(12) United States Patent
Whitehead et al.

(10) Patent No.: US 8,075,903 B2
(45) Date of Patent: *Dec. 13, 2011

(54) DENGUE TETRAVALENT VACCINE CONTAINING A COMMON 30 NUCLEOTIDE DELETION IN THE 3'-UTR OF DENGUE TYPES 1, 2, 3, AND 4 OR ANTIGENIC CHIMERIC DENGUE VIRUSES 1, 2, 3, AND 4

(75) Inventors: Stephen S. Whitehead, Montgomery Village, MD (US); Brian R. Murphy, Bethesda, MD (US); Lewis Markoff, Bethesda, MD (US); Barry Falgout, Rockville, MD (US); Joseph Blaney, Frederick, MD (US); Kathryn Hanley, Las Cruces, NM (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 29 days.

This patent is subject to a terminal disclaimer.

(21) Appl. No.: 12/398,043

(22) Filed: Mar. 4, 2009

(65) Prior Publication Data
US 2009/0258036 A1 Oct. 15, 2009

Related U.S. Application Data

(63) Continuation of application No. 10/970,640, filed on Oct. 21, 2004, now Pat. No. 7,517,531, which is a continuation of application No. PCT/US03/13279, filed on Apr. 25, 2003.

(60) Provisional application No. 60/377,860, filed on May 3, 2002, provisional application No. 60/436,500, filed on Dec. 23, 2002.

(51) Int. Cl.
*A61K 39/295* (2006.01)
(52) U.S. Cl. ............... 424/202.1; 424/218.1; 424/199.1; 424/205.1; 435/320.1; 435/235.1; 435/236
(58) Field of Classification Search ........................ None
See application file for complete search history.

(56) References Cited

U.S. PATENT DOCUMENTS
7,517,531 B2 * 4/2009 Whitehead et al. ........ 424/202.1

FOREIGN PATENT DOCUMENTS
WO  01/91790 A1  12/2001
WO  02/095075  11/2002

OTHER PUBLICATIONS

J.M. Troyer et al., "A live attenuated recombinant dengue-4 virus vaccine candidate with restricted capacity for dissemination in mosquitoes and lack of transmission from vaccine to mosquitoes", Am. J. Trop, Med Hyg., vol. 65, pp. 414-419 (2001).
S.S. Whitehead et al., "A live, attenuated dengue virus type 1 vaccine candidate with a 30-nucleotide deletion in the 3' untranslated region is highly attenuated and immunogenic in monkeys", J. Virol., vol. 77, pp. 1653-1657 (2003).
S.S. Whitehead et al., "Substitution of the structural genes of dengue virus type 4 with those of type 2 results in chimeric vaccine candidates which are attenuated for mosquitoes, mice, and rhesus monkeys", Vaccine, vol. 21, pp. 4307-4316 (2003).
M. Worobey et al., "Widespread intra-serotype recombination in natural populations of dengue virus", PNAS USA, vol. 96, pp. 7352-7357 (1999).
L. Zeng et al., "Identification of specific nucleotide sequences within the conserved 3'-SL in the dengue type 2 virus genome required for replication", J. Virol., vol. 72, pp. 7510-7522 (1998).
N. Bhamarapravati et al., "Live attenuated tetravalent dengue vaccine", Vaccine, vol. 18, pp. 44-47 (2000).
J.E. Blaney, Jr. et al., "Development of a Live Attenuated Dengue Virus Vaccine Using Reverse Genetics", Viral Immunol., vol. 19, pp. 10-32 (2006).
A.P. Durbin et al., "The Recombinant Live Attenuated Dengue 4 Candidate Vaccine rDEN4delta30 is Safe, Immunogenic, and Highly Infectious in Healthy Adults", Am. J. Trop. Med. Hyg., p. 361, Abstract 379 (2003).
K.A. Hanley et al., "Paired Charge-to-Alanine Mutagenesis of Dengue Virus Type 4 NS5 Generates Mutants with Temperature-Sensitive, Host Range, and Mouse Attenuation Phenotypes", J. Virol., vol. 76, pp. 525-531 (2002).
N. Kanesa-Thasan et al., "Safety and immunogenicity of attenuated dengue virus vaccines (Aventis Pasteur) in human volunteers", Vaccine, vol. 19, pp. 3179-3188 (2001).
Durbin et al., Attenuation and immunogenicity in humans of a live dengue virus type-4 vaccine candidate with a 30 nucleotide deletion in its 3'-untranslated region, American Journal of Tropical Medicine and Hygeine, vol. 65, pp. 405-413 (2001).
Lai et al., Clinical and Diagnostic Virology, vol. 10, pp. 173-179 (1998).
Olsthoorn et al., RNA, vol. 7, pp. 1370-1377 (2001).
Blaney et al., Journal of Virology, vol. 79, pp. 5516-5528 (2005).
Proutski et al., Virus Research, vol. 64, pp. 107-123 (1999). J. An et al., "Development of a novel mouse model for dengue virus infection", Virology, vol. 263, pp. 70-77 (1999).
A.D.T. Barrett et al., "Yellow fever vaccines", Biologicals, vol. 25, pp. 17-25 (1997).
J.L. Blackwell et al., "Translation elongation factor-1 alpha interacts with the 3' stem-loop region of West Nile virus genomic RNA", J. Virol., vol. 71, pp. 6433-6444 (1997).
J.E. Blaney, Jr., et al., "Chemical mutagenesis of dengue virus type 4 yields mutant viruses which are temperature sensitive in vero cells or human liver cells and attenuated in mice", J. Virol., vol. 75, pp. 9731-9740 (2001).
J.E. Blaney, Jr., et al., "Genetic basis of attenuation of dengue virus type 4 small plaque mutants with restricted replication in suckling mice and in SCID mice transplanted with human liver cells", Virology, vol. 300, pp. 125-139 (2002).
J.E. Blaney, Jr. et al. "Mutations which enhance the replication of dengue virus type 4 and an antigenic chimeric dengue virus type 2/4 vaccine candidate in Vero cells", Vaccine, vol. 21, pp. 4317-4327 (2003).

(Continued)

*Primary Examiner* — Mary E Mosher
(74) *Attorney, Agent, or Firm* — Edwards Wildman Palmer LLP; Peter F. Corless

(57) ABSTRACT

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

36 Claims, 15 Drawing Sheets

OTHER PUBLICATIONS

J.E. Blaney, Jr., et al., "Genetically modified, live attenuated dengue virus type 3 vaccine candidates", Am. J. Trop. Med. Hyg., vol. 71, pp. 811-821 (2004).

J.E. Blaney, Jr. et al. "Vaccine candidates derived from a novel infectious cDNA clone of an American genotype dengue virus type 2", BMC Infect. Dis., 4(39), 10 pages (2004).

J. Blok et al, "Comparison of a dengue-2 virus and its candidate vaccine derivative: sequence relationships with the flaviviruses and other viruses", Virology, vol. 187, pp. 573-590 (1992).

M. Bray et al., "Construction of intertypic chimeric dengue viruses by substitution of structural protein genes", PNAS USA, vol. 88, pp. 10342-10346 (1991).

M. Bray et al., "Monkeys immunized with intertypic chimeric dengue viruses are protected against wild-type virus challenge", J. Virol., vol. 70, pp. 4162-4166 (1996).

M. Bray et al., "Genetic determinants responsible for acquisition of dengue type 2 virus mouse neurovirulence", J. Virol., vol. 72, pp. 1647-1651 (1998).

M.A. Brinton et al., "The 3'-nucleotides of flavivirus genomic RNA form a conserved secondary structure", Virology, vol. 153, pp. 113-121 (1986).

D.S. Burke et al., "A prospective study of dengue infections in Bangkok", Am. J. Trop. Med. Hyg., vol. 38, pp. 172-180 (1988).

S. Butrapet et al., "Attenuation markers of a candidate dengue type 2 vaccine virus, strain 16681 (PDK-53), are defined by mutations in the 5' noncoding region and nonstructural proteins 1 and 3", J. Virol., vol. 74, pp. 3011-3019 (2000).

T.J. Chambers et al., "Yellow fever virus/dengue-2 virus and yellow fever virus/dengue-4 virus chimeras: biological characterization, immunogenicity, and protection against dengue encephalitis in the mouse model", J. Virol., vol. 77, pp. 3655-3668 (2003).

W. Chen et al., "Construction of intertypic chimeric dengue viruses exhibiting type 3 antigenicity and neurovirulence for mice", J. Virol., vol. 69, pp. 5186-5190 (1995).

D.J. Gubler et al., "Impact of dengue/dengue hemorrhagic fever on the developing world", Adv. Virus Res., vol. 53, pp. 35-70 (1999).

S. Guillot et al., "Natural genetic exchanges between vaccine and wild poliovirus strains in humans", J. Virol., vol. 74, pp. 8434-8443 (2000).

F. Guirakhoo et al., "Construction, safety, and immunogenicity in nonhuman primates of a chimeric yellow fever-dengue virus tetravalent vaccine", J. Virol., vol. 75, pp. 7290-7304 (2001).

F. Guirakhoo et al., "Viremia and immunogenicity in nonhuman primates of a tetravalent yellow fever-dengue chimeric vaccine: genetic reconstructions, dose adjustment, and antibody responses against wild-type dengue virus isolates", Virology, vol. 298, pp. 146-159 (2002).

C.S. Hahn et al., "Conserved elements in the 3' untranslated region of flavivirus RNAs and potential cyclization sequences", J. Mol. Biol., vol. 198, pp. 33-41 (1987).

K.A. Hanley et al., "Introduction of mutations into the non-structural genes or 3' untranslated region of an attenuated dengue virus type 4 vaccine candidate further decreases replication in rhesus monkeys while retaining protective immunity", Vaccine, vol. 22, pp. 3440-3448 (2004).

C.Y. Huang et al., "Chimeric dengue type 2 (vaccine strain PDK-53)/dengue type 1 virus as a potential candidate dengue type 1 virus vaccine", J. Virol., vol. 74, pp. 3020-3028 (2000).

O. Kew et al., "Outbreak of poliomyelitis in Hispaniola associated with circulating type 1 vaccine-derived poliovirus", Science, vol. 296, pp. 356-359 (2002).

A.A. Khromykh et al., "RNA binding properties of core protein of the flavivirus Kunjin", Arch. Virol., vol. 141, pp. 685-699 (1996).

C.J. Lai et al., "Infectious RNA transcribed from stably cloned full-length cDNA of dengue type 4 virus", PNAS USA, vol. 88, pp. 5139-5143 (1991).

L. Markoff et al., "A conserved internal hydrophobic domain mediates the stable membrane integration of the dengue virus capsid protein", Virology, vol. 233, pp. 105-117 (1997).

L. Markoff et al., "Derivation and characterization of a dengue type 1 host range-restricted mutant virus that is attenuated and highly immunogenic in monkeys", J. Virol., vol. 76, pp. 3318-3328 (2002).

A. Mathew et al., "Predominance of HLA-restricted cytotoxic T-lymphocyte responses to serotype-cross-reactive epitopes on nonstructural proteins following natural secondary dengue virus infection", J. Virol., vol. 72, pp. 3999-4004 (1998).

R. Men et al., "Dengue type 4 virus mutants containing deletions in the 3' noncoding region of the RNA genome: analysis of growth restriction in cell culture and altered viremia pattern and immunogenicity in rhesus monkeys", J. Virol., vol. 70, pp. 3930-3937 (1996).

A.G. Pletnev et al., "Construction and characterization of chimeric tick-borne encephalitis/dengue type 4 viruses", PNAS USA, vol. 89, pp. 10532-10536 (1992).

A.G. Platnev et al., "Chimeric tick-borne encephalitis and dengue type 4 viruses: effects of mutations on neurovirulence in mice", J. Virol., vol. 67, pp. 4956-4963 (1993).

A.G. Platnev et al., "Attenuation of the Langat tick-borne flavivirus by chimerization with mosquito-borne flavivirus dengue type 4", PNAS USA, vol. 95, pp. 1746-1751 (1998).

A.G. Pletnev et al., "West Nile virus/dengue type 4 virus chimeras that are reduced in neurovirulence and peripheral virulence without loss of immunogenicity or protective efficacy", PNAS USA, vol. 99, pp. 3036-3041 (2002).

S. Polo et al., "Infectious RNA transcripts from full-length dengue virus type 2 cDNA clones made in yeast", J. Virol., vol. 71, pp. 5366-5374 (1997).

V. Proutski et al., "Secondary structure of the 3' untranslated region of flaviviruses: similarities and differences", Nucleic Acids Res.. vol. 25, pp. 1194-1202 (1997).

B. Puri et al., "Molecular analysis of dengue virus attenuation after serial passage in primary dog kidney cells", J. Gen. Virol., vol. 78, pp. 2287-2291 (1997).

B. Puri et al., "Construction of a full length infectious clone for dengue-1 virus Western Pacific, 74 strain", Virus Genes, vol. 20, pp. 57-63 (2000).

S. Rauscher et al., "Secondary structure of the 3'-noncoding region of flavivirus genomes: comparative analysis of base pairing probabilities", RNA, vol. 3, pp. 779-791 (1997).

C.M. Rice et al., "Nucleotide sequence of yellow fever virus: implications for flavivirus gene expression and evolution", Science, vol. 229, pp. 726-733 (1985).

L. Rosen et al., "Comparative susceptibility of mosquito species and strains to oral and parenteral infection with dengue and Japanese encephalitis viruses", Am. J. Trop. Med. Hyg., vol. 34, pp. 603-615 (1985).

L. Rosen et al., "Comparative suceptibility of five species of Toxorhynchites mosquitoes to parenteral infection with dengue and other flaviviruses", Am. J. Trop. Med. Hyg., vol. 34, pp. 805-809 (1985).

M. Ta et al., "Mov34 protein from mouse brain interacts with the 3' noncoding region of Japanese encephalitis virus", J. Virol., vol. 74, pp. 5108-5115 (2000).

S. Thein et al., "Risk factors in dengue shock syndrome", Am. J. Trop. Med. Hyg., vol. 56, pp. 566-572 (1997).

S.S. Whitehead et al., "Dengue Virus Vaccine Candidates Containing a Common 30 Nucleotide Deletion in the 3'-UTR of Each Serotype or Antigenic Chimeric Viruses Representing Each Serotype are Attenuated and Immunogenic", American Journal of Tropical Medicine & Hygiene, 69(3), pp. 530-531 (2003).

A.P. Durbin et al., "rDEN2/4Delta30(ME), A Live Attenuated Chimeric Dengue Serotype 2 Vaccine is Safe and Highly Immunogenic in Healthy Dengue-Naïve Adults", Human Vaccines, 2(6), pp. 255-260 (2006).

European Search Report for EP Appln. No. 10 17 7735, dated May 10, 2011.

European Search Report for EP Appln. No. 10 17 7740, dated Mar. 25, 2011.

* cited by examiner

```
DEN1      GGGGCCC-AACACCAGGGGAAGCUGUACCCUGGUGGUAAGGACUAGA
DEN1Δ30   GGGGCCC-AA-----------------------------GACUAGA
DEN2      GGGGCCC-AAGGUGAGAUGAAGCUGUAGUCUCACUGGAAGGACUAGA
DEN2Δ30   GGGGCCC-AA-----------------------------GACUAGA
DEN3      GGGGCCCGAGCUCUGAGGGAAGCUGUACCUCCUUGCAAAGGACUAGA
DEN3Δ30   GGGGCCCAA------------------------------GACUAGA
DEN4      GGGGCCCGAAGCCAGGAGGAAGCUGUACUCCUGGUGGAAGGACUAGA
DEN4Δ30   GGGGCCC-AA-----------------------------GACUAGA

DEN1      GGGGCCC-AacaccaggGGAAGCUGUAcccuggugguAAGGACUAGA
DEN2      GGGGCCC-AaggugagauGAAGCUGUAgucucacuggAAGGACUAGA
DEN3      GGGGCCCgAgcucugaggGAAGCUGUAccuccuugcaAAGGACUAGA
DEN4      GGGGCCCgAagccaggagGAAGCUGUAcuccugguggAAGGACUAGA
```

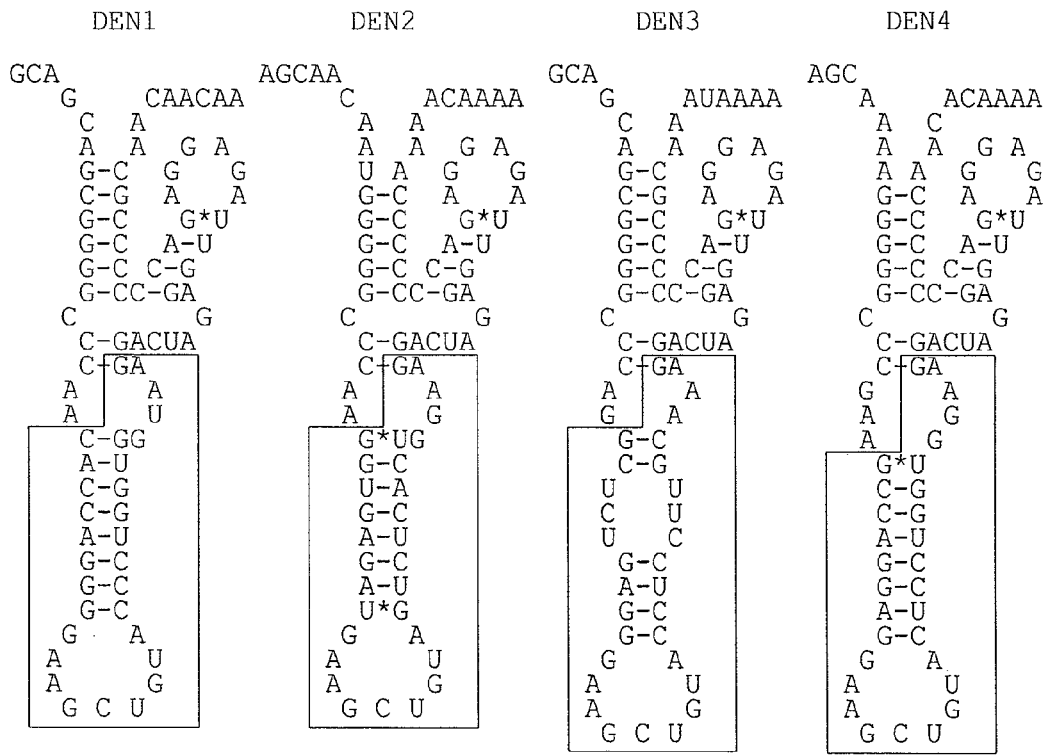

*FIG. 2C*

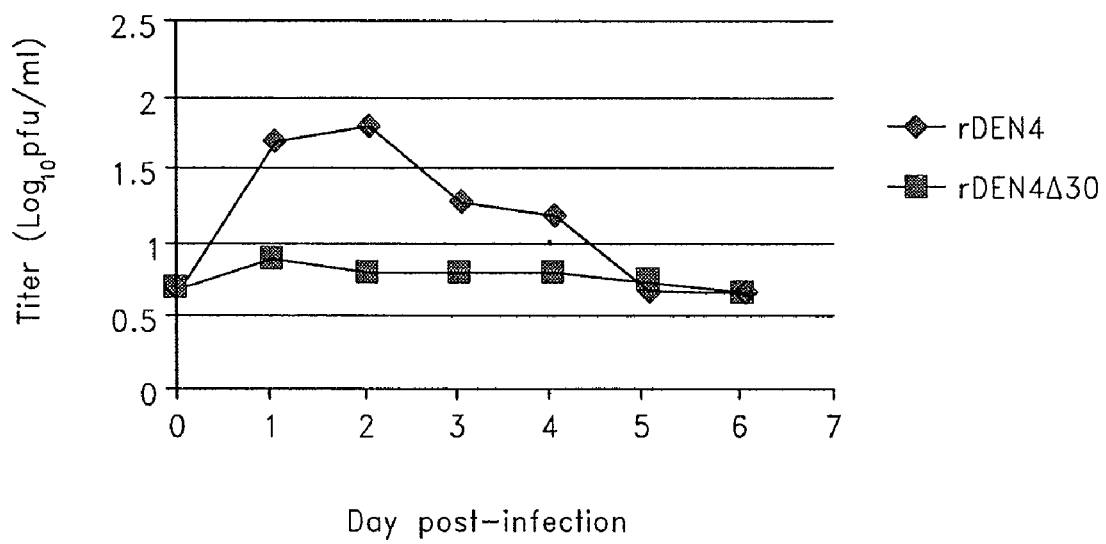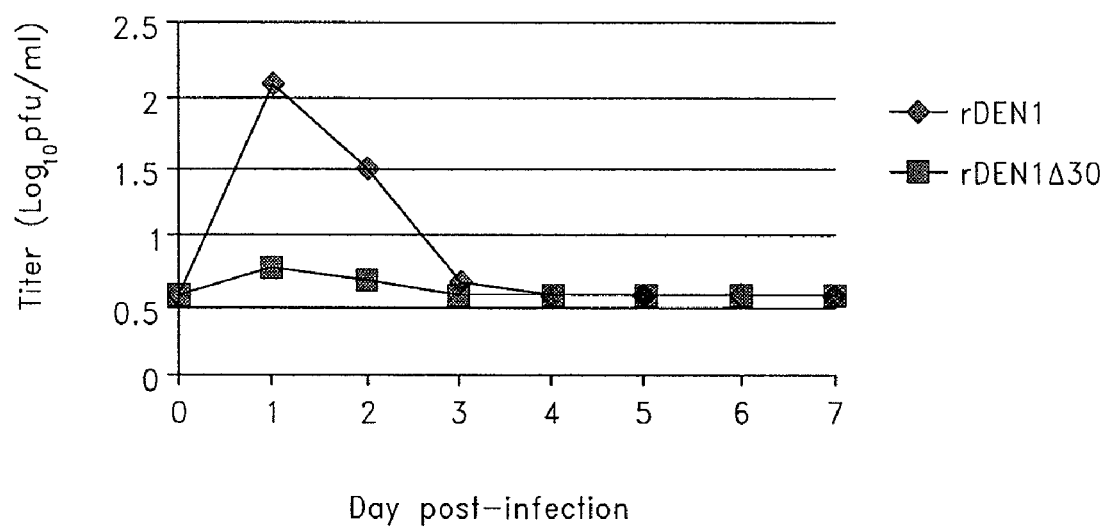
FIG. 5

Junction 1:
```
           BglII
    DEN4  |     DEN2
-CAGTTTGTTTGAATATAGAGAGCAGATCTCTGATGAATAACCAACGAAAAAG

FIG. 12B

```
                 DEN4              BglII          DEN1
Junction 1:  -CAGTTTGTTTGAATAGAGAGCAGATCTCTGGAAAAATGAACAACCAACGG-
                                                   MetAsnAsnGlnArg DEN1                XhoI          DEN4
Junction 2:  -CTGCTGACATGGCTAGGATTAAACTCGAGGAACACTTCAATGGCTATGACG-
              LeuLeuThrTrpLeuGlyLeuAsnSerArgAsnThrSerMetAlaMetThr DEN4               PstI           DEN1
Junction 3:  -ATCTTGAACGGGAGAAAAAGGTCTGCAGCCATGCTCCTCATGCTGCTGCCC-
              IleLeuAsnGlyArgLysArgSerAlaAlaMetLeuLeuMetLeuLeuPro
```

় # DENGUE TETRAVALENT VACCINE CONTAINING A COMMON 30 NUCLEOTIDE DELETION IN THE 3'-UTR OF DENGUE TYPES 1, 2, 3, AND 4 OR ANTIGENIC CHIMERIC DENGUE VIRUSES 1, 2, 3, AND 4

RELATED APPLICATIONS

This application is a continuation of U.S. patent application Ser. No. 10/970,640, filed Oct. 21, 2004, which is a continuation and claims the benefit of priority of International Application No. PCT/US03/13279 filed Apr. 25, 2003, designating the United States of America and published in English on Nov. 13, 2003, as WO 03/092592, which claims the benefit of priority of U.S. Provisional Application No. 60/377,860 filed May 3, 2002 and U.S. Provisional Application No. 60/436,500 filed Dec. 23, 2002, all of which are hereby expressly incorporated by reference in their entireties.

SEQUENCE LISTING

The present application is being filed along with a Sequence Listing in electronic format. The Sequence Listing is provided as a file entitled NIH230-001C1C1_Sequence_Listing.TXT, created Jan. 26, 2008, which is 118 Kb in size. The information in the electronic format of the Sequence Listing is incorporated herein by reference in its entirety.

FIELD OF THE INVENTION

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

BACKGROUND OF THE INVENTION

Dengue virus is a positive-sense RNA virus belonging to the *Flavivirus* genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO 1997 *Dengue Haemorrhagic Fever: Diagnosis, Treatment, Prevention, and Control* 2nd Edition, Geneva). There are four serotypes of dengue virus (DEN1, DEN2, DEN3, and DEN4) that annually cause an estimated 50-100 million cases of dengue fever and 500,000 cases of the more severe form of dengue virus infection known as dengue hemorrhagic fever/dengue shock syndrome (DHF/DSS) (Gubler, D. J. and Meltzer, M. 1999 *Adv Virus Res* 53:35-70). This latter disease is seen predominantly in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-180; Halstead, S. B. et al. 1969 *Am J Trop Med Hyg* 18:997-1021; Thein, S. et al. 1997 *Am J Trop Med Hyg* 56:566-575). A dengue vaccine is needed to lessen disease burden caused by dengue virus, but none is licensed. Because of the association of more severe disease with secondary dengue virus infection, a successful vaccine must simultaneously induce immunity to all four serotypes. Immunity is primarily mediated by neutralizing antibody directed against the envelope (E) glycoprotein, a virion structural protein. Infection with one serotype induces long-lived homotypic immunity and a short-lived heterotypic immunity (Sabin, A. 1955 *Am J Trop Med Hyg* 4:198-207). Therefore, the goal of immunization is to induce a long-lived neutralizing antibody response against DEN1, DEN2, DEN3, and DEN4, which can best be achieved economically using live attenuated virus vaccines. This is a reasonable goal since a live attenuated vaccine has already been developed for the related yellow fever virus, another mosquito-borne flavivirus present in tropical and semitropical regions of the world (Monath, T. P. and Heinz, F. X. 1996 in: *Fields Virology*, Fields, D. M et al. eds. Philadelphia: Lippincott-Raven Publishers, pp. 961-1034).

Several live attenuated dengue vaccine candidates have been developed and evaluated in humans and non-human primates. The first live attenuated dengue vaccine candidates were host range mutants developed by serial passage of wild-type dengue viruses in the brains of mice and selection of mutants attenuated for humans (Kimura, R. and Hotta, S. 1944 *Jpn J Bacteriol* 1:96-99; Sabin, A. B. and Schlesinger, R. W. 1945 *Science* 101:640; Wisserman, C. L. et al. 1963 *Am J Trop Med Hyg* 12:620-623). Although these candidate vaccine viruses were immunogenic in humans, their poor growth in cell culture discouraged further development. Additional live attenuated DEN1, DEN2, DEN3, and DEN4 vaccine candidates have been developed by serial passage in non-human tissue culture (Angsubhakorn, S. et al. 1994 *Southeast Asian J Trop Med Public Health* 25:554-559; Bancroft, W. H. et al. 1981 *Infect Immun* 31:698-703; Bhamarapravati, N. et al. 1987 *Bull World Health Organ* 65:189-195; Eckels, K. H. et al. 1984 *Am J Trop Med Hyg* 33:684-698; Hoke, C. H. Jr. et al. 1990 *Am J Trop Med Hyg* 43:219-226; Kanesa-Thasan, N. et al. 2001 *Vaccine* 19:3179-3188) or by chemical mutagenesis (McKee, K. T. et al. 1987 *Am J Trop Med Hyg* 36:435-442). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-Thasan, N. et al. 2001 *Vaccine* 19:3179-3188; Bhamarapravati, N. and Sutee, Y. 2000 *Vaccine* 18:44-47).

Two major advances using recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations that have been introduced into the cDNA clone by site-directed mutagenesis (Lai, C. J. et al. 1991 *PNAS USA* 88:5139-5143). Second, it is possible to produce antigenic chimeric viruses in which the structural protein coding region of the full-length cDNA clone of dengue virus is replaced by that of a different dengue virus serotype or from a more divergent flavivirus (Bray, M. and Lai, C. J. 1991 *PNAS USA* 88:10342-10346; Chen, W. et al. 1995 *J Virol* 69:5186-5190; Huang, C. Y. et al. 2000 *J Virol* 74:3020-3028; Pletnev, A. G. and Men, R. 1998 *PNAS USA* 95:1746-1751). These techniques have been used to construct intertypic chimeric dengue viruses that have been shown to be effective in protecting monkeys against homologous dengue virus challenge (Bray, M. et al. 1996 *J Virol* 70:4162-4166). A similar strategy is also being used to develop attenuated antigenic chimeric dengue virus vaccines based on the attenuation of the yellow fever vaccine virus or the attenuation of the cell-culture passaged dengue viruses (Monath, T. P. et al. 1999 *Vaccine* 17:1869-1882; Huang, C. Y. et al. 2000 *J Virol* 74:3020-3028).

Another study examined the level of attenuation for humans of a DEN4 mutant bearing a 30-nucleotide deletion (Δ30) introduced into its 3'-untranslated region by site-directed mutagenesis and that was found previously to be attenuated for rhesus monkeys (Men, R. et al. 1996 *J Virol* 70:3930-3937). Additional studies were carried out to examine whether this Δ30 mutation present in the DEN4 vaccine candidate was the major determinant of its attenuation for monkeys. It was found that the Δ30 mutation was indeed the major determinant of attenuation for monkeys, and that it specified a satisfactory balance between attenuation and immunogenicity for humans (Durbin, A. P. et al. 2001 *Am J Trop Med Hyg* 65:405-13).

SUMMARY OF THE INVENTION

The previously identified Δ30 attenuating mutation, created in dengue virus type 4 (DEN4) by the removal of 30 nucleotides from the 3'-UTR, is also capable of attenuating a wild-type strain of dengue virus type 1 (DEN1). Removal of 30 nucleotides from the DEN1 3'-UTR in a highly conserved region homologous to the DEN4 region encompassing the Δ30 mutation yielded a recombinant virus attenuated in rhesus monkeys to a level similar to recombinant virus DEN4Δ30. This establishes the transportability of the Δ30 mutation and its attenuation phenotype to a dengue virus type other than DEN4. The effective transferability of the Δ30 mutation, described by this work, establishes the usefulness of the Δ30 mutation to attenuate and improve the safety of commercializable dengue virus vaccines of any serotype. We envision a tetravalent dengue virus vaccine containing dengue virus types 1, 2, 3, and 4 each attenuated by the Δ30 mutation. We also envision a tetravalent dengue virus vaccine containing recombinant antigenic chimeric viruses in which the structural genes of dengue virus types 1, 2, and 3 replace those of DEN4Δ30; 1, 2, and 4 replace those of DEN3Δ30; 1, 3, and 4 replace those of DEN2Δ30; and 2, 3, and 4 replace those of DEN1Δ30. In some instances, such chimeric dengue viruses are attenuated not only by the Δ30 mutation, but also by their chimeric nature. The presence of the Δ30 attenuating mutation in each virus component precludes the reversion to a wild-type virus by intertypic recombination. In addition, because of the inherent genetic stability of deletion mutations, the Δ30 mutation represents an excellent alternative for use as a common mutation shared among each component of a tetravalent vaccine.

BRIEF DESCRIPTION OF THE DRAWINGS

FIG. 2. A. The Δ30 mutation removes 30 contiguous nucleotides (shaded) from the 3' UTR of DEN4. Nucleotides are numbered from the 3' terminus. B. Nucleotide sequence alignment of the TL2 region of DEN1, DEN2, DEN3, and DEN4 and their Δ30 derivatives. Also shown is the corresponding region for each of the four DEN serotypes. Upper case letters indicate sequence homology among all 4 serotypes, underlining indicates nucleotide pairing to form the stem structure. C. Predicted secondary structure of the TL2 region of each DEN serotype. Nucleotides that are removed by the Δ30 mutation are boxed (DEN1—between nts 10562-10591, DEN2 Tonga/74—between nts 10541-10570, DEN3 Sleman/78—between nts 10535-10565, and DEN4—between nts 10478-10507).

FIG. 5. The Δ30 mutation attenuates both DEN1 and DEN4 for rhesus monkeys. Groups of 4 monkeys were immunized subcutaneously with 5.0 $\log_{10}$ PFU of the indicated virus. Serum was collected each day following immunization and virus titers were determined and are shown as mean $\log_{10}$ PFU/ml.

The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.

FIG. 12. A. Recombinant chimeric dengue viruses were constructed by introducing either the CME or the ME regions of DEN1 (Puerto Rico/94) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.

| Brief Description of the Sequences | |
|---|---|
| Serotype | GenBank Accession No. or description |
| DEN1 | U88535 |
| DEN2 | Tonga/74 |
| DEN3 | Sleman/78 |
| DEN4 | AF326825 |

Figures 6A, 6B:
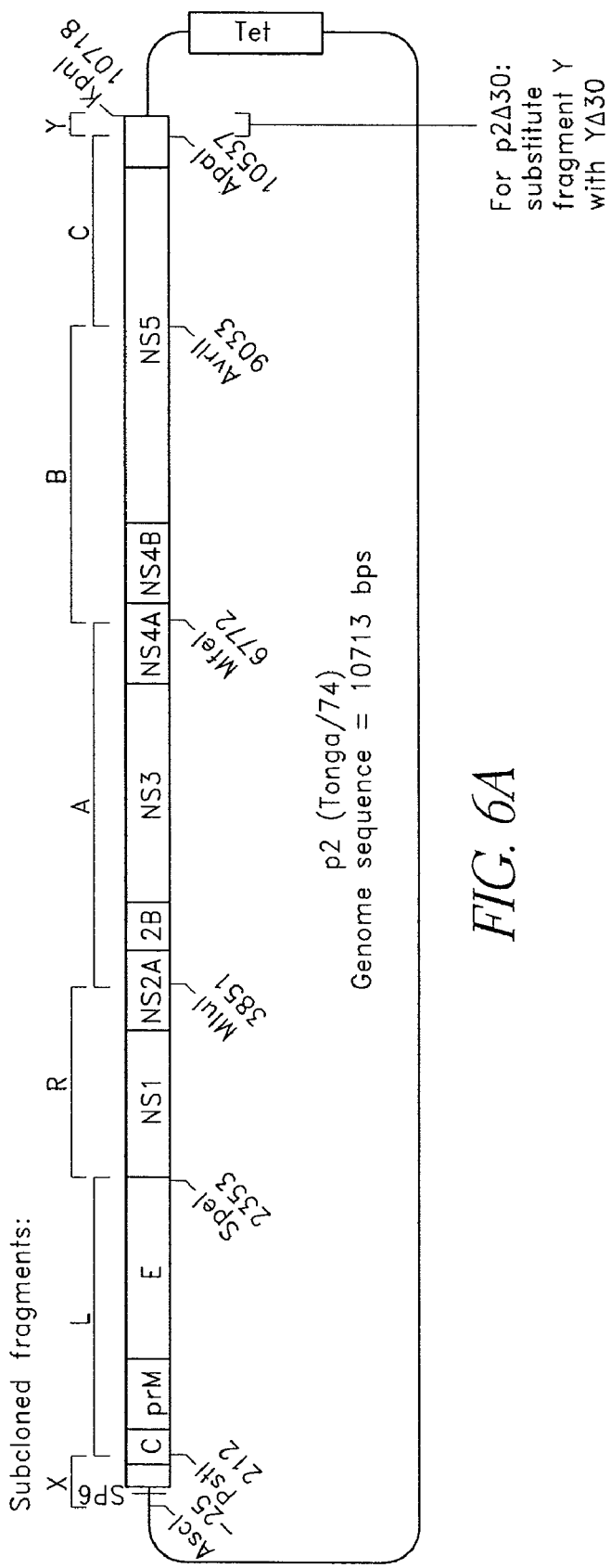
FIG. 6. A. Diagram of the p2 (Tonga/74) full-length cDNA plasmid. Regions subcloned are indicated above the plasmid. Numbering begins at the 5' end of the viral sequence. B. The Δ30 mutation removes the indicated 30 nucleotides from the 3' UTR sequence to create p2Δ30.
Figure 8A:
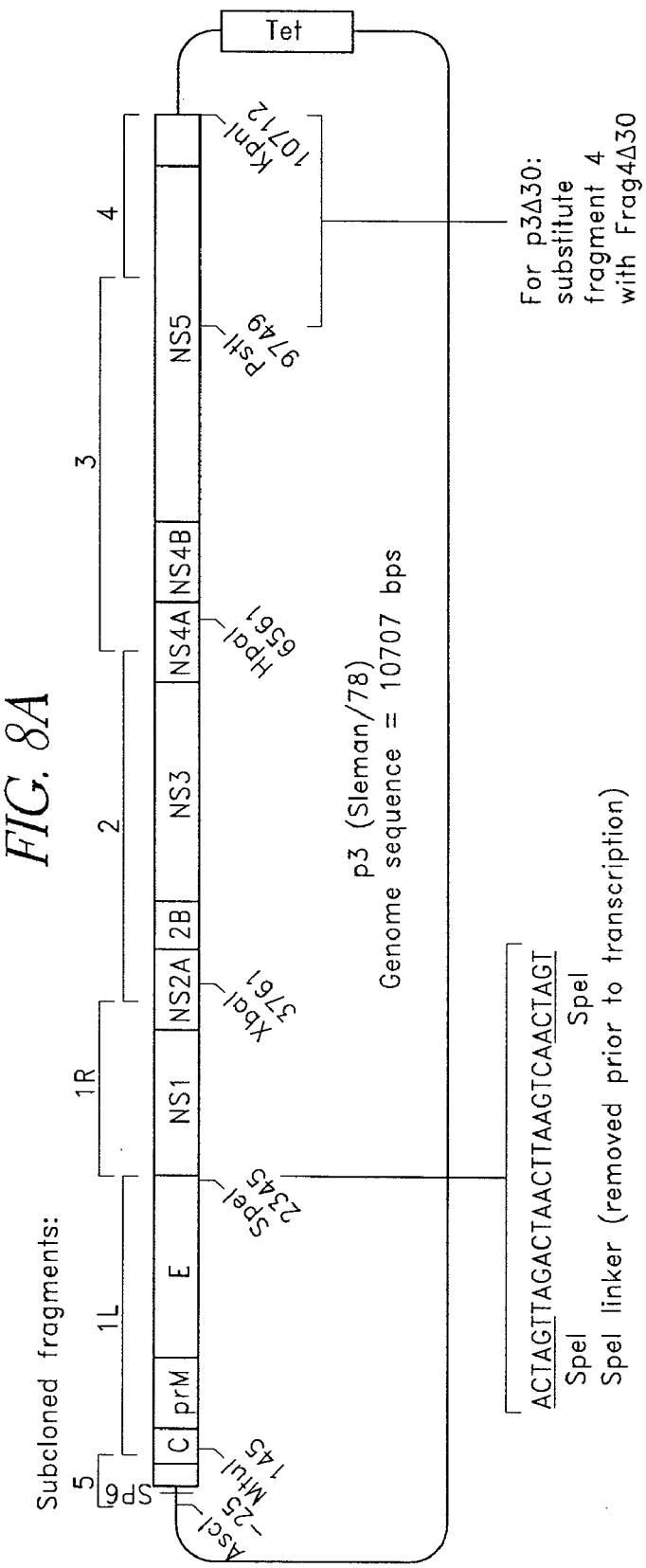
FIG. 8. A. Diagram of the p3 (Sleman/78) full-length cDNA plasmid. Regions subcloned are indicated above the plasmid. Numbering begins at the 5' end of the viral sequence. The sequence and insertion location of the SpeI linker is shown. B. The Δ30 mutation removes the indicated 31 nucleotides from the 3' UTR sequence to create p3Δ30.
Figure 8B:
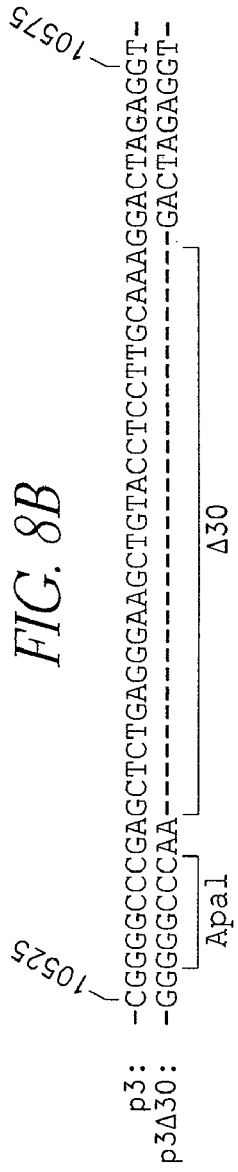
Figure 9A:
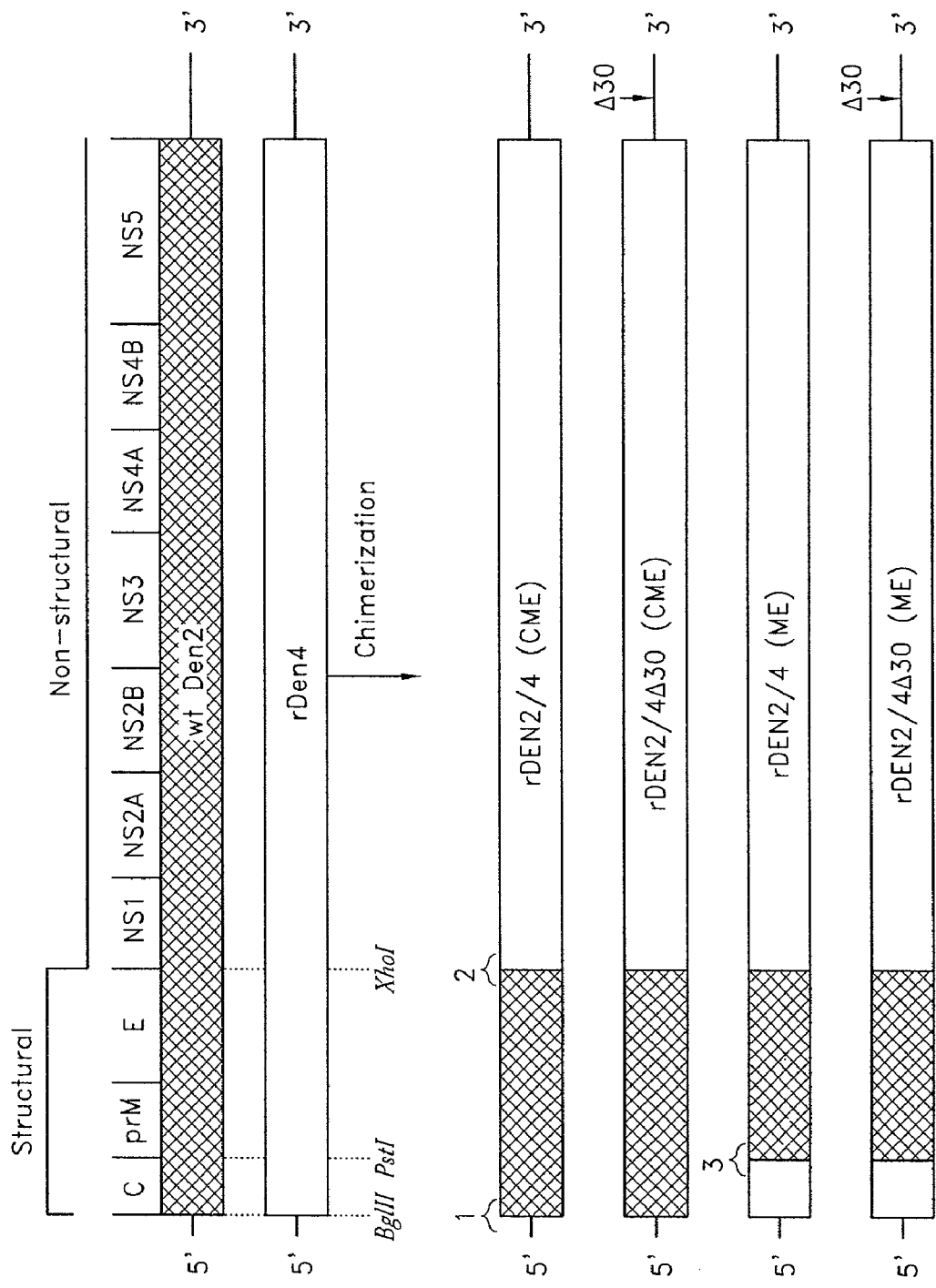
FIG. 9. A. Recombinant chimeric dengue viruses were constructed by introducing either the CME or the ME regions of DEN2 (Tonga/74) into the DEN4 genetic background. The relative location of the Δ30 mutation in the 3' UTR is indicated by an arrow and intertypic junctions 1, 2, and 3 are indicated. B. Nucleotide and amino acid sequence of the intertypic junction regions. Restriction enzyme recognition sites used in assembly of each chimeric cDNA are indicated.
Figure 9B:
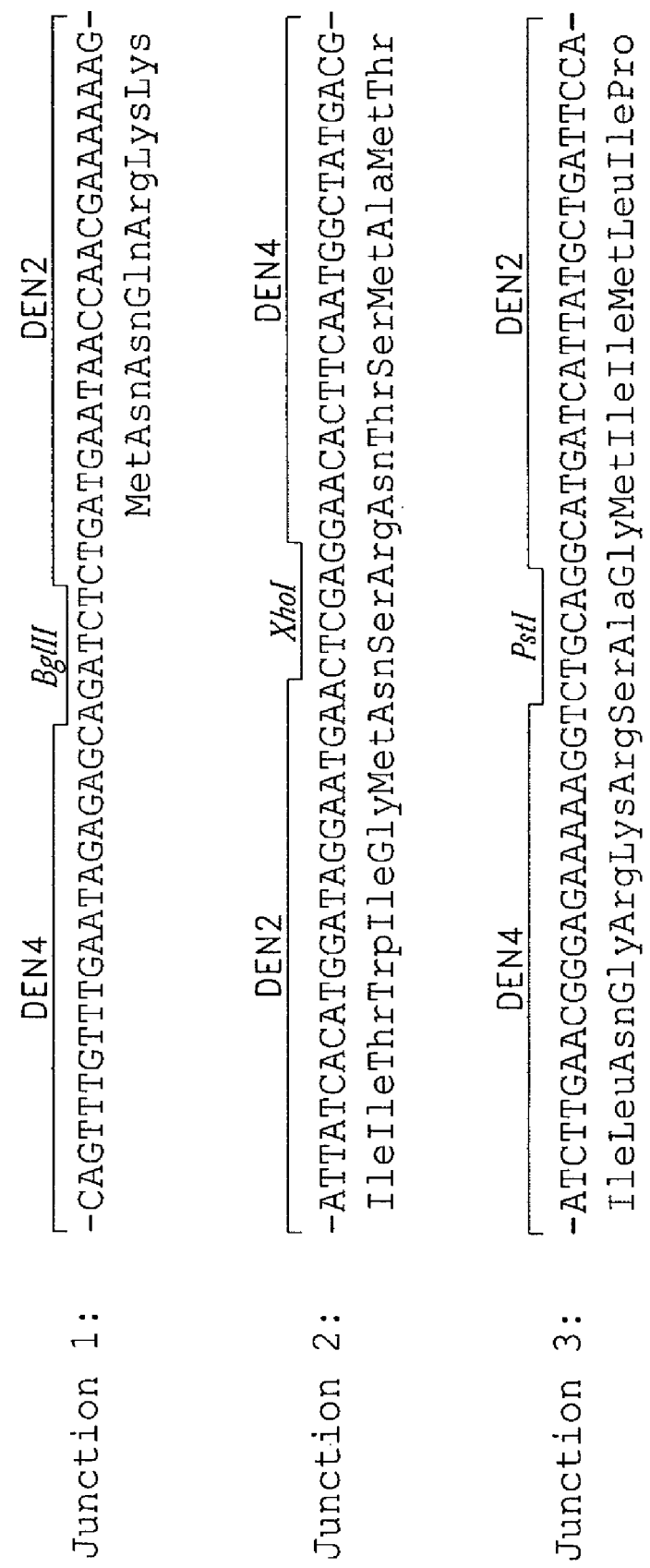
Figure 11A:
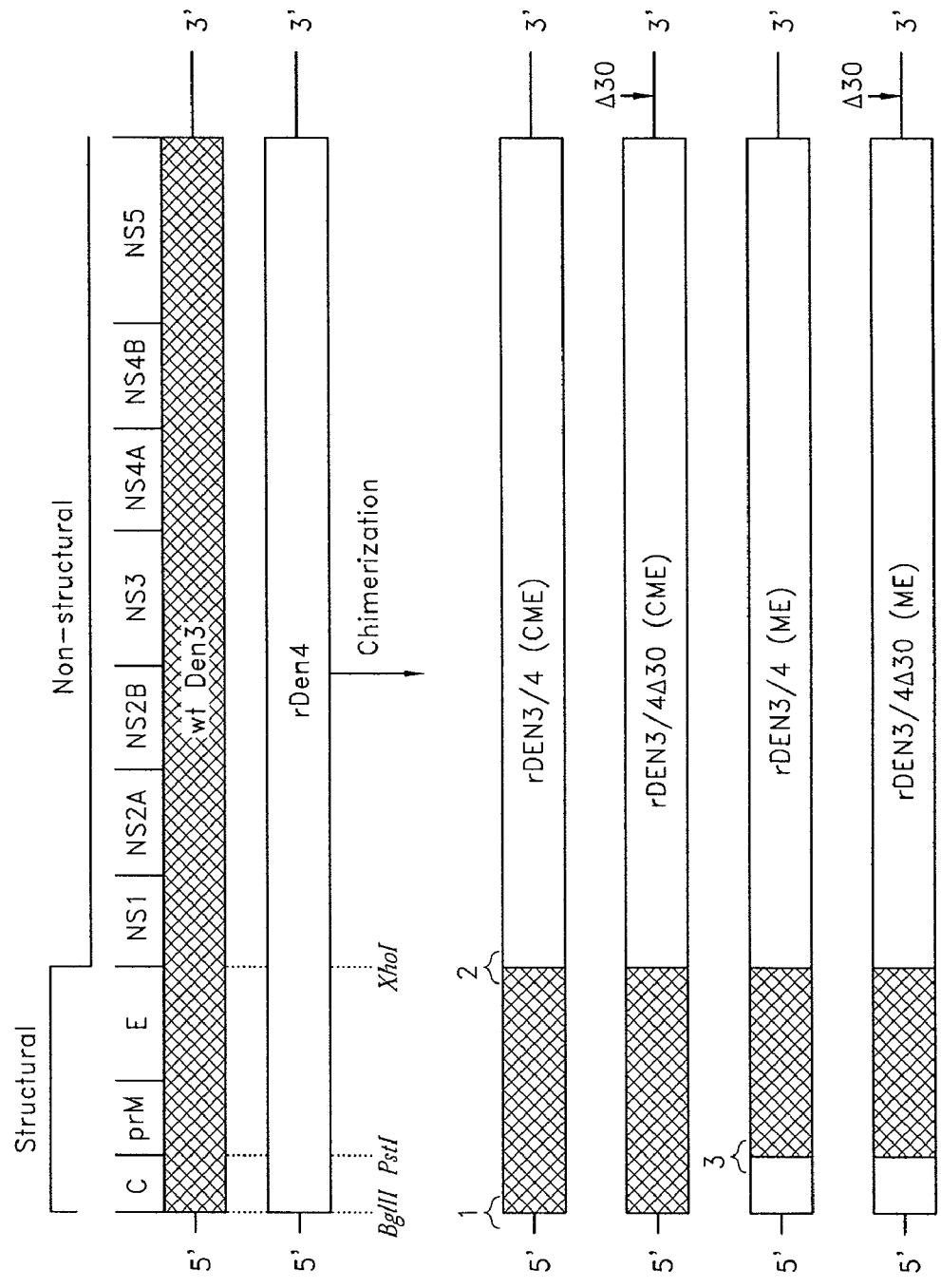
FIG. 11. A. Recombinant chimeric dengue viruses were constructed by introducing either the CME or the ME regions of DEN3 (Sleman/78) into the DEN4 genetic background.
Figure 11B:
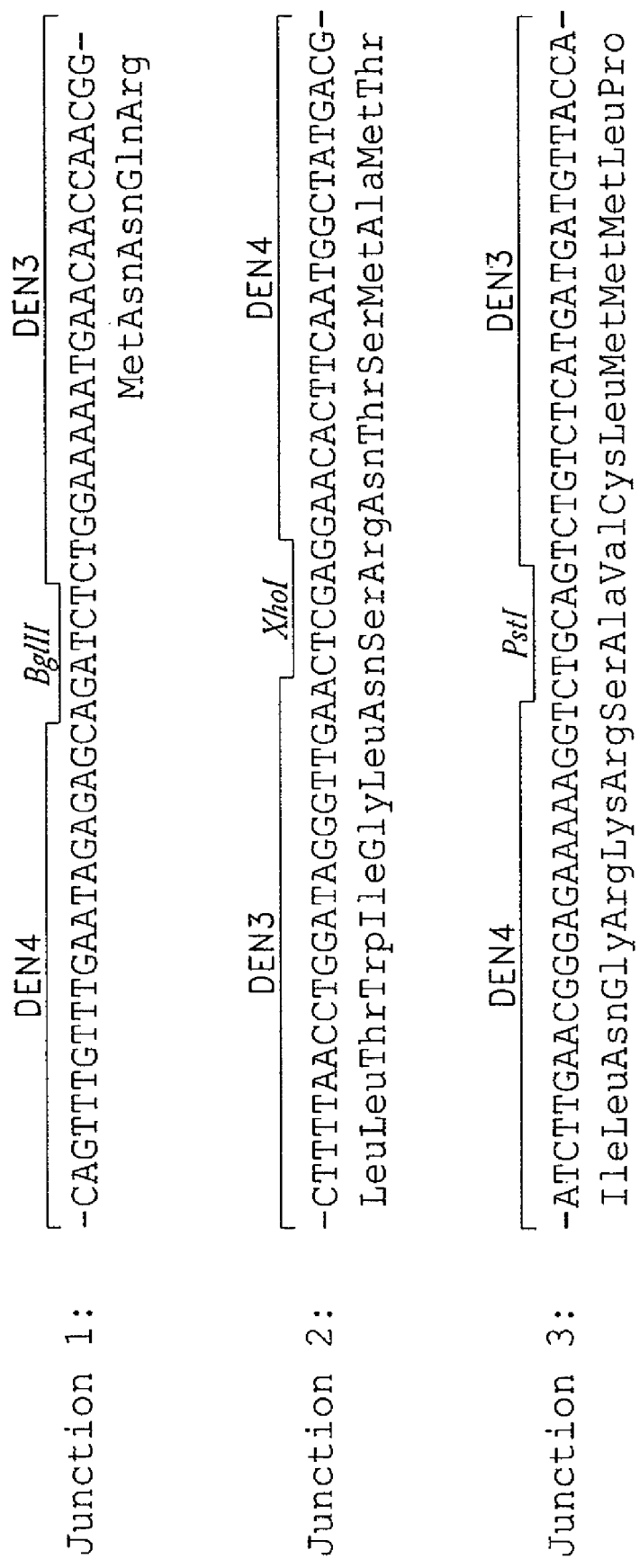

| Brief Description of the SEQ ID NOs | | |
|---|---|---|
| Identification | Figure, Table, or Appendix | SEQ ID NO. |
| TL2 region of DEN1 | Fig. 2C | 1 |
| TL2 region of DEN2 | Fig. 2C | 2 |
| TL2 region of DEN3 | Fig. 2C | 3 |
| TL2 region of DEN4 | Fig. 2C | 4 |
| TL2 region of DEN1Δ30 | Fig. 2B | 5 |
| TL2 region of DEN2Δ30 | Fig. 2B | 6 |
| TL2 region of DEN3Δ30 | Fig. 2B | 7 |
| TL2 region of DEN4Δ30 | Fig. 2B | 8 |
| TL2 region of p2 | Fig. 6B | 9 |
| TL2 region of p2Δ30 | Fig. 6B | 10 |
| TL2 region of p3 | Fig. 8B | 11 |
| TL2 region of p3Δ30 | Fig. 8B | 12 |
| SpeI linker in p3 | Fig. 8A | 13 |
| rDEN2/4 junction 1 | Fig. 9B | 14-nt, 15-aa |
| rDEN2/4 junction 2 | Fig. 9B | 16-nt, 17-aa |
| rDEN2/4 junction 3 | Fig. 9B | 18-nt, 19-aa |
| rDEN3/4 junction 1 | Fig. 11B | 20-nt, 21-aa |
| rDEN3/4 junction 2 | Fig. 11B | 22-nt, 23-aa |
| rDEN3/4 junction 3 | Fig. 11B | 24-nt, 25-aa |
| rDEN1/4 junction 1 | Fig. 12B | 26-nt, 27-aa |
| rDEN1/4 junction 2 | Fig. 12B | 28-nt, 29-aa |
| rDEN1/4 junction 3 | Fig. 12B | 30-nt, 31-aa |
| D4 selected NS4B region | Table 15 | 32-nt, 33-aa |
| D1 selected NS4B region | Table 15 | 34-nt, 35-aa |
| D2 selected NS4B region | Table 15 | 36-nt, 37-aa |
| D3 selected NS4B region | Table 15 | 38-nt, 39-aa |
| CCACGGGCGCCGT | Table 26 | 40 |
| AAGGCCTGGA | Table 26 | 41 |

-continued

Brief Description of the SEQ ID NOs

| Identification | Figure, Table, or Appendix | SEQ ID NO. |
|---|---|---|
| TATCCCCGGGAC | Table 26 | 42 |
| AGAGCTCTCTC | Table 26 | 43 |
| GAATCTCCACCCGGA | Table 26 | 44 |
| CTGTCGAATC | Table 26 | 45 |
| DEN2 (Tonga/74) cDNA plasmid p2 | Appendix 1 | 46-nt, 47-aa |
| DEN3 (Sleman/78) cDNA plasmid p3 | Appendix 2 | 48-nt, 49-aa |
| DEN1 (Puerto Rico/94) CME chimeric region | Appendix 3 | 50-nt, 51-aa |
| DEN1 (Puerto Rico/94) ME chimeric region | Appendix 4 | 52-nt, 53-aa |

DETAILED DESCRIPTION OF THE PREFERRED EMBODIMENT

Introduction

A molecular approach is herewith used to develop a genetically stable live attenuated tetravalent dengue virus vaccine. Each component of the tetravalent vaccine, namely, DEN1, DEN2, DEN3, and DEN4, must be attenuated, genetically stable, and immunogenic. A tetravalent vaccine is needed to ensure simultaneous protection against each of the four dengue viruses, thereby precluding the possibility of developing the more serious illnesses dengue hemorrhagic fever/dengue shock syndrome (DHF/DSS), which occur in humans during secondary infection with a heterotypic wild-type dengue virus. Since dengue viruses can undergo genetic recombination in nature (Worobey, M. et al. 1999 *PNAS USA* 96:7352-7), the tetravalent vaccine should be genetically incapable of undergoing a recombination event between its four virus components that could lead to the generation of viruses lacking attenuating mutations. Previous approaches to develop a tetravalent dengue virus vaccine have been based on independently deriving each of the four virus components through separate mutagenic procedures, such as passage in tissue culture cells derived from a heterologous host. This strategy has yielded attenuated vaccine candidates (Bhamarapravati, N. and Sutee, Y. 2000 *Vaccine* 18:44-7). However, it is possible that gene exchanges among the four components of these independently derived tetravalent vaccines could occur in vaccines, possibly creating a virulent recombinant virus. Virulent polioviruses derived from recombination have been generated in vaccines following administration of a trivalent poliovirus vaccine (Guillot, S. et al. 2000 *J Virol* 74:8434-43).

The present invention describes: (1) improvements to the previously described rDEN4Δ30 vaccine candidate, 2) attenuated rDEN1Δ30, rDEN2Δ30, and rDEN3Δ30 recombinant viruses containing a 30 nucleotide deletion (Δ30) in a section of the 3' untranslated region (UTR) that is homologous to that in the rDEN4Δ30 recombinant virus, (3) a method to generate a tetravalent dengue virus vaccine composed of rDEN1Δ30, rDEN2Δ30, rDEN3Δ30, and rDEN4Δ30, 4) attenuated antigenic chimeric viruses, rDEN1/4Δ30, rDEN2/4Δ30, and rDEN3/4Δ30, for which the CME, ME, or E gene regions of rDEN4Δ30 have been replaced with those derived from DEN1, DEN2, or DEN3; alternatively rDEN1/3Δ30, rDEN2/3Δ30, and rDEN4/3Δ30 for which CME, ME, or E gene regions of rDEN3Δ30 have been replaced with those derived from DEN1, 2, or 4; alternatively rDEN1/2Δ30, rDEN3/2Δ30, and rDEN4/2Δ30 for which CME, ME, or E gene regions of rDEN2Δ30 have been replaced with those derived from DEN1, 3, or, 4; and alternatively rDEN2/1Δ30, rDEN3/1Δ30, and rDEN4/1Δ30 for which CME, ME, or E gene regions of rDEN1Δ30 have been replaced with those derived from DEN2, 3, or 4, and 5) a method to generate a tetravalent dengue virus vaccine composed of rDEN1/4Δ30, rDEN2/4Δ30, rDEN3/4Δ30, and rDEN4Δ30, alternatively rDEN1/3Δ30, rDEN2/3Δ30, rDEN4/3Δ30, and rDEN3Δ30, alternatively rDEN1/2Δ30, rDEN3/2Δ30, rDEN4/2Δ30, and rDEN2Δ30, and alternatively rDEN2/1Δ30, rDEN3/1Δ30, rDEN4/1Δ30, and rDEN1Δ30. These tetravalent vaccines are unique since they contain a common shared attenuating mutation which eliminates the possibility of generating a virulent wild-type virus in a vaccine since each component of the vaccine possesses the same Δ30 attenuating deletion mutation. In addition, the rDEN1Δ30, rDEN2Δ30, rDEN3Δ30, rDEN4Δ30 tetravalent vaccine is the first to combine the stability of the Δ30 mutation with broad antigenicity. Since the Δ30 deletion mutation is in the 3' UTR of each virus, all of the proteins of the four component viruses are available to induce a protective immune response. Thus, the method provides a mechanism of attenuation that maintains each of the proteins of DEN1, DEN2, DEN3, and DEN4 viruses in a state that preserves the full capability of each of the proteins of the four viruses to induce humoral and cellular immune responses against all of the structural and non-structural proteins present in each dengue virus serotype.

Figure 1:
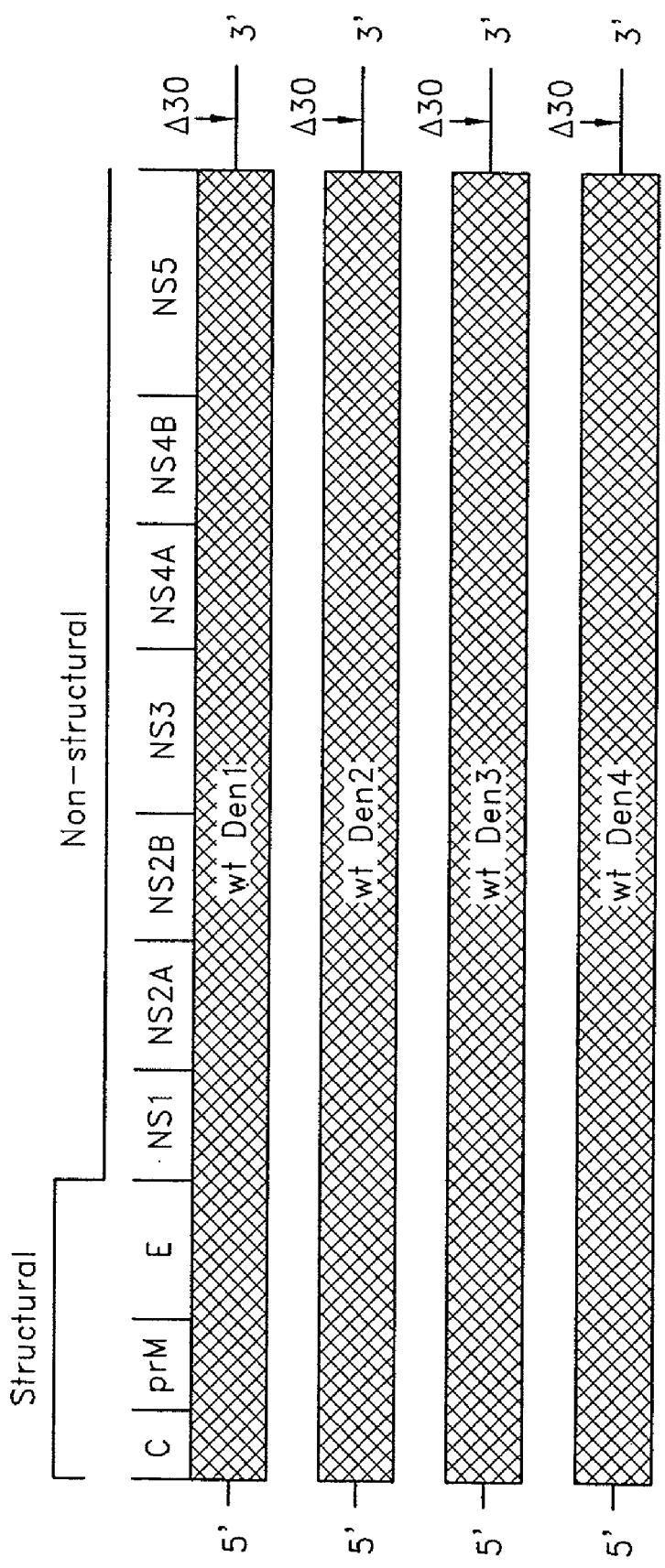
FIG. 1. The live attenuated tetravalent dengue virus vaccine contains dengue viruses representing each of the 4 serotypes, with each serotype containing its full set of unaltered wild-type structural and non-structural proteins and a shared Δ30 attenuating mutation. The relative location of the Δ30 mutation in the 3' untranslated region (UTR) of each component is indicated by an arrow.

As previously described, the DEN4 recombinant virus, rDEN4Δ30 (previously referred to as 2AΔ30), was engineered to contain a 30 nucleotide deletion in the 3' UTR of the viral genome (Durbin, A. P. et al. 2001 *Am J Trop Med Hyg* 65:405-13; Men, R. et al. 1996 *J Virol* 70:3930-7). Evaluation in rhesus monkeys showed the virus to be significantly attenuated relative to wild-type parental virus, yet highly immunogenic and completely protective. Also, a phase I clinical trial with adult human volunteers showed the rDEN4Δ30 recombinant virus to be safe and satisfactorily immunogenic (Durbin, A. P. et al. 2001 *Am J Trop Med Hyg* 65:405-13). To develop a tetravalent vaccine bearing a shared attenuating mutation in a untranslated region, we selected the Δ30 mutation to attenuate wild-type dengue viruses of serotypes 1, 2, and 3 since it attenuated wild-type DEN4 virus for rhesus monkeys and was safe in humans (FIG. 1).

The Δ30 mutation was first described and characterized in the DEN4 virus (Men, R. et al. 1996 *J Virol* 70:3930-7). In DEN4, the mutation consists of the removal of 30 contiguous nucleotides comprising nucleotides 10478-10507 of the 3' UTR (FIG. 2A) which form a putative stem-loop structure referred to as TL2 (Proutski, V. et al. 1997 *Nucleic Acids Res* 25:1194-202). Among the *flaviviruses*, large portions of the UTR form highly conserved secondary structures (Hahn, C. S. et al. 1987 *J Mol Biol* 198:33-41; Proutski, V. et al. 1997 *Nucleic Acids Res* 25:1194-202). Although the individual nucleotides are not necessarily conserved in these regions, appropriate base pairing preserves the stem-loop structure in each serotype, a fact that is not readily apparent when only considering the primary sequence (FIG. 2B, C).

Immunogenic Dengue Chimeras and Methods for their Preparation

Immunogenic dengue chimeras and methods for preparing the dengue chimeras are provided herein. The immunogenic dengue chimeras are useful, alone or in combination, in a pharmaceutically acceptable carrier as immunogenic compositions to minimize, inhibit, or immunize individuals and animals against infection by dengue virus.

Chimeras of the present invention comprise nucleotide sequences encoding the immunogenicity of a dengue virus of one serotype and further nucleotide sequences selected from the backbone of a dengue virus of a different serotype. These chimeras can be used to induce an immunogenic response against dengue virus.

In another embodiment, the preferred chimera is a nucleic acid chimera comprising a first nucleotide sequence encoding at least one structural protein from a dengue virus of a first serotype, and a second nucleotide sequence encoding non-structural proteins from a dengue virus of a second serotype different from the first. In another embodiment the dengue virus of the second serotype is DEN4. In another embodiment, the structural protein can be the C protein of a dengue virus of the first serotype, the prM protein of a dengue virus of the first serotype, the E protein of a dengue virus of the first serotype, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As used herein, the terms "virus chimera," "chimeric virus," "dengue chimera" and "chimeric dengue virus" means an infectious construct of the invention comprising nucleotide sequences encoding the immunogenicity of a dengue virus of one serotype and further nucleotide sequences derived from the backbone of a dengue virus of a different serotype.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a dengue virus of one serotype and further nucleotide sequences derived from the backbone of a dengue virus of a different serotype. Correspondingly, any chimeric virus or virus chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Dengue Chimeras

Dengue virus is a mosquito-borne flavivirus pathogen. The dengue virus genome contains a 5' untranslated region (5' UTR), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' untranslated region (3' UTR). The viral structural proteins are C, prM and E, and the nonstructural proteins are NS1-NS5. The structural and nonstructural proteins are translated as a single polyprotein and processed by cellular and viral proteases.

The dengue chimeras of the invention are constructs formed by fusing structural protein genes from a dengue virus of one serotype, e.g. DEN1, DEN2, DEN3, or DEN4, with non-structural protein genes from a dengue virus of a different serotype, e.g., DEN1, DEN2, DEN3, or DEN4.

The attenuated, immunogenic dengue chimeras provided herein contain one or more of the structural protein genes, or antigenic portions thereof, of the dengue virus of one serotype against which immunogenicity is to be conferred, and the nonstructural protein genes of a dengue virus of a different serotype.

The chimera of the invention contains a dengue virus genome of one serotype as the backbone, in which the structural protein gene(s) encoding C, prM, or E protein(s) of the dengue genome, or combinations thereof, are replaced with the corresponding structural protein gene(s) from a dengue virus of a different serotype that is to be protected against. The resulting viral chimera has the properties, by virtue of being chimerized with a dengue virus of another serotype, of attenuation and is therefore reduced in virulence, but expresses antigenic epitopes of the structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding nonstructural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 *J Virology* 70:3930-3933; Durbin et al. 2001 *Am J Trop Med* 65:405-413, 2001). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of Dengue Chimeras

The dengue virus chimeras described herein can be produced by substituting at least one of the structural protein genes of the dengue virus of one serotype against which immunity is desired into a dengue virus genome backbone of a different serotype, using recombinant engineering techniques well known to those skilled in the art, namely, removing a designated dengue virus gene of one serotype and replacing it with the desired corresponding gene of dengue virus of a different serotype. Alternatively, using the sequences provided in GenBank, the nucleic acid molecules encoding the dengue proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a dengue structural protein of one serotype. Preferably the dengue gene of a different serotype to be inserted is a gene encoding a C protein, a prM protein and/or an E protein. The sequence inserted into the dengue virus backbone can encode both the prM and E structural proteins of the other serotype. The sequence inserted into the dengue virus backbone can encode the C, prM and E structural proteins of the other serotype. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a dengue virus of a different serotype, or the substituted gene(s) that encode the prM and/or E structural protein(s) of a dengue virus of a different serotype.

Suitable chimeric viruses or nucleic acid chimeras containing nucleotide sequences encoding structural proteins of dengue virus of any of the serotypes can be evaluated for usefulness as vaccines by screening them for phenotypic markers of attenuation that indicate reduction in virulence with retention of immunogenicity. Antigenicity and immunogenicity can be evaluated using in vitro or in vivo reactivity with dengue antibodies or immunoreactive serum using routine screening procedures known to those skilled in the art.

Dengue Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a dengue virus of one serotype in a wild-type or an attenuated dengue virus backbone of a different serotype. For example, the chimera may express the structural protein genes of a dengue virus of one serotype in either of a dengue virus or an attenuated dengue virus background of a different serotype.

The strategy described herein of using a genetic background that contains nonstructural regions of a dengue virus genome of one serotype, and, by chimerization, the properties of attenuation, to express the structural protein genes of a dengue virus of a different serotype has lead to the development of live, attenuated dengue vaccine candidates that express structural protein genes of desired immunogenicity. Thus, vaccine candidates for control of dengue pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various dengue serotypes. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue RNA with various primers. Amplified fragments are cloned into the cleavage sites of other intermediate clones. Intermediate, chimeric dengue clones are then sequenced to verify the sequence of the inserted dengue-specific cDNA.

Full genome-length chimeric plasmids constructed by inserting the structural or nonstructural protein gene region of dengue viruses into vectors are obtainable using recombinant techniques well known to those skilled in the art.

Methods of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans, especially individuals travelling to regions where dengue virus infection is present, and also to inhabitants of those regions. The optimal time for administration of the composition is about one to three months before the initial exposure to the dengue virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of dengue virus of one serotype and dengue virus of a different serotype are useful for designing nucleic acid probes and primers for the detection of dengue virus chimeras in a sample or specimen with high sensitivity and specificity. Probes or primers corresponding to dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding dengue virus or complementary sequences thereof. By "selective" or "selectively" is meant a sequence which does not hybridize with other nucleic acids to prevent adequate detection of the dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in Molecular Cloning: A Laboratory Manual, 2nd ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of dengue virus, the degree of complementarity between the hybridizing nucleic acid (probe or primer) and the sequence to which it hybridizes is at least enough to distinguish hybridization with a nucleic acid from other organisms.

The nucleic acid sequences encoding dengue virus can be inserted into a vector, such as a plasmid, and recombinantly expressed in a living organism to produce recombinant dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT/PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer, 1996 *Nature Biotechnology* 14:303-308). Molecular beacon assays employ quencher and reporter dyes that differ from those used in the TaqMan assay. These and other detection systems may used by one skilled in the art.

EXAMPLE 1

Improvement of Dengue Virus Vaccine Candidate rDEN4Δ30

The safety of recombinant live-attenuated dengue-4 vaccine candidate rDEN4Δ30 was evaluated in twenty human volunteers who received a dose of 5.0 $\log_{10}$ plaque forming units (PFU) (Durbin A. P. et al. 2001 *Am J Trop Med Hyg* 65:405-413). The vaccine candidate was found to be safe, well-tolerated and immunogenic in all of the vaccines. However, five of the vaccines experienced a transient elevation in alanine aminotransferase levels, three experienced neutropenia and ten vaccines developed an asymptomatic macular rash, suggesting that it may be necessary to further attenuate this vaccine candidate.

Currently, a randomized, double-blind, placebo-controlled, dose de-escalation study is being conducted to determine the human infectious dose 50 ($HID_{50}$) of rDEN4Δ30. Each dose cohort consists of approximately twenty vaccines and four placebo recipients. To date, complete data for doses of 3.0 $\log_{10}$ PFU and 2.0 $\log_{10}$ PFU has been collected. rDEN4Δ30 infected 100% of vaccines when 3.0 $\log_{10}$ PFU was administered and 95% of vaccines when 2.0 $\log_{10}$ PFU was administered (Table 1). The vaccine candidate caused no symptomatic illness at either dose (Table 1). One vaccine who received 3.0 $\log_{10}$ PFU experienced a transient elevation in alanine aminotransferase levels and approximately one fourth of the vaccines experienced neutropenia at both doses (Table 1). Neutropenia was transient and mild. More than half of the vaccines developed a macular rash at both doses; the occurrence of rash was not correlated with vaccination dose or with viremia (Table 1 and Table 2). Neither peak titer nor onset of viremia differed between the 3.0 $\log_{10}$ PFU and 2.0 $\log_{10}$ PFU doses, though both measures of viremia were significantly lower for these doses than for a dose of 5.0 $\log_{10}$ PFU (Table 3). The vaccine candidate was immunogenic in 95% of vaccines at both doses and neutralizing antibody did not decline between days 28 and 42 post-vaccination (Table 4). Although the $HID_{50}$ has not been determined yet, it is clearly less than 2.0 $\log_{10}$ PFU. Interestingly, decreases in the dose of vaccine have had no consistent effect on immunogenicity, viremia, benign neutropenia or the occurrence of rash. Thus it will not necessarily be possible to further attenuate rDEN4Δ30 by decreasing the dose of virus administered, and other approaches must be developed.

TABLE 1 rDEN4Δ30 clinical summary

| No. of subjects | Dose[a] | No. infected | No. with viremia | Mean peak titer[b] | No. volunteers with: Fever | Rash | Neutropenia[c] | ↑ALT |
|---|---|---|---|---|---|---|---|---|
| 20 | 5.0 | 20 | 14 | 1.2 (0.2) | 1[d] | 10 | 3 | 5 |
| 20 | 3.0 | 20 | 7 | 0.4 (0.0) | 0 | 11 | 5 | 1[e] |
| 20 | 2.0 | 19 | 11 | 0.6 (0.1) | 1[d] | 16 | 4 | 0 |
| 8 | 0 | 0 | 0 | 0 | 0 | 0 | 0 | 0 |

[a]$\log_{10}$ pfu
[b]$\log_{10}$ pfu/mL
[c]Neutropenia defined as ANC < 1500/dl
[d]T Max in volunteer = 100.4° F.
[e]ALT day 0 = 78, ALT max = 91 (day 14)

TABLE 2

Pattern of rash in vaccinees

| Dose[a] | No. with viremia | No. with rash | Viremia & rash | Viremia no rash | Mean day of onset ± SD | Mean duration (days ± SD) |
|---|---|---|---|---|---|---|
| 5 | 14/20 | 10/20 | 9/20 | 5/20 | 8.1 ± 1.3 [A][a] | 3.6 ± 2.0 [A] |
| 3 | 7/20 | 11/20 | 6/20 | 1/20 | 12.2 ± 1.4 [B] | 5.0 ± 2.1 [A] |
| 2 | 11/20 | 16/20 | 9/20 | 2/20 | 11.2 ± 1.4 [B] | 6.9 ± 1.7 [B] |

[a]$\log_{10}$ pfu
[b]Means in each column with different letters are significantly different (α = 0.05)

TABLE 3 rDEN4Δ30 viremia summary

| Dose[a] | # with viremia | Mean peak titer ($\log_{10}$ pfu/mL) | Mean onset of viremia (day ± SD) | Mean duration of viremia (day ± SD) |
|---|---|---|---|---|
| 5 | 14 | 1.2 ± 0.2 [A] | 5.8 ± 2.4 [A][b] | 4.4 ± 2.4 [A] |
| 3 | 7 | 0.4 ± 0.0 [B] | 9.1 ± 2.5 [B] | 1.6 ± 1.0 [B] |
| 2 | 11 | 0.6 ± 0.1 [B] | 8.7 ± 2.4 [B] | 2.6 ± 2.0 [A] |

[a]$\log_{10}$pfu
[b]Means in each column with different letters are significantly different (α = 0.05)

TABLE 4

Immunogenicity of rDEN4Δ30

| No. of subjects | Dose (log₁₀) | No. infected | Geometric mean serum neutralizing antibody titer (range) | | % sero-conversion |
|---|---|---|---|---|---|
| | | | Day 28 | Day 42 | |
| 20 | 5.0 | 20 | 567 (72-2455) | 399 (45-1230) | 100 |
| 20 | 3.0 | 20 | 156 (5-2365) | 158 (25-1222) | 95 |
| 20 | 2.0 | 19 | 163 (5-943) | 165 (5-764) | 95 |
| 8 | 0 | 0 | 0 | 0 | 0 |

Two approaches have been taken to further attenuate rDEN4Δ30. This first is the generation and characterization of attenuating point mutations in rDEN4 using 5' fluorouracil mutagenesis (Blaney, J. E. Jr. et al. 2002 *Virology* 300: 125-139; Blaney, J. E. Jr. et al. 2001 *J. Virol.* 75: 9731-9740). This approach has identified a panel of point mutations that confer a range of temperature sensitivity (ts) and small plaque (sp) phenotypes in Vero and HuH-7 cells and attenuation (att) phenotypes in suckling mouse brain and SCID mice engrafted with HuH-7 cells (SCID-HuH-7 mice). In this example, a subset of these mutations has been introduced to rDEN4Δ30 and the phenotypes of the resulting viruses evaluated.

A second approach was to create a series of paired charge-to-alanine mutations in contiguous pairs of charged amino acid residues in the rDEN4 NS5 gene. As demonstrated previously, mutation of 32 individual contiguous pairs of charged amino acid residues in rDEN4 NS5 conferred a range of ts phenotypes in Vero and HuH-7 cells and a range of att phenotypes in suckling mouse brain (Hanley, K. H. et al. 2002 *J. Virol.* 76 525-531). As demonstrated below, these mutations also confer an att phenotype in SCID-HuH-7 mice. These mutations have been introduced, either as single pairs or sets of two pairs, into rDEN4Δ30 to determine whether they are compatible with the Δ30 mutation and whether they enhance the att phenotypes of rDEN4Δ30.

A panel of rDEN4 viruses bearing individual point mutations have been characterized which possess temperature sensitive and/or small plaque phenotypes in tissue culture and varying levels of attenuated replication in suckling mouse brain when compared to wild type rDEN4 virus (Blaney, J. E. et al. 2002 *Virology* 300:125-139; Blaney, J. E. et al. 2001 *J. Virol.* 75:9731-9740). Three mutations have been selected to combine with the Δ30 deletion mutation to evaluate their ability to further restrict replication of rDEN4Δ30 in rhesus monkeys. First, the missense mutation in NS3 at nucleotide 4995 (Ser>Pro) which confers temperature sensitivity in Vero and HuH-7 cells and restricted replication in suckling mouse brain was previously combined with the Δ30 mutation (Blaney, J. E. et al. 2001 *J Virol.* 75:9731-9740). The resulting virus, rDEN4Δ30-4995, was found to be more restricted (1,000-fold) in mouse brain replication than rDEN4Δ30 virus (<5-fold) when compared to wild type rDEN4 virus. Second, a missense mutation at nucleotide 8092 (Glu>Gly) which also confers temperature sensitivity in Vero and HuH-7 cells and 10,000-fold restricted replication in suckling mouse brain was combined with the Δ30 mutation here. Third, a substitution in the 3' UTR at nucleotide 10634 which confers temperature sensitivity in Vero and HuH-7 cells, small plaque size in HuH-7 cells, and approximately 1,000-fold restricted replication in suckling mouse brain and SCID mice transplanted with HuH-7 cells was combined with the Δ30 mutation here (Blaney, J. E. et al. 2002 *Virology* 300:125-139).

For the present investigation, subcloned fragments of p4 (Durbin, A. P. et al. 2001 *Am J Trop Med Hyg* 65:405-13) containing the above mutations were introduced into the p4Δ30 cDNA clone. For transcription and recovery of virus, cDNA was linearized with Acc65I (isoschizomer of KpnI which cleaves leaving only a single 3' nucleotide) and used as template for transcription by SP6 RNA polymerase as previously described (Blaney, J. E. et al. 2002 *Virology* 300:125-139). C6/36 mosquito cells were transfected using liposome-mediated transfection and cell culture supernatants were harvested between days five and seven. Recovered virus was terminally diluted twice in Vero cells and passaged two (rDEN4Δ30-4995) or three (rDEN4Δ30-8092 and rDEN4Δ30-10634) times in Vero cells.

The complete genomic sequences of rDEN4Δ30-4995, rDEN4Δ30-8092, and rDEN4Δ30-10634 viruses were determined as previously described (Durbin et al. 2001 *Am. J. Trop. Med. Hyg.* 65:405-413). As expected, each rDEN4Δ30 virus derivative contained the Δ30 mutation. Unexpectedly, in rDEN4Δ30-4995 virus, the nucleotide changes in the codon containing nucleotide 4995, resulted in a Ser>Leu amino acid change rather than a Ser>Pro change since the p4Δ30-4995 cDNA was designed to introduce the Ser>Pro change (Table 5). The p4Δ30-4995 cDNA clone was indeed found to encode a Ser>Pro change at nucleotide 4995, so it is unclear how the virus population acquired the Ser>Leu mutation. Nevertheless, this virus was evaluated to assess the phenotype specified by this missense mutation. rDEN4Δ30-4995 virus was also found to contain an incidental mutation at nucleotides 4725-6 which resulted in a single amino acid change (Ser>Asp). The rDEN4Δ30-8092 and rDEN4Δ30-10634 viruses contained the appropriate nucleotide substitutions as well as additional incidental mutations in E, NS4B and NS4B, respectively (Table 5).

TABLE 5

| Missense and UTR mutations present in rDEN4Δ30 virus derivatives bearing introduced point mutations. | | | | | |
|---|---|---|---|---|---|
| Virus | Gene | Nucleotide position | Nucleotide substitution | Amino acid position[a] | Amino acid change |
| rDEN4Δ30-4995 | NS3 | 4725 | U > G | 1542 | Ser > Asp |
| | NS3 | 4726 | C > A | 1542 | Ser > Asp |
| | NS3 | 4995[b] | U > C | 1632 | Ser > Leu |
| rDEN4Δ30-8092 | E | 1612 | A > C | 504 | Asp > Ala |
| | NS4B | 7131 | A > G | 2344 | Thr > Ala |
| | NS5 | 8092[b] | A > G | 2664 | Glu > Gly |
| rDEN4Δ30-10634 | NS4B | 6969 | A > U | 2290 | Met > Leu |
| | NS4B | 7182 | G > C | 2361 | Gly > Arg |
| | 3' UTR | 10634[b] | U > C | none | none |

[a]Amino acid position in DEN4 polyprotein beginning with the methionine residue of the C protein (nucleotides 102-104) as position 1.
[b]Mutation restricts replication in mouse models of DEN4 infection which were introduced by Kunkel mutagenesis.

Replication of the three modified rDEN4Δ30 viruses were compared to rDEN4Δ30 and wild type rDEN4 virus in the suckling mouse brain model and SCID mice transplanted with HuH-7 cells (SCID-HuH-7 mice). Experiments were conducted as previously described (Blaney, J. E. et al. 2002 *Virology* 300:125-139; Blaney, J. E. et al. 2001 *J Virol.* 75:9731-9740). Briefly, for infection of suckling mouse brain, groups of six seven-day-old mice were inoculated intracerebrally with 4.0 $log_{10}$ PFU of virus and the brain of each mouse was removed five days later. Clarified supernatants of 10% brain suspensions were then frozen at −70° C., and the virus titer was determined by plaque assay in Vero cells. For analysis of DEN4 virus replication in SCID-HuH-7 mice, four to six week-old SCID mice were injected intraperitoneally with $10^7$ HuH-7 cells. Five to six weeks after transplantation, mice were infected by direct inoculation into the tumor with 4.0 $\log_{10}$ PFU of virus, and serum for virus titration was obtained by tail-nicking on day 7. The virus titer was determined by plaque assay in Vero cells.

Wild type rDEN4 virus replicated to 6.0 $\log_{10}$PFU/g in suckling mouse brain, and rDEN4Δ30 was restricted in replication by 0.7 $\log_{10}$PFU/g, which is similar to previous observations (Table 6) (Blaney, J. E. et al. 2001 *J Virol.* 75:9731-9740). rDEN4Δ30-4995, rDEN4Δ30-8092, and rDEN4Δ30-10634 viruses were found to have restricted replication in suckling mouse brain when compared to rDEN4 virus of 3.3, 2.8, and 2.4 $\log_{10}$PFU/g, respectively. These results indicate that the additional attenuating mutations serve to further restrict replication of the rDEN4Δ30 virus in mouse brain ranging from 50-fold (rDEN4Δ30-10634) to 400-fold (rDEN4Δ30-4995). In SCID-HuH-7 mice, virus titer of rDEN4Δ30 virus was 0.4 $\log_{10}$PFU/ml lower than rDEN4 virus, which is also similar to previous studies (Blaney, J. E. et al. 2002 *Virology* 300:125-139). Each modified rDEN4Δ30 virus was found to be further restricted in replication in SCID-HuH-7 mice (Table 6). rDEN4Δ30-4995, rDEN4Δ30-8092, and rDEN4Δ30-10634 viruses had restricted replication in SCID-HuH-7 mice when compared to rDEN4 virus of 2.9, 1.1, and 2.3 $\log_{10}$PFU/g below the level of wild type rDEN4 virus, respectively. Two important observations were made: (1) The 4995, 8092 and 10634 mutations were compatible for viability with the Δ30 mutation, and (2) These three modified rDEN4Δ30 viruses had between a 10 and 1,000-fold reduction in replication in comparison to rDEN4 wild-type virus, which allows viruses with a wide range of attenuation in this model to be further evaluated in monkeys or humans.

*Hyg.* 65:405-413). Briefly, groups of four (rDEN4Δ30-4995, rDEN4Δ30-8092, and rDEN4Δ30-10634) or two (rDEN4, rDEN4Δ30, mock) monkeys were inoculated with 5.0 $\log_{10}$PFU virus subcutaneously. Monkeys were observed daily and serum was collected on days 0 to 6, 8, 10, and 12, and virus titers were determined by plaque assay in Vero cells for measurement of viremia. On day 28, serum was drawn and the level of neutralizing antibodies was tested by plaque reduction assay in Vero cells as previously described (Durbin et al. 2001 *Am. J. Trop. Med. Hyg.* 65:405-413).

Figure 3:
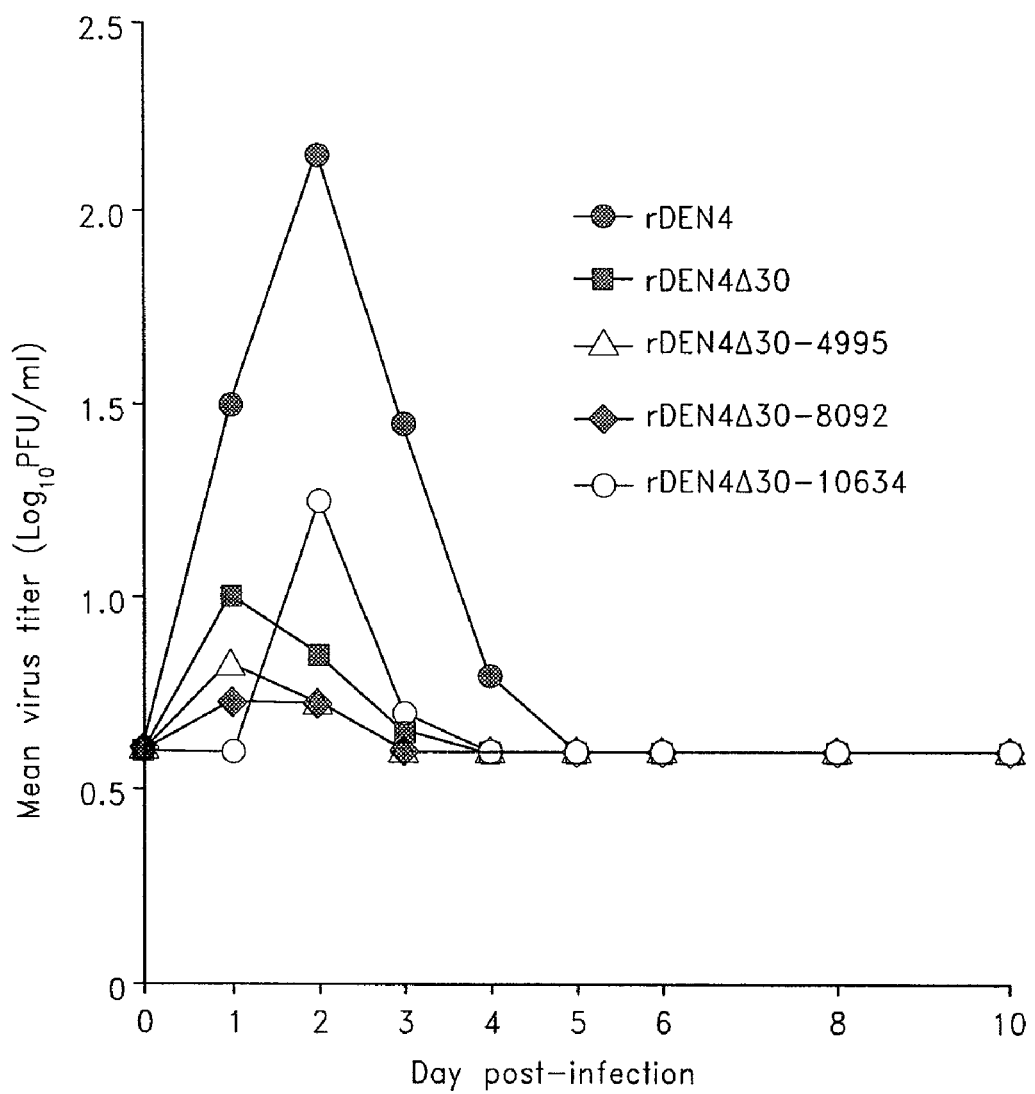
FIG. 3. Viremia levels in rhesus monkeys inoculated with rDEN4 vaccine candidates bearing 5-FU derived mutations. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group.

Viremia was detected beginning on day 1 post-infection and ended by day 4 in all monkeys (Table 7, FIG. 3). Viremia was present in each monkey infected with rDEN4, rDEN4Δ30, or rDEN4Δ30-10634 virus, but only 2 out of 4 monkeys infected with rDEN4Δ30-4995 or rDEN4Δ30-8092 virus had detectable viremia. As expected, infection with rDEN4 virus resulted in the highest mean number of viremic days per monkey (3.0 days) as well as mean peak virus titer (2.2 $\log_{10}$PFU/ml). Monkeys infected with rDEN4Δ30 virus had both a lower mean number of viremic days per monkey (2.0 days) and mean peak virus titer (1.1 $\log_{10}$PFU/ml) compared to rDEN4 virus. Groups of monkeys infected with each of the modified rDEN4Δ30 viruses had a further restricted mean number of viremic days with those inoculated with rDEN4Δ30-8092 virus having the lowest value, 0.5 days, a 4-fold reduction compared to rDEN4Δ30 virus. The mean peak virus titer of monkeys infected with rDEN4Δ30-4995 (0.9 $\log_{10}$PFU/ml) or rDEN4Δ30-8092 (0.7 $\log_{10}$PFU/ml) was also lower than those infected with rDEN4Δ30 virus.

TABLE 6

Addition of point mutations in NS3, NS5, or the 3' UTR to rDEN4Δ30 virus further attenuates the virus for suckling mouse brain and SCID-HuH-7 mice.

| | Replication in suckling mouse brain[a] | | | Replication in SCID-HuH-7 mice[c] | | |
|---|---|---|---|---|---|---|
| Virus | No. of mice | Virus titer ± SE $\log_{10}$ PFU/g brain | Mean $\log_{10}$-unit reduction from wt[b] | No. of mice | Virus titer ± SE $\log_{10}$ PFU/ml serum | Mean $\log_{10}$-unit reduction from wt[b] |
| rDEN4 | 12 | 6.0 ± 0.1 | — | 13 | 6.4 ± 0.2 | — |
| rDEN4Δ30 | 12 | 5.3 ± 0.1 | 0.7 | 20 | 6.0 ± 0.2 | 0.4 |
| rDEN4Δ30-4995 | 6 | 2.7 ± 0.4 | 3.3 | 5 | 3.5 ± 0.3 | 2.9 |
| rDEN4Δ30-8092 | 6 | 3.2 ± 0.2 | 2.8 | 7 | 5.0 ± 0.4 | 1.1 |
| rDEN4Δ30-10634 | 12 | 3.6 ± 0.1 | 2.4 | 5 | 4.4 ± 0.3 | 2.3 |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and concurrent rDEN4 wt control.
[c]Groups of HuH-7-SCID mice were inoculated directly into the tumor with $10^4$ PFU virus. Serum was collected on day 6 and 7 and titered in Vero cells.

Based on the findings in the two mouse models of DEN4 virus infection, each of the rDEN4Δ30-4995, rDEN4Δ30-8092, and rDEN4Δ30-10634 viruses was evaluated in the rhesus macaque model of DEN4 infection which has been previously described (Durbin et al. 2001 *Am. J. Trop. Med.* However, the mean peak virus titer of monkeys infected with rDEN4Δ30-10634 (1.3 $\log_{10}$PFU/ml) was slightly higher than those infected with rDEN4Δ30 particularly on day 2 (FIG. 3).

TABLE 7

Addition of point mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| rDEN4 | 2 | 2 | 3.0 | 2.2 ± 0.6 | <10 | 398 |
| rDEN4Δ30 | 2 | 2 | 2.0 | 1.1 ± 0.4 | <10 | 181 |
| rDEN4Δ30-4995 | 4 | 2 | 0.8 | 0.9 ± 0.2 | <10 | 78 |
| rDEN4Δ30-8092 | 4 | 2 | 0.5 | 0.7 ± 0.1 | <10 | 61 |
| rDEN4Δ30-10634 | 4 | 4 | 1.3 | 1.3 ± 0.2 | <10 | 107 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

Serum collected on day 0 and 28 was tested for the level of neutralizing antibodies against rDEN4. No detectable neutralizing antibodies were found against DEN4 on day 0, as expected, since the monkeys were pre-screened to be negative for neutralizing antibodies against *flaviviruses* (Table 7). On day 28, monkeys infected with rDEN4 had a mean serum neutralizing antibody titer (reciprocal dilution) of 398 which was approximately two-fold higher than monkeys infected with rDEN4Δ30 virus (1:181). This result and the two-fold higher level of viremia in rDEN4 virus-infected monkeys are similar to results obtained previously (Durbin et al. 2001 *Am. J. Trop. Med. Hyg.* 65:405-413). Monkeys infected with rDEN4Δ30-4995 (1:78), rDEN4Δ30-8092 (1:61), and rDEN4Δ30-10634 (1:107) viruses each had a reduced mean serum neutralizing antibody titer compared to monkeys infected with rDEN4Δ30 virus. The four monkeys which had no detectable viremia did have serum neutralizing antibody titers indicating that they were indeed infected. Despite the slight increase in mean peak virus titer of rDEN4Δ30-10634 virus compared with rDEN4Δ30 virus, rDEN4Δ30-10634 virus had a lower mean serum neutralizing antibody titer compared to monkeys infected with rDEN4Δ30 virus. This and the lower mean number of viremic days per monkey suggests that the 10634 mutation can attenuate the replication of rDEN4Δ30 virus in monkeys.

On day 28 after inoculation, all monkeys were challenged with 5.0 $\log_{10}$PFU wild type rDEN4 virus subcutaneously. Monkeys were observed daily and serum was collected on days 28 to 34, 36, and 38, and virus titers were determined by plaque assay in Vero cells for measurement of viremia after challenge. Twenty eight days after rDEN4 virus challenge, serum was drawn and the level of neutralizing antibodies was tested by plaque reduction assay in Vero cells. Mock-inoculated monkeys had a mean peak virus titer of 2.3 $\log_{10}$PFU/ml after challenge with a mean number of viremic days of 3.5 (Table 8). However, monkeys inoculated with rDEN4, rDEN4Δ30, or each of the modified rDEN4Δ30 viruses had no detectable viremia, indicating that despite the decreased replication and immunogenicity of rDEN4Δ30-4995, rDEN4Δ30-8092, and rDEN4Δ30-10634 viruses, each was sufficiently immunogenic to induce protection against wild type rDEN4. Increases in mean neutralizing antibody titer were minimal (<3-fold) following challenge in all inoculation groups except mock-infected providing further evidence that the monkeys were protected from the challenge.

TABLE 8 rDEN4Δ30 containing additional point mutations protects rhesus monkeys from wt DEN4 virus challenge

| Virus[a] | No. of monkeys | Mean no. of viremic days per monkey after rDEN4 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| Mock | 2 | 3.5 | 2.3 ± 0.1 | <10 | 358 |
| rDEN4 | 2 | 0.0 | <0.7 | 398 | 753 |
| rDEN4Δ30 | 2 | 0.0 | <0.7 | 181 | 202 |
| rDEN4Δ30-4995 | 4 | 0.0 | <0.7 | 78 | 170 |
| rDEN4Δ30-8092 | 4 | 0.0 | <0.7 | 61 | 131 |
| rDEN4Δ30-10634 | 4 | 0.0 | <0.7 | 107 | 177 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 38, and 56. Virus titer was determined by plaque assay in Vero cells.

Taken together, these results indicate that the three point mutations, 4995, 8092, and 10634) described above do further attenuate the rDEN4Δ30 vaccine candidate in suckling mouse brain, SCID-HuH-7 mice, and rhesus monkeys. Because of additional incidental mutations (Table 4) present in each modified rDEN4Δ30 virus, the phenotypes cannot be directly attributed to the individual 4995, 8092, and 10634 point mutations. However, the presence of similar mouse-attenuation phenotypes in other rDEN4 viruses bearing one of these three mutations supports the contention that the 4995, 8092, and 10634 point mutations are responsible for the att phenotypes of the modified rDEN4Δ30 viruses. Since rDEN4Δ30-4995, rDEN4Δ30-8092, and rDEN4Δ30-10634 virus demonstrated decreased replication in rhesus monkeys while retaining sufficient immunogenicity to confer protective immunity, these viruses are contemplated as dengue vaccines for humans.

DEN4 viruses carrying both Δ30 and charge-to-alanine mutations were next generated. A subset of seven groups of charge-to-alanine mutations described above were identified that conferred between a 10-fold and 1,000-fold decrease in replication in SCID-HuH-7 mice and whose unmutated sequence was well-conserved across the four dengue serotypes. These mutations were introduced as single pairs and as two sets of pairs to rDEN4Δ30 using conventional cloning techniques. Transcription and recovery of virus and terminal dilution of viruses were conducted as described above. Assay of the level of temperature sensitivity of the charge-cluster-to-alanine mutant viruses in Vero and HuH-7 cells, level of replication in the brain of suckling mice and level of replication in SCID-HuH-7 mice was conducted as described above.

Introduction of one pair of charge-to-alanine mutations to rDEN4 produced recoverable virus in all cases (Table 9). Introduction of two pairs of charge-to-alanine mutations produced recoverable virus in two out of three cases (rDEN4Δ30-436-437-808-809 was not recoverable).

rDEN4Δ30 is not ts in Vero or HuH-7 cells. In contrast, seven of the seven sets of charge-to-alanine mutations used in this example conferred a ts phenotype in HuH-7 cells and five also conferred a ts phenotype in Vero cells. All six viruses carrying both Δ30 and charge-to-alanine mutations showed a ts phenotype in both Vero and HuH-7 cells (Table 9). rDEN4Δ30 is not attenuated in suckling mouse brain, whereas five of the seven sets of charge-to-alanine mutations conferred an att phenotype in suckling mouse brain (Table 10). Four of the viruses carrying both Δ30 and charge-to-alanine mutations were attenuated in suckling mouse brain (Table 10). In one case (rDEN4Δ30-23-24-396-397) combination of two mutations that did not attenuate alone resulted in an attenuated virus. Generally, viruses carrying both Δ30 and charge-to-alanine mutations showed levels of replication in the suckling mouse brain more similar to their charge-to-alanine mutant parent virus than to rDEN4Δ30.

rDEN4Δ30 is attenuated in SCID-HuH-7 mice, as are six of the seven charge-to-alanine mutant viruses used in this example. Viruses carrying both Δ30 and charge-to-alanine mutations tended to show similar or slightly lower levels of replication in SCID-HuH-7 mice compared to their charge-to-alanine mutant parent virus (Table 10). In three cases, viruses carrying both Δ30 and charge-to-alanine mutations showed at least a fivefold greater reduction in SCID-HuH-7 mice than rDEN4Δ30.

The complete genomic sequence of five viruses (rDEN4-200-201, rDEN4Δ30-200-201, rDEN4-436-437 [clone 1], rDEN4Δ30-436-437, and rDEN4-23-24-200-201) that replicated to >$10^5$ PFU/ml in Vero cells at 35° C. and that showed a hundredfold or greater reduction in replication in SCID-HuH-7 mice was determined (Table 11). Each of the five contained one or more incidental mutations. In one virus, rDEN4Δ30-436-437, the one additional mutation has been previously associated with Vero cell adaptation (Blaney, J. E. Jr. et al. 2002 *Virology* 300:125-139). Each of the remaining viruses contained at least one incidental mutation whose phenotypic effect is unknown. Consequently, the phenotypes described cannot be directly attributed to the charge-to-alanine mutations. However, the fact that rDEN4 and rDEN4Δ30 viruses carrying the same charge-to-alanine mutations shared similar phenotypes provides strong support for the ability of charge-to-alanine mutations to enhance the attenuation of rDEN4Δ30. Because rDEN4-436-[clone 1] contained 4 incidental mutations, a second clone of this virus was prepared. rDEN4-436-437 [clone 2] contained only one incidental mutation (Table 11), and showed the same phenotypes as rDEN4-436-437 in cell culture and SCID-HuH-7 mice. rDEN4-436-437 [clone 2] was used in the rhesus monkey study described below.

TABLE 9

Addition of charge-to-alanine mutations to rDEN4Δ30 confers a ts phenotype in both Vero and HuH-7 cells.

| | | | Mean virus titer ($\log_{10}$ PFU/ml) at indicated temperature (° C.)[a] | | | | | | | | | |
|---|---|---|---|---|---|---|---|---|---|---|---|---|
| | AA | No. nt | Vero | | | | | HuH-7 | | | | |
| Virus | changed[b] | changed | 35 | 37 | 38 | 39 | Δ[c] | 35 | 37 | 38 | 39 | Δ |
| rDEN4 | none | 0 | 7.4 | 7.1 | 7.7 | 7.2 | 0.2 | 7.7 | 7.5 | 7.5 | 7.4 | 0.3 |
| rDEN4Δ30 | none | 30 | 6.6 | 6.6 | 6.5 | 6.5 | 0.1 | 7.4 | 6.9 | 7.0 | 6.4 | 1.0 |
| rDEN4-23-24 | KE | 3 | 6.7 | 6.6 | 6.0 | 6.5 | 0.2 | 7.1 | 7.3 | 5.6 | ≤1.7 | >5.4 |
| rDEN4Δ30-23-24 | | | 6.1 | 5.5 | 4.9 | ≤1.7 | 4.4 | 6.5 | 5.9 | 4.7 | ≤1.7 | >4.2 |
| rDEN4-200-201 | KH | 4 | 5.3 | 4.8 | 4.8 | 4.3 | 1.0 | 5.7 | 5.4 | 2.7 | ≤1.7 | >4.0 |
| rDEN4Δ30-200-201 | | | 6.0 | 5.3 | 5.6 | ≤1.7 | >4.3 | 5.8 | 5.0 | 5.9 | ≤1.7 | >4.1 |
| rDEN4-436-437 | DK | 4 | 5.2 | 4.2 | 3.4 | 1.9 | 3.3 | 5.9 | 4.9 | 3.2 | ≤1.7 | >4.2 |
| rDEN4Δ30-436-437 [clone1] | | | 6.3 | 5.7 | 5.5 | ≤1.7 | >4.6 | 6.5 | 5.7 | 5.1 | ≤1.7 | >4.8 |
| rDEN4-808-809 | ED | 3 | 4.6 | 4.1 | ≤1.7 | ≤1.7 | >2.9 | 5.2 | ≤1.7 | ≤1.7 | ≤1.7 | >3.5 |
| rDEN4Δ30-808-809 | | | 5.6 | 4.9 | 4.9 | ≤1.7 | >3.9 | 5.9 | 4.8 | 5.1 | ≤1.7 | >4.2 |
| rDEN4-23-24-200-201 | KE, KH | 7 | 6.0 | 5.2 | 4.2 | ≤1.7 | >4.3 | 6.9 | 6.3 | ≤1.7 | ≤1.7 | >5.2 |
| rDEN4Δ30-23-24-200-201 | | | 4.5 | 4.2 | 4.8 | ≤1.7 | >2.8 | 4.9 | 4.5 | 2.9 | ≤1.7 | >3.2 |
| rDEN4-23-24-396-397 | KE, RE | 7 | 6.5 | 5.8 | 5.5 | ≤1.7 | >4.8 | 7.1 | 5.9 | 5.4 | ≤1.7 | >5.4 |

TABLE 9-continued

Addition of charge-to-alanine mutations to rDEN4Δ30 confers a ts phenotype in both Vero and HuH-7 cells.

| | | | Mean virus titer ($\log_{10}$ PFU/ml) at indicated temperature (° C.)[a] | | | | | | | | |
|---|---|---|---|---|---|---|---|---|---|---|---|
| | AA | No. nt | Vero | | | | | HuH-7 | | | |
| Virus | changed[b] | changed | 35 | 37 | 38 | 39 | Δ[c] | 35 | 37 | 38 | 39 | Δ |
| rDEN4Δ30-23-24-396-397 | | | 6.1 | 5.2 | 4.8 | ≤1.7 | >4.4 | 6.9 | 5.4 | 4.9 | ≤1.7 | >5.2 |
| rDEN-436-437-808-809 | DK, ED | 7 | 4.9 | 4.9 | 5.1 | ≤1.7 | >3.2 | 5.5 | 3.2 | ≤1.7 | ≤1.7 | >3.8 |

[a]Underlined values indicate a 2.5 or 3.5 $\log_{10}$ PFU/ml reduction in titer in Vero or HuH-7 cells, respectively, at the indicated temperature when compared to the permissive temperature (35° C.).
[b]Amino acid pair(s) changed to pair of Ala residues.
[c]Reduction in titer ($\log_{10}$ pfu/ml) compared to the permissive temperature (35° C.).

TABLE 10

Addition of charge-to-alanine mutations attenuates rDEN4Δ30 in suckling mouse brain and enhances attenuation in SCID-HuH-7 mice.

| | Replication in suckling mice[a] | | | Replication in SCID-HuH-7 mice[c] | | |
|---|---|---|---|---|---|---|
| Virus | n | Mean virus titer ± SE ($\log_{10}$ PFU/g brain) | Mean log reduction from wt[b] | n | Mean virus titer ± SE ($\log_{10}$ PFU/ml serum) | Mean log reduction from wt[d] |
| rDEN4 | 18 | 6.2 ± 0.4 | — | 33 | 5.4 ± 0.3 | — |
| rDEN4Δ30 | 12 | 5.9 ± 0.8 | 0.2 | 8 | 3.4 ± 0.3 | 2.3 |
| rDEN4-23-24 | 18 | 4.7 ± 0.1 | 1.6 | 19 | 4.7 ± 0.5 | 1.3 |
| rDEN4Δ30-23-24 | 6 | 5.6 ± 0.3 | 0.7 | 7 | 4.6 ± 0.4 | 1.5 |
| rDEN4-200-201 | 12 | 5.5 ± 0.5 | 0.6 | 12 | 3.7 ± 0.2 | 2.6 |
| rDEN4Δ30-200-201 | 6 | 5.5 ± 0.6 | 0.1 | 4 | 3.3 ± 0.6 | 1.8 |
| rDEN4-436-437 | 18 | 2.7 ± 0.4 | 3.5 | 10 | 2.9 ± 0.7 | 2.5 |
| rDEN4Δ30-436-437 [clone1] | 6 | 2.9 ± 0.3 | 3.4 | 4 | 2.3 ± 0.4 | 2.8 |
| rDEN4-808-809 | 6 | 1.8 ± 0.1 | 3.1 | 8 | 3.2 ± 0.4 | 3.0 |
| rDEN4Δ30-808-809 | 12 | 3.9 ± 0.7 | 2.1 | 4 | 3.7 ± 0.6 | 2.4 |
| rDEN4-23-24-200-201 | 12 | 5.3 ± 0.5 | 0.7 | 13 | 3.4 ± 0.1 | 2.9 |
| rDEN4Δ30-23-24-200-201 | 6 | 3.0 ± 0.2 | 2.6 | 5 | 1.8 ± 0.1 | 3.3 |
| rDEN4-23-24-396-397 | 12 | 4.6 ± 0.9 | 1.5 | 8 | 3.6 ± 0.3 | 2.3 |
| rDEN4Δ30-23-24-396-397 | 6 | 3.0 ± 0.2 | 2.6 | 5 | 2.2 ± 0.3 | 2.9 |
| rDEN-436-437-808-809 | 6 | <1.7 ± 0.0 | 3.6 | 8 | 2.1 ± 0.3 | 2.4 |

[a]Groups of six suckling mice were inoculated i.c. with $10^4$ PFU virus in a 30 μl inoculum. The brain was removed 5 days later, homogenized, and virus was quantitated by titration in Vero cells.
[b]Determined by comparing the mean viral titers in mice inoculated with sample virus and concurrent wt controls (n = 6). The attenuation (att) phenotype is defined as a reduction of ≥1.5 $\log_{10}$ PFU/g compared to wt virus; reductions of ≥1.5 are listed in boldface.
[c]Groups of SCID-HuH-7 mice were inoculated directly into the tumor with $10^4$ PFU virus.
[d]Determined by comparing mean viral titers in mice inoculated with sample virus and concurrent wt controls. The attenuation phenotype is defined as a reduction of ≥1.5 $\log_{10}$ PFU/g compared to wt virus; reductions of ≥1.5 are listed in boldface.

TABLE 11

Missense and UTR mutations present in rDEN4 virus derivatives bearing charge-to-alanine and the Δ30 mutation.

| Virus | Gene[a, b] | Nucleotide position | Nucleotide substitution | Amino acid position[c] | Amino acid change[b] |
|---|---|---|---|---|---|
| rDEN4-200-201 | prM | 626 | A > T | 61 | Glu > Asp |
| | NS4A | 6659 | C > T | 93 | Len > Phe |
| | NS5 | 8160-8165 | AAACA > GCAGC | 200-201 | LysHis > AlaAla |
| rDEN4Δ30-200-201 | NS3 | 4830 | G > A | 102 | Gly > Arg |
| | NS5 | 8106 | G > A | 181 | Val > Ile |
| | NS5 | 8160-8165 | AAACA > GCAGC | 200-201 | LysHis > AlaAla |
| | 3' UTR | 10478-10507 | Δ30 deletion | None | None |
| rDEN4-436-437 [clone 1] | E | 2331 | T > G | 464 | Trp > Gly |
| | NS1 | 2845 | C > T | 140 | Ser > Phe |
| | NS3* | 4891 | T > C | 122 | Ile > Thr |
| | NS5 | 8869-8873 | GACAA > GCAGC | 436-437 | AspLys > AlaAla |
| | NS5 | 9659 | A > G | 699 | Lys > Arg |
| rDEN4-436-437 [clone 2] | NS4B | 7153 | T > C | 108 | Val > Ala |
| | NS5 | 8869-8873 | GACAA > GCAGC | 436-437 | AspLys > AlaAla |

TABLE 11-continued Missense and UTR mutations present in rDEN4 virus derivatives bearing charge-to-alanine and the Δ30 mutation.

| Virus | Gene[a,b] | Nucleotide position | Nucleotide substitution | Amino acid position[c] | Amino acid change[b] |
|---|---|---|---|---|---|
| rDEN4Δ30-436-437 | NS4B* | 7163 | A > C | 111 | Leu > Phe |
|  | NS5 | 8869-73 | GACAA > GCAGC | 436-437 | AspLys > AlaAla |
|  | 3' UTR | 10478-10507 | Δ30 deletion | None | None |
| rDBN4-23-24-200-20 1 | NS3 | 6751 | A > C | 124 | Lys > Thr |
|  | NS5 | 7629-7633 | AAAGA > GCAGC | 23-24 | LysGlu > AlaAla |
|  | NS5 | 8160-8165 | AAACA > GCAGC | 200-201 | LysHis > AlaAla |

[a]Asterisk indicates previously identified Vero cell adaptation mutation.
[b]Bold values indicate mutations designed to occur in the designated virus.
[c]Amino acid position in the protein product of the designated DEN4 gene; numbering starts with the amino terminus of the protein.

Figure 4:
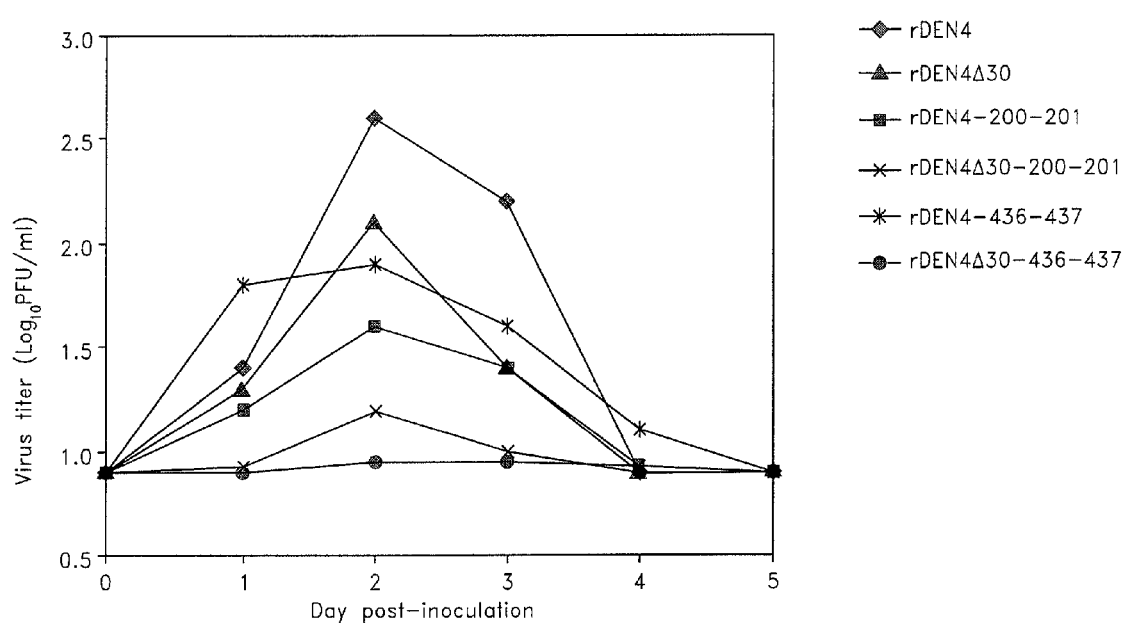
FIG. 4. Viremia levels in rhesus monkeys inoculated with rDEN4 vaccine candidates bearing pairs of charge-to-alanine mutations in NS5. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 1.0 $\log_{10}$PFU/ml. Mean virus titers are indicated for each group. Viremia was not detected in any monkey after day 4.

Based on the attenuation in the SCID-HuH7 mouse model, four of the charge-to-alanine mutant viruses (rDEN4-200-201, rDEN4Δ30-200-201, rDEN4-436-437 [clone 2], rDEN4Δ30-436-437) were evaluated in rhesus macaques as described above. As with the study of viruses carrying attenuating point mutations, viremia was detected on day 1 post-infection and ended by day 4 in all monkeys (FIG. 4, Table 12). Viremia was detected in most of the monkeys infected; only one of the four monkeys infected with rDEN4Δ30-200-201 and one of the four monkeys infected with rDEN4Δ30-436-437 showed no detectable viremia. Monkeys infected with rDEN4 showed the highest mean peak virus titer; and in each case viruses carrying the Δ30 mutation showed an approximately 0.5 log decrease in mean peak virus titer relative to their parental viruses and a 0.5 to 2 day decrease in mean number of viremic days per monkey. Monkeys infected with viruses carrying both the Δ30 and charge-to-alanine mutations showed a two-fold reduction in mean peak viremia relative to those infected with rDEN4Δ30. This suggests that addition of the charge-to-alanine mutations further attenuates rDEN4Δ30 for rhesus macaques.

As expected, none of the monkeys in this study showed detectable levels of neutralizing antibody on day 0. On day 28, every monkey infected with a virus showed a detectable levels of neutralizing antibody, indicating that all of the monkeys, even those that showed no detectable viremia, had indeed been infected. As in the study of attenuating point mutations, monkeys infected with rDEN4 had a mean serum neutralizing antibody titer (reciprocal dilution) which was approximately twice that of monkeys that had been infected with rDEN4Δ30. Monkeys infected with rDEN4-200-201 and rDEN4-436-437 [clone 2] had similar mean neutralizing antibody titers to rDEN4, and those infected with rDEN4Δ30-200-201 and rDEN4Δ30-436-437 had similar mean neutralizing antibody titers to rDEN4. In each case the addition of the Δ30 mutation to a virus resulted in a two-fold decrease in neutralizing antibody. Thus, although the addition of charge-to-alanine mutations to rDEN4Δ30 decreased mean peak viremia below that of rDEN4Δ30 alone, it did not affect levels of neutralizing antibody.

TABLE 12

Addition of paired charge-to-alanine mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
|  |  |  |  |  | Day 0 | Day 28 |
| mock | 2 | 0 | 0 | <0.7 | <5 | <5 |
| rDEN4 | 2 | 2 | 2.5 | 2.6 ± 0.3 | <5 | 276 |
| rDEN4Δ30 | 2 | 2 | 2.0 | 2.1 ± 0.1 | <5 | 131 |
| rDEN4-200, 201 | 4 | 4 | 2.3 | 1.8 ± 0.3 | <5 | 212 |
| rDEN4Δ30-200, 201 | 4 | 3 | 1.5 | 1.3 ± 0.2 | <5 | 139 |
| rDEN4-436, 437 [cl 2] | 4 | 4 | 3.3 | 1.8 ± 0.2 | <5 | 273 |
| rDEN4Δ30-436, 437 | 4 | 3 | 1.3 | 1.0 ± 0.0 | <5 | 143 |

[a]Groups of rhesus monkeys were inoculated subcutaneously with $10^5$ PFU of the indicated virus in a 1 ml dose. Serum was collected on days 0 to 6, 8, 10 and 28. Virus titer was determined by plaque assay in Vero cells.
[b]Viremia was not detected in any monkey after day 4.

After challenge with rDEN4 on day 28, mock-infected monkeys had a mean peak virus titer of 1.5 $\log_{10}$PFU/ml and a mean number of viremic days of 3.0 (Table 13). However, none of the monkeys previously inoculated with rDEN4, rDEN4Δ30 or the charge-to-alanine mutant viruses showed detectable viremia. Additionally, none of the monkeys showed a greater than four-fold increase in serum neutralizing antibody titer. Together these data indicate that infection with any of the viruses, including those carrying both Δ30 and the charge-to-alanine mutations, protected rhesus macaques from challenge with rDEN4.

TABLE 13 rDEN4Δ30 containing charge-to-alanine mutations protects rhesus monkeys from wt DEN4 virus challenge

| Virus[a] | No. of monkeys | Mean no. of viremic days per monkey after rDEN4 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| mock | 2 | 3.0 | 1.5 ± 0.7 | <5 | 284 |
| rDEN4 | 2 | 0.0 | <0.7 | 276 | 316 |
| rDEN4Δ30 | 2 | 0.0 | <0.7 | 131 | 96 |
| rDEN4-200, 201 | 4 | 0.0 | <0.7 | 212 | 356 |
| rDEN4Δ30-200, 201 | 4 | 0.0 | <0.7 | 139 | 132 |
| rDEN4-436, 437 [cl 2] | 4 | 0.0 | <0.7 | 273 | 401 |
| rDEN4Δ30-436, 437 | 4 | 0.0 | <0.7 | 143 | 182 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 10, and 56. Virus titer was determined by plaque assay in Vero cells.

Addition of charge-to-alanine mutations to rDEN4Δ30 can confer a range of ts phenotypes in both Vero and HuH-7 cells and att phenotypes in suckling mouse brain and can either enhance or leave unchanged attenuation in SCID-HuH-7 mice. Most importantly, addition of these mutations can decrease the viremia produced by rDEN4Δ30 in rhesus macaques without decreasing neutralizing antibody titer or protective efficacy. Thus addition of such mutations to rDEN4Δ30 is contemplated as enhancing attenuation in humans. Also, mutations are contemplated as being added that do not change the overall level of attenuation, but stabilize the attenuation phenotype because they themselves are independently attenuating even in the absence of the Δ30 mutation. Charge-to-alanine mutations are particularly useful because they occur outside of the structural gene regions, and so can be used to attenuate structural gene chimeric viruses. Moreover, they involve at least three nucleotide changes, making them unlikely to revert to wild type sequence.

A series of point mutations that enhance the replication of rDEN4 in Vero cells tissue culture have been identified; these are primarily located in the NS4B gene (Blaney, J. E. et. al. 2002 *Virology* 300:125-139; Blaney, J. E. et al. 2001 *J Virol* 75:9731-9740). Vero cell adaptation mutations confer two desirable features upon a vaccine candidate. First, they enhance virus yield in Vero cells, the intended substrate for vaccine production, and thus render vaccine production more cost-effective. Second, although each of these Vero adaptation mutations are point mutations, they are likely to be extremely stable during vaccine manufacture, because they give a selective advantage in Vero cells. At least one Vero cell adaptation mutation, at position 7129, was also shown to decrease mosquito infectivity of rDEN4; poor mosquito infectivity is another desirable characteristic of a dengue vaccine candidate. To investigate the generality of this finding, we tested the effect of the remaining Vero cell adaptation mutations on the ability of rDEN4 to infect *Aedes aegypti* mosquitoes fed on an infectious bloodmeal. Table 14 shows the infectivity of each virus carrying a single Vero cell adaptation mutation at high titer. Of these, only one mutation, at position 7182, was associated with a large decrease in mosquito infectivity. Thus 7182 may be a particularly valuable mutation to include in an rDEN4 vaccine candidate, as it has opposite effects on replication in Vero cells and in mosquitoes.

TABLE 14

Effect of Vero cell adaptation mutations on rDEN4 mosquito infectivity

| | *Aedes aegypti* (oral infection) | | | |
|---|---|---|---|---|
| | Dose[a] | | % infected[b] | |
| Virus | ($\log_{10}$ pfu) | No. tested | Midgut | Head |
| rDEN4 | 4.3 | 27 | 70 | 25 |
| rDEN4-4891 | 4.4 | 23 | 74 | 13 |
| rDEN4-4995 | 4.8 | 20 | 80 | 50 |
| rDEN4-7153 | 4.8 | 20 | 80 | 30 |
| rDEN4-7546 | 4.6 | 20 | 55 | 10 |
| rDEN4-7162 | 5.0 | 20 | 55 | 25 |
| rDEN4-7163 | 4.9 | 15 | 73 | 72 |
| rDEN4-7182 | 5.0 | 20 | 20 | 0 |
| rDEN4-7630 | 4.3 | 10 | 70 | 10 |

[a]Virus titer ingested, assuming a 2 μl bloodmeal.
[b]Percentage of mosquitoes with IFA detectable antigen in midgut or head tissue prepared 21 days after oral infection.

EXAMPLE 2

Generation and Characterization of a Recombinant DEN1 Virus Containing the Δ30 Mutation We first sought to determine if the Δ30 mutation was able to satisfactorily attenuate a wild-type DEN virus other than the DEN4 serotype. To do this, the Δ30 mutation was introduced into the cDNA for DEN1 (Western Pacific). The pRS424DEN1WP cDNA clone (Puri, B. et al. 2000 *Virus Genes* 20:57-63) was digested with BamHI and used as template in a PCR using Pfu polymerase with forward primer 30 (DEN1 nt 10515-10561 and 10592-10607) and the M13 reverse sequencing primer (101 nt beyond the 3' end of DEN1 genome sequence). The resulting PCR product was 292 bp and contained the Δ30 mutation. The pRS424DEN1WP cDNA was partially digested with Apa I, then digested to completion with Sac II and the vector was gel isolated, mixed with PCR product, and used to transform yeast strain YPH857 to yield growth on plates lacking tryptophan (Polo, S. et al. 1997 *J Virol* 71:5366-74). Positive yeast colonies were confirmed by PCR and restriction enzyme analysis. DNA isolated from two independent yeast colonies was used to transform *E. coli* strain STBL2. Plasmid DNA suitable for generating RNA transcripts was prepared and the presence of the Δ30 mutation was verified by sequence analysis.

For transcription and generation of virus, cDNA (designated pRS424DEN1Δ30) that was linearized with Sac II was used as template in a transcription reaction using SP6 RNA polymerase as described (Polo, S. et al. 1997 *J Virol* 71:5366-74). Transcription reactions were electroporated into LLC-MK2 cells and infection was confirmed by observation of CPE and immunofluorescence and harvested on day 14. Virus stocks were amplified on C6/36 mosquito cells and titered on LLC-MK2 cells. The genome of the resulting virus, rDEN1Δ30, was sequenced to confirm the presence of the Δ30 mutation. The Δ30 mutation removes nucleotides 10562-10591 of DEN1 (FIG. 2B, C), which corresponds to the TL2 of DEN1. The virus replicates efficiently in Vero cell culture to titers of 6.5 $\log_{10}$ PFU/ml, indicating that the Δ30 mutation is compatible with efficient growth of DEN1 in cell culture, a property essential for manufacture of the vaccine. Using similar techniques, parent virus rDEN1 was generated. Incidental mutations arising from virus passage in tissue culture were identified in both rDEN1 and rDEN1Δ30 using sequence analysis and are listed in Table 15. An additional rDEN1Δ30 virus was derived by transfection and amplification in Vero cells. Although this virus was not evaluated in the studies described below, its sequence analysis is included in Table 15. The properties of rDEN1Δ30 as a vaccine in vivo were next examined.

Evaluation of the replication, immunogenicity, and protective efficacy of rDEN1Δ30 and wild-type parental rDEN1 virus (derived from the pRS424DEN1WP cDNA) in juvenile rhesus monkeys was performed as follows. Dengue virus-seronegative monkeys were injected subcutaneously with 5.0 $\log_{10}$ PFU of virus in a 1 ml dose divided between two injections in each side of the upper shoulder area. Monkeys were observed daily and blood was collected on days 0-10 and 28 and serum was stored at −70° C. Titer of virus in serum samples was determined by plaque assay in Vero cells as described previously (Durbin, A. P. et al. 2001 *Am J Trop Med Hyg* 65:405-13). Plaque reduction neutralization titers were determined for the day 28 serum samples as previously described (Durbin, A. P. et al. 2001 *Am J Trop Med Hyg* 65:405-13). All monkeys were challenged on day 28 with a single dose of 5.0 $\log_{10}$ PFU of wild-type rDEN1 and blood was collected for 10 days. Virus titer in post-challenge sera was determined by plaque assay in Vero cells. Monkeys inoculated with full-length wild-type rDEN1 were viremic for 2-3 days with a mean peak titer of 2.1 $\log_{10}$ PFU/ml (Table 16), and monkeys inoculated with rDEN1Δ30 were viremic for less than 1 day with a mean peak titer of 0.8 $\log_{10}$ PFU/ml, indicating that the Δ30 mutation is capable of attenuating DEN1. As expected for an attenuated virus, the immune response, as measured by neutralizing antibody titer, was lower following inoculation with rDEN1Δ30 compared to inoculation with wild-type rDEN1 (Table 16), yet sufficiently high to protect the animals against wild-type DEN1 virus challenge. Wild-type rDEN1 virus was not detected in any serum sample collected following virus challenge, indicating that monkeys were completely protected following immunization with either full-length wild-type rDEN1 or recombinant virus rDEN1Δ30. The level of attenuation specified by

TABLE 15

Missense mutations present among the recombinant DEN1 viruses and correlation of NS4B region mutations with those found in DEN4

| Virus | Transfection cell type | Gene | Nucleotide position | Nucleotide change | Amino acid position | Amino acid change |
|---|---|---|---|---|---|---|
| wt rDEN1 | LLC-MK2 | prM | 816 | C > U | 241 | Ala > Val |
| | | NS4B | 7165[a] | U > G | 2357 | Phe > Leu |
| | | NS4B | 7173[b] | U > C | 2360 | Val > Ala |
| rDEN1Δ30 | LLC-MK2 | E | 1748 | A > U | 552 | Thr > Ser |
| rDEN1Δ30 | Vero | E | 1545 | A > G | 484 | Lys > Arg |

[a]Same nucleotide as 7154 in rDEN4.
[b]Same nucleotide as 7162 in rDEN4

Nucleotide and amino acid comparison of selected NS4B region:

```
               7         7         7         7         7         7
DEN4           1         1         1         1         1         1
base           3         4         5         6         7         8
Number:  890123456789012345678901234567890123456789012345678901234567
           ++    ++  + +++++  + + +  + ++  +     ++++++++ ++ ++ ++
D47128-  CCAACAACCUUGACAGCAUCCUUAGUCAUGCUUUUAGUCCAUUAUGCAAUAAUAGGCCCA
          P  T  T  L  T  A  S  L  V  M  L  L  V  H  T  A  I  I  G  P
D17139-  CCGCUGACGCUGACAGCGGCGGUAUUUAUGCUAGUGGCUCAUUAUGCCAUAAUUGGACCC
          P  L  T  L  T  A  A  V  P  M  L  V  A  H  T  A  I  I  G  P
D27135-  CCUAUAACCCUCACAGCGGCUCUUCUUUUAUUGGUAGCACAUUAUGCCAUCAUAGGACCG
          P  I  T  L  T  A  A  L  L  L  V  A  H  T  A  I  I  G  P
D37130-  CCACUAACUCUCACAGCGGCAGUUCUCCUGCUAGUCACGCAUUAUGCUAUUAUAGGUCCA
          P  L  T  L  T  A  A  V  L  L  L  V  T  H  T  A  I  I  G  P
           +    +  +  +                +       +  +  +  +  +  +  +
D4 = rDEN4
D1 = rDEN1(WP)
D2 = rDEN2(Tonga/74)
D3 = rDEN3(Sleman/78)
+ Homology among all four serotypes
Nucleotides are underlined in even multiples of 10.
``` the Δ30 mutation was comparable in both the DEN1 and DEN4 genetic backgrounds (FIG. 5).

TABLE 16

The Δ30 mutation attenuates rDEN1 for rhesus monkeys

| Virus* | n | Mean no. days with viremia | Mean peak titer ($\log_{10}$ pfu/ml) | Mean neutralization titer | Mean peak titer of challenge virus |
|---|---|---|---|---|---|
| rDEN1 | 4 | 2.8 | 2.1 | 1230 | <0.7 |
| rDEN1Δ30 | 4 | 0.5 | 0.8 | 780 | <0.7 |

*Rhesus monkeys were inoculated subcuateously with 5.0 $\log_{10}$ PFU of virus. Serum samples were collected daily for 10 days. Serum for neutralization assay was collected on day 28. All monkeys were challenged on day 28 with 5.0 $\log_{10}$ PFU of rDEN1.

As previously reported, rDEN4 virus replicated to greater than 6.0 $\log_{10}$PFU/ml serum in SCID-HuH-7 mice, while the replication of rDEN4 virus bearing the Δ30 mutation was reduced by about 10-fold (Blaney, J. E. Jr. et al. 2002 *Virology* 300:125-139). The replication of rDEN1Δ30 was compared to that of wt rDEN1 in SCID-HuH-7 mice (Table 17). rDEN1Δ30 replicated to a level approximately 100-fold less than its wt rDEN1 parent. This result further validates the use of the SCID-HuH-7 mouse model for the evaluation of attenuated strains of DEN virus, with results correlating closely with those observed in rhesus monkeys.

TABLE 17

The Δ30 mutation attenuates rDEN1 for HuH-7-SCID mice

| Virus | No. of Mice[5] | Mean peak virus titer[6] ($\log_{10}$ pfu/ml ± SE) |
|---|---|---|
| wt rDEN1 | 9 | 7.3 ± 0.2 |
| rDEN1Δ30 | 8 | 5.0 ± 0.3 |

[5]Groups of HuH-7-SCID mice were inoculated directly into the tumor with 4.0 $\log_{10}$ pfu virus. Serum was collected on day 6 and 7, and virus titer was determined by plaque assay in Vero cells.
[6]Significant difference was found between rDEN1 and rDEN1Δ30 viruses, Tukey-Kramer test (P < 0.005).

Finally, the infectivity of rDEN1 and rDEN1Δ30 for mosquitoes was assessed, using the methods described in detail in Example 5. Previously, the Δ30 mutation was shown to decrease the ability of rDEN4 to cross the mosquito midgut barrier and establish a salivary gland infection (Troyer, J. M. et al. 2001 *Am J Trop Med Hyg* 65:414-419). However neither rDEN1 nor rDEN1Δ30 was able to infect the midgut of *Aedes aegypti* mosquitoes efficiently via an artificial bloodmeal (Table 18), so it was not possible to determine whether Δ30 might further block salivary gland infection. A previous study also showed that the Δ30 had no effect on the infectivity of rDEN4 for *Toxorhynchites splendens* mosquitoes infected via intrathoracic inoculation (Troyer, J. M. et al. 2001 *Am J Trop Med Hyg* 65:414-419), and a similar pattern was seen for rDEN1 and rDEN1Δ30 (Table 18). The genetic basis for the inability of rDEN1 to infect the mosquito midgut has not been defined at this time. However, this important property of restricted infectivity for the mosquito midgut is highly desirable in a vaccine candidate since it would serve to greatly restrict transmission of the vaccine virus from a vaccine to a mosquito vector.

TABLE 18

DEN1 and DEN1Δ30 viruses are both highly infectious for *Toxorhynchites splendens*, but do not infect *Aedes aegypti* efficiently.

| | Toxorhynchites splendens (intrathoracic inoculation) | | | Aedes aegypti (oral infection) | | | |
|---|---|---|---|---|---|---|---|
| Virus | Dose[a] ($\log_{10}$ pfu) | No. tested | % infected[b] | Dose[c] ($\log_{10}$ pfu) | No. tested | % infected[d] Midgut | Head |
| rDEN1 | 3.5 | 7 | 100 | 4.0 | 26 | 11 | 0 |
|  | 2.5 | 8 | 75 |  |  |  |  |
|  | 1.5 | 7 | 71 |  |  |  |  |
|  | 0.5 | 5 | 60 |  |  |  |  |
|  | $MID_{50}$ < 0.5 |  |  |  |  | $MID_{50} \geq 4.4$ |  |
| rDEN1Δ30 | 2.7 | 8 | 100 | 3.2 | 20 | 10 | 0 |
|  | 1.7 | 7 | 100 |  |  |  |  |
|  | 0.7 | 6 | 83 |  |  |  |  |
|  | $MID_{50}$ < 0.7 |  |  |  |  | $MID_{50} \geq 3.6$ |  |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the $MID_{50}$ was estimated by assuming that a 10-fold more concentrated virus dose would infect 100% of the mosquitoes.

Thus, the Δ30 mutation, first described in DEN4, was successfully transferred to rDEN1. The resulting virus, rDEN1Δ30, was shown to be attenuated in monkeys and SCID-HuH-7 mice to levels similar to recombinant virus rDEN4Δ30, thereby establishing the conservation of the attenuation phenotype specified by the Δ30 mutation in a different DEN virus background. Based on the favorable results of rDEN4Δ30 in recent clinical trials (Durbin, A. P. et al. 2001 *Am J Trop Med Hyg* 65:405-13), it is predicted that rDEN1Δ30 will be suitably attenuated in humans. To complete the tetravalent vaccine, attenuated rDEN2 and rDEN3 recombinant viruses bearing the Δ30 mutation are contemplated as being prepared (See Examples 3 and 4 below). The demonstration that the Δ30 mutation specifies a phenotype that is transportable to another DEN serotype has important implications for development of the tetravalent vaccine. This indicates that the Δ30 mutation is expected to have a corresponding effect on DEN2 and DEN3 wild-type viruses.

EXAMPLE 3

Generation and Characterization of a Recombinant DEN2 Virus Containing the Δ30 Mutation Evaluation of rDEN1Δ30 showed that it was satisfactorily attenuated. Based on this result, we sought to extend our technology to the creation of a DEN2 vaccine candidate. To do this, the Δ30 mutation was introduced into the cDNA of DEN2. A DEN2 virus isolate from a 1974 dengue epidemic in the Kingdom of Tonga (Tonga/74) (Gubler, D. J. et al. 1978 *Am J Trop Med Hyg* 27:581-589) was chosen to represent wt DEN2. The genome of DEN2 (Tonga/74) was sequenced in its entirety and served as consensus sequence for the construction of a full-length cDNA clone (Appendix 1). cDNA fragments of DEN2 (Tonga/74) were generated by reverse-transcription of the genome as indicated in FIG. 6A. Each fragment was subcloned into a plasmid vector and sequenced to verify that it matched the consensus sequence as determined for the virus. This yielded seven cloned cDNA fragments spanning the genome. Cloned fragments were modified as follows: Fragment X, representing the 5' end of the genome was abutted to the SP6 promoter; Fragment L was modified to contain a translationally-silent SpeI restriction site at genomic nucleotide 2353; Fragment R was modified to contain a translationally-silent SpeI restriction site also at genomic nucleotide 2353, and to stabilize the eventual full-length clone, two additional translationally-silent mutations at nucleotides 2362-2364 and 2397 were created to ensure that translation stop codons were present in all reading frames other than that used to synthesize the virus polyprotein; Fragment A was modified at nucleotide 3582 to ablate a naturally occurring SpeI restriction site and at nucleotide 4497 to ablate a naturally occurring KpnI restriction site; Fragment C was modified at nucleotide 9374 to ablate a naturally occurring KpnI restriction site; and Fragment Y, representing the 3' end of the genome was abutted to a KpnI restriction site. Each fragment was added incrementally between the AscI and KpnI restriction sites of DEN4 cDNA clone p4 (Durbin, A. P. et al. 2001 *Am J Trop Med Hyg* 65:405-13) to generate a full-length DEN2 cDNA clone (p2) with the same vector background successfully used to generate rDEN4 and rDEN4Δ30. cDNA clone p2 was sequenced to confirm that the virus genome region matched the DEN2 (Tonga/74) consensus sequence, with the exception of the translationally-silent modifications noted above. The Δ30 mutation was introduced into Fragment Y to generate Fragment YΔ30. To create p2Δ30, the Fragment Y region of p2 was replaced with Fragment YΔ30 (FIG. 6A, B).

For transcription and generation of infectious virus, cDNA (p2 and p2Δ30) was linearized with Acc65I (isoschizomer of KpnI which cleaves leaving only a single 3' nucleotide) and used as template in a transcription reaction using SP6 RNA polymerase as previously described (Blaney, J. E. et. al. 2002 *Virology* 300:125-139). Transcripts were introduced into Vero cells or C6/36 mosquito cells using liposome-mediated transfection and cell culture supernatants were harvested on day 7.

rDEN2 virus was recovered from the p2 cDNA in both Vero and C6/36 cells, while rDEN2Δ30 was recovered from the p2Δ30 cDNA clone in only C6/36 cells (Table 19). The level of infectious virus recovered in C6/36 cells was comparable for the p2 and p2Δ30 cDNA clones when assayed by plaque titration and immunostaining in Vero or C6/36 cells. As previously observed, the efficiency of transfection in C6/36 cells was higher than that in Vero cells. Two rDEN2Δ30 viruses were recovered from independent cDNA clones, #2 and #10.

TABLE 19 rDEN2 virus is recovered in Vero and C6/36 cells, but rDEN2Δ30 virus is recovered only in C6/36 cells.

| Transfection cell type | cDNA construct | Clone | Virus | Virus titer of transfection harvest (day 7) determined in the indicated cell type ($log_{10}$ PFU/ml) Vero cells | C6/36 cells |
|---|---|---|---|---|---|
| Vero cells | p2 | #8A | rDEN2 | 3.1 | 4.3 |
| | p2Δ30 | #2 | rDEN2Δ30 | <0.7 | <0.7 |
| | p2Δ30 | #10 | rDEN2Δ30 | <0.7 | <0.7 |
| C6/36 cells | p2 | #8A | rDEN2 | 5.5 | 7.5 |
| | p2Δ30 | #2 | rDEN2Δ30 | 4.8 | 7.6 |
| | p2Δ30 | #10 | rDEN2Δ30 | 4.6 | 7.5 |

To produce working stocks of rDEN2 and rDEN2Δ30 viruses, transfection harvests were passaged and terminally diluted in Vero cells, and genomic sequences of the viruses were determined. The Vero cell transfection harvest of rDEN2 virus was terminally diluted once in Vero cells, and individual virus clones were passaged once in Vero cells. To assess whether any homologous Vero cell adaptation mutations identified in the rDEN4 NS4B 7100-7200 region were present in these virus clones, seven independent terminally diluted clones were sequenced over this region. Each of the seven rDEN2 viruses contained a single nucleotide substitution in this region at nucleotide 7169 (U>C) resulting in a Val>Ala amino acid change. This nucleotide corresponds to the 7162 mutation identified in rDEN4 (Blaney, J. E. et. al. 2002 *Virology* 300:125-139), which has a known Vero cell adaptation phenotype suggesting that this mutation may confer a replication enhancement phenotype in rDEN2 virus. One rDEN2 virus clone was completely sequenced and in addition to the 7169 mutation, a missense mutation (Glu>Ala) was found in NS5 at residue 3051 (Table 20).

TABLE 20

Missense mutations which accumulate in rDEN2 and rDEN2Δ30 viruses after transfection or passage in Vero cells.

| Virus | Gene | Nucleotide position | Nucleotide substitution | Amino acid position[a] | Amino acid change |
|---|---|---|---|---|---|
| rDEN2[b] | NS4B | 7169[c] | U > C | 2358 | Val > Ala |
| (Vero) | NS5 | 9248 | A > C | 3051 | Glu > Ala |
| rDEN2Δ30[d] | NS3 | 4946 | A > G | 1617 | Lys > Arg |
| (Vero) | NS4B | 7169[c] | U > C | 2358 | Val > Ala |

[a]Amino acid position in DEN2 polyprotein beginning with the methionine residue of the C protein (nucleotides 97-99) as position 1.
[b]Virus was recovered in Vero cells and terminally-diluted once in Vero cells. Virus stock was prepared in Vero cells.
[c]Same nucleotide position as 7162 in rDEN4.
[d]Virus was recovered in C6/36 cells and passaged three times in Vero cells. Virus was then terminally diluted and a stock was prepared in Vero cells.

Because both rDEN2 and rDEN2Δ30 viruses grown in Vero cells acquired the same mutation at nucleotide 7169, which corresponds to the Vero cell adaptation mutation previously identified in rDEN4 at nucleotide 7162, it was reasoned that this mutation is associated with growth adaptation of rDEN2 and rDEN2Δ30 in Vero cells. In anticipation that the 7169 mutation may allow rDEN2Δ30 to be recovered directly in Vero cells, the mutation was introduced into the rDEN2Δ30 cDNA plasmid to create p2Δ30-7169. Transcripts synthesized from p2Δ30-7169, as well as p2 and p2Δ30 were introduced into Vero cells or C6/36 mosquito cells using liposome-mediated transfection as described above. Virus rDEN2Δ30-7169 was recovered from the p2Δ30-7169 cDNA in both Vero and C6/36 cells, while rDEN2Δ30 was recovered from the p2Δ30 cDNA clone in only C6/36 cells (Table 21). The 7169 mutation is both necessary and sufficient for the recovery of rDEN2Δ30 in Vero cells.

TABLE 21 rDEN2Δ30-7169 virus containing the 7169 Vero cell adaptation mutation is recovered in both Vero and C6/36 cells

| Transfection cell type | cDNA construct | Clone | Virus | Virus titer of transfection harvest (day 14) determined in C6/36 cells ($\log_{10}$ PFU/ml) |
|---|---|---|---|---|
| Vero cells | p2 | #8A | rDEN2 | 6.8 |
| | p2Δ30 | #2 | rDEN2Δ30 | <0.7 |
| | p2Δ30-7169[a] | #37 | rDEN2Δ30-7169 | 5.1 |
| C6/36 cells | p2 | #8A | rDEN2 | 6.9 |
| | p2Δ30 | #2 | rDEN2Δ30 | 7.1 |
| | p2Δ30-7169 | #37 | rDEN2Δ30-7169 | 7.2 |

[a]Nucleotide 7169 in rDEN2 corresponds to nucleotide 7162 in rDEN4 which has been shown to be associated with growth adaptation in Vero cells.

To initially assess the ability of the Δ30 mutation to attenuate rDEN2 virus in an animal model, the replication of DEN2 (Tonga/74), rDEN2, and rDEN2Δ30 viruses was evaluated in SCID-HuH-7 mice. Previously, attenuation of vaccine candidates in SCID-HuH-7 mice has been demonstrated to be predictive of attenuation in the rhesus monkey model of infection (Examples 1 and 2). The recombinant viruses tested in this experiment were recovered in C6/36 cells. The DEN2 Tonga/74 virus isolate, rDEN2, and two independent rDEN2Δ30 viruses, (clones 20A and 21A) which were derived from two independent p2Δ30 cDNA clones, were terminally diluted twice in C6/36 cells prior to production of a working stock in C6/36 cells. These viruses should not contain any Vero cell adaptation mutations. DEN2 Tonga/74 virus replicated to a mean virus titer of 6.2 $\log_{10}$PFU/ml in the serum of SCID-HuH-7 mice, and rDEN2 virus replicated to a similar level, 5.6 $\log_{10}$PFU/ml (Table 22). Both rDEN2Δ30 viruses were greater than 100-fold restricted in replication compared to rDEN2 virus. These results indicate that the Δ30 mutation has an attenuating effect on replication of rDEN2 virus similar to that observed for rDEN4 and rDEN1 viruses.

TABLE 22

The Δ30 mutation restricts rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 8 | 6.2 ± 0.3 | — |
| rDEN2 | 9 | 5.6 ± 0.2 | — |
| rDEN2Δ30 (clone 20A) | 9 | 3.1 ± 0.2 | 2.5 |
| rDEN2Δ30 (clone 21A) | 9 | 2.9 ± 0.3 | 2.7 |

[a]Groups of SCID-HuH-7 mice were inoculated directly into the tumor with $10^4$ PFU virus grown in C6/36 cells. Serum was collected on day 7 and titered in C6/36 cells.
[b]Comparison of mean virus titers of mice inoculated with mutant virus and concurrent rDEN2 control.

DEN2 virus replication in SCID-HuH-7 mice was also determined using DEN2 (Tonga/74), rDEN2, and rDEN2Δ30 which were passaged in Vero cells (see Table 20, footnotes b and d). Both rDEN2 and rDEN2Δ30 had acquired a mutation in NS4B, nucleotide 7169, corresponding to the 7162 mutation identified in rDEN4 as Vero cell adaptation mutation. In the presence of the 7169 mutation, the Δ30 mutation reduced replication of rDEN2Δ30 by 1.0 $\log_{10}$PFU/ml (Table 23). Previously, using virus grown in C6/36 cells and lacking the 7169 mutation, the Δ30 mutation reduced replication of rDEN2Δ30 by about 2.5 $\log_{10}$PFU/ml (Table 22). These results indicate that Vero cell growth adaptation in DEN2 may also confer a slight growth advantage in HuH-7 liver cells. Nevertheless, the attenuation conferred by the Δ30 mutation is still discernible in these Vero cell growth adapted viruses.

TABLE 23

The Δ30 mutation restricts Vero cell adapted rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 6 | 5.9 ± 0.3 | — |
| rDEN2 | 7 | 5.9 ± 0.2 | — |
| rDEN2Δ30 | 9 | 4.9 ± 0.3 | 1.0 |

[a]Groups of SCID-HuH-7 mice were inoculated directly into the tumor with $10^4$ PFU virus. Serum was collected on day 7 and titered in C6/36 cells.
[b]Comparison of mean virus titers of mice inoculated with rDEN2Δ30 and rDEN2 control.

Evaluation of the replication, immunogenicity, and protective efficacy of rDEN2Δ30 and wild-type parental rDEN2 virus in juvenile rhesus monkeys was performed as follows. Dengue virus-seronegative monkeys were injected subcutaneously with 5.0 $\log_{10}$ PFU of virus in a 1 ml dose divided between two injections in each side of the upper shoulder area. Monkeys were observed daily and blood was collected on days 0-10 and 28 and serum was stored at −70° C. Viruses used in this experiment were passaged in Vero cells, and recombinant viruses contained the mutations shown in Table 20 (See footnotes b and d). Titer of virus in serum samples was determined by plaque assay in Vero cells as described previously (Durbin, A. P. et al. 2001 *Am J Trop Med Hyg* 65:405-13). Plaque reduction neutralization titers were determined for the day 28 serum samples as previously described (Durbin, A. P. et al. 2001 *Am J Trop Med Hyg* 65:405-13). All monkeys were challenged on day 28 with a single dose of 5.0 $\log_{10}$ PFU of wt DEN2 (Tonga/74) and blood was collected for 10 days. Virus titer in post-challenge sera was determined by plaque assay in Vero cells. Monkeys inoculated with wt DEN2 (Tonga/74) or rDEN2 were viremic for 4-5 days with a mean peak titer of 2.1 or 1.9 $\log_{10}$ PFU/ml, respectively.

Figure 7:
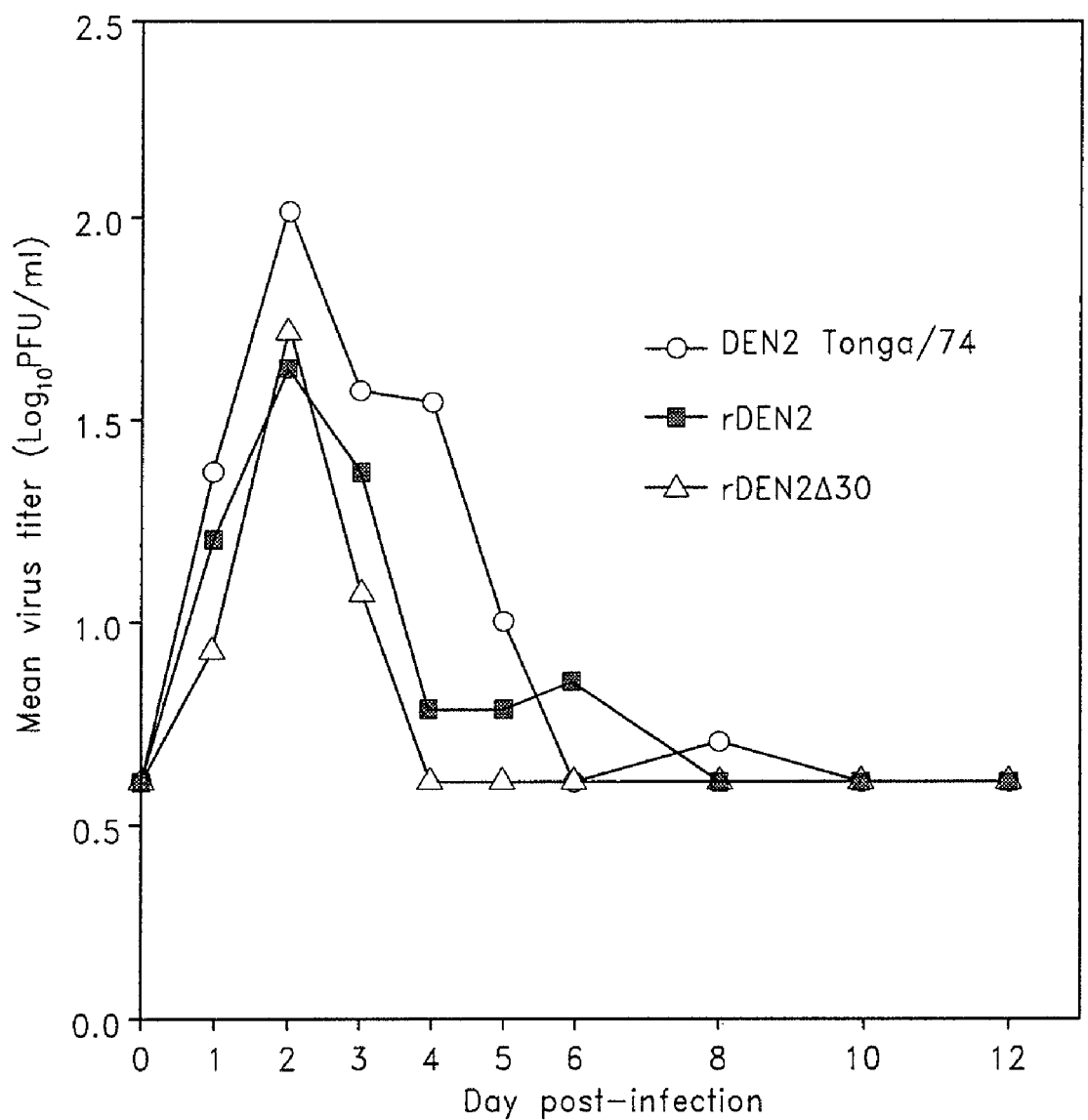
FIG. 7. Viremia levels in rhesus monkeys inoculated with DEN2 (Tonga/74), rDEN2, and rDEN2Δ30 vaccine candidate. Groups of four monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group. Viremia was not detected in any monkey after day 8.

Monkeys inoculated with rDEN2Δ30 were viremic for 2-3 days with a mean peak titer of 1.7 $\log_{10}$ PFU/ml (Table 24, FIG. 7), indicating that the Δ30 mutation is capable of attenuating DEN2, although not to the same low level observed in rDEN1Δ30 (Table 16). As expected for an attenuated virus, the immune response, as measured by neutralizing antibody titer, was lower following inoculation with rDEN2Δ30 compared to inoculation with wt DEN2 (Tonga/74) or rDEN2 (Table 24), yet sufficiently high to protect the animals against wt DEN2 virus challenge (Table 25). Thus, the decreased number of days of viremia for rDEN2Δ30, the decreased mean peak titer, and the decreased serum antibody response indicate that the Δ30 mutation attenuates rDEN2 for rhesus monkeys.

TABLE 24 rDEN2Δ30 is slightly more attenuated for rhesus monkeys than rDEN2

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| DEN2 (Tonga/74) | 4 | 4 | 4.5 | 2.1 ± 0.3 | <10 | 311 |
| rDEN2 (Vero) | 4 | 4 | 4.0 | 1.9 ± 0.1 | <10 | 173 |
| rDEN2Δ30 (Vero) | 4 | 4 | 2.8 | 1.7 ± 0.2 | <10 | 91 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 8.

TABLE 25 rDEN2Δ30 protects rhesus monkeys from wt DEN2 virus challenge

| Virus[a] | No. of monkeys | Mean no. of viremic days per monkey after DEN2 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| Mock | 2 | 4.0 | 2.1 ± 0.1 | <10 | 338 |
| DEN2 (Tonga/74) | 4 | 0 | <0.7 | 311 | 334 |
| rDEN2 (Vero) | 4 | 0 | <0.7 | 173 | 318 |
| rDEN2Δ30 (Vero) | 4 | 0 | <0.7 | 91 | 267 |

[a]28 days after inoculation with the indicated viruses, monkeys were challenged subcutaneously with $10^5$ PFU DEN2 (Tonga/74) in a 1 ml dose. Serum was collected on days 28 to 34, 36, 38, and 56. Virus titer was determined by plaque assay in Vero cells.

The infectivity of DEN2 (Tonga/74), rDEN2 and rDEN2Δ30 for *Aedes aegypti* mosquitoes via an artificial bloodmeal was evaluated using the methods described in detail in Example 5. However at doses of 3.3 to 3.5 $\log_{10}$ pfu ingested, none of these three viruses infected any mosquitoes, indicating that DEN2 (Tonga/74) is poorly infectious for *Aedes aegypti*. As with rDEN1, the genetic basis for this lack of infectivity remains to be defined. The important property of restricted infectivity for the mosquito midgut is highly desirable in a vaccine candidate because it would serve to greatly restrict transmission of the virus from a vaccine to a mosquito vector.

Several missense mutation identified in rDEN4 have been demonstrated to confer attenuated replication in suckling mouse brain and/or SCID-HuH-7 mice (Blaney, J. E. et al. 2002 *Virology* 300:125-139; Blaney, J. E. et al. 2001 *J Virol* 75:9731-9740). In addition, missense mutations that enhance replication of rDEN4 virus in Vero cells have been characterized. The significant sequence conservation among the DEN virus serotypes provides a strategy by which the mutations identified in rDEN4 viruses are contemplated as being used to confer similar phenotypes upon rDEN2 virus. Six mutations identified in rDEN4 virus that are at a site conserved in rDEN2 virus are being introduced into the p2 and p2Δ30 cDNA clones (Table 26). Specifically, two rDEN4 mutations, NS3 4891 and 4995, which confer Vero cell adaptation phenotypes and decreased replication in mouse brain, one mutation, NS4B 7182, which confers a Vero cell adaptation phenotype, and three mutations, NS12650, NS3 5097, and 3' UTR 10634 which confer decreased replication in mouse brain and SCID-HuH-7 mice are being evaluated. These mutations have been introduced into sub-cloned fragments of the p2 and p2Δ30 cDNA clones, and have been used to generate mutant full-length cDNA clones (Table 26), from which virus has been recovered in C6/36 cells (Table 27). The evaluation of these mutant rDEN2 viruses is contemplated as determining that such point mutations can be transported into a different DEN virus serotype and confer a similar useful phenotype, as has been demonstrated for the Δ30 deletion mutation.

TABLE 26

Introduction of conserved point mutations characterized in rDEN4 viruses into rDEN2 Tonga/74 virus.

| Phenotype in rDEN4 virus | | | Mutation in rDEN4 virus | | | | Mutation introduced into DEN2 virus | | | | |
|---|---|---|---|---|---|---|---|---|---|---|---|
| Vero Ad-ap-tation[a] | Mouse brain att[b] | SCID-HuH-7 att[c] | Gene/region | Nucleotide position | Amino acid position[d] | Amino acid change | Nucleotide position | Amino acid position[d] | Amino acid change | RE site/mutagenic region[e] |
| + | + | − | NS3 | 4891 | 1597 | Ile > Thr | 4889 | 1598 | Ile > Thr | Nar I CCAcgGGcGCCCGT |

TABLE 26-continued

Introduction of conserved point mutations characterized in rDEN4 viruses into rDEN2 Tonga/74 virus.

| Phenotype in rDEN4 virus | | | Mutation in rDEN4 virus | | | | Mutation introduced into DEN2 virus | | | |
|---|---|---|---|---|---|---|---|---|---|---|
| Vero Adaptation[a] | Mouse brain att[b] | SCID-HuH-7 att[c] | Gene/ region | Nucleotide position | Amino acid position[d] | Amino acid change | Nucleotide position | Amino acid position[d] | Amino acid change | RE site/ mutagenic region[e] |
| + | + | − | NS3 | 4995 | 1632 | Ser > Pro | 4993 | 1633 | Ser > Pro | Stu I AAGGccTGGA |
| + | − | − | NS4b | 7182 | 2361 | Gly > Ser | 7189 | 2365 | Gly > Ser | Xma I TAtccCCGGGAC |
| − | + | + | NS1 | 2650 | 850 | Asn > Ser | 2648 | 851 | Asn > Ser | Sac I AGAgcTctcTC |
| − | + | + | NS3 | 5097 | 1666 | Asp > Asn | 5095 | 1667 | Asp > Asn | Xma I GaATCTCCACCCgGA |
| − | + | + | 3' UTR | 10634 | n/a[f] | n/a | 10698 | n/a | n/a | none CTGTcGAATC |

[a]Presence of the indicated mutation increases plaque size in Vero cells two-fold or greater than rDEN4 virus.
[b]Presence of the indicated mutation restricts replication in 7-day-old mouse brain greater than 100-fold compared to rDEN4 virus.
[c]Presence of the indicated mutation restricts replication in SCID-HuH-7 mice greater than 100-fold compared to rDEN4 virus.
[d]Amino acid position in DEN4 or DEN2 polyprotein beginning with the methionine residue of the C protein (nucleotides 102-104 or 97-99, respectively) as position 1.
[e]Primers were engineered which introduced (underline) translationally-silent restriction enzyme (RE) sites.
Lowercase letters indicate nt changes and bold letters indicate the site of the 5-FU mutation, which in some oligonucleotides differs from the original nucleotide substitution change in order to create a unique RE site. The change preserves the codon for the amino acid substitution.
[f]Nucleotide substitution in the 3' UTR is U > C in DEN4 and DEN2 virus.

TABLE 27 rDEN2 viruses containing conserved 5-FU mutations are recovered in C6/36 cells.

| Virus (nucleotide position in rDEN2) | Nucleotide position in rDEN4 | Virus titer of transfection harvest (day 7) determined in C6/36 cells ($\log_{10}$ PFU/ml) |
|---|---|---|
| rDEN2-4889 | 4891 | 7.6 |
| rDEN2-4993 | 4995 | 7.2 |
| rDEN2-7189 | 7182 | 3.5 |
| rDEN2-2648 | 2650 | —[a] |
| rDEN2-5095 | 5097 | —[a] |
| rDEN2-10698 | 10634 | 7.7 |

[a]Transfection has not yet been attempted.

EXAMPLE 4

Generation and Characterization of a Recombinant DEN3 Virus Containing the Δ30 Mutation Because rDEN1Δ30 was satisfactorily attenuated, we sought to extend our technology to the creation of a DEN3 vaccine candidate. To do this, the Δ30 mutation was introduced into the cDNA of DEN3, similar to the method used to create rDEN2Δ30. A DEN3 virus isolate from a 1978 dengue epidemic in rural Sleman, Central Indonesia (Sleman/78) (Gubler, D. J. et al. 1981 *Am J Trop Med Hyg* 30:1094-1099) was chosen to represent wt DEN3. The genome of DEN3 (Sleman/78) was sequenced in its entirety and served as consensus sequence for the construction of a full-length cDNA clone (Appendix 2). cDNA fragments of DEN3 (Sleman/78) were generated by reverse-transcription of the genome as indicated in FIG. 8A. Each fragment was subcloned into a plasmid vector and sequenced to verify that it matched the consensus sequence as determined for the virus. This yielded six cloned cDNA fragments spanning the genome. Cloned fragments were modified as follows: Fragment 5, representing the 5' end of the genome was abutted to the SP6 promoter preceded by an AscI restriction site; Fragment 1L was modified to contain a translationally-silent SpeI restriction site at genomic nucleotide 2345; Fragment 1R was modified to contain a translationally-silent SpeI restriction site also at genomic nucleotide 2345, and to stabilize the eventual full-length clone, three additional translationally-silent mutations at nucleotides 2354-2356, 2360-2362, and 2399 were created to ensure that translation stop codons were present in all reading frames other than that used to synthesize the virus polyprotein; Fragment 3 was modified at nucleotide 9007 to ablate a naturally occurring KpnI restriction site; and Fragment 4, representing the 3' end of the genome was abutted to a KpnI restriction site. Each fragment was added incrementally between the AscI and KpnI restriction sites of DEN4 cDNA clone p4 (Durbin, A. P. et al. 2001 *Am J Trop Med Hyg* 65:405-13) to generate a full-length DEN3 cDNA clone with the same vector background successfully used to generate rDEN4 and rDEN2. However, a stable, full-length clone could not be recovered in *E. coli* when fragments 1L and 1R were combined into the same cDNA molecule. To overcome this instability, a synthetic DNA linker (FIG. 8A) containing redundant termination codons in each of the forward and reverse open reading frames was introduced into the SpeI restriction site at the same time that fragment 1L was added to complete the full-length cDNA construct. The resulting p3 clone containing the linker sequence was stable in *E. coli*, indicating that the linker sequence was sufficient to interrupt whatever deleterious element exists in this region. cDNA clone p3 was sequenced and the virus genome was found to match the DEN3 (Sleman/78) consensus sequence, with the exception of the linker sequence and translationally-silent modifications noted above (Appendix 2—shown with the linker sequence removed). The Δ30 mutation was introduced into Fragment 4 to generate Fragment 4Δ30. To create p3Δ30, the Fragment 4 region of p3 was replaced with Fragment 4Δ30 (FIG. 8A, B).

For transcription and generation of infectious virus, cDNA plasmids p3 and p3Δ30 were digested with SpeI and re-ligated to remove the linker sequence, linearized with Acc65I (isoschizomer of KpnI which cleaves leaving only a single 3' nucleotide), and used as templates in a transcription reaction using SP6 RNA polymerase as previously described (Blaney, J. E. et. al 2002 *Virology* 300:125-139). Transcripts were introduced into Vero cells or C6/36 mosquito cells using liposome-mediated transfection and cell culture supernatants were harvested on day 14.

rDEN3 virus was recovered from the p3 cDNA in both Vero and C6/36 cells, while rDEN3Δ30 was recovered from the p3Δ30 cDNA clone in only C6/36 cells (Table 28). The level of infectious virus recovered in C6/36 cells was comparable for the p3 and p3Δ30 cDNA clones when assayed by plaque titration in Vero or C6/36 cells. As previously observed, the efficiency of transfection in C6/36 cells was higher than that in Vero cells. Two rDEN3Δ30 viruses were recovered from independent cDNA clones, #22 and #41.

TABLE 28 rDEN3 virus is recovered in Vero and C6/36 cells, but rDEN3Δ30 virus is recovered only in C6/36 cells.

| Transfection cell type | cDNA construct | Clone | Virus | Virus titer of transfection harvest (day 14) determined in the indicated cell type ($\log_{10}$ PFU/ml) | |
|---|---|---|---|---|---|
| | | | | Vero cells | C6/36 cells |
| Vero cells | p3 | #50 | rDEN3 | 5.2 | 6.3 |
| | p3Δ30 | #22 | rDEN3Δ30 | <0.7 | <0.7 |
| | p3Δ30 | #41 | rDEN3Δ30 | <0.7 | <0.7 |
| C6/36 cells | p3 | #50 | rDEN3 | 5.2 | 6.0 |
| | p3Δ30 | #22 | rDEN3Δ30 | 5.9 | 6.9 |
| | p3Δ30 | #41 | rDEN3Δ30 | 5.1 | 7.2 |

To produce working stocks of viruses, transfection harvests will be passaged and terminally diluted in Vero cells, and genomic sequences of the viruses will be determined. To improve virus yield in Vero cells, the Vero cell adaptation mutation previously identified in rDEN4 at nucleotide 7162 was introduced into the homologous NS4B region of p3 and p3Δ30 to create p3-7164 and p3Δ30-7164. This mutation creates a Val to Ala substitution at amino acid position 2357. As demonstrated for rDEN2Δ30, this mutation allowed for the direct recovery of virus in Vero cells (Table 27) and is anticipated to have the same effect for rDEN3Δ30.

To initially assess the ability of the Δ30 mutation to attenuate rDEN3 virus in an animal model, the replication of DEN3 (Sleman/78), rDEN3, and rDEN3Δ30 viruses will be evaluated in SCID-HuH-7 mice and rhesus monkeys. Previously, attenuation of vaccine candidates in SCID-HuH-7 mice has been demonstrated to be predictive of attenuation in the rhesus monkey model of infection (Examples 1 and 2). The evaluation of these mutant rDEN3 viruses is contemplated as determining that the Δ30 deletion mutations can be transported into the DEN3 virus serotype and confer a similar useful phenotype, as has been demonstrated for DEN1, DEN2, and DEN4.

In summary, the strategy of introducing the Δ30 mutation into wild-type DEN viruses of each serotype to generate a suitably attenuated tetravalent vaccine formulation is a unique and attractive approach for several reasons. First, the mutation responsible for attenuation is a 30-nucleotide deletion in the 3' UTR, thus assuring that all of the structural and non-structural proteins expressed by each of the four components of the tetravalent vaccine are authentic wild-type proteins. Such wild-type proteins should elicit an antibody response that is broad based, rather than based solely on the M and E proteins that are present in chimeric dengue virus vaccine candidates (Guirakhoo, F. et al. 2001 *J Virol* 75:7290-304; Huang, C. Y. et al. 2000 *J Virol* 74:3020-8). The uniqueness of this approach derives from the fact that other live attenuated dengue virus vaccines have mutations in their structural or non-structural proteins (Butrapet, S. et al. 2000 *J Virol* 74:3011-9; Puri, B. et al. 1997 *J Gen Virol* 78:2287-91), therefore the immune response induced by these viruses will be to a mutant protein, rather than a wild-type protein. Second, deletion mutations are genetically more stable than point mutations, and reversion of the attenuation phenotype is unlikely. In humans, DEN4Δ30 present in serum of vaccines retained its Δ30 mutation, confirming its genetic stability in vivo (Durbin, A. P. et al. 2001 *Am J Trop Med Hyg* 65:405-13). The attenuating mutations in other existing dengue live attenuated vaccine candidates are based on less stable point mutations (Butrapet, S. et al. 2000 *J Virol* 74:3011-9: Puri, B. et al. 1997 *J Gen Virol* 78:2287-91). Third, since the Δ30 mutation is common to each of the four viruses of the tetravalent vaccine, recombination between any of the four vaccine serotypes would not lead to loss of the attenuating mutation or reversion to a wild-type phenotype. Recombination between components of the trivalent polio vaccine has been observed (Guillot, S. et al. 2000 *J Virol* 74:8434-43), and naturally occurring recombinant dengue viruses have been described (Worobey, M. et al. 1999 *PNAS USA* 96:7352-7) indicating the ability of this flavivirus to exchange genetic elements between two different viruses. Clearly, gene exchange is readily achieved between different DEN virus serotypes using recombinant cDNA techniques (Bray, M. and Lai, C. J. 1991 *PNAS USA* 88:10342-6). Fourth, viruses with wild-type structural proteins appear more infectious than viruses with altered structural proteins (Huang, C. Y. et al. 2000 *J Virol* 74:3020-80). This permits the use of a low quantity of each of the four virus components in the final vaccine, contributing to the low cost of manufacture. Low-cost manufacture is an essential element in defining the ultimate utility of a dengue virus vaccine.

EXAMPLE 5

Generation and Characterization of Intertypic Chimeric DEN2 Viruses Containing the Δ30 Mutation The four serotypes of dengue virus are defined by antibody responses induced by the structural proteins of the virus, primarily by a neutralizing antibody response to the envelope (E) protein. These structural proteins include the E glycoprotein, a membrane protein (M), and a capsid (C) protein. The mature virus particle consists of a well-organized outer protein shell surrounding a lipid bilayer membrane and a less-well-defined inner nucleocapsid core (Kuhn, R. J. et al. 2002 *Cell* 108:717-25). The E glycoprotein is the major protective antigen and readily induces virus neutralizing antibodies that confer protection against dengue virus infection. An effective dengue vaccine must therefore minimally contain the E protein of all four serotypes, namely DEN1, DEN2, DEN3, and DEN4, thereby inducing broad immunity and precluding the possibility of developing the more serious illnesses DHF/DSS, which occur in humans during secondary infection with a heterotypic wild-type dengue virus. Based on a previously reported strategy (Bray, M. and Lai, C. J. 1991 *PNAS USA* 88:10342-6), a recombinant cDNA technology is being used to develop a live attenuated tetravalent dengue virus vaccine composed of a set of intertypic chimeric dengue viruses bearing the structural proteins of each serotype.

Following the identification of a suitably attenuated and immunogenic DEN4 recombinant virus, namely DEN4Δ30 (Durbin, A. P et al. 2001 *Am J Trop Med Hyg* 65:405-13), chimeric viruses based on the DEN4 cDNA have been generated in which the C-M-E (CME) or M-E (ME) genes have been replaced with the corresponding genes derived from the prototypic DEN2 New Guinea C(NGC) strain (FIG. 9A). To create the CME chimeric viruses, the BglII/XhoI region of the cDNA for either rDEN4 or rDEN4Δ30 was replaced with a similar region derived from DEN2. Likewise, to create the ME chimeric viruses, the PstI/XhoI region of the cDNA for either rDEN4 or rDEN4Δ30 was replaced with a homologous region derived from DEN2. The nucleotide and amino acid sequences of the resulting junctions are shown in FIG. 9B. The GenBank accession number for the nucleotide sequence of rDEN4Δ30 is AF326837. The GenBank accession number for DEN2 NGC is M29095, which represents the mouse neurovirulent strain of DEN2 NGC and differs from the prototypic strain used here as previously documented (Bray, M. et al. 1998 *J Virol* 72:1647-51).

For transcription and generation of virus, chimeric cDNA clones were linearized and used as template in a transcription reaction using SP6 RNA polymerase as described (Durbin, A. P et al. 2001 *Am J Trop Med Hyg* 65:405-13). Transcripts were introduced into Vero cells using liposome-mediated transfection and recombinant dengue virus was harvested on day 7. The genomes of the resulting viruses were confirmed by sequence analysis of viral RNA isolated from recovered virus as previously described (Durbin, A. P et al. 2001 *Am J Trop Med Hyg* 65:405-13). Incidental mutations arising from virus passage in tissue culture were identified in all viruses and are listed in Table 29. Notably, each virus contained a missense mutation in NS4B corresponding to a previously identified mutation from rDEN4 and associated with adaptation to replication in Vero cells (See Table 30 for correlation of nucleotide positions between rDEN4 and chimeric viruses). All viruses replicated in Vero cells to titers in excess of 6.0 log$_{10}$ PFU/ml, indicating that the chimeric viruses, even those containing the Δ30 mutation, replicate efficiently in cell culture, a property essential for manufacture of the vaccine.

TABLE 29

Missense mutations observed among the Vero cell-grown chimeric DEN2/4 viruses

| Virus | Gene | Nucleotide position | Nucleotide change | Amino acid position | Amino acid change |
|---|---|---|---|---|---|
| rDEN2/4 (CME) | NS4B | 7161[a] | A > U | 2355 | Leu > Phe |
| rDEN2/4Δ30 (CME) | M | 743 | G > A | 216 | Gly > Glu |
|  | E | 1493 | C > U | 466 | Ser > Phe |
|  | NS4B | 7544[b] | C > T | 2483 | Ala > Val |

TABLE 29-continued

Missense mutations observed among the Vero cell-grown chimeric DEN2/4 viruses

| Virus | Gene | Nucleotide position | Nucleotide change | Amino acid position | Amino acid change |
|---|---|---|---|---|---|
| rDEN2/4 (ME) | E | 1065 | U > C | 322 | Phe > Leu |
|  | NS4B | 7163[a] | A > U | 2354 | Leu > Phe |
| rDEN2/4Δ30 (ME) | NS4B | 7163[a] | A > C | 2354 | Leu > Phe |

[a]Same nucleotide position as 7163 in rDEN4.
[b]Same nucleotide position as 7546 in rDEN4.

TABLE 30

Nucleotide (nt) length differences for DEN chimeric viruses compared to rDEN4.

| rDEN chimeric virus | nt difference from rDEN4 (following CME region) | ORF start (nt position) | Amino acid length | | |
|---|---|---|---|---|---|
|  |  |  | C | M | E |
| 1/4 ME | 0 | 102 | 113 | 166 | 495 |
| 1/4 CME | +3 | 102 | 114 | 166 | 495 |
| 2/4 ME | 0 | 102 | 113 | 166 | 495 |
| 2/4 CME | −2 | 97 | 114 | 166 | 495 |
| 3/4 ME | −6 | 102 | 113 | 166 | 493 |
| 3/4 CME | −3 | 102 | 114 | 166 | 493 |
| rDEN4 | — | 102 | 113 | 166 | 495 |

Results of a safety, immunogenicity, and efficacy study in monkeys are presented in Table 31. Monkeys inoculated with wild-type DEN2 were viremic for approximately 5 days with a mean peak titer of 2.1 log$_{10}$ PFU/ml, while monkeys inoculated with any of the chimeric DEN2 viruses were viremic for 1.2 days or less and had a mean peak titer of less than 1.0 log$_{10}$ PFU/ml. This reduction in the magnitude and duration of viremia clearly indicates that the chimeric viruses containing either the CME or ME proteins of DEN2 were more attenuated than the parental DEN2 NGC virus. Neither the animals receiving the wild-type DEN2 nor the DEN2/4 chimeric viruses were ill. The decreased replication of the attenuated viruses in monkeys is accompanied by a reduction in the immune response of inoculated monkeys. This is indicated in Table 31 by approximately a 5-fold reduction in the level of neutralizing antibody following inoculation with the chimeric viruses in comparison to titers achieved in animals inoculated with wild-type virus. Addition of the Δ30 mutation to the CME chimeric virus further attenuated the virus, such that rDEN2/4Δ30(CME) did not replicate in monkeys to a detectable level and did not induce a detectable immune response. This virus appeared over-attenuated, and if similar results were seen in humans, this virus would not be suitable for use as a vaccine. However, addition of the Δ30 mutation to the ME chimeric virus did not further attenuate this chimeric virus and the resulting rDEN2/4Δ30(ME) virus appears satisfactorily attenuated and immunogenic for use as a vaccine.

TABLE 31

Chimerization between dengue virus types 2 and 4 results in recombinant viruses which are attenuated for rhesus monkeys.

| Group* | Virus | n | Mean no. days with viremia | Mean peak virus titer ($\log_{10}$ pfu/ml) | Geometric mean neutralizing antibody titer (reciprocal) |
|---|---|---|---|---|---|
| 1 | rDEN2/4 (CME) | 6 | 1.2 | 0.9 | 50 |
| 2 | rDEN2/4Δ30 (CME) | 8 | 0 | <0.7 | <5 |
| 3 | rDEN2/4 (ME) | 4 | 1.0 | 0.8 | 76 |
| 4 | rDEN2/4Δ30 (ME) | 4 | 0.3 | 0.7 | 62 |
| 5 | DEN2 NGC | 6 | 5.5 | 2.1 | 312 |

*Rhesus monkeys were inoculated subcutaneously with 5.0 $\log_{10}$ PFU of virus. Serum samples were collected daily for 10 days. Serum for neutralization assay was collected on day 28. Serum samples obtained before virus inoculation had a neutralizing antibody titer of <5.

As described in the previous examples, SCID mice transplanted with the cells are a sensitive model for the evaluation of dengue virus attenuation. Each chimeric DEN2/4 virus was inoculated into groups of SCID-HuH-7 mice and levels of virus in the serum were determined (Table 32). Chimeric viruses replicated to levels between 20- and 150-fold lower than either of the parental viruses (rDEN4 and DEN2-NGC). CME chimeric viruses were slightly more attenuated than the comparable ME chimeric viruses, with the Δ30 mutation providing a 0.5 $\log_{10}$ reduction in replication. This level of attenuation exerted by the Δ30 mutation was similar to that observed previously for rDEN4Δ30.

TABLE 32

Chimerization between dengue virus types 2 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN2-NGC | 9 | 6.1 ± 0.2 | A |
| rDEN2/4 (CME) | 7 | 4.4 ± 0.3 | B |
| rDEN2/4Δ30 (CME) | 7 | 3.9 ± 0.3 | B |
| rDEN2/4 (ME) | 6 | 4.8 ± 0.5 | B |
| rDEN2/4Δ30 (ME) | 9 | 4.3 ± 0.2 | B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

To evaluate the replication levels of each DEN2/4 chimeric virus in mosquitoes, two different genera of mosquitoes were experimentally infected. *Aedes aegypti* were infected by ingesting a virus-containing blood meal. By evaluating the presence of virus antigen in both the midgut and head tissue, infectivity could be determined for the local tissues (midgut), and the ability of virus to disseminate and replicate in tissues beyond the midgut barrier (head) could also be measured. The presence of virus in the head is limited by the ability of the ingested virus to replicate in the midgut and then disseminate to the salivary glands in the head, as well as the innate ability of the virus to replicate in the salivary glands. Intrathoracic inoculation of virus into *Toxorhynchites splendens* bypasses the mosquito midgut barrier. Parental viruses rDEN4 and DEN2-NGC readily infect *Ae. aegypti* and *T. splendens* (Table 33), with DEN2-NGC appearing to be much more infectious in *T. splendens*. Each of the rDEN2/4 chimeric viruses was also tested in both mosquito types. In many cases it was not possible to inoculate *Ae. aegypti* with an undiluted virus stock of sufficient titer to achieve a detectable infection due to the very low infectivity of several of the viruses. Nevertheless, it is clear that the rDEN2/4 chimeric viruses are less infectious for the midgut and head. Parental viruses rDEN4 and DEN2-NGC, administered at a maximum dose of approximately 4.0 $\log_{10}$PFU, were detectable in 74% and 94% of midgut preparations, and 32% and 71% of head preparations, respectively. Among the chimeric viruses, the highest level of infectivity, as observed for rDEN2/4Δ30 (CME), resulted in only 26% infected midgut samples and 6% head samples. In the more permissive *T. splendens*, the rDEN2/4 chimeric viruses were generally less infectious than either parental virus, with CME chimeric viruses being less infectious than ME viruses. It has previously been reported for DEN4 that the Δ30 mutation does not have a discernable effect on virus infectivity in *T. splendens* similar to that observed here for the rDEN2/4 chimeric viruses (Troyer, J. M. et al. 2001 *Am J Trop Med Hyg* 65:414-419).

TABLE 33

Dengue 2/4 chimeric viruses are less infectious compared to either parental virus strain in mosquitoes

| Virus | Toxorhynchites splendens (intrathoracic inoculation) | | | Aedes aegypti (oral infection) | | | |
|---|---|---|---|---|---|---|---|
| | Dose[a] log$_{10}$ pfu | No. tested | % infected[b] | Dose[c] log$_{10}$ pfu | No. tested | % infected[d] Midgut | Head |
| rDEN4 | 3.3 | 6 | 83 | 3.8 | 38 | 74 | 32 |
| | 2.3 | 7 | 57 | 2.8 | 15 | 26 | 6 |
| | 1.3 | 6 | 0 | 1.8 | 20 | 10 | 5 |
| | | | MID$_{50}$ = 2.2 | | | MID$_{50}$ = 3.4 | MID$_{50}$ ≧ 4.1 |
| DEN2-NGC | 2.5 | 5 | 100 | 4.0 | 17 | 94 | 71 |
| | 1.2 | 15 | 93 | 3.0 | 25 | 36 | 16 |
| | 0.2 | 4 | 75 | 2.0 | 30 | 0 | 0 |
| | 0.02 | 8 | 38 | | | MID$_{50}$ = 3.2 | MID$_{50}$ = 3.6 |
| | | | MID$_{50}$ = 0.5 | | | | |
| rDEN2/4 (CME) | 3.9 | 9 | 11 | 4.4 | 11 | 9 | 0 |
| | 2.9 | 5 | 0 | 3.4 | 10 | 0 | 0 |
| | | | MID$_{50}$ ≧ 4.3 | | | MID$_{50}$ ≧ 4.9 | Nc[e] |
| rDEN2/4Δ30 (CME) | 3.5 | 6 | 17 | 4.0 | 15 | 26 | 6 |
| | 2.5 | 6 | 17 | 3.0 | 10 | 0 | 0 |
| | | | MID$_{50}$ ≧ 3.9 | | | MID$_{50}$ ≧ 4.3 | MID$_{50}$ ≧ 4.5 |
| rDEN2/4 (ME) | 3.4 | 6 | 100 | 3.9 | 23 | 4 | 0 |
| | 2.4 | 5 | 20 | | | MID$_{50}$ ≧ 4.4 | Nc |
| | 1.4 | 5 | 0 | | | | |
| | | | MID$_{50}$ = 2.8 | | | | |
| rDEN2/4Δ30 (ME) | 2.6 | 11 | 9 | 3.1 | 30 | 0 | 0 |
| | | | MID$_{50}$ ≧ 3.0 | | | nc | Nc |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the MID$_{50}$ was estimated by assuming that a 10-fold more concentrated virus dose would infect 100% of the mosquitoes.
[e]nc = not calculated, since virus antigen was not detected.

Chimerization of the DEN2 structural genes with rDEN4Δ30 virus resulted in a virus, rDEN2/4Δ30(CME), that had decreased replication in Vero cells compared to either parent virus. To evaluate Vero cell adaptation mutations (Blaney, J. E. et al. 2002 *Virology* 300:125-139) as a means of increasing the virus yield of a DEN vaccine candidate in Vero cells, selected mutations were introduced into this chimeric virus. Accordingly, rDEN2/4Δ30(CME) viruses bearing adaptation mutations were recovered, terminally diluted, and propagated in C6/36 cells to determine if the virus yield in Vero cells could be increased.

rDEN2/4Δ30(CME) viruses bearing Vero cell adaptation mutations were generated as follows. DNA fragments were excised from rDEN4 cDNA constructs encompassing single or double DEN4 Vero cell adaptation mutations and introduced into the cDNA clone of rDEN2/4Δ30(CME). The presence of the Vero cell adaptation mutation was confirmed by sequence analysis, and RNA transcripts derived from the mutant cDNA clones were transfected, terminally diluted, and propagated in C6/36 cells.

For evaluation of growth kinetics, Vero cells were infected with the indicated viruses at a multiplicity of infection (MOI) of 0.01. Confluent cell monolayers in duplicate 25-cm² tissue culture flasks were washed and overlaid with a 1 ml inoculum containing the indicated virus. After a two hour incubation at 37° C., cells were washed three times in MEM and 5 ml of MEM supplemented with 2% FBS was added. A 1 ml aliquot of tissue culture medium was removed, replaced with fresh medium, and designated the day 0 time-point. At the indicated time points post-infection, 1 ml samples of tissue culture medium were removed, clarified by centrifugation, and frozen at −80° C. The level of virus replication was assayed by plaque titration in C6/36 cells and visualized by immunoperoxidase staining. The limit of detection was <0.7 log$_{10}$PFU/ml.

Figure 10:
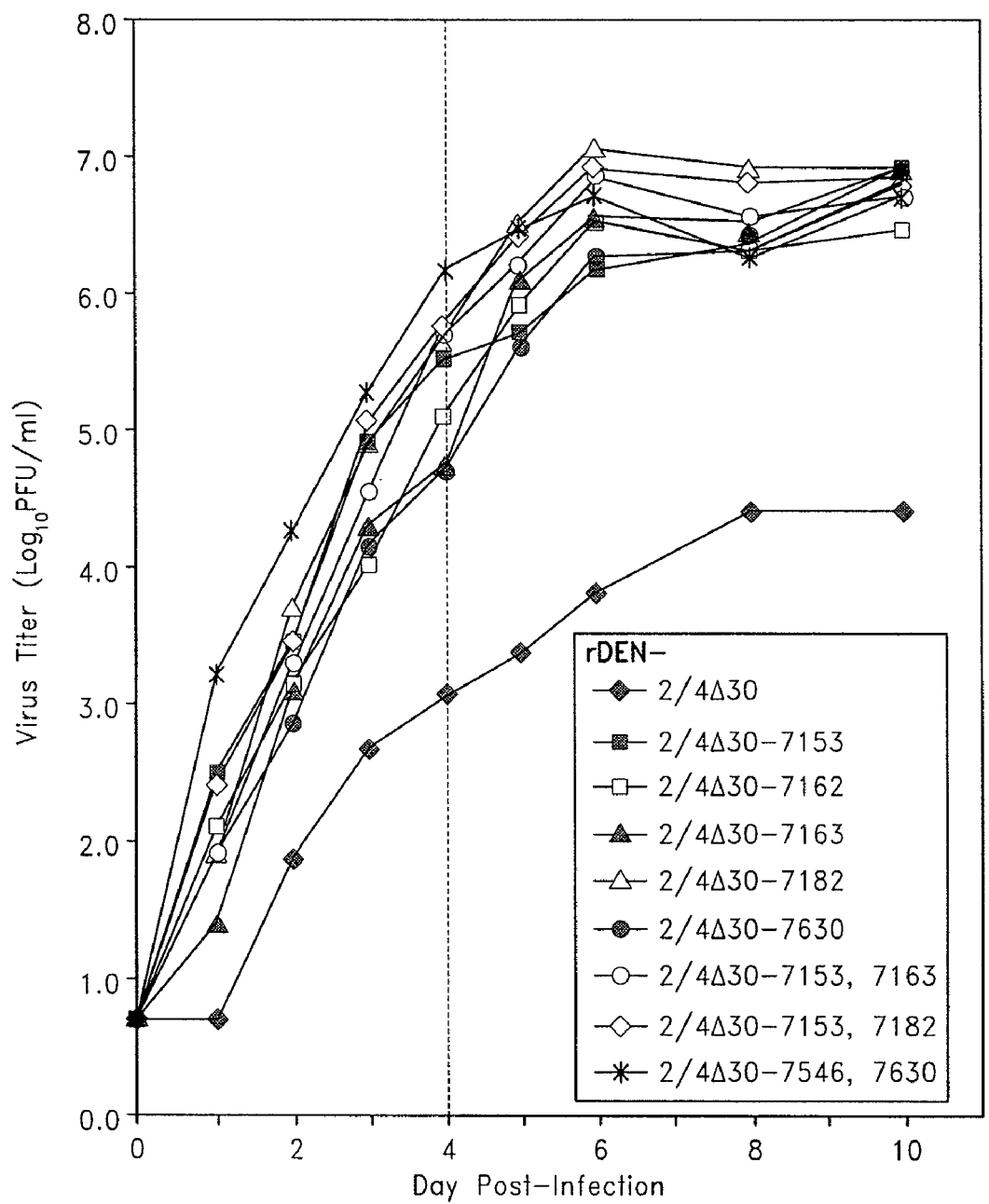
FIG. 10. Growth kinetics in Vero cells of chimeric rDEN2/4Δ30 viruses encoding single or combined Vero cell adaptation mutations. Vero cells were infected with the indicated viruses at an MOI of 0.01. At the indicated time points post-infection, 1 ml samples of tissue culture medium were removed, clarified by centrifugation, and frozen at −80° C. The level of virus replication was assayed by plaque titration in C6/36 cells. Lower limit of detection was 0.7 $\log_{10}$PFU/ml. Replication levels on day 4 post-infection are indicated by the dashed line.

The growth properties of rDEN2/4Δ30(CME) viruses bearing single Vero cell adaptation mutations at NS4B -7153, -7162, -7163, -7182, NS5-7630 or three combinations of mutations were compared in Vero cells with rDEN2/4Δ30 (CME) virus (FIG. 10). Without an introduced Vero cell adaptation mutation, rDEN2/4Δ30(CME) virus yield peaked at 4.4 log$_{10}$PFU/ml. Each individual adaptation mutation and the combined mutations conferred a substantial increase in replication. Specifically, rDEN2/4Δ30(CME)-7182 grew to the highest titer of 7.1 log$_{10}$PFU/ml, which was a 500-fold increase in yield. rDEN2/4Δ30(CME)-7162 had the lowest yield but still was increased 125-fold over the level of replication by rDEN2/4Δ30(CME) virus. Introduction of two adaptation mutations into rDEN2/4Δ30(CME) virus did not significantly increase virus yield over that of viruses bearing single Vero cell adaptation mutations. The observed increase of up to 500-fold in virus yield by the introduction of a Vero cell adaptation mutation into this chimeric vaccine candidate demonstrates the value of identifying and characterizing specific replication-promoting sequences in DEN viruses.

These results have particular significance for the development of a live attenuated dengue virus vaccine. First, it is clear that chimerization leads to attenuation of the resulting virus, as indicated by studies in rhesus monkeys, HuH7-SCID mice and mosquitoes. Although this conclusion was not made in the previous study with DEN2/DEN4 or DEN1/DEN4 chimeric viruses (Bray, M. et al. 1996 *J Virol* 70:4162-6), careful examination of the data would suggest that the chimeric viruses are more attenuated in monkeys compared to the wild-type parent viruses. Second, the Δ30 mutation can further augment this attenuation in a chimeric-dependent manner. Specifically, in this example, chimeric viruses bearing the CME region of DEN2 were over-attenuated by the addition of Δ30, whereas the attenuation phenotype of chimeric viruses bearing just the ME region of DEN2 was unaltered by the addition of the Δ30 mutation. This unexpected finding indicates that in a tetravalent vaccine comprised of individual component viruses bearing a shared attenuating mutation, such as the Δ30 mutation, only ME chimeric viruses can be utilized since CME chimeric viruses bearing the Δ30 mutation can be over-attenuated in rhesus monkeys and might provide only limited immunogenicity in humans.

EXAMPLE 6

Generation and Characterization of Intertypic Chimeric DEN3 Viruses Containing the Δ30 Mutation Chimeric viruses based on the DEN4 cDNA have been generated in which the CME or ME genes have been replaced with the corresponding genes derived from DEN3 (Sleman/78), a virus isolate from the 1978 dengue outbreak in the Sleman region of Indonesia (Gubler, D. J. et al. 1981 *Am J Trop Med Hyg* 30:1094-1099) (Appendix 2). As described in Example 5 for the DEN2 chimeric viruses, CME chimeric viruses for DEN3 were generated by replacing the BglII/XhoI region of the cDNA for either rDEN4 or rDEN4Δ30 with a similar region derived from DEN3 (Sleman/78) (FIG. 11A). Likewise, to create the ME chimeric viruses, the PstI/XhoI region of the cDNA for either rDEN4 or rDEN4Δ30 was replaced with a similar region derived from DEN3 (Sleman/78). The nucleotide and amino acid sequences of the resulting junctions are shown in FIG. 1B. The genomes of the resulting viruses were confirmed by sequence analysis of viral RNA isolated from recovered virus as previously described (Durbin, A. P et al. 2001 *Am J Trop Med Hyg* 65:405-13). Incidental mutations arising from virus passage in tissue culture were identified in all viruses and are listed in Table 34. Notably, each virus contained a missense mutation in NS4B corresponding to a previously identified mutation from rDEN4 and associated with adaptation to growth in Vero cells (See Table 30 for correlation of nucleotide positions between rDEN4 and chimeric viruses). All viruses replicated in Vero cells to titers in excess of 5.7 $\log_{10}$ PFU/ml, indicating that the chimeric viruses, even those containing the Δ30 mutation, replicate efficiently in cell culture, a property essential for manufacture of the vaccine.

TABLE 34

Missense mutations observed among Vero cell-grown chimeric DEN3/4 viruses

| Virus | Gene | Nucleotide position | Nucleotide change | Amino acid position | Amino acid change |
|---|---|---|---|---|---|
| rDEN3/4Δ30 (CME) | M | 825 | T > C | 242 | Phe > Leu |
|  | E | 1641 | C > T | 514 | Leu > Phe |
|  | E | 2113 | A > G | 671 | Lys > Arg |
|  | NS4B | 7159[a] | T > C | 2353 | Leu > Ser |
| rDEN3/4 (ME) | M | 460 | A > G | 120 | Asp > Gly |
|  | NS4B | 7177[b] | G > U | 2359 | Gly > Val |
|  | NS5 | 7702 | C > U | 2534 | Ser > Phe |
| rDEN3/4Δ30 | E | 1432 | A > U | 444 | Gln > Leu |

TABLE 34-continued

Missense mutations observed among Vero cell-grown chimeric DEN3/4 viruses

| Virus | Gene | Nucleotide position | Nucleotide change | Amino acid position | Amino acid change |
|---|---|---|---|---|---|
| (ME) | NS4B | 7156[a] | U > C | 2352 | Leu > Ser |
|  | NS5 | 8692 | A > C | 2864 | Asn > His |

[a]Same nucleotide position as 7162 in rDEN4.
[b]Same nucleotide position as 7183 in rDEN4.

As described in the previous examples, SCID mice transplanted with HuH-7 cells are a sensitive model for the evaluation of dengue virus attenuation. Each chimeric DEN3/4 virus was inoculated into groups of SCID-HuH-7 mice and levels of virus in the serum were determined (Table 35). While chimeric virus rDEN3/4 (CME) was not attenuated, the remaining chimeric viruses replicated to levels between 40- and 400-fold lower than either of the parental viruses (rDEN4 and DEN3-Sleman/78). In the CME chimeric virus, the Δ30 mutation providing a remarkable 2.7 $\log_{10}$ reduction in replication. This level of attenuation conferred by the Δ30 mutation in the CME chimeric virus was much greater than that observed previously for rDEN4Δ30. The rDEN3/4 (ME) virus was 100-fold reduced in replication compared to either parent virus indicating that the ME chimerization was attenuating per se. Addition of the Δ30 mutation to rDEN3/4 (ME) did not result in additional attenuation.

TABLE 35

Chimerization between dengue virus types 3 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN3-Sleman/78 | 23 | 6.4 ± 0.2 | A |
| rDEN3/4 (CME) | 7 | 6.4 ± 0.6 | A |
| rDEN3/4Δ30 (CME) | 5 | 3.7 ± 0.4 | B |
| rDEN3/4 (ME) | 6 | 4.2 ± 0.7 | B |
| rDEN3/4Δ30 (ME) | 7 | 4.7 ± 0.4 | A, B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

Evaluation of the replication and immunogenicity of the DEN3 chimeric recombinant viruses and wild-type DEN3 virus in monkeys was performed as described in Example 5. Results of this safety and immunogenicity study in monkeys are presented in Table 36. Monkeys inoculated with rDEN3/4(CME) and wild-type DEN (Sleman/78) were viremic for approximately 2 days with a mean peak titer of between 1.6 and 1.8 $\log_{10}$ PFU/ml, respectively, indicating that chimerization of the CME structural genes of DEN3 did not lead to attenuation of virus replication, a different pattern than that observed for DEN2 chimerization (Table 31). However, chimerization of the ME structural genes resulted in attenuated viruses with undetectable viremia in monkeys, although all monkeys seroconverted with a greater than 10-fold increase in serum antibody levels. As expected for an attenuated virus, the immune response, as measured by neutralizing antibody titer, was lower following inoculation with any of the chimeric viruses compared to inoculation with wt (Sleman/78), yet sufficiently high to protect the animals against wt DEN3 virus challenge (Table 37). It is clear that addition of the Δ30 mutation to rDEN3/4(CME) was capable of further attenuating the resulting virus rDEN3/4Δ30(CME).

TABLE 36

The Δ30 mutation further attenuates rDEN3/4 (CME) for rhesus monkeys

| Virus[a] | No. of monkeys | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|
| DEN3 (Sleman/78) | 4 | 2.3 | 1.8 | <5 | 707 |
| rDEN3/4 (CME) | 4 | 2.0 | 1.6 | <5 | 211 |
| rDEN3/4Δ30 (CME) | 4 | 0 | <1.0 | <5 | 53 |
| rDEN3/4 (ME) | 4 | 0 | <1.0 | <5 | 70 |
| rDEN3/4Δ30 (ME) | 4 | 0 | <1.0 | <5 | 58 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

TABLE 37 rDEN3/4 chimeric viruses protect rhesus monkeys from wt DEN3 virus challenge

| Virus[a] | No. of monkeys | Mean no. of viremic days per monkey after rDEN3 challenge | Mean peak virus titer ($\log_{10}$ PFU/ml ± SE) | Geometric mean serum neutralizing antibody titer (reciprocal dilution) Day 28 | Day 56 |
|---|---|---|---|---|---|
| Mock | 2 | 5.0 | 2.5 ± 0.4 | <5 | 372 |
| DEN3 (Sleman/78) | 4 | 0 | <1.0 | 707 | 779 |
| rDEN3/4 (CME) | 4 | 0 | <1.0 | 211 | 695 |
| rDEN3/4Δ30 (CME) | 4 | 0.8 | 1.1 ± 0.2 | 53 | 364 |
| rDEN3/4 (ME) | 4 | 0 | <1.0 | 70 | 678 |
| rDEN3/4Δ30 (ME) | 4 | 0 | <1.0 | 58 | 694 |

[a]28 days after primary inoculation with the indicated viruses, rhesus monkeys were challenged subcutaneously with $10^5$ PFU DEN3 (Sleman/78) virus in a 1 ml dose. Serum was collected on days 28 to 34, 36, 38, and 56. Virus titer was determined by plaque assay in Vero cells.

To evaluate the replication levels of each DEN3/4 chimeric virus in mosquitoes, *Aedes aegypti* were infected by ingesting a virus-containing blood meal (Table 38). Parental viruses rDEN4 and DEN3 (Sleman/78) readily infect *Ae. aegypti*. Each of the rDEN3/4 chimeric viruses was also tested. In many cases it was not possible to infect *Ae. aegypti* with an undiluted virus stock of sufficient titer to achieve a detectable infection due to the very low infectivity of several of the viruses. At a dose of approximately 2.8-2.9 $\log_{10}$PFU, rDEN4, DEN3 (Sleman/78), and rDEN3/4(CME) were equally infectious and disseminated to the head with equal efficiency. For the remaining chimeric viruses, infection was not detectable even at a dose of 3.4 $\log_{10}$PFU, indicating that replication of rDEN3/4(ME) and rDEN3/4Δ30(CME) is restricted in *Ae. aegypti*. By comparing infectivity of rDEN3/4(CME) and rDEN3/4Δ30(CME), it is clear that the Δ30 mutation is capable of further attenuating the chimeric virus for mosquitoes.

TABLE 38

Ability of DEN3/4 chimeric viruses to infect *Aedes aegypti* fed an infectious bloodmeal.

| Virus Tested | Dose Ingested ($\log_{10}$ pfu)[a] | No. Mosquitoes Tested | No. (%) Midgut Infections[b,c,d] | No. (%) Disseminated Infections[e] |
|---|---|---|---|---|
| rDEN4 | 3.8 | 18 | 14 (77%) | 2 (14%) |
| | 2.8 | 20 | 7 (34%) | 2 (10%) |
| | 1.8 | 18 | 0 | 0 |
| | | | $MID_{50}$ = 3.4 | $MID_{50}$ ≥ 4.4 |
| DEN3 (Sleman) | 2.9 | 16 | 3 (18%) | 2 (12%) |
| | 1.9 | 10 | 1 (10%) | 0 |
| | | | $MID_{50}$ ≥ 3.5 | $MID_{50}$ ≥ 3.5 |
| rDEN3/4 (CME) | 3.9 | 20 | 6 (30%) | 2 (10%) |
| | 2.9 | 18 | 4 (22%) | 0 |
| | 1.9 | 13 | 1 (7%) | 0 |
| | | | $MID_{50}$ ≥ 4.2 | $MID_{50}$ ≥ 4.5 |
| DEN3/4Δ30 (CME) | 3.3 | 20 | 0 | 0 |
| | | | $MID_{50}$ ≥ 4.3 | $MID_{50}$ ≥ 4.3 |
| DEN3/4 (ME) | 3.4 | 15 | 0 | 0 |
| | | | $MID_{50}$ ≥ 4.4 | $MID_{50}$ ≥ 4.4 |

[a]Amount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

EXAMPLE 7

Figure 12A:
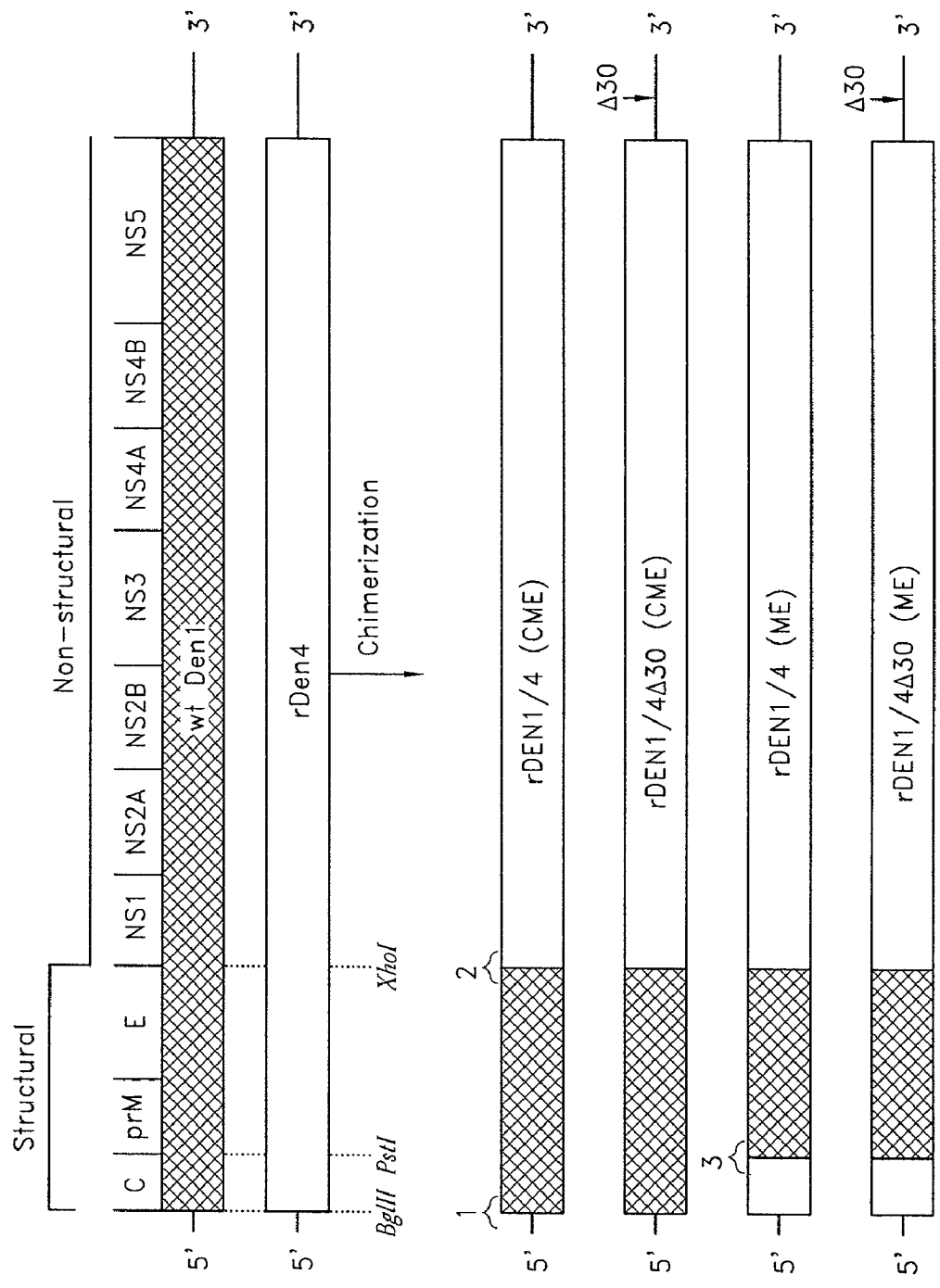

Generation and Characterization of Intertypic Chimeric DEN1 Viruses Containing the Δ30 Mutation Chimeric viruses based on the DEN4 cDNA have been generated in which the CME or ME genes have been replaced with the corresponding genes derived from DEN1 (Puerto Rico/94), a virus isolate from a 1994 dengue outbreak in Puerto Rico (Appendices 3 and 4). As described in Example 4 for the DEN2 chimeric viruses, CME chimeric viruses for DEN1 were generated by replacing the BglII/XhoI region of the cDNA for either rDEN4 or rDEN4Δ30 with a similar region derived from DEN1 (Puerto Rico/94) (FIG. 12A). Likewise, to create the ME chimeric viruses, the PstI/XhoI region of the cDNA for either rDEN4 or rDEN4Δ30 was replaced with a similar region derived from DEN1 (Puerto Rico/94). The nucleotide and amino acid sequences of the resulting junctions are shown in FIG. 12B.

For transcription and generation of virus, chimeric cDNA clones were linearized and used as template in a transcription reaction using SP6 RNA polymerase as described. Transcripts were introduced into C6/36 mosquito cells using liposome-mediated transfection and recombinant dengue virus was harvested between day 7 and 14. Viruses were subsequently grown in Vero cells and biologically cloned by terminal dilution in Vero cells. All viruses replicated in Vero cells to titers in excess of $6.0 \log_{10}$ PFU/ml, indicating that the chimeric viruses, even those containing the $\Delta 30$ mutation, replicate efficiently in cell culture. Genomic sequence analysis is currently underway to identify incidental mutations arising from virus passage in tissue culture.

To evaluate the replication levels of DEN1/4 (CME) and rDEN1/4Δ30(CME) chimeric virus in mosquitoes, *Aedes aegypti* were infected by ingesting a virus-containing blood meal (Table 39). Parental virus rDEN4 infects *Ae. aegypti* with an MID50 of $4.0 \log_{10}$PFU. However, parental virus DEN1 (Puerto Rico/94), is unable to infect *Ae. aegypti* at a dose of up to $3.4 \log_{10}$PFU. Thus CME chimeric viruses DEN1/4 and rDEN1/4Δ30 share this inability to infect *Ae. aegypti*. Therefore, it is unnecessary in *Ae. aegypti* to evaluate the effect of the Δ30 mutation on the infectivity of the DEN1/4 chimeric viruses, in a manner similar to that used for the DEN2/4 and DEN3/4 chimeric viruses.

TABLE 39

Inability of DEN1/4 chimeric viruses to infect *Aedes aegypti* fed an infectious bloodmeal.

| Virus tested | Dose ingested $(\log_{10} \text{pfu})^a$ | No. Mosquitoes Tested | No. (%) Midgut Infections[b,c,d] | No. (%) Disseminated Infections[e] |
|---|---|---|---|---|
| rDEN4 | 4.3 | 21 | 18 (85%) | 8 (44%) |
| | 3.3 | 15 | 3 (20%) | 0 |
| | 2.3 | 20 | 0 | 0 |
| | | | $\text{MID}_{50} = 4.0$ | $\text{MID}_{50} \geq 4.3$ |
| DEN1 (Puerto Rico/94) | 3.4 | 21 | 0 | 0 |
| | | | $\text{MID}_{50} \geq 4.4$ | $\text{MID}_{50} \geq 4.4$ |
| rDEN 1/4 | 3.8 | 20 | 0 | 0 |

TABLE 39-continued

Inability of DEN1/4 chimeric viruses to infect *Aedes aegypti* fed an infectious bloodmeal.

| Virus tested | Dose ingested $(\log_{10} \text{pfu})^a$ | No. Mosquitoes Tested | No. (%) Midgut Infections[b,c,d] | No. (%) Disseminated Infections[e] |
|---|---|---|---|---|
| (CME) | | | $\text{MID}_{50} \geq 4.8$ | $\text{MID}_{50} \geq 4.8$ |
| rDEN1/4Δ30 (CME) | 2.8 | 20 | 0 | 0 |
| | | | $\text{MID}_{50} \geq 3.8$ | $\text{MID}_{50} \geq 3.8$ |

[a]Amount of virus ingested, assuming a 2 μl bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the MID$_{50}$ was estimated by assuming that a 10-fold more concentrated virus dose would infect 100% of the mosquitoes.
[d]When no infection was detected, the MID$_{50}$ was assumed to be greater than a 10-fold higher dose of virus than the one used.
[e]Number (percentage) of mosquitoes with detectable dengue virus antigen in both midgut and head tissue.

As described in the previous examples, SCID mice transplanted with the cells are a sensitive model for the evaluation of dengue virus attenuation. Each chimeric DEN1/4 virus was inoculated into groups of SCID-HuH-7 mice and levels of virus in the serum were determined (Table 40). Chimeric viruses replicated to levels between 15- and 250-fold lower than either of the parental viruses, rDEN4 and DEN1 (Puerto Rico/94). CME chimeric viruses were more attenuated than the comparable ME chimeric viruses, with the Δ30 mutation providing a $0.8 \log_{10}$ reduction in replication. This level of attenuation exerted by the Δ30 mutation in the CME chimeric viruses was similar to that observed previously for rDEN4Δ30. However, the attenuating effect of the Δ30 mutation in the ME chimeric viruses is indiscernible.

TABLE 40

Chimerization between dengue virus types 1 and 4 results in recombinant viruses which are attenuated for HuH-7-SCID mice.

| Virus[a] | No. of mice | Mean peak virus titer $(\log_{10} \text{pfu/ml} \pm \text{SE})$ | Statistical group[b] |
|---|---|---|---|
| rDEN4 | 32 | 6.3 ± 0.2 | A |
| DEN1 (Puerto Rico/94) | 4 | 6.4 ± 0.2 | A |
| rDEN1/4 (CME) | 8 | 4.7 ± 0.2 | B, C |
| rDEN1/4Δ30 (CME) | 6 | 3.9 ± 0.4 | C |
| rDEN1/4 (ME) | 6 | 5.0 ± 0.2 | B |
| rDEN1/4Δ30 (ME) | 6 | 5.1 ± 0.3 | B |

[a]Groups of HuH-7-SCID mice were inoculated into the tumor with $4.0 \log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

APPENDIX 1

Nucleotide and amino acid sequence of DEN2 (Tonga/74) cDNA plasmid p2

```
         10        20        30        40        50        60        70        80        90       100
AGTTGTTAGTCTACGTGGACCGACAAAGACAGATTCTTTGAGGGAGCTAAGCTCAACGTAGTTCTAACTGTTTTTTGATTAGAGAGCAGATCTCTGATGA
Met>

110       120       130       140       150       160       170       180       190       200
ATAACCAACGGAAAAAGGCGAGAAACACGCCTTTCAATATGCTGAAACGCGAGAGAAACCGCGTGTCAACTGTACAACAGTTGACAAAGAGATTCTCACT
AsnAsnGlnArgLysLysAlaArgAsnThrProPheAsnMetLeuLysArgGluArgAsnArgValSerThrValGlnGlnLeuThrLysArgPheSerLeu>

210       220       230       240       250       260       270       280       290       300
TGGAATGCTGCAGGGACGAGGACCACTAAAATTGTTCATGGCCCTGGTGGCATTCCTTCGTTTCCTAACAATCCCACCAACAGCAGGGATATTAAAAAGA
GlyMetLeuGlnGlyArgGlyProLeuLysLeuPheMetAlaLeuValAlaPheLeuArgPheLeuThrIleProProThrAlaGlyIleLeuLysArg>

310       320       330       340       350       360       370       380       390       400
TGGGGAACAATTAAAAAATCAAAGGCTATTAATGTTCTGAGAGGCTTCAGGAAAGAGATTGGAAGGATGCTGAATATCTTAAACAGGAGACGTAGAACTG
TrpGlyThrIleLysLysSerLysAlaIleAsnValLeuArgGlyPheArgLysGluIleGlyArgMetLeuAsnIleLeuAsnArgArgArgArgThr>
```

APPENDIX 1-continued

Nucleotide and amino acid sequence of DEN2 (Tonga/74) cDNA plasmid p2

```
         410       420       430       440       450       460       470       480       490       500
TAGGCATGATCATCATGCTGACTCCAACAGTGATGGCGTTTCATCTGACCACACGCAACGGAGAACCACACATGATTGTCAGTAGACAAGAAAAAGGGAA
ValGlyMetIleIleMetLeuThrProThrValMetAlaPheHisLeuThrThrArgAsnGlyGluProHisMetIleValSerArgGlnGluLysGlyLys>

510       520       530       540       550       560       570       580       590       600
AAGCCTTCTGTTCAAGACAAAGGATGGCACGAACATGTGTACCCTCATGGCCATGGACCTTGGTGAGTTGTGTGAAGACACAATCACGTATAAATGTCCT
SerLeuLeuPheLysThrLysAspGlyThrAsnMetCysThrLeuMetAlaMetAspLeuGlyGluLeuCysGluAspThrIleThrTyrLysCysPro>

610       620       630       640       650       660       670       680       690       700
TTTCTCAAGCAGAACGAACCAGAAGACATAGATTGTTGGTGCAACTCCACGTCCACATGGGTAACTTATGGGACATGTACCACCACAGGAGAGCACAGAA
PheLeuLysGlnAsnGluProGluAspIleAspCysTrpCysAsnSerThrSerThrTrpValThrTyrGlyThrCysThrThrThrGlyGluHisArg>

710       720       730       740       750       760       770       780       790       800
GAGAAAAAGATCAGTGGCGCTTGTTCCACACGTGGGAATGGGATTGGAGACACGAACTGAAACATGGATGTCATCAGAAGGGGCCTGGAAACATGCCCA
ArgGluLysArgSerValAlaLeuValProHisValGlyMetGlyLeuGluThrArgThrGluThrTrpMetSerSerGluGlyAlaTrpLysHisAlaGln>

810       820       830       840       850       860       870       880       890       900
GAGAATTGAAACTTGGATTCTGAGACATCCAGGCTTTACCATAATGGCCGCAATCCTGGCATACACCATAGGGACGACGCATTTCCAAAGAGTCCTGATA
ArgIleGluThrTrpIleLeuArgHisProGlyPheThrIleMetAlaAlaIleLeuAlaTyrThrIleGlyThrThrHisPheGlnArgValLeuIle>

910       920       930       940       950       960       970       980       990      1000
TTCATCCTACTGACAGCCATCGCTCCTTCAATGACAATGCGCTGCATAGGAATATCAAATAGGGACTTTGTGGAAGGAGTGTCAGGAGGGAGTTGGGTTG
PheIleLeuLeuThrAlaIleAlaProSerMetThrMetArgCysIleGlyIleSerAsnArgAspPheValGluGlyValSerGlyGlySerTrpVal>

1010      1020      1030      1040      1050      1060      1070      1080      1090      1100
ACATAGTTTTAGAACATGGAAGTTGTGTGACGACGATGGCAAAAAACAAACCAACACTGGACTTTGAACTGATAAAAACAGAAGCCAAACAACCTGCCAC
AspIleValLeuGluHisGlySerCysValThrThrMetAlaLysAsnLysProThrLeuAspPheGluLeuIleLysThrGluAlaLysGlnProAlaThr>

1110      1120      1130      1140      1150      1160      1170      1180      1190      1200
CTTAAGGAAGTACTGTATAGAGGCCAAACTGACCAACACGACAACAGACTCGCGCTGCCCAACACAAGGGGAACCCACCCTGAATGAAGAGCAGGACAAA
LeuArgLysTyrCysIleGluAlaLysLeuThrAsnThrThrThrAspSerArgCysProThrGlnGlyGluProThrLeuAsnGluGluGlnAspLys>

1210      1220      1230      1240      1250      1260      1270      1280      1290      1300
AGGTTTGTCTGCAAACATTCCATGGTAGACAGAGGATGGGGAAATGGATGTGGATTGTTTGGAAAAGGAGGCATCGTGACCTGTGCTATGTTCACATGCA
ArgPheValCysLysHisSerMetValAspArgGlyTrpGlyAsnGlyCysGlyLeuPheGlyLysGlyGlyIleValThrCysAlaMetPheThrCys>

1310      1320      1330      1340      1350      1360      1370      1380      1390      1400
AAAAGAACATGGAAGGAAAAATTGTGCAGCCAGAAAACCTGGAATACACTGTCGTGATAACACCTCATTCAGGGGAAGAACATGCAGTGGGAAATGACAC
LysLysAsnMetGluGlyLysIleValGlnProGluAsnLeuGluTyrThrValValIleThrProHisSerGlyGluGluHisAlaValGlyAsnAspThr>

1410      1420      1430      1440      1450      1460      1470      1480      1490      1500
AGGAAAACATGGTAAAGAAGTCAAGATAACACCACAGAGCTCCATCACAGAGGCGGAACTGACAGGCTATGGCACTGTTACGATGGAGTGCTCTCCAAGA
GlyLysHisGlyLysGluValLysIleThrProGlnSerSerIleThrGluAlaGluLeuThrGlyTyrGlyThrValThrMetGluCysSerProArg>

1510      1520      1530      1540      1550      1560      1570      1580      1590      1600
ACGGGCCTCGACTTCAATGAGATGGTGTTGCTGCAAATGGAAGACAAAGCCTGGCTGGTGCACAGACAATGGTTCCTAGACCTACCGTTGCCATGGCTGC
ThrGlyLeuAspPheAsnGluMetValLeuLeuGlnMetGluAspLysAlaTrpLeuValHisArgGlnTrpPheLeuAspLeuProLeuProTrpLeu>

1610      1620      1630      1640      1650      1660      1670      1680      1690      1700
CCGGAGCAGACACACAAGGATCAAATTGGATACAGAAAGAAACACTGGTCACCTTCAAAAATCCCCATGCGAAAAAACAGGATGTTGTTGTCTTAGGATC
ProGlyAlaAspThrGlnGlySerAsnTrpIleGlnLysGluThrLeuValThrPheLysAsnProHisAlaLysLysGlnAspValValValLeuGlySer>

1710      1720      1730      1740      1750      1760      1770      1780      1790      1800
CCAAGAGGGGCCATGCATACAGCACTCACAGGGGCTACGGAAATCCAGATGTCATCAGGAAACCTGCTGTTCACAGGACATCTCAAGTGCAGGCTGAGA
GlnGluGlyAlaMetHisThrAlaLeuThrGlyAlaThrGluIleGlnMetSerSerGlyAsnLeuLeuPheThrGlyHisLeuLysCysArgLeuArg>

1810      1820      1830      1840      1850      1860      1870      1880      1890      1900
ATGGACAAATTACAACTTAAAGGGATGTCATACTCCATGTGCACAGGAAAGTTTAAAATTGTGAAGGAAATAGCAGAAACACAACATGGAACAATAGTCA
MetAspLysLeuGlnLeuLysGlyMetSerTyrSerMetCysThrGlyLysPheLysIleValLysGluIleAlaGluThrGlnHisGlyThrIleVal>

1910      1920      1930      1940      1950      1960      1970      1980      1990      2000
TTAGAGTACAATATGAAGGAGACGGCTCTCCATGCAAGATCCCCTTTGAGATAATGGATCTGGAAAAAAGACATGTTTTGGGCCGCCTGATCACAGTCAA
IleArgValGlnTyrGluGlyAspGlySerProCysLysIleProPheGluIleMetAspLeuGluLysArgHisValLeuGlyArgLeuIleThrValAsn>

2010      2020      2030      2040      2050      2060      2070      2080      2090      2100
CCCAATTGTAACAGAAAAGGACAGTCCAGTCAACATAGAAGCAGAACCTCCATTCGGAGACAGCTACATCATCATAGGAGTGGAACCAGGACAATTGAAG
ProIleValThrGluLysAspSerProValAsnIleGluAlaGluProProPheGlyAspSerTyrIleIleIleGlyValGluProGlyGlnLeuLys>

2110      2120      2130      2140      2150      2160      2170      2180      2190      2200
CTGGACTGGTTCAAGAAAGGAAGTTCCATCGGCCAAATGTTTGAGACAACAATGAGGGGAGCGAAAAGAATGGCCATTTTGGGTGACACAGCCTGGGATT
LeuAspTrpPheLysLysGlySerSerIleGlyGlnMetPheGluThrThrMetArgGlyAlaLysArgMetAlaIleLeuGlyAspThrAlaTrpAsp>

2210      2220      2230      2240      2250      2260      2270      2280      2290      2300
TTGGATCTCTGGGAGGAGTGTTCACATCAATAGGAAAGGCTCTCCACCAGGTTTTTGGAGCAATCTACGGGGCTGCTTTCAGTGGGGTCTCATGGACTAT
PheGlySerLeuGlyGlyValPheThrSerIleGlyLysAlaLeuHisGlnValPheGlyAlaIleTyrGlyAlaAlaPheSerGlyValSerTrpThrMet>
```

APPENDIX 1-continued

Nucleotide and amino acid sequence of DEN2 (Tonga/74) cDNA plasmid p2

```
         2310      2320      2330      2340      2350      2360      2370      2380      2390      2400
GAAGATCCTCATAGGAGTTATCATCACATGGATAGGAATGAACTCACGTAGCACTAGTCTGAGCGTGTCACTGGTGTTAGTGGGAATCGTGACACTTTAC
LysIleLeuIleGlyValIleIleThrTrpIleGlyMetAsnSerArgSerThrSerLeuSerValSerLeuValLeuValGlyIleValThrLeuTyr>

2410      2420      2430      2440      2450      2460      2470      2480      2490      2500
TTGGGAGTTATGGTGCAGGCCGATAGTGGTTGCGTTGTGAGCTGGAAGAACAAAGAACTAAAATGTGGCAGTGGAATATTCGTCACAGATAACGTGCATA
LeuGlyValMetValGlnAlaAspSerGlyCysValValSerTrpLysAsnLysGluLeuLysCysGlySerGlyIlePheValThrAspAsnValHis>

2510      2520      2530      2540      2550      2560      2570      2580      2590      2600
CATGGACAGAACAATACAAGTTCCAACCAGAATCCCCTTCAAAACTGGCCTCAGCCATCCAGAAAGCGCATGAAGAGGGCATCTGTGGAATCCGCTCAGT
ThrTrpThrGluGlnTyrLysPheGlnProGluSerProLysLeuAlaSerAlaIleGlnLysAlaHisGluGluGlyIleCysGlyIleArgSerVal>

2610      2620      2630      2640      2650      2660      2670      2680      2690      2700
AACAAGACTGGAAAATCTTATGTGGAAACAGATAACATCAGAATTGAATCATATTCTATCAGAAATGAAGTGAAACTGACCATCATGACAGGAGACATC
ThrArgLeuGluAsnLeuMetTrpLysGlnIleThrSerGluLeuAsnHisIleLeuSerGluAsnGluValLysLeuThrIleMetThrGlyAspIle>

2710      2720      2730      2740      2750      2760      2770      2780      2790      2800
AAAGGAATCATGCAGGTAGGAAAACGATCTCTTTCGGCCTCAACCCACTGAGTTGAGGTATTCATGGAAAACATGGGGTAAAGCGAAAATGCTCTCCACAG
LysGlyIleMetGlnValGlyLysArgSerLeuArgProGlnProThrGluLeuArgTyrSerTrpLysThrTrpGlyLysAlaLysMetLeuSerThr>

2810      2820      2830      2840      2850      2860      2870      2880      2890      2900
AACTCCACAATCAGACCTTCCTCATTGATGGTCCCGAAACAGCAGAATGCCCCAACACAAACAGAGCTTGGAATTCACTGGAAGTTGAGGACTACGGCTT
GluLeuHisAsnGlnThrPheLeuIleAspGlyProGluThrAlaGluCysProAsnThrAsnArgAlaTrpAsnSerLeuGluValGluAspTyrGlyPhe>

2910      2920      2930      2940      2950      2960      2970      2980      2990      3000
TGGAGTATTCACTACCAATATATGGCTAAGATTGAGAGAAAAGCAGGATGTATTTTGTGACTCAAAACTCATGTCAGCGGCCATAAAGGACAACAGAGCC
GlyValPheThrThrAsnIleTrpLeuArgLeuArgGluLysGlnAspValPheCysAspSerLysLeuMetSerAlaAlaIleLysAspAsnArgAla>

3010      3020      3030      3040      3050      3060      3070      3080      3090      3100
GTCCATGCTGATATGGGTTATTGGATAGAAAGCGCACTCAATGATACATGGAAGATAGAGAAAGCTTCTTTCATTGAAGTCAAAAGTTGCCACTGGCCAA
ValHisAlaAspMetGlyTyrTrpIleGluSerAlaLeuAsnAspThrTrpLysIleGluLysAlaSerPheIleGluValLysSerCysHisTrpPro>

3110      3120      3130      3140      3150      3160      3170      3180      3190      3200
AGTCACACACCCTATGGAGTAATGGAGTGCTAGAAAGCGAGATGGTCATTCCAAAGAATTTCGCTGGACCAGTGTCACAACATAATAACAGACCAGGCTA
LysSerHisThrLeuTrpSerAsnGlyValLeuGluSerGluMetValIleProLysAsnPheAlaGlyProValSerGlnHisAsnAsnArgProGlyTyr>

3210      3220      3230      3240      3250      3260      3270      3280      3290      3300
TTACACACAAACAGCAGGACCTTGGCATCTAGGCAAGCTTGAGATGGACTTTGATTTCTGCGAAGGGACTACAGTGGTGGTAACCGAGAACTGTGGAAAC
TyrThrGlnThrAlaGlyProTrpHisLeuGlyLysLeuGluMetAspPheAspPheCysGluGlyThrThrValValValThrGluAsnCysGlyAsn>

3310      3320      3330      3340      3350      3360      3370      3380      3390      3400
AGAGGGCCCTCTTTAAGAACAACCACTGCCTCAGGAAAACTCATAACGGAATGGTGTTGTCGATCTTGCACACTACCACCACTAAGATACAGAGGTGAGG
ArgGlyProSerLeuArgThrThrThrAlaSerGlyLysLeuIleThrGluTrpCysCysArgSerCysThrLeuProProLeuArgTyrArgGlyGlu>

3410      3420      3430      3440      3450      3460      3470      3480      3490      3500
ATGGATGTTGGTACGGGATGGAAATCAGACCATTGAAAGAGAAAGAAGAAAATCTGGTCAGTTCTCTGGTTACAGCCGGACATGGGCAGATTGACAATTT
AspGlyCysTrpTyrGlyMetGluIleArgProLeuLysGluLysGluGluAsnLeuValSerSerLeuValThrAlaGlyHisGlyGlnIleAspAsnPhe>

3510      3520      3530      3540      3550      3560      3570      3580      3590      3600
CTCATTAGGAATCTTGGGAATGGCACTGTTCCTTGAAGAAATGCTCAGGACTCGAGTAGGAACAAAACATGCAATATTACTCGTCGCAGTTTCTTTCGTG
SerLeuGlyIleLeuGlyMetAlaLeuPheLeuGluGluMetLeuArgThrArgValGlyThrLysHisAlaIleLeuLeuValAlaValSerPheVal>

3610      3620      3630      3640      3650      3660      3670      3680      3690      3700
ACGCTAATCACAGGGAACATGTCTTTTAGAGACCTGGGAAGAGTGATGGTTATGGTGGGTGCCACCATGACAGATGACATAGGCATGGGTGTGACTTATC
ThrLeuIleThrGlyAsnMetSerPheArgAspLeuGlyArgValMetValMetValGlyAlaThrMetThrAspAspIleGlyMetGlyValThrTyr>

3710      3720      3730      3740      3750      3760      3770      3780      3790      3800
TCGCTCTACTAGCAGCTTTTAGAGTCAGACCAACCTTTGCAGCTGGACTGCTCTTGAGAAAACTGACCTCCAAGGAATTAATGATGACTACCATAGGAAT
LeuAlaLeuLeuAlaAlaPheArgValArgProThrPheAlaAlaGlyLeuLeuLeuArgLysLeuThrSerLysGluLeuMetMetThrThrIleGlyIle>

3810      3820      3830      3840      3850      3860      3870      3880      3890      3900
CGTTCTTCTCTCCCAGAGTAGCATACCAGAGACCATTCTTGAACTGACCGACGCGTTAGCTCTAGGCATGATGGTCCTCAAGATGGTGAGAAACATGGAA
ValLeuLeuSerGlnSerSerIleProGluThrIleLeuGluLeuThrAspAlaLeuAlaLeuGlyMetMetValLeuLysMetValArgAsnMetGlu>

3910      3920      3930      3940      3950      3960      3970      3980      3990      4000
AAATATCAGCTGGCAGTGACCATCATGGCTATTTTGTGCGTCCCAAATGCTGTGATATTACAGAACGCATGGAAAGTGAGTTGCACAATATTGGCAGTGG
LysTyrGlnLeuAlaValThrIleMetAlaIleLeuCysValProAsnAlaValIleLeuGlnAsnAlaTrpLysValSerCysThrIleLeuAlaVal>

4010      4020      4030      4040      4050      4060      4070      4080      4090      4100
TGTCTGTTTCCCCCCTGCTCTTAACATCCTCACAACAGAAAGCGGACTGGATACCATTAGCGTTGACGATCAAAGGTCTTAATCCAACAGCCATTTTTCT
ValSerValSerProLeuLeuLeuThrSerSerGlnGlnLysAlaAspTrpIleProLeuAlaLeuThrIleLysGlyLeuAsnProThrAlaIlePheLeu>

4110      4120      4130      4140      4150      4160      4170      4180      4190      4200
AACAACCCTCTCAAGAACCAACAAGAAAAGGAGCTGGCCTTTAAATGAGGCCATCATGGCCGTTGGGATGGTGAGTATCTTGGCCAGCTCTCTCTTAAAG
ThrThrLeuSerArgThrAsnLysLysArgSerTrpProLeuAsnGluAlaIleMetAlaValGlyMetValSerIleLeuAlaSerSerLeuLeuLys>
```

APPENDIX 1-continued

Nucleotide and amino acid sequence of DEN2 (Tonga/74) cDNA plasmid p2

```
      4210      4220      4230      4240      4250      4260      4270      4280      4290      4300
AATGACATCCCCATGACAGGACCATTAGTGGCTGGAGGGCTCCTTACTGTGTGCTACGTGCTAACTGGGCGGTCAGCCGATCTGGAATTAGAGAGAGCTA
AsnAspIleProMetThrGlyProLeuValAlaGlyGlyLeuLeuThrValCysTyrValLeuThrGlyArgSerAlaAspLeuGluLeuGluArgAla>

4310      4320      4330      4340      4350      4360      4370      4380      4390      4400
CCGATGTCAAATGGGATGACCAGGCAGAGATATCAGGTAGCAGTCCAATCCTGTCAATAACAATATCAGAAGATGGCAGCATGTCAATAAAGAATGAAGA
ThrAspValLysTrpAspAspGlnAlaGluIleSerGlySerSerProIleLeuSerIleThrIleSerGluAspGlySerMetSerIleLysAsnGluGlu>

4410      4420      4430      4440      4450      4460      4470      4480      4490      4500
GGAAGAGCAAACACTGACTATACTCATTAGAACAGGATTGCTTGTGATCTCAGGACTCTTTCCGGTATCAATACCAATTACAGCAGCAGCATGGTATCTG
GluGluGlnThrLeuThrIleLeuIleArgThrGlyLeuLeuValIleSerGlyLeuPheProValSerIleProIleThrAlaAlaAlaTrpTyrLeu>

4510      4520      4530      4540      4550      4560      4570      4580      4590      4600
TGGGAAGTAAAGAAACAACGGGCTGGAGTGCTGTGGGATGTCCCCTCACCACCACCCGTGGGAAAAGCTGAATTGGAAGATGGAGCCTACAGAATCAAGC
TrpGluValLysLysGlnArgAlaGlyValLeuTrpAspValProSerProProProValGlyLysAlaGluLeuGluAspGlyAlaTyrArgIleLys>

4610      4620      4630      4640      4650      4660      4670      4680      4690      4700
AAAAAGGAATCCTTGGATATTCCCAGATCGGAGCTGGAGTTTACAAAGAAGGAACATTTCACACAATGTGGCACGTCACACGTGGCGCTGTCCTAATGCA
GlnLysGlyIleLeuGlyTyrSerGlnIleGlyAlaGlyValTyrLysGluGlyThrPheHisThrMetTrpHisValThrArgGlyAlaValLeuMetHis>

4710      4720      4730      4740      4750      4760      4770      4780      4790      4800
TAAGGGGAAGAGGATTGAACCATCATGGGCGGACGTCAAGAAAGACTTAATATCATATGGAGGAGGTTGGAAGCTAGAAGGAGAATGGAAAGAAGGAGAA
LysGlyLysArgIleGluProSerTrpAlaAspValLysLysAspLeuIleSerTyrGlyGlyGlyTrpLysLeuGluGlyGluTrpLysGluGlyGlu>

4810      4820      4830      4840      4850      4860      4870      4880      4890      4900
GAAGTCCAGGTCTTGGCATTGGAGCCAGGGAAAAATCCAAGAGCCGTCCAAACAAAGCCTGGCCTTTTTAGAACCAACACTGGAACCATAGGTGCCGTAT
GluValGlnValLeuAlaLeuGluProGlyLysAsnProArgAlaValGlnThrLysProGlyLeuPheArgThrAsnThrGlyThrIleGlyAlaVal>

4910      4920      4930      4940      4950      4960      4970      4980      4990      5000
CTCTGGACTTTTCCCCTGGGACGTCAGGATCTCCAATCGTCGACAAAAAAGGAAAAGTTGTAGGTCTCTATGGCAATGGTGTCGTTACAAGGAGTGGAGC
SerLeuAspPheSerProGlyThrSerGlySerProIleValAspLysLysGlyLysValValGlyLeuTyrGlyAsnGlyValValThrArgSerGlyAla>

5010      5020      5030      5040      5050      5060      5070      5080      5090      5100
ATATGTGAGTGCCATAGCTCAGACTGAAAAAAGCATTGAAGACAATCCAGAGATTGAAGATGACATCTTTCGAAAGAGAAGATTGACTATCATGGATCTC
TyrValSerAlaIleAlaGlnThrGluLysSerIleGluAspAsnProGluIleGluAspAspIlePheArgLysArgArgLeuThrIleMetAspLeu>

5110      5120      5130      5140      5150      5160      5170      5180      5190      5200
CACCCAGGAGCAGGAAAGACAAAGAGATACCTCCCGGCCATAGTCAGAGAGGCCATAAAAAGAGGCTTGAGAACACTAATCCTAGCCCCCACTAGAGTCG
HisProGlyAlaGlyLysThrLysArgTyrLeuProAlaIleValArgGluAlaIleLysArgGlyLeuArgThrLeuIleLeuAlaProThrArgVal>

5210      5220      5230      5240      5250      5260      5270      5280      5290      5300
TGGCAGCTGAAATGGAGGAAGCCCTTAGAGGACTTCCAATAAGATACCAAACTCCAGCTATCAGGGCTGAGCACACCGGGCGGGAGATTGTAGACTTAAT
ValAlaAlaGluMetGluGluAlaLeuArgGlyLeuProIleArgTyrGlnThrProAlaIleArgAlaGluHisThrGlyArgGluIleValAspLeuMet>

5310      5320      5330      5340      5350      5360      5370      5380      5390      5400
GTGTCATGCCACATTTACCATGAGGCTGCTATCACCAATCAGGGTGCCAAATTACAACCTGATCATCATGGACGAAGCCCATTTTACAGATCCAGCAAGC
CysHisAlaThrPheThrMetArgLeuLeuSerProIleArgValProAsnTyrAsnLeuIleIleMetAspGluAlaHisPheThrAspProAlaSer>

5410      5420      5430      5440      5450      5460      5470      5480      5490      5500
ATAGCAGCTAGGGGATACATCTCAACTCGAGTGGAGATGGGGGAGGCAGCTGGAATTTTTATGACAGCCACTCCTCCGGGTAGTAGAGATCCATTTCCTC
IleAlaAlaArgGlyTyrIleSerThrArgValGluMetGlyGluAlaAlaGlyIlePheMetThrAlaThrProProGlySerArgAspProPhePro>

5510      5520      5530      5540      5550      5560      5570      5580      5590      5600
AGAGCAATGCACCAATTATGGACGAAGAAAGAGAAATTCCGGAACGTTCATGGAACTCTGGGCACGAGTGGGTCACGGATTTTAAAGGAAAGACTGTCTG
GlnSerAsnAlaProIleMetAspGluGluArgGluIleProGluArgSerTrpAsnSerGlyHisGluTrpValThrAspPheLysGlyLysThrValTrp>

5610      5620      5630      5640      5650      5660      5670      5680      5690      5700
GTTTGTTCCAAGCATAAAAACCGGAAATGACATAGCAGCCTGCCTGAGAAAGAATGGAAAGAGGGTGATACAACTCAGTAGGAAGACCTTTGATTCTGAA
PheValProSerIleLysThrGlyAsnAspIleAlaAlaCysLeuArgLysAsnGlyLysArgValIleGlnLeuSerArgLysThrPheAspSerGlu>

5710      5720      5730      5740      5750      5760      5770      5780      5790      5800
TATGTCAAGACTAGAACCAATGACTGGGATTTCGTGGTTACAACTGACATCTCGGAAATGGGCGCCAACTTTAAAGCTGAGAGGGTCATAGACCCCAGAC
TyrValLysThrArgThrAsnAspTrpAspPheValValThrThrAspIleSerGluMetGlyAlaAsnPheLysAlaGluArgValIleAspProArg>

5810      5820      5830      5840      5850      5860      5870      5880      5890      5900
GCTGCATGAAACCAGTTATATTGACAGACGGCGAAGAGCGGGTGATTCTGGCAGGACCCATGCCAGTGACCCACTCTAGTGCAGCACAAAGAAGAGGGAG
ArgCysMetLysProValIleLeuThrAspGlyGluGluArgValIleLeuAlaGlyProMetProValThrHisSerSerAlaAlaGlnArgArgGlyArg>

5910      5920      5930      5940      5950      5960      5970      5980      5990      6000
AATAGGAAGGAATCCAAGGAATGAAAATGATCAATATATATATATGGGGGAACCACTGGAAAATGATGAAGACTGTGCGCACTGGAAGGAAGCTAAGATG
IleGlyArgAsnProArgAsnGluAsnAspGlnTyrIleTyrMetGlyGluProLeuGluAsnAspGluAspCysAlaHisTrpLysGluAlaLysMet>

6010      6020      6030      6040      6050      6060      6070      6080      6090      6100
CTCCTAGATAATATCAACACACCTGAAGGAATCATTCCCAGCTTGTTCGAGCCAGAGCGTGAAAAGGTGGATGCCATTGACGGTGAATATCGCTTGAGAG
LeuLeuAspAsnIleAsnThrProGluGlyIleIleProSerLeuPheGluProGluArgGluLysValAspAlaIleAspGlyGluTyrArgLeuArg>
```

APPENDIX 1-continued

Nucleotide and amino acid sequence of DEN2 (Tonga/74) cDNA plasmid p2

```
      6110      6120      6130      6140      6150      6160      6170      6180      6190      6200
GAGAAGCACGGAAAACTTTTGTGGACCTAATGAGAAGAGGAGACCTACCAGTCTGGTTGGCTTATAAAGTGGCAGCTGAAGGTATCAACTACGCAGACAG
GlyGluAlaArgLysThrPheValAspLeuMetArgArgGlyAspLeuProValTrpLeuAlaTyrLysValAlaAlaGluGlyIleAsnTyrAlaAspArg>

6210      6220      6230      6240      6250      6260      6270      6280      6290      6300
AAGATGGTGTTTTGACGGAACCAGAAACAATCAAATCTTGGAAGAAAATGTGGAAGTGGAAATCTGGACAAAGGAAGGGGAAAGGAAAAAATTGAAACCT
ArgTrpCysPheAspGlyThrArgAsnAsnGlnIleLeuGluGluAsnValGluValGluIleTrpThrLysGluGlyGluArgLysLysLeuLysPro>

6310      6320      6330      6340      6350      6360      6370      6380      6390      6400
AGATGGTTAGATGCTAGGATCTACTCCGACCCACTGGCGCTAAAAGAGTTCAAGGAATTTGCAGCCGGAAGAAAGTCCCTAACCCTGAACCTAATTACAG
ArgTrpLeuAspAlaArgIleTyrSerAspProLeuAlaLeuLysGluPheLysGluPheAlaAlaGlyArgLysSerLeuThrLeuAsnLeuIleThr>

6410      6420      6430      6440      6450      6460      6470      6480      6490      6500
AGATGGGCAGACTCCCAACTTTTATGACTCAGAAGGCCAGAGATGCACTAGACAACTTGGCGGTGCTGCACACGGCTGAAGCGGGTGGAAAGGCATACAA
GluMetGlyArgLeuProThrPheMetThrGlnLysAlaArgAspAlaLeuAspAsnLeuAlaValLeuHisThrAlaGluAlaGlyGlyLysAlaTyrAsn>

6510      6520      6530      6540      6550      6560      6570      6580      6590      6600
TCATGCTCTCAGTGAATTACCGGAGACCCTGGAGACATTGCTTTTGCTGACACTGTTGGCCACAGTCACGGGAGGAATCTTCCTATTCCTGATGAGCGGA
HisAlaLeuSerGluLeuProGluThrLeuGluThrLeuLeuLeuThrLeuLeuAlaThrValThrGlyGlyIlePheLeuPheLeuMetSerGly>

6610      6620      6630      6640      6650      6660      6670      6680      6690      6700
AGGGGTATGGGGAAGATGACCCTGGGAATGTGCTGCATAATCACGGCCAGCATCCTCTTATGGTATGCACAAATACAGCCACATTGGATAGCAGCCTCAA
ArgGlyMetGlyLysMetThrLeuGlyMetCysCysIleIleThrAlaSerIleLeuLeuTrpTyrAlaGlnIleGlnProHisTrpIleAlaAlaSer>

6710      6720      6730      6740      6750      6760      6770      6780      6790      6800
TAATATTGGAGTTCTTTCTCATAGTCTTGCTCATTCCAGAACCAGAAAAGCAGAGGACACCTCAGGATAATCAATTGACTTATGTCATCATAGCCATCCT
IleIleLeuGluPhePheLeuIleValLeuLeuIleProGluProGluLysGlnArgThrProGlnAspAsnGlnLeuThrTyrValIleIleAlaIleLeu>

6810      6820      6830      6840      6850      6860      6870      6880      6890      6900
CACAGTGGTGGCCGCAACCATGGCAAACGAAATGGGTTTTCTGGAAAAAACAAAGAAAGACCTCGGACTGGGAAACATTGCAACTCAGCAACCTGAGAGC
ThrValValAlaAlaThrMetAlaAsnGluMetGlyPheLeuGluLysThrLysLysAspLeuGlyLeuGlyAsnIleAlaThrGlnGlnProGluSer>

6910      6920      6930      6940      6950      6960      6970      6980      6990      7000
AACATTCTGGACATAGATCTACGTCCTGCATCAGCATGGACGTTGTATGCCGTGGCTACAACATTTATCACACCAATGTTGAGACATAGCATTGAAAATT
AsnIleLeuAspIleAspLeuArgProAlaSerAlaTrpThrLeuTyrAlaValAlaThrThrPheIleThrProMetLeuArgHisSerIleGluAsn>

7010      7020      7030      7040      7050      7060      7070      7080      7090      7100
CCTCAGTAAATGTGTCCCTAACAGCCATAGCTAACCAAGCCACAGTGCTAATGGGTCTCGGAAAAGGATGGCCATTGTCAAAGATGGACATTGGAGTTCC
SerSerValAsnValSerLeuThrAlaIleAlaAsnGlnAlaThrValLeuMetGlyLeuGlyLysGlyTrpProLeuSerLysMetAspIleGlyValPro>

7110      7120      7130      7140      7150      7160      7170      7180      7190      7200
CCTCCTTGCTATTGGGTGTTACTCACAAGTCAACCCTATAACCCTCACAGCGGCTCTTCTTTTATTGGTAGCACATTATGCCATCATAGGACCGGGACTT
LeuLeuAlaIleGlyCysTyrSerGlnValAsnProIleThrLeuThrAlaAlaLeuLeuLeuLeuValAlaHisTyrAlaIleIleGlyProGlyLeu>

7210      7220      7230      7240      7250      7260      7270      7280      7290      7300
CAAGCCAAAGCAACTAGAGAAGCTCAGAAAAGAGCAGCAGCGGGCATCATGAAAAACCCAACTGTGGATGGAATAACAGTGATAGATCTAGATCCAATAC
GlnAlaLysAlaThrArgGluAlaGlnLysArgAlaAlaAlaGlyIleMetLysAsnProThrValAspGlyIleThrValIleAspLeuAspProIle>

7310      7320      7330      7340      7350      7360      7370      7380      7390      7400
CCTATGATCCAAAGTTTGAAAAGCAGTTGGGACAAGTAATGCTCCTAGTCCTCTGCGTGACCCAAGTGCTGATGATGAGGACTACGTGGGCTTTGTGTGA
ProTyrAspProLysPheGluLysGlnLeuGlyGlnValMetLeuLeuValLeuCysValThrGlnValLeuMetMetArgThrThrTrpAlaLeuCysGlu>

7410      7420      7430      7440      7450      7460      7470      7480      7490      7500
AGCCTTAACTCTAGCAACTGGACCCGTGTCCACATTGTGGGAAGGAAATCCAGGGAGATTCTGGAACACAACCATTGCAGTGTCAATGGCAAACATCTTT
AlaLeuThrLeuAlaThrGlyProValSerThrLeuTrpGluGlyAsnProGlyArgPheTrpAsnThrThrIleAlaValSerMetAlaAsnIlePhe>

7510      7520      7530      7540      7550      7560      7570      7580      7590      7600
AGAGGGAGTTACCTGGCTGGAGCTGGACTTCTCTTTTCTATCATGAAGAACACAACCAGCACGAGAAGAGGAACTGGCAATATAGGAGAAACGTTAGGAG
ArgGlySerTyrLeuAlaGlyAlaGlyLeuLeuPheSerIleMetLysAsnThrThrSerThrArgArgGlyThrGlyAsnIleGlyGluThrLeuGly>

7610      7620      7630      7640      7650      7660      7670      7680      7690      7700
AGAAATGGAAAAGCAGACTGAACGCATTGGGGAAAAGTGAATTCCAGATCTACAAAAAAAGTGGAATTCAAGAAGTGGACAGAACCTTAGCAAAAGAAGG
GluLysTrpLysSerArgLeuAsnAlaLeuGlyLysSerGluPheGlnIleTyrLysLysSerGlyIleGlnGluValAspArgThrLeuAlaLysGluGly>

7710      7720      7730      7740      7750      7760      7770      7780      7790      7800
CATTAAAAGAGGAGAAACGGATCATCACGCTGTGTCGCGAGGCTCAGCAAAACTGAGATGGTTCGTTGAAAGGAATTTGGTCACACCAGAAGGGAAAGTA
IleLysArgGlyGluThrAspHisHisAlaValSerArgGlySerAlaLysLeuArgTrpPheValGluArgAsnLeuValThrProGluGlyLysVal>

7810      7820      7830      7840      7850      7860      7870      7880      7890      7900
GTGGACCTTGGTTGTGGCAGAGGGGGCTGGTCATACTATTGTGGAGGATTAAAGAATGTAAGAGAAGTTAAAGGCTTAACAAAAGGAGGACCAGGACACG
ValAspLeuGlyCysGlyArgGlyGlyTrpSerTyrTyrCysGlyGlyLeuLysAsnValArgGluValLysGlyLeuThrLysGlyGlyProGlyHis>

7910      7920      7930      7940      7950      7960      7970      7980      7990      8000
AAGAACCTATCCCTATGTCAACATATGGGTGGAATCTAGTACGCTTACAGAGCGGAGTTGATGTTTTTTTGTTCCACCAGAGAAGTGTGACACATTGTT
GluGluProIleProMetSerThrTyrGlyTrpAsnLeuValArgLeuGlnSerGlyValAspValPhePheValProProGluLysCysAspThrLeuLeu>
```

APPENDIX 1-continued

Nucleotide and amino acid sequence of DEN2 (Tonga/74) cDNA plasmid p2

```
        8010      8020      8030      8040      8050      8060      8070      8080      8090      8100
GTGTGACATAGGGGAATCATCACCAAATCCCACGGTAGAAGCGGGACGAACACTCAGAGTCCTCAACCTAGTGGAAAATTGGCTGAACAATAACACCCAA
CysAspIleGlyGluSerSerProAsnProThrValGluAlaGlyArgThrLeuArgValLeuAsnLeuValGluAsnTrpLeuAsnAsnAsnThrGln>

8110      8120      8130      8140      8150      8160      8170      8180      8190      8200
TTTTGCGTAAAGGTTCTTAACCCGTACATGCCCTCAGTCATTGAAAGAATGGAAACCTTACAACGGAAATACGGAGGAGCCTTGGTGAGAAATCCACTCT
PheCysValLysValLeuAsnProTyrMetProSerValIleGluArgMetGluThrLeuGlnArgLysTyrGlyGlyAlaLeuValArgAsnProLeu>

8210      8220      8230      8240      8250      8260      8270      8280      8290      8300
CACGGAATTCCACACATGAGATGTACTGGGTGTCCAATGCTTCCGGGAACATAGTGTCATCAGTGAACATGATTTCAAGAATGCTGATCAACAGATTCAC
SerArgAsnSerThrHisGluMetTyrTrpValSerAsnAlaSerGlyAsnIleValSerSerValAsnMetIleSerArgMetLeuIleAsnArgPheThr>

8310      8320      8330      8340      8350      8360      8370      8380      8390      8400
TATGAGACACAAGAAGGCCACCTATGAGCCAGATGTCGACCTCGGAAGCGGAACCCGCAATATTGGAATTGAAAGTGAGACACCGAACCTAGACATAATT
MetArgHisLysLysAlaThrTyrGluProAspValAspLeuGlySerGlyThrArgAsnIleGlyIleGluSerGluThrProAsnLeuAspIleIle>

8410      8420      8430      8440      8450      8460      8470      8480      8490      8500
GGGAAAAGAATAGAAAAAATAAAACAAGAGCATGAAACGTCATGGCACTATGATCAAGACCACCCATACAAAACATGGGCTTACCATGGCAGCTATGAAA
GlyLysArgIleGluLysIleLysGlnGluHisGluThrSerTrpHisTyrAspGlnAspHisProTyrLysThrTrpAlaTyrHisGlySerTyrGlu>

8510      8520      8530      8540      8550      8560      8570      8580      8590      8600
CAAAACAGACTGGATCATCATCCATGGTGAACGGAGTAGTCAGATTGCTGACAAAACCCTGGGACGTTGTTCCAATGGTGACACAGATGGCAATGAC
ThrLysGlnThrGlySerAlaSerSerMetValAsnGlyValValArgLeuLeuThrLysProTrpAspValValProMetValThrGlnMetAlaMetThr>

8610      8620      8630      8640      8650      8660      8670      8680      8690      8700
AGACACAACTCCTTTTGGACAACAGCGCGTCTTCAAAGAGAAGGTGGATACGAGAACCCAAGAACCAAAGAAGGCACAAAAAAACTAATGAAAATCACG
AspThrThrProPheGlyGlnGlnArgValPheLysGluLysValAspThrArgThrGlnGluProLysGluGlyThrLysLysLeuMetLysIleThr>

8710      8720      8730      8740      8750      8760      8770      8780      8790      8800
GCAGAGTGGCTCTGGAAAGAACTAGGAAAGAAAAAGACACCTAGAATGTGTACCAGAGAAGAATTCACAAAAAAGGTGAGAAGCAATGCAGCCTTGGGGG
AlaGluTrpLeuTrpLysGluLeuGlyLysLysLysThrProArgMetCysThrArgGluGluPheThrLysLysValArgSerAsnAlaAlaLeuGly>

8810      8820      8830      8840      8850      8860      8870      8880      8890      8900
CCATATTCACCGATGAGAACAAGTGGAAATCGGCGCGTGAAGCCGTTGAAGATAGTAGGTTTTGGGAGCTGGTTGACAAGGAAAGGAACCTCCATCTTGA
AlaIlePheThrAspGluAsnLysTrpLysSerAlaArgGluAlaValGluAspSerArgPheTrpGluLeuValAspLysGluArgAsnLeuHisLeuGlu>

8910      8920      8930      8940      8950      8960      8970      8980      8990      9000
AGGGAAATGTGAAACATGTGTATACAACATGATGGGGAAAGAGAGAAAAAACTAGGAGAGTTTGGTAAAGCAAAAGGCAGCAGAGCCATATGGTACATG
GlyLysCysGluThrCysValTyrAsnMetMetGlyLysArgGluLysLysLeuGlyGluPheGlyLysAlaLysGlySerArgAlaIleTrpTyrMet>

9010      9020      9030      9040      9050      9060      9070      9080      9090      9100
TGGCTCGGAGCACGCTTCTTAGAGTTTGAAGCCCTAGGATTTTTGAATGAAGACCATTGGTTCTCCAGAGAGAACTCCCTGAGTGGAGTGGAAGGAGAAG
TrpLeuGlyAlaArgPheLeuGluPheGluAlaLeuGlyPheLeuAsnGluAspHisTrpPheSerArgGluAsnSerLeuSerGlyValGluGlyGlu>

9110      9120      9130      9140      9150      9160      9170      9180      9190      9200
GGCTGCATAAGCTAGGTTACATCTTAAGAGAGGTGAGCAAGAAAGAAGGAGGAGCAATGTATGCCGATGACACCGCAGGCTGGGACACAAGAATCACAAT
GlyLeuHisLysLeuGlyTyrIleLeuArgGluValSerLysLysGluGlyGlyAlaMetTyrAlaAspAspThrAlaGlyTrpAspThrArgIleThrIle>

9210      9220      9230      9240      9250      9260      9270      9280      9290      9300
AGAGGATTTGAAAAATGAAGAAATGATAACGAACCACATGGCAGGAGAACACAAGAAACTTGCCGAGGCCATTTTTAAATTGACGTACCAAAACAAGGTG
GluAspLeuLysAsnGluGluMetIleThrAsnHisMetAlaGlyGluHisLysLysLeuAlaGluAlaIlePheLysLeuThrTyrGlnAsnLysVal>

9310      9320      9330      9340      9350      9360      9370      9380      9390      9400
GTGCGTGTGCAAAGACCAACACCAAGAGGCACAGTAATGGACATCATATCGAGAAGAGACCAAAGGGGTAGTGGACAAGTTGGCACCTATGGCCTCAACA
ValArgValGlnArgProThrProArgGlyThrValMetAspIleIleSerArgArgAspGlnArgGlySerGlyGlnValGlyThrTyrGlyLeuAsn>

9410      9420      9430      9440      9450      9460      9470      9480      9490      9500
CTTTTCACCAACATGGAAGCACAACTAATTAGGCAAATGGAGGGGAAGGAATCTTCAAAAGCATCCAGCACTTGACAGCCTCAGAAGAAATCGCTGTGCA
ThrPheThrAsnMetGluAlaGlnLeuIleArgGlnMetGluGlyGluGlyIlePheLysSerIleGlnHisLeuThrAlaSerGluGluIleAlaValGln>

9510      9520      9530      9540      9550      9560      9570      9580      9590      9600
AGATTGGCTAGTAAGAGTAGGGCGTGAAAGGTTGTCAAGAATGGCCATCAGTGGAGATGATTGTGTTGTGAAACCTTTAGATGATAGATTTGCAAGAGCT
AspTrpLeuValArgValGlyArgGluArgLeuSerArgMetAlaIleSerGlyAspAspCysValValLysProLeuAspAspArgPheAlaArgAla>

9610      9620      9630      9640      9650      9660      9670      9680      9690      9700
CTAACAGCTCTAAATGACATGGGAAAGGTTAGGAAGGACATACAGCAATGGGAGCCCTCAAGAGGATGGAACGACTGGACGCAGGTGCCCTTCTGTTCAC
LeuThrAlaLeuAsnAspMetGlyLysValArgLysAspIleGlnGlnTrpGluProSerArgGlyTrpAsnAspTrpThrGlnValProPheCysSer>

9710      9720      9730      9740      9750      9760      9770      9780      9790      9800
ACCATTTTCACGAGTTAATTATGAAAGATGGTCGCACACTCGTAGTTCCATGCAGAAACCAAGATGAATTGATCGGCAGAGCCCGAATTTCCCAGGGAGC
HisHisPheHisGluLeuIleMetLysAspGlyArgThrLeuValValProCysArgAsnGlnAspGluLeuIleGlyArgAlaArgIleSerGlnGlyAla>

9810      9820      9830      9840      9850      9860      9870      9880      9890      9900
TGGGTGGTCTTTACGGGAGACGGCCTGTTTGGGAAGTCTTACGCCCAAATGTGGAGCTTGATGTACTTCCACAGACGTGATCTCAGGCTAGCGGCAAAT
GlyTrpSerLeuArgGluThrAlaCysLeuGlyLysSerTyrAlaGlnMetTrpSerLeuMetTyrPheHisArgArgAspLeuArgLeuAlaAlaAsn>
```

APPENDIX 1-continued

Nucleotide and amino acid sequence of DEN2 (Tonga/74) cDNA plasmid p2

```
         9910      9920      9930      9940      9950      9960      9970      9980      9990     10000
GCCATCTGCTCGGCAGTCCCATCACACTGGATTCCAACAAGCCGGACAACCTGGTCCATACACGCCAGCCATGAATGGATGACGACGGAAGACATGTTGA
AlaIleCysSerAlaValProSerHisTrpIleProThrSerArgThrThrTrpSerIleHisAlaSerHisGluTrpMetThrThrGluAspMetLeu>

10010     10020     10030     10040     10050     10060     10070     10080     10090     10100
CAGTTTGGAACAGAGTGTGGATCCTAGAAAATCCATGGATGGAAGACAAAACTCCAGTGGAATCATGGGAGGAAATCCCATACCTGGGAAAAAGAGAAGA
ThrValTrpAsnArgValTrpIleLeuGluAsnProTrpMetGluAspLysThrProValGluSerTrpGluGluIleProTyrLeuGlyLysArgGluAsp>

10110     10120     10130     10140     10150     10160     10170     10180     10190     10200
CCAATGGTGCGGCTCGCTGATTGGGCTGACAAGCAGAGCCACCTGGGCGAAGAATATCCAGACAGCAATAAACCAAGTCAGATCCCTCATTGGCAATGAG
GlnTrpCysGlySerLeuIleGlyLeuThrSerArgAlaThrTrpAlaLysAsnIleGlnThrAlaIleAsnGlnValArgSerLeuIleGlyAsnGlu>

10210     10220     10230     10240     10250     10260     10270     10280     10290     10300
GAATACACAGATTACATGCCATCCATGAAAAGATTCAGAAGAGAAGAGGAAGAGGCAGGAGTTTTGTGGTAGAAAAACATGAAACAAAACAGAAGTCAGG
           GluTyrThrAspTyrMetProSerMetLysArgPheArgArgGluGluGluGluAlaGlyValLeuTrp***>

10310     10320     10330     10340     10350     10360     10370     10380     10390     10400
TCGGATTAAGCCATAGTACGGGAAAAACTATGCTACCTGTGAGCCCCGTCCAAGGACGTTAAAAGAAGTCAGGCCATTTTGATGCCATAGCTTGAGCAAA 10410     10420     10430     10440     10450     10460     10470     10480     10490     10500
CTGTGCAGCCTGTAGCTCCACCTGAGAAGGTGTAAAAAATCCGGGAGGCCACAAACCATGGAAGCTGTACGCATGGCGTAGTGGACTAGCGGTTAGAGGA 10510     10520     10530     10540     10550     10560     10570     10580     10590     10600
GACCCCTCCCTTACAGATCGCAGCAACAATGGGGGCCCAAGGTGAGATGAAGCTGTAGTCTCACTGGAAGGACTAGAGGTTAGAGGAGACCCCCCCAAAA 10610     10620     10630     10640     10650     10660     10670     10680     10690     10700
CAAAAAACAGCATATTGACGCTGGGAAAGACCAGAGATCCTGCTGTCTCCTCAGCATCATTCCAGGCACAGGACGCCAGAAAATGGAATGGTGCTGTTGA 10710     10720     10730     10740     10750     10760     10770     10780     10790     10800
ATCAACAGGTTCTGGTACCGGTAGGCATCGTGGTGTCACGCTCGTCGTTTGGTATGGCTTCATTCAGCTCCGGTTCCCAACGATCAAGGCGAGTTACATG 10810     10820     10830     10840     10850     10860     10870     10880     10890     10900
ATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCA 10910     10920     10930     10940     10950     10960     10970     10980     10990     11000
CTGCATAATTCTCTTACTGTCATGCCATCCGTAAGATGCTTTTCTGTGACTGGTGAGTACTCAACCAAGTCATTCTGAGAATAGTGTATGCGGCGACCGA 11010     11020     11030     11040     11050     11060     11070     11080     11090     11100
GTTGCTCTTGCCCGGCGTCAACACGGGATAATACCGCGCCACATAGCAGAACTTTAAAAGTGCTCATCATTGGAAAACGTTCTTCGGGGCGAAAACTCTC 11110     11120     11130     11140     11150     11160     11170     11180     11190     11200
AAGGATCTTACCGCTGTTGAGATCCAGTTCGATGTAACCCACTCGTGCACCCAACTGATCTTCAGCATCTTTTACTTTCACCAGCGTTTCTGGGTGAGCA 11210     11220     11230     11240     11250     11260     11270     11280     11290     11300
AAAACAGGAAGGCAAAATGCCGCAAAAAAGGGAATAAGGGCGACACGGAAATGTTGAATACTCATACTCTTCCTTTTTCAATATTATTGAAGCATTTATC 11310     11320     11330     11340     11350     11360     11370     11380     11390     11400
AGGGTTATTGTCTCATGAGCGGATACATATTTGAATGTATTTAGAAAAATAAACAAATAGGGGTTCCGCGCACATTTCCCCGAAAAGTGCCACCTGACGT 11410     11420     11430     11440     11450     11460     11470     11480     11490     11500
CTAAGAAACCATTATTATCATGACATTAACCTATAAAAATAGGCGTATCACGAGGCCCTTTCGTCTTCAAGAATTCTCATGTTTGACAGCTTATCATCGA 11510     11520     11530     11540     11550     11560     11570     11580     11590     11600
TAAGCTTTAATGCGGTAGTTTATCACAGTTAAATTGCTAACGCAGTCAGGCACCGTGTATGAAATCTAACAATGCGCTCATCGTCATCCTCGGCACCGTC 11610     11620     11630     11640     11650     11660     11670     11680     11690     11700
ACCCTGGATGCTGTAGGCATAGGCTTGGTTATGCCGGTACTGCCGGGCCTCTTGCGGGATATCGTCCATTCCGACAGCATCGCCAGTCACTATGGCGTGC 11710     11720     11730     11740     11750     11760     11770     11780     11790     11800
TGCTGGCGCTATATGCGTTGATGCAATTTCTATGCGCACCCGTTCTCGGAGCACTGTCCGACCGCTTTGGCCGCCGCCCAGTCCTGCTCGCTTCGCTACT 11810     11820     11830     11840     11850     11860     11870     11880     11890     11900
TGGAGCCACTATCGACTACGCGATCATGGCGACCACACCCGTCCTGTGGATCCTCTACGCCGGACGCATCGTGGCCGGCATCACCGGCGCCACAGGTGCG 11910     11920     11930     11940     11950     11960     11970     11980     11990     12000
GTTGCTGGCGCCTATATCGCCGACATCACCGATGGGAAGATCGGGCTCGCCACTTCGGGCTCATGAGCGCTTGTTTCGGCGTGGGTATGGTGGCAGGCC 12010     12020     12030     12040     12050     12060     12070     12080     12090     12100
CCGTGGCCGGGGACTGTTGGGCGCCATCTCCTTGCATGCACCATTCCTTGCGGCGGCGGTGCTCAACGGCCTCAACCTACTACTGGGCTGCTTCCTAAT 12110     12120     12130     12140     12150     12160     12170     12180     12190     12200
GCAGGAGTCGCATAAGGGAGAGCGTCGACCGATGCCCTTGAGAGCCTTCAACCCAGTCAGCTCCTTCCGGTGGGCGCGGGGCATGACTATCGTCGCCGCA 12210     12220     12230     12240     12250     12260     12270     12280     12290     12300
CTTATGACTGTCTTCTTTATCATGCAACTCGTAGGACAGGTGCCGGCAGCGCTCTGGGTCATTTTCGGCGAGGACCGCTTTCGCTGGAGCGCGACGATGA
```

APPENDIX 1-continued

Nucleotide and amino acid sequence of DEN2 (Tonga/74) cDNA plasmid p2

```
     12310      12320      12330      12340      12350      12360      12370      12380      12390      12400
TCGGCCTGTCGCTTGCGGTATTCGGAATCTTGCACGCCCTCGCTCAAGCCTTCGTCACTGGTCCCGCCACCAAACGTTTCGGCGAGAAGCAGGCCATTAT 12410      12420      12430      12440      12450      12460      12470      12480      12490      12500
CGCCGGCATGGCGGCCGACGCGCTGGGCTACGTCTTGCTGGCGTTCGCGACGCGAGGCTGGATGGCCTTCCCCATTATGATTCTTCTCGCTTCCGGCGGC 12510      12520      12530      12540      12550      12560      12570      12580      12590      12600
ATCGGGATGCCCGCGTTGCAGGCCATGCTGTCCAGGCAGGTAGATGACGACCATCAGGGACAGCTTCAAGGATCGCTCGCGGCTCTTACCAGCCTAACTT 12610      12620      12630      12640      12650      12660      12670      12680      12690      12700
CGATCACTGGACCGCTGATCGTCACGGCGATTTATGCCGCCTCGGCGAGCACATGGAACGGGTTGGCATGGATTGTAGGCGCCGCCCTATACCTTGTCTG 12710      12720      12730      12740      12750      12760      12770      12780      12790      12800
CCTCCCCGCGTTGCGTCGCGGTGCATGGAGCCGGGCCACCTCGACCTGAATGGAAGCCGGCGGCACCTCGCTAACGGATTCACCACTCCAAGAATTGGAG 12810      12820      12830      12840      12850      12860      12870      12880      12890      12900
CCAATCAATTCTTGCGGAGAACTGTGAATGCGCAAACCAACCCTTGGCAGAACATATCCATCGCGTCCGCCATCTCCAGCAGCCGCACGCGGCGCATCTC 12910      12920      12930      12940      12950      12960      12970      12980      12990      13000
GGGCAGCGTTGGGTCCTGGCCACGGGTGCGCATGATCGTGCTCCTGTCGTTGAGGACCCGGCTAGGCTGGCGGGGTTGCCTTACTGGTTAGCAGAATGAA 13010      13020      13030      13040      13050      13060      13070      13080      13090      13100
TCACCGATACGCGAGCGAACGTGAAGCGACTGCTGCTGCAAAACGTCTGCGACCTGAGCAACAACATGAATGGTCTTCGGTTTCCGTGTTTCGTAAAGTC 13110      13120      13130      13140      13150      13160      13170      13180      13190      13200
TGGAAACGCGGAAGTCAGCGCCCTGCACCATTATGTTCCGGATCTGCATCGCAGGATGCTGCTGGCTACCCTGTGGAACACCTACATCTGTATTAACGAA 13210      13220      13230      13240      13250      13260      13270      13280      13290      13300
GCGCTGGCATTGACCCTGAGTGATTTTTCTCTGGTCCCGCCGCATCCATACCGCCAGTTGTTTACCCTCACAACGTTCCAGTAACCGGGCATGTTCATCA 13310      13320      13330      13340      13350      13360      13370      13380      13390      13400
TCAGTAACCCGTATCGTGAGCATCCTCTCTCGTTTCATCGGTATCATTACCCCCATGAACAGAAATCCCCCTTACACGGAGGCATCAGTGACCAAACAGG 13410      13420      13430      13440      13450      13460      13470      13480      13490      13500
AAAAAACCGCCCTTAACATGGCCCGCTTTATCAGAAGCCAGACATTAACGCTTCTGGAGAAACTCAACGAGCTGGACGCGGATGAACAGGCAGACATCTG 13510      13520      13530      13540      13550      13560      13570      13580      13590      13600
TGAATCGCTTCACGACCACGCTGATGAGCTTTACCGCAGCTGCCTCGCGCGTTTCGGTGATGACGGTGAAAACCTCTGACACATGCAGCTCCCGGAGACG 13610      13620      13630      13640      13650      13660      13670      13680      13690      13700
GTCACAGCTTGTCTGTAAGCGGATGCCGGGAGCAGACAAGCCCGTCAGGGCGCGTCAGCGGGTGTTGGCGGGTGTCGGGGCGCAGCCATGACCCAGTCAC 13710      13720      13730      13740      13750      13760      13770      13780      13790      13800
GTAGCGATAGCGGAGTGTATACTGGCTTAACTATGCGGCATCAGAGCAGATTGTACTGAGAGTGCACCATATGCGGTGTGAAATACCGCACAGATGCGTA 13810      13820      13830      13840      13850      13860      13870      13880      13890      13900
AGGAGAAAATACCGCATCAGGCGCTCTTCCGCTTCCTCGCTCACTGACTCGCTGCGCTCGGTCGTTCGGCTGCGGCGAGCGGTATCAGCTCACTCAAAGG 13910      13920      13930      13940      13950      13960      13970      13980      13990      14000
CGGTAATACGGTTATCCACAGAATCAGGGGATAACGCAGGAAAGAACATGTGAGCAAAAGGCCAGCAAAAGGCCAGGAACCGTAAAAAGGCCGCGTTGCT 14010      14020      14030      14040      14050      14060      14070      14080      14090      14100
GGCGTTTTTCCATAGGCTCCGCCCCCCTGACGAGCATCACAAAAATCGACGCTCAAGTCAGAGGTGGCGAAACCCGACAGGACTATAAAGATACCAGGCG 14110      14120      14130      14140      14150      14160      14170      14180      14190      14200
TTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTC 14210      14220      14230      14240      14250      14260      14270      14280      14290      14300
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATC 14310      14320      14330      14340      14350      14360      14370      14380      14390      14400
CGGTAACTATCGTCTTGAGTCCAACCCGGTAAGACACGACTTATCGCCACTGGCAGCAGCCACTGGTAACAGGATTAGCAGAGCGAGGTATGTAGGCGGT 14410      14420      14430      14440      14450      14460      14470      14480      14490      14500
GCTACAGAGTTCTTGAAGTGGTGGCCTAACTACGGCTACACTAGAAGGACAGTATTTGGTATCTGCGCTCTGCTGAAGCCAGTTACCTTCGGAAAAAGAG 14510      14520      14530      14540      14550      14560      14570      14580      14590      14600
TTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGA 14610      14620      14630      14640      14650      14660      14670      14680      14690      14700
TCCTTTGATCTTTTCTACGGGGTCTGACGCTCAGTGGAACGAAAACTCACGTTAAGGGATTTTGGTCATGAGATTATCAAAAAGGATCTTCACCTAGATC 14710      14720      14730      14740      14750      14760      14770      14780      14790      14800
CTTTTAAATTAAAAATGAAGTTTTAAATCAATCTAAAGTATATATGAGTAAACTTGGTCTGACAGTTACCAATGCTTAATCAGTGAGGCACCTATCTCAG 14810      14820      14830      14840      14850      14860      14870      14880      14890      14900
```

APPENDIX 1-continued

Nucleotide and amino acid sequence of DEN2 (Tonga/74) cDNA plasmid p2

```
CGATCTGTCTATTTCGTTCATCCATAGTTGCCTGACTCCCCGTCGTGTAGATAACTACGATACGGGAGGGCTTACCATCTGGCCCCAGTGCTGCAATGAT 14910     14920     14930     14940     14950     14960     14970     14980     14990     15000
ACCGCGAGACCCACGCTCACCGGCTCCAGATTTATCAGCAATAAACCAGCCAGCCGGAAGGGCCGAGCGCAGAAGTGGTCCTGCAACTTTATCCGCCTCC 15010     15020     15030     15040     15050     15060     15070     15080     15090     15100
ATCCAGTCTATTAATTGTTGCCGGGAAGCTAGAGTAAGTAGTTCGCCAGTTAATAGTTTGCGCAACGTTGTTGCCATTGCTGCAAGATCTGGCTAGCGAT 15110     15120     15130     15140     15150
GACCCTGCTGATTGGTTCGCTGACCATTTCCGGGCGCGCCGATTTAGGTGACACTATAG
```

```
Bases 1 to 10713: DEN2 virus genome cDNA
Bases 97 to 10269: DEN2 polyprotein ORF
Bases 97 to 438: C protein ORF
Bases 439 to 936: prM protein ORF
Bases 937 to 2421: E protein ORF
Bases 2422 to 3477: NS1 protein ORF
Bases 3478 to 4131: NS2A protein ORF
Bases 4132 to 4521: NS2B protein ORF
Bases 4522 to 6375: NS3 protein ORF
Bases 6376 to 6756: NS4A protein ORF
Bases 6757 to 6825: 2K protein ORF
Bases 6826 to 7569: NS4B protein ORF
Bases 7570 to 10269: NS5 protein ORF
```

APPENDIX 2

Nucleotide and amino acid sequence of DEN3 (Sleman/78) cDNA plasmid p3

```
          10        20        30        40        50        60        70        80        90       100
AGTTGTTAGTCTACGTGGACCGACAAGAACAGTTTCGACTCGGAAGCTTGCTTAACGTAGTACTGACAGTTTTTTATTAGAGAGCAGATCTCTGATGAAC
                                                                                                MetAsn>

110       120       130       140       150       160       170       180       190       200
AACCAACGGAAAAAGACGGGAAAACCGTCTATCAATATGCTGAAACGCGTGAGAAACCGTGTGTCAACTGGATCACAGTTGGCGAAGAGATTCTCAAGAG
AsnGlnArgLysLysThrGlyLysProSerIleAsnMetLeuLysArgValArgAsnArgValSerThrGlySerGlnLeuAlaLysArgPheSerArg>

210       220       230       240       250       260       270       280       290       300
GACTGCTGAACGGCCAAGGACCAATGAAATTGGTTATGGCGTTCATAGCTTTCCTCAGATTTCTAGCCATTCCACCGACAGCAGGAGTCTTGGCTAGATG
GlyLeuLeuAsnGlyGlnGlyProMetLysLeuValMetAlaPheIleAlaPheLeuArgPheLeuAlaIleProProThrAlaGlyValLeuAlaArgTrp>

310       320       330       340       350       360       370       380       390       400
GGGAACCTTTAAGAAGTCGGGGGCTATTAAGGTCCTGAGAGGCTTCAAGAAGGAGATCTCAAACATGCTGAGCATTATCAACAGACGGAAAAAGACATCG
GlyThrPheLysLysSerGlyAlaIleLysValLeuArgGlyPheLysLysGluIleSerAsnMetLeuSerIleIleAsnArgArgLysLysThrSer>

410       420       430       440       450       460       470       480       490       500
CTCTGTCTCATGATGATGTTACCAGCAACACTTGCTTTCCACTTGACTTCACGAGATGGAGAGCCGCGCATGATTGTGGGGAAGAATGAAAGAGGAAAAT
LeuCysLeuMetMetMetLeuProAlaThrLeuAlaPheHisLeuThrSerArgAspGlyGluProArgMetIleValGlyLysAsnGluArgGlyLys>

510       520       530       540       550       560       570       580       590       600
CCCTACTTTTTAAGACAGCCTCTGGAATCAACATGTGCACACTCATAGCCATGGATTTGGGAGAGATGTGTGATGACACGGTCACCTACAAATGCCCCCT
SerLeuLeuPheLysThrAlaSerGlyIleAsnMetCysThrLeuIleAlaMetAspLeuGlyGluMetCysAspAspThrValThrTyrLysCysProLeu>

610       620       630       640       650       660       670       680       690       700
CATTACTGAAGTGGAGCCTGAAGACATTGACTGCTGGTGCAACCTTACATCGACATGGGTGACCTACGGAACGTGCAATCAAGCTGGAGAGCACAGACGC
IleThrGluValGluProGluAspIleAspCysTrpCysAsnLeuThrSerThrTrpValThrTyrGlyThrCysAsnGlnAlaGlyGluHisArgArg>

710       720       730       740       750       760       770       780       790       800
GACAAAAGATCGGTGGCGTTAGCTCCCCATGTCGGCATGGGACTGGACACACGCACCCAAACCTGGATGTCGGCTGAAGGAGCTTGGAGACAGGTCGAGA
AspLysArgSerValAlaLeuAlaProHisValGlyMetGlyLeuAspThrArgThrGlnThrTrpMetSerAlaGluGlyAlaTrpArgGlnValGlu>

810       820       830       840       850       860       870       880       890       900
AGGTAGAGACATGGGCCTTTAGGCACCCAGGGTTCACAATACTAGCCCTATTTCTTGCCCATTACATAGGCACTTCCTTGACCCAGAAAGTGGTTATTTT
LysValGluThrTrpAlaPheArgHisProGlyPheThrIleLeuAlaLeuPheLeuAlaHisTyrIleGlyThrSerLeuThrGlnLysValValIlePhe>

910       920       930       940       950       960       970       980       990      1000
CATACTACTAATGCTGGTCACCCCATCCATGACAATGAGATGCGTGGGAGTAGGAAACAGAGATTTTGTGGAAGGCCTATCAGGAGCTACGTGGGTTGAC
IleLeuLeuMetLeuValThrProSerMetThrMetArgCysValGlyValGlyAsnArgAspPheValGluGlyLeuSerGlyAlaThrTrpValAsp>

1010      1020      1030      1040      1050      1060      1070      1080      1090      1100
GTGGTGCTCGAGCACGGTGGGTGTGTGACTACCATGGCTAAGAACAAGCCCACGCTGGATATAGAGCTCCAGAAGACCGAGGCCACCCAACTGGCGACCC
ValValLeuGluHisGlyGlyCysValThrThrMetAlaLysAsnLysProThrLeuAspIleGluLeuGlnLysThrGluAlaThrGlnLeuAlaThr>

1110      1120      1130      1140      1150      1160      1170      1180      1190      1200
```

APPENDIX 2-continued

Nucleotide and amino acid sequence of DEN3 (Sleman/78) cDNA plasmid p3

APPENDIX 2-continued

Nucleotide and amino acid sequence of DEN3 (Sleman/78) cDNA plasmid p3

```
CGACATGGGCTATTGGATAGAAAGCCAAAAGAATGGAAGTTGGAAGCTAGAAAAGGCATCCCTCATAGAGGTAAAAACCTGCACATGGCCAAAATCACAC
AspMetGlyTyrTrpIleGluSerGlnLysAsnGlySerTrpLysLeuGluLysAlaSerLeuIleGluValLysThrCysThrTrpProLysSerHis>

3110      3120      3130      3140      3150      3160      3170      3180      3190      3200
ACTCTTTGGAGCAATGGTGTGCTAGAGAGTGACATGATCATCCCAAAGAGTCTGGCTGGTCCCATTTCGCAACACAACTACAGGCCCGGATACCACACCC
ThrLeuTrpSerAsnGlyValLeuGluSerAspMetIleIleProLysSerLeuAlaGlyProIleSerGlnHisAsnTyrArgProGlyTyrHisThr>

3210      3220      3230      3240      3250      3260      3270      3280      3290      3300
AAACGGCAGGACCCTGGCACTTAGGAAAATTGGAGCTGGACTTCAACTATTGTGAAGGAACAACAGTTGTCATCACAGAAAATTGTGGGACAAGAGGCCC
GlnThrAlaGlyProTrpHisLeuGlyLysLeuGluLeuAspPheAsnTyrCysGluGlyThrThrValValIleThrGluAsnCysGlyThrArgGlyPro>

3310      3320      3330      3340      3350      3360      3370      3380      3390      3400
ATCACTGAGAACAACAACAGTGTCAGGGAAGTTGATACACGAATGGTGTTGCCGCTCGTGTACACTTCCTCCCCTGCGATACATGGGAGAAGACGGCTGC
SerLeuArgThrThrThrValSerGlyLysLeuIleHisGluTrpCysCysArgSerCysThrLeuProProLeuArgTyrMetGlyGluAspGlyCys>

3410      3420      3430      3440      3450      3460      3470      3480      3490      3500
TGGTATGGCATGGAAATTAGACCCATTAATGAGAAAGAAGAGAACATGGTAAAGTCTTTAGTCTCAGCAGGGAGTGGAAAGGTGGATAACTTCACAATGG
TrpTyrGlyMetGluIleArgProIleAsnGluLysGluGluAsnMetValLysSerLeuValSerAlaGlySerGlyLysValAspAsnPheThrMet>

3510      3520      3530      3540      3550      3560      3570      3580      3590      3600
GTGTCTTGTGTTTGGCAATCCTTTTTGAAGAGGTGATGAGAGGAAAATTTGGGAAAAAGCACATGATTGCAGGGGTTCTCTTCACGTTTGTACTCCTTCT
GlyValLeuCysLeuAlaIleLeuPheGluGluValMetArgGlyLysPheGlyLysLysHisMetIleAlaGlyValLeuPheThrPheValLeuLeuLeu>

3610      3620      3630      3640      3650      3660      3670      3680      3690      3700
CTCAGGGCAAATAACATGGAGAGACATGGCGCACACACTCATAATGATTGGGTCCAACGCCTCTGACAGAATGGGAATGGGCGTCACTTACCTAGCATTG
SerGlyGlnIleThrTrpArgAspMetAlaHisThrLeuIleMetIleGlySerAsnAlaSerAspArgMetGlyMetGlyValThrTyrLeuAlaLeu>

3710      3720      3730      3740      3750      3760      3770      3780      3790      3800
ATTGCAACATTTAAAATTCAGCCATTTTTGGCTTTGGGATTCTTCCTGAGGAAACTGACATCTAGAGAAAATTTATTGTTGGGAGTTGGGTTGGCCATGG
IleAlaThrPheLysIleGlnProPheLeuAlaLeuGlyPhePheLeuArgLysLeuThrSerArgGluAsnLeuLeuLeuGlyValGlyLeuAlaMet>

3810      3820      3830      3840      3850      3860      3870      3880      3890      3900
CAACAACGTTACAACTGCCAGAGGACATTGAACAAATGGCGAATGGAATAGCTTTAGGGCTCATGGCTCTTAAATTAATAACACAATTTGAAACATACCA
AlaThrThrLeuGlnLeuProGluAspIleGluGlnMetAlaAsnGlyIleAlaLeuGlyLeuMetAlaLeuLysLeuIleThrGlnPheGluThrTyrGln>

3910      3920      3930      3940      3950      3960      3970      3980      3990      4000
ACTATGGACGGCATTAGTCTCCCTAATGTGTTCAAATACAATTTTCACGTTGACTGTTGCCTGGAGAACAGCCACCCTGATTTTGGCCGGAATTTCTCTT
LeuTrpThrAlaLeuValSerLeuMetCysSerAsnThrIlePheThrLeuThrValAlaTrpArgThrAlaThrLeuIleLeuAlaGlyIleSerLeu>

4010      4020      4030      4040      4050      4060      4070      4080      4090      4100
TTGCCAGTGTGCCAGTCTTCGAGCATGAGGAAAACAGATTGGCTCCCAATGGCTGTGGCAGCTATGGGAGTTCCACCCCTACCACTTTTTATTTTCAGTT
LeuProValCysGlnSerSerSerMetArgLysThrAspTrpLeuProMetAlaValAlaAlaMetGlyValProProLeuProLeuPheIlePheSer>

4110      4120      4130      4140      4150      4160      4170      4180      4190      4200
TGAAAGATACGCTCAAAAGGAGAAGCTGGCCACTGAATGAGGGGGTGATGGCTGTTGGACTTGTGAGTATTCTAGCTAGTTCTCTCCTTAGGAATGACGT
LeuLysAspThrLeuLysArgArgSerTrpProLeuAsnGluGlyValMetAlaValGlyLeuValSerIleLeuAlaSerSerLeuLeuArgAsnAspVal>

4210      4220      4230      4240      4250      4260      4270      4280      4290      4300
GCCCATGGCTGGACCATTAGTGGCTGGGGGCTTGCTGATAGCGTGCTACGTCATAACTGGCACGTCAGCAGACCTCACTGTAGAAAAAGCAGCAGATGTG
ProMetAlaGlyProLeuValAlaGlyGlyLeuLeuIleAlaCysTyrValIleThrGlyThrSerAlaAspLeuThrValGluLysAlaAlaAspVal>

4310      4320      4330      4340      4350      4360      4370      4380      4390      4400
ACATGGGAGGAAGAGGCTGAGCAAACAGGAGTGTCCCACAATTTAATGATCACAGTTGATGACGATGGAACAATGAGAATAAAAGATGATGAGACTGAGA
ThrTrpGluGluGluAlaGluGlnThrGlyValSerHisAsnLeuMetIleThrValAspAspAspGlyThrMetArgIleLysAspAspGluThrGlu>

4410      4420      4430      4440      4450      4460      4470      4480      4490      4500
ACATCTTAACAGTGCTTTTGAAAACAGCATTACTAATAGTGTCAGGCATTTTTCCATACTCCATACCCGCAACACTGTTGGTCTGGCACACTTGGCAAAA
AsnIleLeuThrValLeuLeuLysThrAlaLeuLeuIleValSerGlyIlePheProTyrSerIleProAlaThrLeuLeuValTrpHisThrTrpGlnLys>

4510      4520      4530      4540      4550      4560      4570      4580      4590      4600
GCAAACCCAAAGATCCGGTGTCCTATGGGACGTTCCCAGCCCCCCAGAGACACAGAAAGCAGAACTGGAAGAAGGGGTTTATAGGATCAAGCAGCAAGGA
GlnThrGlnArgSerGlyValLeuTrpAspValProSerProProGluThrGlnLysAlaGluLeuGluGluGlyValTyrArgIleLysGlnGlnGly>

4610      4620      4630      4640      4650      4660      4670      4680      4690      4700
ATTTTTGGGAAAACCCAAGTGGGGGTTGGAGTACAAAAAGAAGGAGTTTTCCACACCATGTGGCACGTCACAAGAGGAGCAGTGTTGACACACAATGGGA
IlePheGlyLysThrGlnValGlyValGlyValGlnLysGluGlyValPheHisThrMetTrpHisValThrArgGlyAlaValLeuThrHisAsnGly>

4710      4720      4730      4740      4750      4760      4770      4780      4790      4800
AAAGACTGGAACCAAACTGGGCTAGCGTGAAAAAAGATCTGATTTCATACGGAGGAGGATGGAAATTGAGTGCACAATGGCAAAAAGGAGAGGAGGTGCA
LysArgLeuGluProAsnTrpAlaSerValLysLysAspLeuIleSerTyrGlyGlyGlyTrpLysLeuSerAlaGlnTrpGlnLysGlyGluGluValGln>

4810      4820      4830      4840      4850      4860      4870      4880      4890      4900
GGTTATTGCCGTAGAGCCTGGGAAGAACCCAAAGAACTTTCAAACCATGCCAGGCATTTTCCAGACAACAACAGGGGAGATAGGAGCGATTGCACTGGAC
ValIleAlaValGluProGlyLysAsnProLysAsnPheGlnThrMetProGlyIlePheGlnThrThrThrGlyGluIleGlyAlaIleAlaLeuAsp>

4910      4920      4930      4940      4950      4960      4970      4980      4990      5000
```

APPENDIX 2-continued

Nucleotide and amino acid sequence of DEN3 (Sleman/78) cDNA plasmid p3

```
TTCAAGCCTGGAACTTCAGGATCTCCCATCATAAACAGAGAGGGAAAGGTACTGGGATTGTATGGCAATGGAGTGGTCACAAAGAATGGTGGCTATGTCA
PheLysProGlyThrSerGlySerProIleIleAsnArgGluGlyLysValLeuGlyLeuTyrGlyAsnGlyValValThrLysAsnGlyGlyTyrVal>

5010      5020      5030      5040      5050      5060      5070      5080      5090      5100
GTGGAATAGCACAAACAAATGCAGAACCAGACGGACCGACACCAGAGTTGGAAGAAGAGATGTTCAAAAAGCGAAATCTAACCATAATGGATCTCCATCC
SerGlyIleAlaGlnThrAsnAlaGluProAspGlyProThrProGluLeuGluGluGluMetPheLysLysArgAsnLeuThrIleMetAspLeuHisPro>

5110      5120      5130      5140      5150      5160      5170      5180      5190      5200
CGGGTCAGGAAAGACGCGGAAATATCTTCCAGCTATTGTTAGAGAGGCAATCAAGAGACGCTTAAGGACTCTAATTTTGGCACCAACAAGGGTAGTTGCA
GlySerGlyLysThrArgLysTyrLeuProAlaIleValArgGluAlaIleLysArgArgLeuArgThrLeuIleLeuAlaProThrArgValValAla>

5210      5220      5230      5240      5250      5260      5270      5280      5290      5300
GCTGAGATGGAAGAAGCATTGAAAGGGCTCCCAATAAGGTATCAAACAACTGCAACAAAATCTGAACACACAGGGAGAGAGATTGTTGATCTAATGTGCC
AlaGluMetGluGluAlaLeuLysGlyLeuProIleArgTyrGlnThrThrAlaThrLysSerGluHisThrGlyArgGluIleValAspLeuMetCys>

5310      5320      5330      5340      5350      5360      5370      5380      5390      5400
ACGCAACGTTCACAATGCGTTTGCTGTCACCAGTCAGGGTTCCAAACTACAACTTGATAATAATGGATGAGGCTCATTTCACAGACCCAGCCAGTATAGC
HisAlaThrPheThrMetArgLeuLeuSerProValArgValProAsnTyrAsnLeuIleIleMetAspGluAlaHisPheThrAspProAlaSerIleAla>

5410      5420      5430      5440      5450      5460      5470      5480      5490      5500
GGCTAGAGGGTACATATCAACTCGTGTAGGAATGGGAGAGGCAGCCGCAATTTTCATGACAGCCACACCCCCTGGAACAGCTGATGCCTTTCCTCAGAGC
AlaArgGlyTyrIleSerThrArgValGlyMetGlyGluAlaAlaAlaIlePheMetThrAlaThrProProGlyThrAlaAspAlaPheProGlnSer>

5510      5520      5530      5540      5550      5560      5570      5580      5590      5600
AACGCTCCAATTCAAGATGAAGAAAGAGACATACCAGAACGCTCATGGAATTCAGGCAATGAATGGATTACCGACTTTGCCGGGAAGACGGTGTGGTTTG
AsnAlaProIleGlnAspGluGluArgAspIleProGluArgSerTrpAsnSerGlyAsnGluTrpIleThrAspPheAlaGlyLysThrValTrpPhe>

5610      5620      5630      5640      5650      5660      5670      5680      5690      5700
TCCCTAGCATCAAAGCTGGAAATGACATAGCAAACTGCTTGCGGAAAAATGGAAAAAAGGTCATTCAACTTAGTAGGAAGACTTTTGACACAGAATATCA
ValProSerIleLysAlaGlyAsnAspIleAlaAsnCysLeuArgLysAsnGlyLysLysValIleGlnLeuSerArgLysThrPheAspThrGluTyrGln>

5710      5720      5730      5740      5750      5760      5770      5780      5790      5800
AAAGACTAAACTAAATGATTGGGACTTTGTGGTGACAACAGACATTTCAGAAATGGGAGCCAATTTCAAAGCAGACAGAGTGATCGACCCAAGAAGATGT
LysThrLysLeuAsnAspTrpAspPheValValThrThrAspIleSerGluMetGlyAlaAsnPheLysAlaAspArgValIleAspProArgArgCys>

5810      5820      5830      5840      5850      5860      5870      5880      5890      5900
CTCAAGCCAGTGATTTTGACAGACGGACCCGAGCGCGTGATCCTGGCGGGACCAATGCCAGTCACCGTAGCGAGCGCTGCGCAAAGGAGAGGGAGAGTTG
LeuLysProValIleLeuThrAspGlyProGluArgValIleLeuAlaGlyProMetProValThrValAlaSerAlaAlaGlnArgArgGlyArgVal>

5910      5920      5930      5940      5950      5960      5970      5980      5990      6000
GCAGGAACCCACAAAAAGAAAATGACCAATACATATTCATGGGCCAGCCCCTCAATAATGATGAAGACCATGCTCACTGGACAGAAGCAAAAATGCTGCT
GlyArgAsnProGlnLysGluAsnAspGlnTyrIlePheMetGlyGlnProLeuAsnAsnAspGluAspHisAlaHisTrpThrGluAlaLysMetLeuLeu>

6010      6020      6030      6040      6050      6060      6070      6080      6090      6100
AGACAACATCAACACACCAGAAGGGATCATACCAGCTCTCTTTGAACCAGAAAGGGAGAAGTCAGCCGCCATAGACGGCGAATACCGCCTGAAGGGTGAG
AspAsnIleAsnThrProGluGlyIleIleProAlaLeuPheGluProGluArgGluLysSerAlaAlaIleAspGlyGluTyrArgLeuLysGlyGlu>

6110      6120      6130      6140      6150      6160      6170      6180      6190      6200
TCCAGGAAGACCTTCGTGGAACTCATGAGGAGGGGTGACCTCCCAGTTTGGCTAGCCCATAAAGTAGCATCAGAAGGGATCAAATATACAGATAGAAAGT
SerArgLysThrPheValGluLeuMetArgArgGlyAspLeuProValTrpLeuAlaHisLysValAlaSerGluGlyIleLysTyrThrAspArgLys>

6210      6220      6230      6240      6250      6260      6270      6280      6290      6300
GGTGTTTTGATGGAGAACGCAACAATCAAATTTTAGAGGAGAATATGGATGTGGAAATCTGGACAAAGGAAGGAGAAAAGAAAAAATTGAGACCTAGGTG
TrpCysPheAspGlyGluArgAsnAsnGlnIleLeuGluGluAsnMetAspValGluIleTrpThrLysGluGlyGluLysLysLysLeuArgProArgTrp>

6310      6320      6330      6340      6350      6360      6370      6380      6390      6400
GCTTGATGCCCGCACTTATTCAGATCCCTTAGCGCTCAAGGAATTCAAGGACTTTGCGGCTGGTAGAAAGTCAATTGCCCTTGATCTTGTGACAGAAATA
LeuAspAlaArgThrTyrSerAspProLeuAlaLeuLysGluPheLysAspPheAlaAlaGlyArgLysSerIleAlaLeuAspLeuValThrGluIle>

6410      6420      6430      6440      6450      6460      6470      6480      6490      6500
GGAAGAGTGCCTTCACACTTAGCTCACAGAACGAGAAACGCCCTGGACAATCTGGTGATGTTGCACACGTCAGAACATGGCGGGAGGGCCTACAGGCATG
GlyArgValProSerHisLeuAlaHisArgThrArgAsnAlaLeuAspAsnLeuValMetLeuHisThrSerGluHisGlyGlyArgAlaTyrArgHis>

6510      6520      6530      6540      6550      6560      6570      6580      6590      6600
CAGTGGAGGAACTACCAGAAACAATGGAAACACTCTTACTCCTGGGACTCATGATCCTGTTAACAGGTGGAGCAATGCTTTTCTTGATATCAGGTAAAGG
AlaValGluGluLeuProGluThrMetGluThrLeuLeuLeuLeuGlyLeuMetIleLeuLeuThrGlyGlyAlaMetLeuPheLeuIleSerGlyLysGly>

6610      6620      6630      6640      6650      6660      6670      6680      6690      6700
GATTGGAAAGACTTCAATAGGACTCATTTGTGTAGCTGCTTCCAGCGGTATGTTATGGATGGCTGATGTCCCACTCCAATGGATCGCGTCTGCCATAGTC
IleGlyLysThrSerIleGlyLeuIleCysValAlaAlaSerSerGlyMetLeuTrpMetAlaAspValProLeuGlnTrpIleAlaSerAlaIleVal>

6710      6720      6730      6740      6750      6760      6770      6780      6790      6800
CTGGAGTTTTTTATGATGGTGTTACTTATACCAGAACCAGAAAAGCAGAGAACTCCCCAAGACAATCAACTCGCATATGTCGTGATAGGCATACTCACAC
LeuGluPhePheMetMetValLeuLeuIleProGluProGluLysGlnArgThrProGlnAspAsnGlnLeuAlaTyrValValIleGlyIleLeuThr>

6810      6820      6830      6840      6850      6860      6870      6880      6890      6900
```

APPENDIX 2-continued

Nucleotide and amino acid sequence of DEN3 (Sleman/78) cDNA plasmid p3

```
TGGCTGCAATAGTAGCAGCCAATGAAATGGGACTGTTGGAAACCACAAAGAGAGATTTAGGAATGTCCAAAGAACCAGGTGTTGTTTCTCCAACCAGCTA
LeuAlaAlaIleValAlaAlaAsnGluMetGlyLeuLeuGluThrThrLysArgAspLeuGlyMetSerLysGluProGlyValValSerProThrSerTyr>

6910      6920      6930      6940      6950      6960      6970      6980      6990      7000
TTTGGATGTGGACTTGCACCCAGCATCAGCCTGGACATTGTACGCTGTGGCCACAACAGTAATAACACCAATGTTGAGACATACCATAGAGAATTCCACA
LeuAspValAspLeuHisProAlaSerAlaTrpThrLeuTyrAlaValAlaThrThrValIleThrProMetLeuArgHisThrIleGluAsnSerThr>

7010      7020      7030      7040      7050      7060      7070      7080      7090      7100
GCAAATGTGTCCCTGGCAGCTATAGCCAACCAGGCAGTGGTCCTGATGGGTTTAGACAAAGGATGGCCGATATCGAAAATGGACTTAGGCGTGCCACTAT
AlaAsnValSerLeuAlaAlaIleAlaAsnGlnAlaValValLeuMetGlyLeuAspLysGlyTrpProIleSerLysMetAspLeuGlyValProLeu>

7110      7120      7130      7140      7150      7160      7170      7180      7190      7200
TGGCACTGGGTTGTTATTCACAAGTGAACCCACTAACTCTCACAGCGGCAGTTCTCCTGCTAGTCACGCATTATGCTATTATAGGTCCAGGATTGCAGGC
LeuAlaLeuGlyCysTyrSerGlnValAsnProLeuThrLeuThrAlaAlaValLeuLeuLeuValThrHisTyrAlaIleIleGlyProGlyLeuGlnAla>

7210      7220      7230      7240      7250      7260      7270      7280      7290      7300
AAAAGCCACTCGTGAAGCTCAAAAAAGGACAGCTGCTGGAATAATGAAGAATCCAACGGTGGATGGGATAATGACAATAGACCTAGATCCTGTAATATAC
LysAlaThrArgGluAlaGlnLysArgThrAlaAlaGlyIleMetLysAsnProThrValAspGlyIleMetThrIleAspLeuAspProValIleTyr>

7310      7320      7330      7340      7350      7360      7370      7380      7390      7400
GATTCAAAATTTGAAAAGCAACTAGGACAGGTTATGCTCCTGGTTCTGTGTGCAGTTCAACTTTTGTTAATGAGAACATCATGGGCTTTTTGTGAAGCTC
AspSerLysPheGluLysGlnLeuGlyGlnValMetLeuLeuValLeuCysAlaValGlnLeuLeuLeuMetArgThrSerTrpAlaPheCysGluAla>

7410      7420      7430      7440      7450      7460      7470      7480      7490      7500
TAACCCTAGCCACAGGACCAATAACAACACTCTGGGAAGGATCACCTGGGAAGTTCTGGAACACCACGATAGCTGTTTCCATGGCGAACATCTTTAGAGG
LeuThrLeuAlaThrGlyProIleThrThrLeuTrpGluGlySerProGlyLysPheTrpAsnThrThrIleAlaValSerMetAlaAsnIlePheArgGly>

7510      7520      7530      7540      7550      7560      7570      7580      7590      7600
GAGCTATTTAGCAGGAGCTGGGCTTGCTTTTTCTATCATGAAATCAGTTGGAACAGGAAAGAGAGGGACAGGGTCACAGGGTGAAACCTTGGGAGAAAAG
SerTyrLeuAlaGlyAlaGlyLeuAlaPheSerIleMetLysSerValGlyThrGlyLysArgGlyThrGlySerGlnGlyGluThrLeuGlyGluLys>

7610      7620      7630      7640      7650      7660      7670      7680      7690      7700
TGGAAAAAGAAATTGAATCAATTACCCCGGAAAGAGTTTGACCTTTACAAGAAATCCGGAATCACTGAAGTGGATAGAACAGAAGCCAAAGAAGGGTTGA
TrpLysLysLysLeuAsnGlnLeuProArgLysGluPheAspLeuTyrLysLysSerGlyIleThrGluValAspArgThrGluAlaLysGluGlyLeu>

7710      7720      7730      7740      7750      7760      7770      7780      7790      7800
AAAGAGGAGAAATAACACACCATGCCGTGTCCAGAGGCAGCGCAAAACTTCAATGGTTCGTGGAGAGAAACATGGTCATCCCCGAAGGAAGAGTCATAGA
LysArgGlyGluIleThrHisHisAlaValSerArgGlySerAlaLysLeuGlnTrpPheValGluArgAsnMetValIleProGluGlyArgValIleAsp>

7810      7820      7830      7840      7850      7860      7870      7880      7890      7900
CTTAGGCTGTGGAAGAGGAGGCTGGTCATATTATTGTGCAGGACTGAAAAAAGTTACAGAAGTGCGAGGATACACAAAAGGCGGCCCAGGACATGAAGAA
LeuGlyCysGlyArgGlyGlyTrpSerTyrTyrCysAlaGlyLeuLysLysValThrGluValArgGlyTyrThrLysGlyGlyProGlyHisGluGlu>

7910      7920      7930      7940      7950      7960      7970      7980      7990      8000
CCAGTACCTATGTCTACATACGGATGGAACATAGTCAAGTTAATGAGTGGAAAGGATGTGTTTTATCTTCCACCTGAAAAGTGTGATACTCTATTGTGTG
ProValProMetSerThrTyrGlyTrpAsnIleValLysLeuMetSerGlyLysAspValPheTyrLeuProProGluLysCysAspThrLeuLeuCys>

8010      8020      8030      8040      8050      8060      8070      8080      8090      8100
ACATTGGAGAATCTTCACCAAGCCCAACAGTGGAAGAAAGCAGAACCATAAGAGTCTTGAAGATGGTTGAACCATGGCTAAAAAATAACCAGTTTTGCAT
AspIleGlyGluSerSerProSerProThrValGluGluSerArgThrIleArgValLeuLysMetValGluProTrpLeuLysAsnAsnGlnPheCysIle>

8110      8120      8130      8140      8150      8160      8170      8180      8190      8200
TAAAGTATTGAACCCTTACATGCCAACTGTGATTGAGCACCTAGAAAGACTACAAAGGAAACATGGAGGAATGCTTGTGAGAAATCCACTCTCACGAAAC
LysValLeuAsnProTyrMetProThrValIleGluHisLeuGluArgLeuGlnArgLysHisGlyGlyMetLeuValArgAsnProLeuSerArgAsn>

8210      8220      8230      8240      8250      8260      8270      8280      8290      8300
TCCACGCACGAAATGTACTGGATATCTAATGGCACAGGCAATATCGTTTCTTCAGTCAACATGGTATCCAGATTGCTACTTAACAGATTCACAATGACAC
SerThrHisGluMetTyrTrpIleSerAsnGlyThrGlyAsnIleValSerSerValAsnMetValSerArgLeuLeuLeuAsnArgPheThrMetThr>

8310      8320      8330      8340      8350      8360      8370      8380      8390      8400
ATAGGAGACCCACCATAGAAAAGATGTGGATTTAGGAGCGGGGACCCGACATGTCAATGCGGAACCAGAAACACCCAACATGGATGTCATTGGGGAAAG
HisArgArgProThrIleGluLysAspValAspLeuGlyAlaGlyThrArgHisValAsnAlaGluProGluThrProAsnMetAspValIleGlyGluArg>

8410      8420      8430      8440      8450      8460      8470      8480      8490      8500
AATAAGAAGGATCAAGGAGGAGCATAGTTCAACATGGCACTATGATGATGAAAATCCTTATAAAACGTGGGCTTACCATGGATCCTATGAAGTTAAGGCC
IleArgArgIleLysGluGluHisSerSerThrTrpHisTyrAspAspGluAsnProTyrLysThrTrpAlaTyrHisGlySerTyrGluValLysAla>

8510      8520      8530      8540      8550      8560      8570      8580      8590      8600
ACAGGCTCAGCCTCCTCCATGATAAATGGAGTCGTGAAACTCCTCACGAAACCATGGGATGTGGTGCCCATGGTGACACAGATGGCAATGACGGATACAA
ThrGlySerAlaSerSerMetIleAsnGlyValValLysLeuLeuThrLysProTrpAspValValProMetValThrGlnMetAlaMetThrAspThr>

8610      8620      8630      8640      8650      8660      8670      8680      8690      8700
CCCCATTCGGCCAGCAAAGGGTTTTTAAAGAGAAGTGGACACCAGGACACCCAGACCTATGCCAGGAACAAGAAAGGTTATGGAGATCACAGCGGAATG
ThrProPheGlyGlnGlnArgValPheLysGluLysValAspThrArgThrProArgProMetProGlyThrArgLysValMetGluIleThrAlaGluTrp>

8710      8720      8730      8740      8750      8760      8770      8780      8790      8800
```

APPENDIX 2-continued

Nucleotide and amino acid sequence of DEN3 (Sleman/78) cDNA plasmid p3

```
GCTTTGGAGAACCCTGGGAAGGAACAAAAGACCCAGATTATGTACGAGAGAGGAGTTCACAAAAAAGGTCAGAACCAACGCAGCTATGGGCGCCGTTTTT
LeuTrpArgThrLeuGlyArgAsnLysArgProArgLeuCysThrArgGluGluPheThrLysLysValArgThrAsnAlaAlaMetGlyAlaValPhe>

8810      8820      8830      8840      8850      8860      8870      8880      8890      8900
ACAGAGGAGAACCAATGGGACAGTGCTAGAGCTGCTGTTGAGGATGAAGAATTCTGGAAACTCGTGGACAGAGAACGTGAACTCCACAAATTGGGCAAGT
ThrGluGluAsnGlnTrpAspSerAlaArgAlaAlaValGluAspGluGluPheTrpLysLeuValAspArgGluArgGluLeuHisLysLeuGlyLys>

8910      8920      8930      8940      8950      8960      8970      8980      8990      9000
GTGGAAGCTGCGTTTACAACATGATGGGCAAGAGAGAGAAGAAACTTGGAGAGTTTGGCAAAGCAAAAGGCAGTAGAGCCATATGGTACATGTGGTTGGG
CysGlySerCysValTyrAsnMetMetGlyLysArgGluLysLysLeuGlyGluPheGlyLysAlaLysGlySerArgAlaIleTrpTyrMetTrpLeuGly>

9010      9020      9030      9040      9050      9060      9070      9080      9090      9100
AGCCAGATACCTTGAGTTCGAAGCACTCGGATTCTTAAATGAAGACCATTGGTTCTCGCGTGAAAACTCTTACAGTGGAGTAGAAGGAGAAGGACTGCAC
AlaArgTyrLeuGluPheGluAlaLeuGlyPheLeuAsnGluAspHisTrpPheSerArgGluAsnSerTyrSerGlyValGluGlyGluGlyLeuHis>

9110      9120      9130      9140      9150      9160      9170      9180      9190      9200
AAGCTGGGATACATCTTAAGAGACATTTCCAAGATACCCGGAGGAGCTATGTATGCTGATGACACAGCTGGTTGGGACACAAGAATAACAGAAGATGACC
LysLeuGlyTyrIleLeuArqAspIleSerLysIleProGlyGlyAlaMetTyrAlaAspAspThrAlaGlyTrpAspThrArgIleThrGluAspAsp>

9210      9220      9230      9240      9250      9260      9270      9280      9290      9300
TGCACAATGAGGAAAAAATCACACAGCAAATGGACCCTGAACACAGGCAGTTAGCAAACGCTATATTCAAGCTCACATACCAAAACAAAGTGGTCAAAGT
LeuHisAsnGluGluLysIleThrGlnGlnMetAspProGluHisArgGlnLeuAlaAsnAlaIlePheLysLeuThrTyrGlnAsnLysValValLysVal>

9310      9320      9330      9340      9350      9360      9370      9380      9390      9400
TCAACGACCAACTCCAAAGGGCACGGTAATGGACATCATATCTAGGAAAGACCAAAGAGGCAGTGGACAGGTGGGAACTTATGGTCTGAATACATTCACC
GlnArgProThrProLysGlyThrValMetAspIleIleSerArgLysAspGlnArgGlySerGlyGlnValGlyThrTyrGlyLeuAsnThrPheThr>

9410      9420      9430      9440      9450      9460      9470      9480      9490      9500
AACATGGAAGCCCAGTTAATCAGACAAATGGAAGGAGAAGGTGTGTTGTCGAAGGCAGACCTCGAGAACCCTCATCTGCTAGAGAAGAAAGTTACACAAT
AsnMetGluAlaGlnLeuIleArgGlnMetGluGlyGluGlyValLeuSerLysAlaAspLeuGluAsnProHisLeuLeuGluLysLysValThrGln>

9510      9520      9530      9540      9550      9560      9570      9580      9590      9600
GGTTGGAAACAAAAGGAGTGGAGAGGTTAAAAAGAATGGCCATCAGCGGGGATGATTGCGTGGTGAAACCAATTGATGACAGGTTCGCCAATGCCCTGCT
TrpLeuGluThrLysGlyValGluArgLeuLysArgMetAlaIleSerGlyAspAspCysValValLysProIleAspAspArgPheAlaAsnAlaLeuLeu>

9610      9620      9630      9640      9650      9660      9670      9680      9690      9700
TGCCCTGAATGACATGGGAAAAGTTAGGAAGGACATACCTCAATGGCAGCCATCAAAGGGATGGCATGATTGGCAACAGGTCCCTTTCTGCTCCCACCAC
AlaLeuAsnAspMetGlyLysValArgLysAspIleProGlnTrpGlnProSerLysGlyTrpHisAspTrpGlnGlnValProPheCysSerHisHis>

9710      9720      9730      9740      9750      9760      9770      9780      9790      9800
TTTCATGAATTGATCATGAAAGATGGAAGAAAGTTGGTAGTTCCCTGCAGACCTCAGGATGAATTAATCGGGAGAGCGAGAATCTCTCAAGGAGCAGGAT
PheHisGluLeuIleMetLysAspGlyArgLysLeuValValProCysArgProGlnAspGluLeuIleGlyArgAlaArgIleSerGlnGlyAlaGly>

9810      9820      9830      9840      9850      9860      9870      9880      9890      9900
GGAGCCTTAGAGAAACTGCATGCCTAGGGAAAGCCTACGCCCAAATGTGGACTCTCATGTACTTTCACAGAAGAGATCTTAGACTAGCATCCAACGCCAT
TrpSerLeuArgGluThrAlaCysLeuGlyLysAlaTyrAlaGlnMetTrpThrLeuMetTyrPheHisArgArgAspLeuArgLeuAlaSerAsnAlaIle>

9910      9920      9930      9940      9950      9960      9970      9980      9990     10000
ATGTTCAGCAGTACCAGTCCATTGGGTCCCCACAAGCAGAACGACGTGGTCTATTCATGCTCACCATCAGTGGATGACTACAGAAGACATGCTTACTGTT
CysSerAlaValProValHisTrpValProThrSerArgThrThrTrpSerIleHisAlaHisHisGlnTrpMetThrThrGluAspMetLeuThrVal>

10010     10020     10030     10040     10050     10060     10070     10080     10090     10100
TGGAACAGGGTGTGGATAGAGGATAATCCATGGATGGAAGACAAAACTCCAGTCAAAACCTGGGAAGATGTTCCATATCTAGGGAAGAGAGAAGACCAAT
TrpAsnArgValTrpIleGluAspAsnProTrpMetGluAspLysThrProValLysThrTrpGluAspValProTyrLeuGlyLysArgGluAspGln>

10110     10120     10130     10140     10150     10160     10170     10180     10190     10200
GGTGCGGATCACTCATTGGTCTCACTTCCAGAGCAACCTGGGCCCAGAACATACTTACGGCAATCCAACAGGTGAGAAGCCTTATAGGCAATGAAGAGTT
TrpCysGlySerLeuIleGlyLeuThrSerArgAlaThrTrpAlaGlnAsnIleLeuThrAlaIleGlnGlnValArgSerLeuIleGlyAsnGluGluPhe>

10210     10220     10230     10240     10250     10260     10270     10280     10290     10300
TCTGGACTACATGCCTTCGATGAAGAGATTCAGGAAGGAGGAGGAGTCAGAGGGAGCCATTTGGTAAACGTAGGAAGTGAAAAAGAGGCAAACTGTCAGG
             LeuAspTyrMetProSerMetLysArgPheArgLysGluGluGluSerGluGlyAlaIleTrp***>

10310     10320     10330     10340     10350     10360     10370     10380     10390     10400
CCACCTTAAGCCACAGTACGGAAGAAGCTGTGCAGCCTGTGAGCCCCGTCCAAGGACGTTAAAAGAAGAAGTCAGGCCCAAAAGCCACGGTTTGAGCAAA 10410     10420     10430     10440     10450     10460     10470     10480     10490     10500
CCGTGCTGCCTGTGGCTCCGTCGTGGGGACGTAAAACCTGGGAGGCTGCAAACTGTGGAAGCTGTACGCACGGTGTAGCAGACTAGCGGTTAGAGGAGAC 10510     10520     10530     10540     10550     10560     10570     10580     10590     10600
CCCTCCCATGACACAACGCAGCAGCGGGGCCCGAGCTCTGAGGGAAGCTGTACCTCCTTGCAAAGGACTAGAGGTTAGAGGAGACCCCCCGCAAATAAAA 10610     10620     10630     10640     10650     10660     10670     10680     10690     10700
ACAGCATATTGACGCTGGGAGAGACCAGAGATCCTGCTGTCTCCTCAGCATCATTCCAGGCACAGAACGCCAGAAAATGGAATGGTGCTGTTGAATCAAC 10710     10720     10730     10740     10750     10760     10770     10780     10790     10800
```

APPENDIX 2-continued

Nucleotide and amino acid sequence of DEN3 (Sleman/78) cDNA plasmid p3

```
AGGTTCTGGTACCGGTAGGCATCGTGGTGTCACGCTCGTCGTTTGGTATGGCTTCATTCAGCTCCGGTTCCCAACGATCAAGGCGAGTTACATGATCCCC 10810      10820      10830      10840      10850      10860      10870      10880      10890      10900
CATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCAT 10910      10920      10930      10940      10950      10960      10970      10980      10990      11000
AATTCTCTTACTGTCATGCCATCCGTAAGATGCTTTTCTGTGACTGGTGAGTACTCAACCAAGTCATTCTGAGAATAGTGTATGCGGCGACCGAGTTGCT 11010      11020      11030      11040      11050      11060      11070      11080      11090      11100
CTTGCCCGGCGTCAACACGGGATAATACCGCGCCACATAGCAGAACTTTAAAAGTGCTCATCATTGGAAAACGTTCTTCGGGGCGAAAACTCTCAAGGAT 11110      11120      11130      11140      11150      11160      11170      11180      11190      11200
CTTACCGCTGTTGAGATCCAGTTCGATGTAACCCACTCGTGCACCCAACTGATCTTCAGCATCTTTTACTTTCACCAGCGTTTCTGGGTGAGCAAAAACA 11210      11220      11230      11240      11250      11260      11270      11280      11290      11300
GGAAGGCAAAATGCCGCAAAAAAGGGAATAAGGGCGACACGGAAATGTTGAATACTCATACTCTTCCTTTTTCAATATTATTGAAGCATTTATCAGGGTT 11310      11320      11330      11340      11350      11360      11370      11380      11390      11400
ATTGTCTCATGAGCGGATACATATTTGAATGTATTTAGAAAAATAAACAAATAGGGGTTCCGCGCACATTTCCCCGAAAAGTGCCACCTGACGTCTAAGA 11410      11420      11430      11440      11450      11460      11470      11480      11490      11500
AACCATTATTATCATGACATTAACCTATAAAAATAGGCGTATCACGAGGCCCTTTCGTCTTCAAGAATTCTCATGTTTGACAGCTTATCATCGATAAGCT 11510      11520      11530      11540      11550      11560      11570      11580      11590      11600
TTAATGCGGTAGTTTATCACAGTTAAATTGCTAACGCAGTCAGGCACCGTGTATGAAATCTAACAATGCGCTCATCGTCATCCTCGGCACCGTCACCCTG 11610      11620      11630      11640      11650      11660      11670      11680      11690      11700
GATGCTGTAGGCATAGGCTTGGTTATGCCGGTACTGCCGGGCCTCTTGCGGGATATCGTCCATTCCGACAGCATCGCCAGTCACTATGGCGTGCTGCTGG 11710      11720      11730      11740      11750      11760      11770      11780      11790      11800
CGCTATATGCGTTGATGCAATTTCTATGCGCACCCGTTCTCGGAGCACTGTCCGACCGCTTTGGCCGCCGCCCAGTCCTGCTCGCTTCGCTACTTGGAGC 11810      11820      11830      11840      11850      11860      11870      11880      11890      11900
CACTATCGACTACGCGATCATGGCGACCACACCCGTCCTGTGGATCCTCTACGCCGGACGCATCGTGGCCGGCATCACCGGCGCCACAGGTGCGGTTGCT 11910      11920      11930      11940      11950      11960      11970      11980      11990      12000
GGCGCCTATATCGCCGACATCACCGATGGGGAAGATCGGGCTCGCCACTTCGGGCTCATGAGCGCTTGTTTCGGCGTGGGTATGGTGGCAGGCCCCGTGG 12010      12020      12030      12040      12050      12060      12070      12080      12090      12100
CCGGGGGACTGTTGGGCGCCATCTCCTTGCATGCACCATTCCTTGCGGCGGCGGTGCTCAACGGCCTCAACCTACTACTGGGCTGCTTCCTAATGCAGGA 12110      12120      12130      12140      12150      12160      12170      12180      12190      12200
GTCGCATAAGGGAGAGCGTCGACCGATGCCCTTGAGAGCCTTCAACCCAGTCAGCTCCTTCCGGTGGGCGCGGGGCATGACTATCGTCGCCGCACTTATG 12210      12220      12230      12240      12250      12260      12270      12280      12290      12300
ACTGTCTTCTTTATCATGCAACTCGTAGGACAGGTGCCGGCAGCGCTCTGGGTCATTTTCGGCGAGGACCGCTTTCGCTGGAGCGCGACGATGATCGGCC 12310      12320      12330      12340      12350      12360      12370      12380      12390      12400
TGTCGCTTGCGGTATTCGGAATCTTGCACGCCCTCGCTCAAGCCTTCGTCACTGGTCCCGCCACCAAACGTTTCGGCGAGAAGCAGGCCATTATCGCCGG 12410      12420      12430      12440      12450      12460      12470      12480      12490      12500
CATGGCGGCCGACGCGCTGGGCTACGTCTTGCTGGCGTTCGCGACGCGAGGCTGGATGGCCTTCCCCATTATGATTCTTCTCGCTTCCGGCGGCATCGGG 12510      12520      12530      12540      12550      12560      12570      12580      12590      12600
ATGCCCGCGTTGCAGGCCATGCTGTCCAGGCAGGTAGATGACGACCATCAGGGACAGCTTCAAGGATCGCTCGCGGCTCTTACCAGCCTAACTTCGATCA 12610      12620      12630      12640      12650      12660      12670      12680      12690      12700
CTGGACCGCTGATCGTCACGGCGATTTATGCCGCCTCGGCGAGCACATGGAACGGGTTGGCATGGATTGTAGGCGCCGCCCTATACCTTGTCTGCCTCCC 12710      12720      12730      12740      12750      12760      12770      12780      12790      12800
CGCGTTGCGTCGCGGTGCATGGAGCCGGGCCACCTCGACCTGAATGGAAGCCGGCGGCACCTCGCTAACGGATTCACCACTCCAAGAATTGGAGCCAATC 12810      12820      12830      12840      12850      12860      12870      12880      12890      12900
AATTCTTGCGGAGAACTGTGAATGCGCAAACCAACCCTTGGCAGAACATATCCATCGCGTCCGCCATCTCCAGCAGCCGCACGCGGCGCATCTCGGGCAG 12910      12920      12930      12940      12950      12960      12970      12980      12990      13000
CGTTGGGTCCTGGCCACGGGTGCGCATGATCGTGCTCCTGTCGTTGAGGACCCGGCTAGGCTGGCGGGGTTGCCTTACTGGTTAGCAGAATGAATCACCG 13010      13020      13030      13040      13050      13060      13070      13080      13090      13100
ATACGCGAGCGAACGTGAAGCGACTGCTGCTGCAAAACGTCTGCGACCTGAGCAACAACATGAATGGTCTTCGGTTTCCGTGTTTCGTAAAGTCTGGAAA 13110      13120      13130      13140      13150      13160      13170      13180      13190      13200
CGCGGAAGTCAGCGCCCTGCACCATTATGTTCCGGATCTGCATCGCAGGATGCTGCTGGCTACCCTGTGGAACACCTACATCTGTATTAACGAAGCGCTG 13210      13220      13230      13240      13250      13260      13270      13280      13290      13300
GCATTGACCCTGAGTGATTTTTCTCTGGTCCCGCCGCATCCATACCGCCAGTTGTTTACCCTCACAACGTTCCAGTAACCGGGCATGTTCATCATCAGTA
```

APPENDIX 2-continued

Nucleotide and amino acid sequence of DEN3 (Sleman/78) cDNA plasmid p3

```
     13310      13320      13330      13340      13350      13360      13370      13380      13390      13400
ACCCGTATCGTGAGCATCCTCTCTCGTTTCATCGGTATCATTACCCCCATGAACAGAAATCCCCCTTACACGGAGGCATCAGTGACCAAACAGGAAAAAA 13410      13420      13430      13440      13450      13460      13470      13480      13490      13500
CCGCCCTTAACATGGCCCGCTTTATCAGAAGCCAGACATTAACGCTTCTGGAGAAACTCAACGAGCTGGACGCGGATGAACAGGCAGACATCTGTGAATC 13510      13520      13530      13540      13550      13560      13570      13580      13590      13600
GCTTCACGACCACGCTGATGAGCTTTACCGCAGCTGCCTCGCGCGTTTCGGTGATGACGGTGAAAACCTCTGACACATGCAGCTCCCGGAGACGGTCACA 13610      13620      13630      13640      13650      13660      13670      13680      13690      13700
GCTTGTCTGTAAGCGGATGCCGGGAGCAGACAAGCCCGTCAGGGCGCGTCAGCGGGTGTTGGCGGGTGTCGGGGCGCAGCCATGACCCAGTCACGTAGCG 13710      13720      13730      13740      13750      13760      13770      13780      13790      13800
ATAGCGGAGTGTATACTGGCTTAACTATGCGGCATCAGAGCAGATTGTACTGAGAGTGCACCATATGCGGTGTGAAATACCGCACAGATGCGTAAGGAGA 13810      13820      13830      13840      13850      13860      13870      13880      13890      13900
AAATACCGCATCAGGCGCTCTTCCGCTTCCTCGCTCACTGACTCGCTGCGCTCGGTCGTTCGGCTGCGGCGAGCGGTATCAGCTCACTCAAAGGCGGTAA 13910      13920      13930      13940      13950      13960      13970      13980      13990      14000
TACGGTTATCCACAGAATCAGGGGATAACGCAGGAAAGAACATGTGAGCAAAAGGCCAGCAAAAGGCCAGGAACCGTAAAAAGGCCGCGTTGCTGGCGTT 14010      14020      14030      14040      14050      14060      14070      14080      14090      14100
TTTCCATAGGCTCCGCCCCCCTGACGAGCATCACAAAAATCGACGCTCAAGTCAGAGGTGGCGAAACCCGACAGGACTATAAAGATACCAGGCGTTTCCC 14110      14120      14130      14140      14150      14160      14170      14180      14190      14200
CCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCT 14210      14220      14230      14240      14250      14260      14270      14280      14290      14300
CACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAA 14310      14320      14330      14340      14350      14360      14370      14380      14390      14400
CTATCGTCTTGAGTCCAACCCGGTAAGACACGACTTATCGCCACTGGCAGCAGCCACTGGTAACAGGATTAGCAGAGCGAGGTATGTAGGCGGTGCTACA 14410      14420      14430      14440      14450      14460      14470      14480      14490      14500
GAGTTCTTGAAGTGGTGGCCTAACTACGGCTACACTAGAAGGACAGTATTTGGTATCTGCGCTCTGCTGAAGCCAGTTACCTTCGGAAAAAGAGTTGGTA 14510      14520      14530      14540      14550      14560      14570      14580      14590      14600
GCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTT 14610      14620      14630      14640      14650      14660      14670      14680      14690      14700
GATCTTTTCTACGGGGTCTGACGCTCAGTGGAACGAAAACTCACGTTAAGGGATTTTGGTCATGAGATTATCAAAAAGGATCTTCACCTAGATCCTTTTA 14710      14720      14730      14740      14750      14760      14770      14780      14790      14800
AATTAAAAATGAAGTTTTAAATCAATCTAAAGTATATATGAGTAAACTTGGTCTGACAGTTACCAATGCTTAATCAGTGAGGCACCTATCTCAGCGATCT 14810      14820      14830      14840      14850      14860      14870      14880      14890      14900
GTCTATTTCGTTCATCCATAGTTGCCTGACTCCCCGTCGTGTAGATAACTACGATACGGGAGGGCTTACCATCTGGCCCCAGTGCTGCAATGATACCGCG 14910      14920      14930      14940      14950      14960      14970      14980      14990      15000
AGACCCACGCTCACCGGCTCCAGATTTATCAGCAATAAACCAGCCAGCCGGAAGGGCCGAGCGCAGAAGTGGTCCTGCAACTTTATCCGCCTCCATCCAG 15010      15020      15030      15040      15050      15060      15070      15080      15090      15100
TCTATTAATTGTTGCCGGGAAGCTAGAGTAAGTAGTTCGCCAGTTAATAGTTTGCGCAACGTTGTTGCCATTGCTGCAAGATCTGGCTAGCGATGACCCT 15110      15120      15130      15140      15150
GCTGATTGGTTCGCTGACCATTTCCGGGCGCGCCGATTTAGGTGACACTATAG
```

Bases 1 to 10707: DEN3 virus genome cDNA
Bases 95 to 10264: DEN3 polyprotein ORF
Bases 95 to 436: C protein ORF
Bases 437 to 934: prM protein ORF
Bases 935 to 2413: E protein ORF
Bases 2414 to 3469: NS1 protein ORF
Bases 3470 to 4123: NS2A protein ORF
Bases 4124 to 4513: NS2B protein ORF
Bases 4514 to 6370: NS3 protein ORF
Bases 6371 to 6751: NS4A protein ORF
Bases 6752 to 6820: 2K protein ORF
Bases 6821 to 7564: NS4B protein ORF
Bases 7575 to 10264: NS5 protein ORF

APPENDIX 3

Nucleotide and amino acid sequence of DENt (Puerto Rico/94) CME chimeric region

Bases 1 to 88 (BglII): DEN4
Bases 89 (BglII) to 2348 (XhoI): DEN1
Bases 2349 (XhoI) to 2426: DEN4

Bases 102 to 443: C protein ORF
Bases 444 to 941: prM protein ORF
Bases 942 to 2426: B protein ORF

```
                10        20        30        40        50        60        70        80        90
100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA
               110       120       130       140       150       160       170       180       190
200
AATGAACAACCAACGGAAAAAGACGGGTCGACCGTCTTTCAATATGCTGAAACGCGCGAGAAACCGCGTGTCAACTGGTTCACAGTTGGCGAAGAGATTC
MetAsnAsnGlnArgLysLysThrGlyArgProSerPheAsnMetLeuLysArgAlaArgAsnArgValSerThrGlySerGlnLeuAlaLysArgPhe>
               210       220       230       240       250       260       270       280       290
300
TCAAAAGGATTGCTTTCAGGCCAAGGACCCATGAAATTGGTGATGGCTTTCATAGCATTTCTAAGATTTCTAGCCATACCCCCAACAGCAGGAATTTTGG
SerLysGlyLeuLeuSerGlyGlnGlyProMetLysLeuValMetAlaPheIleAlaPheLeuArgPheLeuAlaIleProProThrAlaGlyIleLeu>
               310       320       330       340       350       360       370       380       390
400
CTAGATGGAGCTCATTCAAGAAGAATGGAGCGATCAAAGTGTTACGGGGTTTCAAAAAGAGATCTCAAGCATGTTGAACATTATGAACAGGAGGAAAAA
AlaArgTrpSerSerPheLysLysAsnGlyAlaIleLysValLeuArgGlyPheLysLysGluIleSerSerMetLeuAsnIleMetAsnArgArgLysLys>
               410       420       430       440       450       460       470       480       490
500
ATCTGTGACCATGCTCCTCATGCTGCTGCCCACAGCCCTGGCGTTCCATTTGACCACACGAGGGGGAGAGCCACACATGATAGTTAGTAAGCAGGAAAGA
SerValThrMetLeuLeuMetLeuLeuProThrAlaLeuAlaPheHisLeuThrThrArgGlyGlyGluProHisMetIleValSerLysGlnGluArg>
               510       520       530       540       550       560       570       580       590
600
GGAAAGTCACTGTTGTTTAAGACCTCTGCAGGCATCAATATGTGCACTCTCATTGCGATGGATTTGGGAGAGTTATGCGAGGACACAATGACCTACAAAT
GlyLysSerLeuLeuPheLysThrSerAlaGlyIleAsnMetCysThrLeuIleAlaMetAspLeuGlyGluLeuCysGluAspThrMetThrTyrLys>
               610       620       630       640       650       660       670       680       690
700
GCCCCCGGATCACTGAGGCGGAACCAGATGACGTTGACTGCTGGTGCAATGCCACAGACACATGGGTGACCTATGGGACGTGTTCTCAAACCGGCGAACA
CysProArgIleThrGluAlaGluProAspAspValAspCysTrpCysAsnAlaThrAspThrTrpValThrTyrGlyThrCysSerGlnThrGlyGluHis>
               710       720       730       740       750       760       770       780       790
800
CCGACGAGACAAACGTTCCGTGGCACTGGCCCCACACGTGGGACTTGGTCTAGAAACAAGAACCGAAACATGGATGTCCTCTGAAGGTGCCTGGAAACAA
ArgArgAspLysArgSerValAlaLeuAlaProHisValGlyLeuGlyLeuGluThrArgThrGluThrTrpMetSerSerGluGlyAlaTrpLysGln>
               810       820       830       840       850       860       870       880       890
900
GTACAAAAAGTGGAGACTTGGGCTTTGAGACACCCAGGATTCACGGTGACAGCCCTTTTTTTAGCACATGCCATAGCAACATCCATTACTCAGAAAGGGA
ValGlnLysValGluThrTrpAlaLeuArgHisProGlyPheThrValThrAlaLeuPheLeuAlaHisAlaIleGlyThrSerIleThrGlnGlyGly>
               910       920       930       940       950       960       970       980       990
1000
TCATTTTCATTCTGCTGATGCTAGTAACACCATCAATGGCCATGCGATGTGTGGGAATAGGCAACAGAGACTTCGTTGAAGGACTGTCAGGAGCAACGTG
IleIlePheIleLeuLeuMetLeuValThrProSerMetAlaMetArgCysValGlyIleGlyAsnArgAspPheValGluGlyLeuSerGlyAlaThrTrp>
               1010      1020      1030      1040      1050      1060      1070      1080      1090
1100
GGTTGGACGTGGTATTGGAGCATGGAAGCTGCGTCACCACCATGGCAAAAGATAAACCAACATTGGACATTGAACTCTTGAAGACGGAGGTCACAAACCCT
ValAspValValLeuGluHisGlySerCysValThrThrMetAlaLysAspLysProThrLeuAspIleGluLeuLeuLysThrGluValThrAsnPro>
               1110      1120      1130      1140      1150      1160      1170      1180      1190
1200
GCCGTCTTGCGCAAACTGTGCATTGAAGCTAAAATATCAAACACCACCACCGATTCAAGGTGTCCAACACAAGGAGAGGCTACACTGGTGGAAGAACAGG
AlaValLeuArgLysLeuCysIleGluAlaLysIleSerAsnThrThrThrAspSerArgCysProThrGlnGlyGluAlaThrLeuValGluGluGln>
               1210      1220      1230      1240      1250      1260      1270      1280      1290
1300
ACTCGAACTTTGTGTGTCGACGAACGTTTGTGGACAGAGGCTGGGGTAATGGCTGCGGACTATTGGAAAAGGAAGCCTACTGACGTGTGCTAAGTTCAA
AspSerAsnPheValCysArgArgThrPheValAspArgGlyTrpGlyAsnGlyCysGlyLeuPheGlyLysGlySerLeuLeuThrCydAlaLysPheLys>
               1310      1320      1330      1340      1350      1360      1370      1380      1390
1400
GTGTGTGACAAAACTAGAAGGAAAGATAGTTCAATATGAAAACTTAAAATATTCAGTGATAGTCACTGTCCACACTGGGGACCAGCACCAGGTGGGAAAC
CysValThrLysLeuGluGlyLysIleValGlnTyrGluAsnLeuLysTyrSerValIleValThrValHisThrGlyAspGlnHisGlnValGlyAsn>
```

APPENDIX 3-continued

Nucleotide and amino acid sequence of DENt (Puerto Rico/94) CME chimeric region

```
               1410      1420      1430      1440      1450      1460      1470      1480      1490
1500
GAGACTACAGAACATGGAACAATTGCAACCATAACACCTCAAGCTCCTACGTCGGAAATACAGCTGACTGACTACGGAGCCCTCACATTGGACTGCTCGC
GluThrThrGluHisGLyThrIleAlaThrIleThrProGlnAlaProThrSerGluIleGlnLeuThrAspTyrGlyAlaLeuThrLeuAspCysSer>
               1510      1520      1530      1540      1550      1560      1570      1580      1590
1600
CTAGAACAGGGCTGGACTTTAATGAGATGGTTCTATTGACAATGAAAGAAAAATCATGGCTTGTCCACAAACAATGGTTTCTAGACTTACCACTGCCTTG
ProArgThrGlyLeuAspPheAsnGluMetValLeuLeuThrMetLysGluLysSerTrpLeuValHisLysGlnTrpPheLeuAspLeuProLeuProTrp>
               1610      1620      1630      1640      1650      1660      1670      1680      1690
1700
GACTTCAGGAGCTTCAACATCTCAAGAGACTTGGAACAGACAAGATTTGCTGGTCACATTCAAGACAGCTCATGCAAAGAAACAGGAAGTAGTCGTACTG
ThrSerGlyAlaSerThrSerGlnGluThrTrpAsnArgGlnAspLeuLeuValThrPheLysThrAlaHisAlaLysLysGlnGluValValValLeu>
               1710      1720      1730      1740      1750      1760      1770      1780      1790
1800
GGATCACAGGAAGGAGCAATGCACACTGCGTTGACTGGGGCGACAGAAATCCAGACGTCAGGAACGACAACAATCTTTGCAGGACACCTGAAATGCAGAC
GlySerGlnGluGLyAlaMetHisThrAlaLeuThrGlyAlaThrGluIleGlnThrSerGlyThrThrThrIlePheAlaGlyHisLeuLyscysArg>
               1810      1820      1830      1840      1850      1860      1870      1880      1890
1900
TAAAAATGGATAAACTGACTTTAAAAGGGATGTCATATGTAATGTGCACAGGCTCATTTAAGCTAGAGAAGGAAGTGGCTGAGACCCAGCATGGAACTGT
LeuLysMetAspLysLeuThrLeuLysGlyMetSerTyrValMetCysThrGlySerPheLysLeuGluLysGluValAlaGluThrGlnHisGlyThrVal>
               1910      1920      1930      1940      1950      1960      1970      1980      1990
2000
TTTAGTGCAGGTTAAATACGAAGGAACAGATGCGCCATGCAAGATCCCTTTTTCGGCCCAAGATGAGAAAGGAGTGACCCAGAATGGGAGATTGATAACA
LeuValGlnValLysTyrGluGLyThrAspAlaProCysLysIleProPheSerAlaGlnAspGluLysGlyValThrGlnAsnGlyArgLeuIleThr>
               2010      2020      2030      2040      2050      2060      2070      2080      2090
2100
GCCAACCCCATAGTCACTGACAAAGAAAAACCAGTCAACATTGAGACAGAACCACCTTTTGGTGAGAGCTACATCGTGGTAGGGGCAGGTGAAAAAGCTT
AlaAsnProIleValThrAspLysGluLysProValAsnIleGluThrGluProProPheGlyGluSerTyrIleValValGlyAlaGlyGluLysAla>
               2110      2120      2130      2140      2150      2160      2170      2180      2190
2200
TGAAACTGAGCTGGTTCAAGAAAGGGAGCAGCATAGGGAAAATGTTCGAAGCAACTGCCCGAGGAGCGCGAAGGATGGCTATCCTGGGAGACACCGCATG
LeuLysLeuSerTrpPheLysLysGlySerSerIleGlyLysMetPheGluAlaThrAlaArgGlyAlaArgArgMetAlaIleLeuGlyAspThrAlaTrp>
               2210      2220      2230      2240      2250      2260      2270      2280      2290
2300
GGACTTTGGCTCTATAGGAGGAGTGTTCACATCAGTGGGAAAATTGGTACACCAGGTTTTTGGAGCCGCATATGGGGTTCTGTTCAGCGGTGTTTCTTGG
AspPheGlySerIleGlyGLyValPheThrSerValGlyLysLeuValHisGlnValPheGlyAlaAlatyrGlyValLeuPheSerGlyValSerTrp>
               2310      2320      2330      2340      2350      2360      2370      2380      2390
2400
ACCATGAAAATAGGAATAGGGATTCTGCTGACATGGCTAGGATTAAACTCGAGGAACACTTCAATGGCTATGACGTGCATAGCTGTTGGAGGAATCACTC
ThrMetLysIleGLyIleGlyIleLeuLeuThrTrpLeuGlyLeuAsnSerArgAsnThrSerMetAlaMetThrCysIleAlaValGlyGlyIleThr>
               2410      2420
TGTTTCTGGGCTTCACAGTTCAAGCA
LeuPheLeuGlyPheThrValGlnAla>
```

APPENDIX 4

Nucleotide and amino acid sequence of DEN1 (Puerto Rico/94) ME chimeric region

```
Bases 1 to 404 (PstI): DEN4
Bases 405 (PstI) to 2345 (XhoI): DEN1
Bases 2346 (XhoI) to 2423: DEN4

Bases 102 to 440: C protein ORF
Bases 441 to 938: prM protein ORF
Bases 939 to 2423: B protein ORF 10        20        30        40        50        60        70        80        90
100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA
               110       120       130       140       150       160       170       180       190
200
AATGAACCAACGAAAAAAGGTGGTTAGACCACCTTCAATATGCTGAAACGCGAGAGAAACCGCGTATCAACCCCTCAAGGGTTGGTGAAGAGGATTCTCA
MetAsnGlnArgLysLysValValArgProProPheAsnMetLeuLysArgGluArgAsnArgValSerThrProGlnGlyLeuValLysArgPheSer>
```

APPENDIX 4-continued

Nucleotide and amino acid sequence of DEN1 (Puerto Rico/94) ME chimeric region

```
         210       220       230       240       250       260       270       280       290
300
ACCGGACTTTTTTCTGGGAAAGGACCCTTACGGATGGTGCTAGCATTCATCACGTTTTTGCGAGTCCTTTCCATCCCACCAACAGCAGGGATTCTGAAGA
ThrGlyLeuPheSerGlyLysGlyProLeuArgMetValLeuAlaPheIleThrPheLeuArgValLeuSerIleProProThrALaGlyIleLeuLys>
         310       320       330       340       350       360       370       380       390
400
GATGGGGACAGTTGAAGAAAAATAAGGCCATCAAGATACTGATTGGATTCAGGAAGGAGATAGGCCGCATGCTGAACATCTTGAACGGGAGAAAAAGGTC
ArgTrpGlyGlnLeuLysLysAsnLysAlaIleLysIleLeuIleGlyPheArgLysGluIleGlyArgMetLeuAsnIleLeuAsnGlyArgLysArgSer>
         410       420       430       440       450       460       470       480       490
500
TGCAGCCATGCTCCTCATGCTGCTGCCCACAGCCCTGGCGTTCCATTTGACCACACGAGGGGGAGAGCCACACATGATAGTTAGTAAGCAGGAAAGAGGA
AlaAlaMetLeuLeuMetLeuLeuProThrALaLeuAlaPheHisLeuThrThrArgGlyGlyGluProHisMetIleValSerLysGlnGluArgGly>
         510       520       530       540       550       560       570       580       590
600
AAGTCACTGTTGTTTAAGACCTCTGCAGGCATCAATATGTGCACTCTCATTGCGATGGATTTGGGAGAGTTATGCGAGGACACAATGACCTACAAATGCC
LysSerLeuLeuPheLysThrSerAlaGlyIleAsnMetCysThrLeuIleAlaMetAspLeuGlyGluLeuCysGluAspThrMetThrTyrLysCys>
         610       620       630       640       650       660       670       680       690
700
CCCGGATCACTGAGGCGGAACCAGATGACGTTGACTGCTGGTGCAATGCCACAGACACATGGGTGACCTATGGGACGTGTTCTCAAACCGGCGAACACCG
ProArgIleThrGluAlaGluProAspAspValAspCysTrpCysAsnAlaThrAspThrTrpValThrTyrGlyThrCysSerGlnThrGlyGluHisArg>
         710       720       730       740       750       760       770       780       790
800
ACGAGACAAACGTTCCGTGGCACTGGCCCCACACGTGGGACTTGGTCTAGAAACAAGAACCGAAACATGGATGTCCTCTGAAGGTGCCTGGAAACAAGTA
ArgAspLysArgSerValAlaLeuAlaProHisValGlyLeuGlyLeuGluThrArgThrGluThrTrpMetSerSerGluGlyAlaTrpLysGlnVal>
         810       820       830       840       850       860       870       880       890
900
CAAAAAGTGGAGACTTGGGCTTTGAGACACCCAGGATTCACGGTGACAGCCCTTTTTTTAGCACATGCCATAGGAACATCCATTACTCAGAAAGGGATCA
GlyLysValGluThrTrpAlaLeuArgHisProGlyPheThrValThrAlaLeuPheLeuAlaHisAlaIleGlyThrSerIleThrGlnLysGlyIle>
         910       920       930       940       950       960       970       980       990
1000
TTTTCATTCTGCTGATGCTAGTAACACCATCAATGGCCATGCGATGTGTGGGAATAGGCAACAGAGACTTCGTTGAAGGACTGTCAGGAGCAACGTGGGT
IlePheIleLeuLeuMetLeuValThrProSerMetALaMetArgCysValGlyIleGlyAsnArgAspPheValGluGlyLeuSerGlyAlaThrTrpVal>
         1010      1020      1030      1040      1050      1060      1070      1080      1090
1100
GGACGTGGTATTGGAGCATGGAAGCTGCGTCACCACCATGGCAAAAGATAAACCAACATTGGACATTGAACTCTTGAAGACGGAGGTCACAAACCCTGCC
AspValValLeuGluHisGlySerCysValThrThrMetAlaLysAspLysProThrLeuAspIleGluLeuLeuLysThrGluValThrAsnProAla>
         1110      1120      1130      1140      1150      1160      1170      1180      1190
1200
GTCTTGCGCAAACTGTGCATTGAAGCTAAAATATCAAACACCACCACCGATTCAAGGTGTCCAACACAAGGAGAGGCTACACTGGTGGAAGAACAGGACT
ValLeuArgLysLeuCysIleGlyAlaLysIleSerAsnThrThrThrAspSerArgCysProThrGlnGlyGLuAlaThrLeuValGluGluGlnAsp>
         1210      1220      1230      1240      1250      1260      1270      1280      1290
1300
CGAACTTTGTGTGTCGACGAACGTTTGTGGACAGAGGCTGGGGTAATGGCTGCGGACTATTTGGAAAAGGAAGCCTACTGACGTGTGCTAAGTTCAAGTG
SerAsnPheValCysArgArgThrPheValAspArgGlyTrpGlyAsnGlyCysGlyLeuPheGlyLysGlySerLeuLeuThrCysALaLysPheLysCys>
         1310      1320      1330      1340      1350      1360      1370      1380      1390
1400
TGTGACAAAACTAGAAGGAAAGATAGTTCAATATGAAAACTTAAAATATTCAGTGATAGTCACTGTCCACACTGGGGACCAGCACCAGGTGGGAAACGAG
ValThrLysLeuGluGlyLysIleValGlnTyrGluAsnLeuLysTyrSerValIleValThrValHisThrGlyAspGlnHisGlnValGlyAsnGlu>
         1410      1420      1430      1440      1450      1460      1470      1480      1490
1500
ACTACAGAACATGGAACAATTGCAACCATAACACCTCAAGCTCCTACGTCGGAAATACAGCTGACTGACTACGGAGCCCTCACATTGGACTGCTCGCCTA
ThrThrGluHisGlyThrIleAlaThrIleThrProGlnAlaProThrSerGluIleGlnLeuThrAspTyrGlyAlaLeuThrLeuAspCysSerPro>
         1510      1520      1530      1540      1550      1560      1570      1580      1590
1600
GAACAGGGCTGGACTTTAATGAGATGGTTCTATTGACAATGAAAGAAAAATCATGGCTTGTCCACAAACAATGGTTTCTAGACTTACCACTGCCTTGGAC
ArgThrGlyLeuAspPheAsnGluMetValLeuLeuThrMetLysGluLysSerTrpLeuValHisLysGlnTrpPheLeuAspLeuProLeuProTrpThr>
         1610      1620      1630      1640      1650      1660      1670      1680      1690
1700
TTCAGGAGCTTCAACATCTCAAGAGACTTGGAACAGACAAGATTTGCTGGTCACATTCAAGACAGCTCATGCAAAGAAACAGGAAGTAGTCGTACTGGGA
SerGlyAlaSerThrSerGlnGluThrTrpAsnArgGlnAspLeuLeuValThrPheLysThrAlaHisAlaLysLysGlnGluValValValLeuGly>
```

APPENDIX 4-continued

Nucleotide and amino acid sequence of DEN1 (Puerto Rico/94) ME chimeric region

```
                   1710       1720       1730       1740       1750       1760       1770       1780       1790

1800
TCACAGGAAGGAGCAATGCACACTGCGTTGACTGGGGCGACAGAAATCCAGACGTCAGGAACGACAACAATCTTTGCAGGACACCTGAAATGCAGACTAA
SerGlnGluGLyAlaMetHisThrAlaLeuThrGlyAlaThrGluIleGlnThrSerGlyThrThrThrIlePheAlaGlyHisLeuLysCysArgLeu>
                   1810       1820       1830       1840       1850       1860       1870       1880       1890

1900
AAATGGATAAACTGACTTTAAAAGGGATGTCATATGTAATGTGCACAGGCTCATTTAAGCTAGAGAAGGAAGTGGCTGAGACCCAGCATGGAACTGTTTT
LysMetAspLysLeuThrLeuLysGlyMetSerTyrValmetCysThrGlySerPheLysLeuGluLysGluValAlaGluThrGlnHisGlyThrValLeu>
                   1910       1920       1930       1940       1950       1960       1970       1980       1990

2000
AGTGCAGGTTAAATACGAAGGAACAGATGCGCCATGCAAGATCCCTTTTTCGGCCCAAGATGAGAAAGGAGTGACCCAGAATGGGAGATTGATAACAGCC
ValGlnValLysTyrGluGlyThrAspAlaProCysLysIleProPheSerAlaGlnAspGluLysGlyValThrGlnAsnGlyArgLeuIleThrAla>
                   2010       2020       2030       2040       2050       2060       2070       2080       2090

2100
AACCCCATAGTCACTGACAAAGAAAAACCAGTCAACATTGAGACAGAACCACCTTTTGGTGAGAGCTACATCGTGGTAGGGGCAGGTGAAAAAGCTTTGA
AsnProIleValThrAspLysGluLysProValAsnIleGluThrGluProProPheGlyGluSerTyrIleValValGlyAlaGlyGluLysAlaLeu>
                   2110       2120       2130       2140       2150       2160       2170       2180       2190

2200
AACTGAGCTGGTTCAAGAAAGGGAGCAGCATAGGGAAAATGTTCGAAGCAACTGCCCGAGGAGCGCGAAGGATGGCTATCCTGGGAGACACCGCATGGGA
LysLeuSerTrpPheLysLysGlySerSerIleGlyLysMetPheGluAlaThrAlaArgGlyAlaArgArgMetAlaIleLeuGlyAspThrAlaTrpAsp>
                   2210       2220       2230       2240       2250       2260       2270       2280       2290

2300
CTTTGGCTCTATAGGAGGAGTGTTCACATCAGTGGGAAAATTGGTACACCAGGTTTTGGAGCCGCATATGGGGTTCTGTTCAGCGGTGTTTCTTGGACC
PheGlySerIleGlyGlyValPheThrSerValGlyLysLeuValHisGlnValPheGlyAlaAlaTyrGlyValLeuPheSerGlyValSerTrpThr>
                   2310       2320       2330       2340       2350       2360       2370       2380       2390

2400
ATGAAAATAGGAATAGGGATTCTGCTGACATGGCTAGGATTAAACTCGAGGAACACTTCAATGGCTATGACGTGCATAGCTGTTGGAGGAATCACTCTGT
MetLysIleGlyIleGlyIleLeuLeuThrTrpLeuGlyLeuAsnSerArgAsnThrSerMetAlaMerThrCysIleAlaValGlyGlyIleThrLeu>
                   2410       2420
TTCTGGGCTTCACAGTTCAAGCA
PheLeuGlyPheThrValGlnAla
```

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

SEQUENCE LISTING

```
<160> NUMBER OF SEQ ID NOS: 53

<210> SEQ ID NO 1
<211> LENGTH: 82
<212> TYPE: RNA
<213> ORGANISM: Dengue 1 virus

<400> SEQUENCE: 1
gcagcagcgg ggcccaacac caggggaagc uguacccugg ugguaaggac uagagguuag      60
aggagacccc ccgcaacaac aa                                               82

<210> SEQ ID NO 2
<211> LENGTH: 84
<212> TYPE: RNA
<213> ORGANISM: Dengue 2 virus

<400> SEQUENCE: 2
agcaacaaug ggggcccaag gugagaugaa gcuguagucu cacuggaagg acuagagguu      60
agaggagacc cccccaaaac aaaa                                             84
```

```
<210> SEQ ID NO 3
<211> LENGTH: 83
<212> TYPE: RNA
<213> ORGANISM: Dengue 3 virus

<400> SEQUENCE: 3
gcagcagcgg ggcccgagcu cugagggaag cguaccucc uugcaaagga cuagagguua    60
gaggagaccc cccgcaaaua aaa                                          83

<210> SEQ ID NO 4
<211> LENGTH: 83
<212> TYPE: RNA
<213> ORGANISM: Dengue 4 virus

<400> SEQUENCE: 4
agcaaaaggg ggcccgaagc caggaggaag cguacuccu gguggaagga cuagagguua    60
gaggagaccc ccccaacaca aaa                                          83

<210> SEQ ID NO 5
<211> LENGTH: 16
<212> TYPE: RNA
<213> ORGANISM: Artificial Sequence
<220> FEATURE:
<223> OTHER INFORMATION: Dengue 1 delta 30

<400> SEQUENCE: 5
ggggcccaag acuaga                                                  16

<210> SEQ ID NO 6
<211> LENGTH: 16
<212> TYPE: RNA
<213> ORGANISM: Artificial Sequence
<220> FEATURE:
<223> OTHER INFORMATION: Dengue 2 delta 30

<400> SEQUENCE: 6
ggggcccaag acuaga                                                  16

<210> SEQ ID NO 7
<211> LENGTH: 16
<212> TYPE: RNA
<213> ORGANISM: Artificial Sequence
<220> FEATURE:
<223> OTHER INFORMATION: Dengue 3 delta 30

<400> SEQUENCE: 7
ggggcccaag acuaga                                                  16

<210> SEQ ID NO 8
<211> LENGTH: 16
<212> TYPE: RNA
<213> ORGANISM: Artificial Sequence
<220> FEATURE:
<223> OTHER INFORMATION: Dengue 4 delta 30

<400> SEQUENCE: 8
ggggcccaag acuaga                                                  16

<210> SEQ ID NO 9
<211> LENGTH: 51
<212> TYPE: DNA
<213> ORGANISM: Artificial Sequence
<220> FEATURE:
<223> OTHER INFORMATION: TL2 region of p2 plasmid
```

```
<400> SEQUENCE: 9
tgggggccca aggtgagatg aagctgtagt ctcactggaa ggactagagg t          51

<210> SEQ ID NO 10
<211> LENGTH: 21
<212> TYPE: DNA
<213> ORGANISM: Artificial Sequence
<220> FEATURE:
<223> OTHER INFORMATION: TL2 region of p2 delta 30

<400> SEQUENCE: 10
tgggggccca agactagagg t                                           21

<210> SEQ ID NO 11
<211> LENGTH: 51
<212> TYPE: DNA
<213> ORGANISM: Artificial Sequence
<220> FEATURE:
<223> OTHER INFORMATION: TL2 region of p3 plasmid

<400> SEQUENCE: 11
cggggcccga gctctgaggg aagctgtacc tccttgcaaa ggactagagg t          51

<210> SEQ ID NO 12
<211> LENGTH: 20
<212> TYPE: DNA
<213> ORGANISM: Artificial Sequence
<220> FEATURE:
<223> OTHER INFORMATION: TL2 region of p3 delta 30

<400> SEQUENCE: 12
gggggcccaa gactagaggt                                             20

<210> SEQ ID NO 13
<211> LENGTH: 29
<212> TYPE: DNA
<213> ORGANISM: Artificial Sequence
<220> FEATURE:
<223> OTHER INFORMATION: Spe1 linker in p3

<400> SEQUENCE: 13
actagttaga ctaacttaag tcaactagt                                   29

<210> SEQ ID NO 14
<211> LENGTH: 51
<212> TYPE: DNA
<213> ORGANISM: Artificial Sequence
<220> FEATURE:
<223> OTHER INFORMATION: rDEN2/4 junction 1

<400> SEQUENCE: 14
cagtttgttt gaatagagag cagatctctg atgaataacc aacgaaaaaa g          51

<210> SEQ ID NO 15
<211> LENGTH: 7
<212> TYPE: PRT
<213> ORGANISM: Artificial Sequence
<220> FEATURE:
<223> OTHER INFORMATION: rDEN2/4 junction 1

<400> SEQUENCE: 15

Met Asn Asn Gln Arg Lys Lys
  1               5

<210> SEQ ID NO 16
```

```
<211> LENGTH: 51
<212> TYPE: DNA
<213> ORGANISM: Artificial Sequence
<220> FEATURE:
<223> OTHER INFORMATION: rDEN2/4 junction 2

<400> SEQUENCE: 16
attatcacat ggataggaat gaactcgagg aacacttcaa tggctatgac g        51

<210> SEQ ID NO 17
<211> LENGTH: 17
<212> TYPE: PRT
<213> ORGANISM: Artificial Sequence
<220> FEATURE:
<223> OTHER INFORMATION: rDEN2/4 junction 2

<400> SEQUENCE: 17

Ile Ile Thr Trp Ile Gly Met Asn Ser Arg Asn Thr Ser Met Ala Met
 1               5                  10                  15

Thr

<210> SEQ ID NO 18
<211> LENGTH: 51
<212> TYPE: DNA
<213> ORGANISM: Artificial Sequence
<220> FEATURE:
<223> OTHER INFORMATION: rDEN2/4 junction 3

<400> SEQUENCE: 18
atcttgaacg ggagaaaaag gtctgcaggc atgatcatta tgctgattcc a        51

<210> SEQ ID NO 19
<211> LENGTH: 17
<212> TYPE: PRT
<213> ORGANISM: Artificial Sequence
<220> FEATURE:
<223> OTHER INFORMATION: rDEN2/4 junction 3

<400> SEQUENCE: 19

Ile Leu Asn Gly Arg Lys Arg Ser Ala Gly Met Ile Ile Met Leu Ile
 1               5                  10                  15

Pro

<210> SEQ ID NO 20
<211> LENGTH: 50
<212> TYPE: DNA
<213> ORGANISM: Artificial Sequence
<220> FEATURE:
<223> OTHER INFORMATION: rDEN3/4 junction 1

<400> SEQUENCE: 20
cagtttgttt gaatagagag cagatctctg gaaaaatgaa caaccaacgg            50

<210> SEQ ID NO 21
<211> LENGTH: 5
<212> TYPE: PRT
<213> ORGANISM: Artificial Sequence
<220> FEATURE:
<223> OTHER INFORMATION: rDEN3/4 junction 1

<400> SEQUENCE: 21

Met Asn Asn Gln Arg
 1               5

<210> SEQ ID NO 22
<211> LENGTH: 51
```

```
<212> TYPE: DNA
<213> ORGANISM: Artificial Sequence
<220> FEATURE:
<223> OTHER INFORMATION: rDEN3/4 junction 2

<400> SEQUENCE: 22
cttttaacct ggatagggtt gaactcgagg aacacttcaa tggctatgac g          51

<210> SEQ ID NO 23
<211> LENGTH: 17
<212> TYPE: PRT
<213> ORGANISM: Artificial Sequence
<220> FEATURE:
<223> OTHER INFORMATION: rDEN3/4 junction 2

<400> SEQUENCE: 23

Leu Leu Thr Trp Ile Gly Leu Asn Ser Arg Asn Thr Ser Met Ala Met
 1               5                  10                  15

Thr

<210> SEQ ID NO 24
<211> LENGTH: 51
<212> TYPE: DNA
<213> ORGANISM: Artificial Sequence
<220> FEATURE:
<223> OTHER INFORMATION: rDEN3/4 junction 3

<400> SEQUENCE: 24
atcttgaacg ggagaaaaag gtctgcagtc tgtctcatga tgatgttacc a          51

<210> SEQ ID NO 25
<211> LENGTH: 17
<212> TYPE: PRT
<213> ORGANISM: Artificial Sequence
<220> FEATURE:
<223> OTHER INFORMATION: rDEN3/4 junction 3

<400> SEQUENCE: 25

Ile Leu Asn Gly Arg Lys Arg Ser Ala Val Cys Leu Met Met Met Leu
 1               5                  10                  15

Pro

<210> SEQ ID NO 26
<211> LENGTH: 50
<212> TYPE: DNA
<213> ORGANISM: Artificial Sequence
<220> FEATURE:
<223> OTHER INFORMATION: rDEN1/4 junction 1

<400> SEQUENCE: 26
cagtttgttt gaatagagag cagatctctg gaaaaatgaa caaccaacgg            50

<210> SEQ ID NO 27
<211> LENGTH: 5
<212> TYPE: PRT
<213> ORGANISM: Artificial Sequence
<220> FEATURE:
<223> OTHER INFORMATION: rDEN1/4 junction 1

<400> SEQUENCE: 27

Met Asn Asn Gln Arg
 1               5

<210> SEQ ID NO 28
<211> LENGTH: 51
<212> TYPE: DNA
```

<213> ORGANISM: Artificial Sequence
<220> FEATURE:
<223> OTHER INFORMATION: rDEN1/4 junction 2

<400> SEQUENCE: 28
ctgctgacat ggctaggatt aaactcgagg aacacttcaa tggctatgac g 51

<210> SEQ ID NO 29
<211> LENGTH: 17
<212> TYPE: PRT
<213> ORGANISM: Artificial Sequence
<220> FEATURE:
<223> OTHER INFORMATION: rDEN1/4 junction 2

<400> SEQUENCE: 29

Leu Leu Thr Trp Leu Gly Leu Asn Ser Arg Asn Thr Ser Met Ala Met
1 5 10 15

Thr

<210> SEQ ID NO 30
<211> LENGTH: 51
<212> TYPE: DNA
<213> ORGANISM: Artificial Sequence
<220> FEATURE:
<223> OTHER INFORMATION: rDEN1/4 junction 3

<400> SEQUENCE: 30
atcttgaacg ggagaaaaag gtctgcagcc atgctcctca tgctgctgcc c 51

<210> SEQ ID NO 31
<211> LENGTH: 17
<212> TYPE: PRT
<213> ORGANISM: Artificial Sequence
<220> FEATURE:
<223> OTHER INFORMATION: rDEN1/4 junction 3

<400> SEQUENCE: 31

Ile Leu Asn Gly Arg Lys Arg Ser Ala Ala Met Leu Leu Met Leu Leu
1 5 10 15

Pro

<210> SEQ ID NO 32
<211> LENGTH: 60
<212> TYPE: RNA
<213> ORGANISM: Dengue 4 virus

<400> SEQUENCE: 32
ccaacaaccu ugacagcauc cuuagucaug cuuuuagucc auuaugcaau aauaggccca 60

<210> SEQ ID NO 33
<211> LENGTH: 20
<212> TYPE: PRT
<213> ORGANISM: Dengue 4 virus

<400> SEQUENCE: 33

Pro Thr Thr Leu Thr Ala Ser Leu Val Met Leu Leu Val His Thr Ala
1 5 10 15

Ile Ile Gly Pro
20

<210> SEQ ID NO 34
<211> LENGTH: 60
<212> TYPE: RNA
<213> ORGANISM: Dengue 1 virus

<400> SEQUENCE: 34
ccgcugacgc ugacagcggc gguauuuaug cuaguggcuc auuaugccau aauuggaccc    60

<210> SEQ ID NO 35
<211> LENGTH: 20
<212> TYPE: PRT
<213> ORGANISM: Dengue 1 virus

<400> SEQUENCE: 35

Pro Leu Thr Leu Thr Ala Ala Val Pro Met Leu Val Ala His Thr Ala
 1               5                  10                  15

Ile Ile Gly Pro
            20

<210> SEQ ID NO 36
<211> LENGTH: 60
<212> TYPE: RNA
<213> ORGANISM: Dengue 2 virus

<400> SEQUENCE: 36 ccauaaccc ucacagcggc ucuucuuuua uugguagcac auuaugccau cauaggaccg    60

<210> SEQ ID NO 37
<211> LENGTH: 20
<212> TYPE: PRT
<213> ORGANISM: Dengue 2 virus

<400> SEQUENCE: 37

Pro Ile Thr Leu Thr Ala Ala Leu Leu Leu Leu Val Ala His Thr Ala
 1               5                  10                  15

Ile Ile Gly Pro
            20

<210> SEQ ID NO 38
<211> LENGTH: 60
<212> TYPE: RNA
<213> ORGANISM: Dengue 3 virus

<400> SEQUENCE: 38
ccacuaacuc ucacagcggc aguucuccug cuagucacgc auuaugcuau uauaggucca    60

<210> SEQ ID NO 39
<211> LENGTH: 20
<212> TYPE: PRT
<213> ORGANISM: Dengue 3 virus

<400> SEQUENCE: 39

Pro Leu Thr Leu Thr Ala Ala Val Leu Leu Leu Val Thr His Thr Ala
 1               5                  10                  15

Ile Ile Gly Pro
            20

<210> SEQ ID NO 40
<211> LENGTH: 13
<212> TYPE: DNA
<213> ORGANISM: Artificial Sequence
<220> FEATURE:
<223> OTHER INFORMATION: primer

<400> SEQUENCE: 40
ccacgggcgc cgt    13

```
<210> SEQ ID NO 41
<211> LENGTH: 10
<212> TYPE: DNA
<213> ORGANISM: Artificial Sequence
<220> FEATURE:
<223> OTHER INFORMATION: primer

<400> SEQUENCE: 41
aaggcctgga                                                              10

<210> SEQ ID NO 42
<211> LENGTH: 12
<212> TYPE: DNA
<213> ORGANISM: Artificial Sequence
<220> FEATURE:
<223> OTHER INFORMATION: primer

<400> SEQUENCE: 42
tatccccggg ac                                                           12

<210> SEQ ID NO 43
<211> LENGTH: 11
<212> TYPE: DNA
<213> ORGANISM: Artificial Sequence
<220> FEATURE:
<223> OTHER INFORMATION: primer

<400> SEQUENCE: 43
agagctctct c                                                            11

<210> SEQ ID NO 44
<211> LENGTH: 15
<212> TYPE: DNA
<213> ORGANISM: Artificial Sequence
<220> FEATURE:
<223> OTHER INFORMATION: primer

<400> SEQUENCE: 44
gaatctccac ccgga                                                        15

<210> SEQ ID NO 45
<211> LENGTH: 10
<212> TYPE: DNA
<213> ORGANISM: Artificial Sequence
<220> FEATURE:
<223> OTHER INFORMATION: primer

<400> SEQUENCE: 45
ctgtcgaatc                                                              10

<210> SEQ ID NO 46
<211> LENGTH: 15159
<212> TYPE: DNA
<213> ORGANISM: Artificial Sequence
<220> FEATURE:
<223> OTHER INFORMATION: Dengue 2 plasmid p2

<400> SEQUENCE: 46
agttgttagt ctacgtggac cgacaaagac agattctttg agggagctaa gctcaacgta        60
gttctaactg ttttttgatt agagagcaga tctctgatga ataaccaacg gaaaaggcg        120 agaaacacgc ctttcaatat gctgaaacgc gagagaaacc gcgtgtcaac tgtacaacag       180
ttgacaaaga gattctcact tggaatgctg cagggacgag gaccactaaa attgttcatg       240
gccctggtgg cattccttcg tttcctaaca atcccaccaa cagcagggat attaaaaaga       300
```

```
tggggaacaa ttaaaaaatc aaaggctatt aatgttctga gaggcttcag gaaagagatt      360
ggaaggatgc tgaatatctt aaacaggaga cgtagaactg taggcatgat catcatgctg      420
actccaacag tgatggcgtt tcatctgacc acacgcaacg gagaaccaca catgattgtc      480
agtagacaag aaaaagggaa aagccttctg ttcaagacaa aggatggcac gaacatgtgt      540
accctcatgg ccatggacct tggtgagttg tgtgaagaca caatcacgta taaatgtcct      600
tttctcaagc agaacgaacc agaagacata gattgttggt gcaactccac gtccacatgg      660
gtaacttatg gacatgtac caccacagga gagcacagaa gagaaaaaag atcagtggcg       720
cttgttccac acgtgggaat gggattggag acacgaactg aaacatggat gtcatcagaa      780
ggggcctgga acatgccca gagaattgaa acttggattc tgagacatcc aggctttacc       840
ataatggccg caatcctggc atacaccata gggacgacgc atttccaaag agtcctgata      900
ttcatcctac tgacagccat cgctccttca atgacaatgc gctgcatagg aatatcaaat      960
agggactttg tggaaggagt gtcaggaggg agttgggttg acatagtttt agaacatgga      1020
agttgtgtga cgacgatggc aaaaaacaaa ccaacactgg actttgaact gataaaaaca      1080
gaagccaaac aacctgccac cttaaggaag tactgtatag aggccaaact gaccaacacg      1140
acaacagact cgcgctgccc aacacaaggg gaacccaccc tgaatgaaga gcaggacaaa      1200
aggtttgtct gcaaacattc catggtagac agaggatggg gaaatggatg tggattgttt      1260
ggaaaaggag gcatcgtgac ctgtgctatg ttcacatgca aaagaacat ggaaggaaaa       1320 attgtgcagc cagaaaacct ggaatacact gtcgtgataa cacctcattc agggaagaa      1380 catgcagtgg gaaatgacac aggaaaacat ggtaaagaag tcaagataac accacagagc      1440
tccatcacag aggcggaact gacaggctat ggcactgtta cgatggagtg ctctccaaga      1500
acgggcctcg acttcaatga gatggtgttg ctgcaaatgg aagacaaagc ctggctggtg      1560
cacagacaat ggttcctaga cctaccgttg ccatggctgc ccggagcaga cacacaagga      1620
tcaaattgga tacagaaaga aacactggtc accttcaaaa atcccccatgc gaaaaaacag      1680 gatgttgttg tcttaggatc ccaagagggg gccatgcata cagcactcac aggggctacg      1740
gaaatccaga tgtcatcagg aaacctgctg ttcacaggac atctcaagtg caggctgaga      1800
atggacaaat acaacttaa agggatgtca tactccatgt gcacaggaaa gtttaaaatt      1860
gtgaaggaaa tagcagaaac acaacatgga acaaatgtca ttagagtaca atatgaagga      1920
gacggctctc catgcaagat ccccttttgag ataatggatc tggaaaaaag acatgttttg     1980
ggccgcctga tcacagtcaa cccaattgta acagaaaagg acagtccagt caacatagaa      2040
gcagaacctc cattcggaga cagctacatc atcataggag tggaaccagg acaattgaag      2100
ctggactggt tcaagaaagg aagttccatc ggccaaatgt ttgagacaac aatgagggga      2160
gcgaaaagaa tggccatttt gggtgacaca gcctgggatt ttggatctct gggaggagtg      2220
ttcacatcaa taggaaaggc tctccaccag ttttttggag caatctacgg ggctgctttc      2280 agtgggtct catggactat gaagatcctc ataggagtta tcatcacatg gataggaatg      2340
aactcacgta gcactagtct gagcgtgtca ctggtgttag tgggaatcgt gacactttac      2400
ttgggagtta tggtgcaggc cgatagtggt tgcgttgtga ctggaagaa caaagaacta      2460 aaatgtggca gtggaatatt cgtcacagat aacgtgcata catggacaga acaatacaag      2520
ttccaaccag aatccccttc aaaactggcc tcagccatcc agaaagcgca tgaagagggc      2580
atctgtggaa tccgctcagt aacaagactg gaaaatctta tgtggaaaca gataacatca      2640
gaattgaatc atattctatc agaaaatgaa gtgaaactga ccatcatgac aggagacatc      2700
```

-continued

| | |
|---|---|
| aaaggaatca tgcaggtagg aaaacgatct ttgcggcctc aacccactga gttgaggtat | 2760 |
| tcatggaaaa catggggtaa agcgaaaatg ctctccacag aactccacaa tcagaccttc | 2820 |
| ctcattgatg gtcccgaaac agcagaatgc cccaacacaa acagagcttg gaattcactg | 2880 |
| gaagttgagg actacggctt tggagtattc actaccaata tatggctaag attgagagaa | 2940 |
| aagcaggatg tattttgtga ctcaaaactc atgtcagcgg ccataaagga caacagagcc | 3000 |
| gtccatgctg atatgggtta ttggatagaa agcgcactca atgatacatg gaagatagag | 3060 |
| aaagcttctt tcattgaagt caaaagttgc cactggccaa agtcacacac cctatggagt | 3120 |
| aatggagtgc tagaaagcga gatggtcatt ccaaagaatt cgctggacc agtgtcacaa | 3180 |
| cataataaca gaccaggcta ttacacacaa acagcaggac cttggcatct aggcaagctt | 3240 |
| gagatggact ttgatttctg cgaagggact acagtggtgg taaccgagaa ctgtggaaac | 3300 |
| agagggccct ctttaagaac aaccactgcc tcaggaaaac tcataacgga atggtgttgt | 3360 |
| cgatcttgca cactaccacc actaagatac agaggtgagg atggatgttg gtacgggatg | 3420 |
| gaaatcagac cattgaaaga gaaagaagaa aatctggtca gttctctggt tacagccgga | 3480 |
| catgggcaga ttgacaattt ctcattagga atcttgggaa tggcactgtt ccttgaagaa | 3540 |
| atgctcagga ctcgagtagg aacaaaacat gcaatattac tcgtcgcagt ttctttcgtg | 3600 |
| acgctaatca cagggaacat gtcttttaga gacctgggaa gagtgatggt tatggtgggt | 3660 |
| gccaccatga cagatgacat aggcatgggt gtgacttatc tcgctctact agcagctttt | 3720 |
| agagtcgagc caacctttgc agctggactg ctcttgagaa aactgacctc caaggaatta | 3780 |
| atgatgacta ccataggaat cgttcttctc tcccagagta gcataccaga gaccattctt | 3840 |
| gaactgaccg acgcgttagc tctaggcatg atggtcctca agatggtgag aaacatggaa | 3900 |
| aaatatcagc tggcagtgac catcatggct attttgtgcg tcccaaatgc tgtgatatta | 3960 |
| cagaacgcat ggaaagtgag ttgcacaata ttggcagtgg tgtctgtttc cccccctgctc | 4020 |
| ttaacatcct cacaacagaa agcggactgg ataccattag cgttgacgat caaaggtctt | 4080 |
| aatccaacag ccattttcct aacaaccctc tcaagaacca acaagaaaag gagctggcct | 4140 |
| ttaaatgagg ccatcatggc ggttgggatg gtgagtatct tggccagctc tctcttaaag | 4200 |
| aatgacatcc ccatgacagg accattagtg gctggagggc tccttactgt gtgctacgtg | 4260 |
| ctaactgggc ggtcagccga tctggaatta gagagagcta ccgatgtcaa atgggatgac | 4320 |
| caggcagaga tatcaggtag cagtccaatc tgtcaataa caatatcaga agatggcagc | 4380 |
| atgtcaataa agaatgaaga ggaagagcaa acactgacta tactcattag aacaggattg | 4440 |
| cttgtgatct caggactctt tccggtatca ataccaatta cagcagcagc atggtatctg | 4500 |
| tgggaagtaa agaaacaacg ggctggagtg ctgtgggatg tcccctcacc accacccgtg | 4560 |
| ggaaaagctg aattggaaga tggagcctac agaatcaagc aaaaaggaat ccttggatat | 4620 |
| tcccagatcg gagctggagt ttacaaagaa ggaacatttc acacaatgtg gcacgtcaca | 4680 |
| cgtggcgctg tcctaatgca taggggaag aggattgaac catcatgggc ggacgtcaag | 4740 |
| aaagacttaa tatcatatgg aggaggttgg aagctagaag gagaatggaa agaaggagaa | 4800 |
| gaagtccagg tcttggcatt ggagccaggg aaaaatccaa gagccgtcca aacaaagcct | 4860 |
| ggccttttta gaaccaacac tggaaccata ggtgccgtat ctctggactt ttcccctggg | 4920 |
| acgtcaggat ctccaatcgt cgacaaaaaa ggaaaagttg taggtctcta tggcaatggt | 4980 |
| gtcgttacaa ggagtggagc atatgtgagt gccatagctc agactgaaaa aagcattgaa | 5040 |
| gacaatccag agattgaaga tgacatcttt cgaaagagaa gattgactat catggatctc | 5100 |

```
cacccaggag caggaaagac aaagagatac ctcccggcca tagtcagaga ggccataaaa    5160
agaggcttga gaacactaat cctagccccc actagagtcg tggcagctga aatggaggaa    5220
gcccttagag gacttccaat aagataccaa actccagcta tcaggctgaa gcacaccggg    5280
cgggagattg tagacttaat gtgtcatgcc acatttacca tgaggctgct atcaccaatc    5340
agggtgccaa attacaacct gatcatcatg gacgaagccc attttacaga tccagcaagc    5400
atagcagcta ggggatacat ctcaactcga gtggagatgg gggaggcagc tggaattttt    5460
atgacagcca ctcctccggg tagtagagat ccatttcctc agagcaatgc accaattatg    5520
gacgaagaaa gagaaattcc ggaacgttca tggaactctg gcacgagtg ggtcacggat     5580 tttaaaggaa agactgtctg gtttgttcca agcataaaaa ccggaaatga catagcagcc    5640
tgcctgagaa agaatggaaa gagggtgata caactcagta ggaagacctt tgattctgaa    5700
tatgtcaaga ctagaaccaa tgactgggat ttcgtggtta caactgacat ctcggaaatg    5760
ggcgccaact ttaaagctga gagggtcata daccccagac gctgcatgaa accagttata    5820
ttgacagacg gcgaagagcg ggtgattctg gcaggaccca tgccagtgac ccactctagt    5880
gcagcacaaa aagagggag aataggaagg aatccaagga tgaaaatga tcaatatata      5940 tatatggggg aaccactgga aaatgatgaa gactgtgcgc actggaagga agctaagatg    6000
ctcctagata atatcaacac acctgaagga atcattccca gcttgttcga gccagagcgt    6060
gaaaaggtgg atgccattga cggtgaatat cgcttgagag agaagcacg gaaaactttt     6120 gtggacctaa tgagaagagg agacctacca gtctggttgg cttataaagt ggcagctgaa    6180
ggtatcaact acgcagacag aagatggtgt tttgacggaa ccagaaacaa tcaaatcttg    6240
gaagaaaatg tggaagtgga aatctggaca aaggaagggg aaaggaaaaa attgaaacct    6300
agatggttag atgctaggat ctactccgac ccactggcgc taaaagagtt caaggaattt    6360
gcagccggaa gaaagtccct aaccctgaac ctaattacag agatgggcag actcccaact    6420
tttatgactc agaaggccag agatgcacta gacaacttgg cggtgctgca cacggctgaa    6480
gcgggtggaa aggcatacaa tcatgctctc agtgaattac cggagaccct ggagacattg    6540
cttttgctga cactgttggc cacagtcacg ggaggaatct tcctattcct gatgagcgga    6600
aggggtatgg ggaagatgac cctgggaatg tgctgcataa tcacggccag catcctctta    6660
tggtatgcac aaatacagcc acattggata gcagcctcaa taatattgga gttctttctc    6720
atagtcttgc tcattccaga accagaaaag cagaggacac ctcaggataa tcaattgact    6780
tatgtcatca tagccatcct cacagtggtg gccgcaacca tggcaaacga aatgggtttt    6840
ctggaaaaaa caaagaaaga cctcggactg ggaaacattg caactcagca acctgagagc    6900
aacattctgg acatagatct acgtcctgca tcagcatgga cgttgtatgc cgtggctaca    6960
acatttatca caccaatgtt gagacatagc attgaaaatt cctcagtaaa tgtgtcccta    7020
acagccatag ctaaccaagc cacagtgcta atgggtctcg gaaaaggatg gccattgtca    7080
aagatggaca ttggagttcc cctccttgct attgggtgtt actcacaagt caaccctata    7140
accctcacag cggctcttct tttattggta gcacattatg ccatcatagg accgggactt    7200
caagccaaag caactagaga agctcagaaa agagcagcag cggcatcat gaaaaaccca    7260 actgtggatg gaataacagt gatagatcta gatccaatac cctatgatcc aaagtttgaa    7320
aagcagttgg gacaagtaat gctcctagtc ctctgcgtga cccaagtgct gatgatgagg    7380
actacgtggg ctttgtgtga agccttaact ctagcaactg gacccgtgtc cacattgtgg    7440
gaaggaaatc cagggagatt ctggaacaca accattgcag tgtcaatggc aaacatcttt    7500
```

```
agagggagtt acctggctgg agctggactt ctcttttcta tcatgaagaa cacaaccagc    7560
acgagaagag gaactggcaa tataggagaa acgttaggag agaaatggaa aagcagactg    7620
aacgcattgg ggaaaagtga attccagatc tacaaaaaaa gtggaattca agaagtggac    7680
agaaccttag caaaagaagg cattaaaaga ggagaaacgg atcatcacgc tgtgtcgcga    7740
ggctcagcaa aactgagatg gttcgttgaa aggaatttgg tcacaccaga agggaaagta    7800
gtggaccttg gttgtggcag aggggggctgg tcatactatt gtggaggatt aaagaatgta   7860
agagaagtta aaggcttaac aaaaggagga ccaggacacg aagaacctat ccctatgtca    7920
acatatgggt ggaatctagt acgcttacag agcggagttg atgtttttttt tgttccacca   7980 gagaagtgtg acacattgtt gtgtgacata ggggaatcat caccaaatcc cacggtagaa    8040
gcgggacgaa cactcagagt cctcaaccta gtggaaaatt ggctgaacaa taacacccaa    8100 tttttgcgtaa aggttcttaa cccgtacatg ccctcagtca ttgaaagaat ggaaaacctta  8160 caacggaaat acgaggagc cttggtgaga atccactct cacggaattc cacacatgag      8220
atgtactggg tgtccaatgc ttccgggaac atagtgtcat cagtgaacat gatttcaaga    8280
atgctgatca acagattcac tatgagacac aagaaggcca cctatgagcc agatgtcgac    8340
ctcggaagcg gaacccgcaa tattggaatt gaaagtgaga caccgaacct agacataatt    8400
gggaaaagaa tagaaaaaat aaaacaagag catgaaacgt catggcacta tgatcaagac    8460
caccatacaa aaacatgggc ttaccatggc agctatgaaa caaaacagac tggatcagca    8520
tcatccatgg tgaacggagt agtcagattg ctgacaaaac cctgggacgt tgttccaatg    8580
gtgacacaga tggcaatgac agacacaact ccttttggac aacagcgcgt cttcaaagag    8640
aaggtggata cgagaaccca agaaccaaaa gaaggcacaa aaaaactaat gaaaatcacg    8700
gcagagtggc tctggaaaga actaggaaag aaaaagacac ctagaatgtg taccagagaa    8760
gaattcacaa aaaaggtgag aagcaatgca gccttggggg ccatattcac cgatgagaac    8820
aagtggaaat cggcgcgtga agccgttgaa gatagtaggt tttgggagct ggttgacaag    8880
gaaaggaacc tccatcttga agggaaatgt gaaacatgtg tatacaacat gatggggaaa    8940
agagagaaaa aactaggaga gtttggtaaa gcaaaaggca gcagagccat atggtacatg    9000
tggctcggag cacgcttctt agagtttgaa gccctaggat ttttgaatga agaccattgg    9060
ttctccagag agaactccct gagtggagtg aaggagaag ggctgcataa gctaggttac    9120
atcttaagag aggtgagcaa gaaagaagga ggagcaatgt atgccgatga caccgcaggc    9180
tgggacacaa gaatcacaat agaggatttg aaaaatgaag aaatgataac gaaccacatg    9240
gcaggagaac acaagaaact tgccgaggcc atttttaaat tgacgtacca aaacaaggtg    9300
gtgcgtgtgc aaagaccaac accaagaggc acagtaatgg acatcatatc gagaagagac    9360 caaagggta gtggacaagt tggcacctat ggcctcaaca ctttcaccaa catgaagca    9420 caactaatta ggcaaatgga gggggaagga atcttcaaaa gcatccagca cttgacagcc    9480
tcagaagaaa tcgctgtgca agattggcta gtaagagtag ggcgtgaaag gttgtcaaga    9540
atggccatca gtgagatga ttgtgttgtg aaacctttag atgatagatt tgcaagagct    9600
ctaacagctc taaatgacat gggaaaggtt aggaaggaca tacagcaatg ggagccctca    9660
agaggatgga acgactggac gcaggtgccc ttctgttcac accatttca cgagttaatt    9720 atgaaagatg gtcgcacact cgtagttcca tgcagaaacc aagatgaatt gatcggcaga    9780
gcccgaattt cccagggagc tgggtggtct ttacggggaga cggcctgttt ggggaagtct    9840
tacgcccaaa tgtggagctt gatgtacttc cacagacgtg atctcaggct agcggcaaat    9900
```

```
gccatctgct cggcagtccc atcacactgg attccaacaa gccggacaac ctggtccata   9960
cacgccagcc atgaatggat gacgacggaa gacatgttga cagtttggaa cagagtgtgg  10020
atcctagaaa atccatggat ggaagacaaa actccagtgg aatcatggga ggaaatccca  10080
tacctgggaa aaagagaaga ccaatggtgc ggctcgctga ttgggctgac aagcagagcc  10140
acctgggcga agaatatcca gacagcaata aaccaagtca gatccctcat tggcaatgag  10200
gaatacacag attacatgcc atccatgaaa agattcagaa gagaagagga agaggcagga  10260
gttttgtggt agaaaaacat gaaacaaaac agaagtcagg tcggattaag ccatagtacg  10320
ggaaaaacta tgctacctgt gagccccgtc caaggacgtt aaaagaagtc aggccatttt  10380
gatgccatag cttgagcaaa ctgtgcagcc tgtagctcca cctgagaagg tgtaaaaaat  10440
ccgggaggcc acaaaccatg gaagctgtac gcatggcgta gtggactagc ggttagagga  10500
gaccctccc ttacagatcg cagcaacaat ggggccccaa ggtgagatga agctgtagtc  10560
tcactggaag gactagaggt tagaggagac ccccccaaaa caaaaaacag catattgacg  10620
ctgggaaaga ccagagatcc tgctgtctcc tcagcatcat tccaggcaca ggacgccaga  10680
aaatggaatg gtgctgttga atcaacaggt tctggtaccg gtaggcatcg tggtgtcacg  10740
ctcgtcgttt ggtatggctt cattcagctc cggttcccaa cgatcaaggc gagttacatg  10800
atcccccatg ttgtgcaaaa aagcggttag ctccttcggt cctccgatcg ttgtcagaag  10860
taagttggcc gcagtgttat cactcatggt tatggcagca ctgcataatt ctcttactgt  10920
catgccatcc gtaagatgct tttctgtgac tggtgagtac tcaaccaagt cattctgaga  10980
atagtgtatg cggcgaccga gttgctcttg cccggcgtca acacgggata ataccgcgcc  11040
acatagcaga actttaaaag tgctcatcat tggaaaacgt tcttcgggc gaaaactctc  11100
aaggatctta ccgctgttga gatccagttc gatgtaaccc actcgtgcac ccaactgatc  11160
ttcagcatct tttactttca ccagcgtttc tgggtgagca aaaacaggaa ggcaaaatgc  11220
cgcaaaaaag ggaataaggg cgacacggaa atgttgaata ctcatactct ccttttttca  11280
atattattga agcatttatc agggttattg tctcatgagc ggatacatat ttgaatgtat  11340
ttagaaaaat aaacaaatag gggttccgcg cacatttccc cgaaaagtgc cacctgacgt  11400
ctaagaaacc attattatca tgacattaac ctataaaaat aggcgtatca cgaggccctt  11460
tcgtcttcaa gaattctcat gtttgacagc ttatcatcga taagctttaa tgcggtagtt  11520
tatcacagtt aaattgctaa cgcagtcagg caccgtgtat gaaatctaac aatgcgctca  11580
tcgtcatcct cggcaccgtc acccctggatg ctgtaggcat aggcttggtt atgccggtac  11640
tgccgggcct cttgcgggat atcgtccatt ccgacagcat cgccagtcac tatggcgtgc  11700
tgctggcgct atatgcgttg atgcaatttc tatgcgcacc cgttctcgga gcactgtccg  11760
accgctttgg ccgccgccca gtcctgctcg cttcgctact tggagccact atcgactacg  11820
cgatcatggc gaccacaccc gtcctgtgga tcctctacgc cggacgcatc gtggccggca  11880
tcaccgcgc cacaggtgcg gttgctggcg cctatatcgc cgacatcacc gatggggaag  11940
atcgggctcg ccacttcggg ctcatgagcg cttgtttcgg cgtgggtatg gtggcaggcc  12000
ccgtggccgg gggactgttg gcgccatct ccttgcatgc accattcctt gcggcggcgg  12060
tgctcaacgg cctcaaccta ctactgggct gcttcctaat gcaggagtcg cataaggag  12120
agcgtcgacc gatgcccttg agagccttca acccagtcag ctccttccgg tgggcgcggg  12180
gcatgactat cgtcgccgca cttatgactg tcttctttat catgcaactc gtaggacagg  12240
tgccggcagc gctctgggtc attttcggcg aggaccgctt tcgctggagc gcgacgatga  12300
```

```
tcggcctgtc gcttgcggta ttcggaatct tgcacgccct cgctcaagcc ttcgtcactg   12360
gtcccgccac caaacgtttc ggcgagaagc aggccattat cgccggcatg gcggccgacg   12420
cgctgggcta cgtcttgctg gcgttcgcga cgcgaggctg gatggccttc cccattatga   12480
ttcttctcgc ttccggcggc atcgggatgc ccgcgttgca ggccatgctg tccaggcagg   12540
tagatgacga ccatcaggga cagcttcaag gatcgctcgc ggctcttacc agcctaactt   12600
cgatcactgg accgctgatc gtcacggcga tttatgccgc ctcggcgagc acatggaacg   12660
ggttggcatg gattgtaggc gccgccctat accttgtctg cctccccgcg ttgcgtcgcg   12720
gtgcatggag ccgggccacc tcgacctgaa tggaagccgg cggcacctcg ctaacggatt   12780
caccactcca agaattggag ccaatcaatt cttgcggaga actgtgaatg cgcaaaccaa   12840
cccttggcag aacatatcca tcgcgtccgc catctccagc agccgcacgc ggcgcatctc   12900
gggcagcgtt gggtcctggc cacgggtgcg catgatcgtg ctcctgtcgt tgaggacccg   12960
gctaggctgg cggggttgcc ttactggtta gcagaatgaa tcaccgatac gcgagcgaac   13020
gtgaagcgac tgctgctgca aaacgtctgc gacctgagca caacatgaa tggtcttcgg    13080 tttccgtgtt tcgtaaagtc tggaaacgcg gaagtcagcg ccctgcacca ttatgttccg   13140
gatctgcatc gcaggatgct gctggctacc ctgtggaaca cctacatctg tattaacgaa   13200
gcgctggcat tgaccctgag tgatttttct ctggtcccgc cgcatccata ccgccagttg   13260
tttaccctca caacgttcca gtaaccgggc atgttcatca tcagtaaccc gtatcgtgag   13320
catcctctct cgtttcatcg gtatcattac ccccatgaac agaaatcccc cttacacgga   13380
ggcatcagtg accaaacagg aaaaaaccgc ccttaacatg gcccgcttta tcagaagcca   13440
gacattaacg cttctggaga aactcaacga gctggacgcg gatgaacagg cagacatctg   13500
tgaatcgctt cacgaccacg ctgatgagct ttaccgcagc tgcctcgcgc gtttcggtga   13560
tgacggtgaa aacctctgac acatgcagct cccggagacg gtcacagctt gtctgtaagc   13620
ggatgccggg agcagacaag cccgtcaggg gcgtcagcg ggtgttggcg ggtgtcgggg    13680
cgcagccatg acccagtcac gtagcgatag cggagtgtat actggcttaa ctatgcggca   13740
tcagagcaga ttgtactgag agtgcaccat atgcggtgtg aaataccgca cagatgcgta   13800
aggagaaaat accgcatcag gcgctcttcc gcttcctcgc tcactgactc gctgcgctcg   13860
gtcgttcggc tgcggcgagc ggtatcagct cactcaaagg cggtaatacg gttatccaca   13920
gaatcagggg ataacgcagg aaagaacatg tgagcaaaag gccagcaaaa ggccaggaac   13980
cgtaaaaagg ccgcgttgct ggcgtttttc cataggctcc gcccccctga cgagcatcac   14040
aaaaatcgac gctcaagtca gaggtggcga aacccgacag gactataaag ataccaggcg   14100
tttccccctg gaagctccct cgtgcgctct cctgttccga ccctgccgct taccggatac   14160
ctgtccgcct ttctcccttc gggaagcgtg gcgctttctc atagctcacg ctgtaggtat   14220
ctcagttcgg tgtaggtcgt tcgctccaag ctgggctgtg tgcacgaacc ccccgttcag   14280
cccgaccgct gcgccttatc cggtaactat cgtcttgagt ccaacccggt aagacacgac   14340
ttatcgccac tggcagcagc cactggtaac aggattagca gagcgaggta tgtaggcggt   14400
gctacagagt tcttgaagtg gtggcctaac tacggctaca ctagaaggac agtatttggt   14460
atctgcgctc tgctgaagcc agttaccttc ggaaaaagag ttggtagctc ttgatccggc   14520
aaacaaacca ccgctggtag cggtggtttt tttgtttgca agcagcagat tacgcgcaga   14580
aaaaaaggat ctcaagaaga tcctttgatc ttttctacgg ggtctgacgc tcagtggaac   14640
gaaaactcac gttaagggat tttggtcatg agattatcaa aaaggatctt cacctagatc   14700
```

```
cttttaaatt aaaaatgaag ttttaaatca atctaaagta tatatgagta aacttggtct  14760
gacagttacc aatgcttaat cagtgaggca cctatctcag cgatctgtct atttcgttca  14820
tccatagttg cctgactccc cgtcgtgtag ataactacga tacgggaggg cttaccatct  14880
ggccccagtg ctgcaatgat accgcgagac ccacgctcac cggctccaga tttatcagca  14940
ataaaccagc cagccggaag ggccgagcgc agaagtggtc ctgcaacttt atccgcctcc  15000
atccagtcta ttaattgttg ccgggaagct agagtaagta gttcgccagt taatagtttg  15060
cgcaacgttg ttgccattgc tgcaagatct ggctagcgat gaccctgctg attggttcgc  15120
tgaccatttc cgggcgcgcc gatttaggtg acactatag                         15159

<210> SEQ ID NO 47
<211> LENGTH: 3391
<212> TYPE: PRT
<213> ORGANISM: Dengue 2 virus (Tonga/74)

<400> SEQUENCE: 47

Met Asn Asn Gln Arg Lys Lys Ala Arg Asn Thr Pro Phe Asn Met Leu
 1               5                  10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Val Gly Met Ile Ile Met Leu Thr Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Lys Asp Gly
    130                 135                 140

Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
```

-continued

```
            290                 295                 300
Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
                340                 345                 350

Arg Cys Pro Thr Gln Gly Glu Pro Thr Leu Asn Glu Glu Gln Asp Lys
                355                 360                 365

Arg Phe Val Cys Lys His Ser Met Val Asp Arg Gly Trp Gly Asn Gly
                370                 375                 380

Cys Gly Leu Phe Gly Lys Gly Ile Val Thr Cys Ala Met Phe Thr
385                 390                 395                 400

Cys Lys Lys Asn Met Glu Gly Lys Ile Val Gln Pro Glu Asn Leu Glu
                405                 410                 415

Tyr Thr Val Val Ile Thr Pro His Ser Gly Glu His Ala Val Gly
                420                 425                 430

Asn Asp Thr Gly Lys His Gly Lys Glu Val Lys Ile Thr Pro Gln Ser
                435                 440                 445

Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
                515                 520                 525

Asp Val Val Leu Gly Ser Gln Glu Gly Ala Met His Thr Ala Leu
                530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Ile Val Lys Glu Ile
                580                 585                 590

Ala Glu Thr Gln His Gly Thr Ile Val Ile Arg Val Gln Tyr Glu Gly
                595                 600                 605

Asp Gly Ser Pro Cys Lys Ile Pro Phe Glu Ile Met Asp Leu Glu Lys
                610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
                675                 680                 685

Ala Lys Arg Met Ala Ile Leu Gly Asp Thr Ala Trp Asp Phe Gly Ser
                690                 695                 700

Leu Gly Gly Val Phe Thr Ser Ile Gly Lys Ala Leu His Gln Val Phe
705                 710                 715                 720
```

```
Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Ser Leu Val Leu Val Gly Ile Val Thr Leu Tyr
                755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
                820                 825                 830

Arg Ser Val Thr Arg Leu Glu Asn Leu Met Trp Lys Gln Ile Thr Ser
                835                 840                 845

Glu Leu Asn His Ile Leu Ser Glu Asn Glu Val Lys Leu Thr Ile Met
850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
                900                 905                 910

Pro Glu Thr Ala Glu Cys Pro Asn Thr Asn Arg Ala Trp Asn Ser Leu
                915                 920                 925

Glu Val Glu Asp Tyr Gly Phe Gly Val Phe Thr Thr Asn Ile Trp Leu
                930                 935                 940

Arg Leu Arg Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Ser Cys His Trp Pro Lys Ser His Thr Leu Trp Ser
                995                 1000                1005

Asn Gly Val Leu Glu Ser Glu Met Val Ile Pro Lys Asn Phe Ala Gly
    1010                1015                1020

Pro Val Ser Gln His Asn Asn Arg Pro Gly Tyr Tyr Thr Gln Thr Ala
1025                1030                1035                1040

Gly Pro Trp His Leu Gly Lys Leu Glu Met Asp Phe Asp Phe Cys Glu
                1045                1050                1055

Gly Thr Thr Val Val Val Thr Glu Asn Cys Gly Asn Arg Gly Pro Ser
                1060                1065                1070

Leu Arg Thr Thr Thr Ala Ser Gly Lys Leu Ile Thr Glu Trp Cys Cys
                1075                1080                1085

Arg Ser Cys Thr Leu Pro Pro Leu Arg Tyr Arg Gly Glu Asp Gly Cys
                1090                1095                1100

Trp Tyr Gly Met Glu Ile Arg Pro Leu Lys Glu Lys Glu Glu Asn Leu
1105                1110                1115                1120

Val Ser Ser Leu Val Thr Ala Gly His Gly Gln Ile Asp Asn Phe Ser
                1125                1130                1135

Leu Gly Ile Leu Gly Met Ala Leu Phe Leu Glu Glu Met Leu Arg Thr
```

```
                1140                1145                1150
Arg Val Gly Thr Lys His Ala Ile Leu Leu Val Ala Val Ser Phe Val
            1155                1160                1165

Thr Leu Ile Thr Gly Asn Met Ser Phe Arg Asp Leu Gly Arg Val Met
        1170                1175                1180

Val Met Val Gly Ala Thr Met Thr Asp Asp Ile Gly Met Gly Val Thr
1185                1190                1195                1200

Tyr Leu Ala Leu Leu Ala Ala Phe Arg Val Arg Pro Thr Phe Ala Ala
            1205                1210                1215

Gly Leu Leu Leu Arg Lys Leu Thr Ser Lys Glu Leu Met Met Thr Thr
        1220                1225                1230

Ile Gly Ile Val Leu Leu Ser Gln Ser Ser Ile Pro Glu Thr Ile Leu
            1235                1240                1245

Glu Leu Thr Asp Ala Leu Ala Leu Gly Met Met Val Leu Lys Met Val
        1250                1255                1260

Arg Asn Met Glu Lys Tyr Gln Leu Ala Val Thr Ile Met Ala Ile Leu
1265                1270                1275                1280

Cys Val Pro Asn Ala Val Ile Leu Gln Asn Ala Trp Lys Val Ser Cys
            1285                1290                1295

Thr Ile Leu Ala Val Val Ser Val Ser Pro Leu Leu Leu Thr Ser Ser
        1300                1305                1310

Gln Gln Lys Ala Asp Trp Ile Pro Leu Ala Leu Thr Ile Lys Gly Leu
            1315                1320                1325

Asn Pro Thr Ala Ile Phe Leu Thr Thr Leu Ser Arg Thr Asn Lys Lys
        1330                1335                1340

Arg Ser Trp Pro Leu Asn Glu Ala Ile Met Ala Val Gly Met Val Ser
1345                1350                1355                1360

Ile Leu Ala Ser Ser Leu Leu Lys Asn Asp Ile Pro Met Thr Gly Pro
            1365                1370                1375

Leu Val Ala Gly Gly Leu Leu Thr Val Cys Tyr Val Leu Thr Gly Arg
        1380                1385                1390

Ser Ala Asp Leu Glu Leu Glu Arg Ala Thr Asp Val Lys Trp Asp Asp
            1395                1400                1405

Gln Ala Glu Ile Ser Gly Ser Ser Pro Ile Leu Ser Ile Thr Ile Ser
        1410                1415                1420

Glu Asp Gly Ser Met Ser Ile Lys Asn Glu Glu Glu Gln Thr Leu
1425                1430                1435                1440

Thr Ile Leu Ile Arg Thr Gly Leu Leu Val Ile Ser Gly Leu Phe Pro
            1445                1450                1455

Val Ser Ile Pro Ile Thr Ala Ala Ala Trp Tyr Leu Trp Glu Val Lys
        1460                1465                1470

Lys Gln Arg Ala Gly Val Leu Trp Asp Val Pro Ser Pro Pro Pro Val
            1475                1480                1485

Gly Lys Ala Glu Leu Glu Asp Gly Ala Tyr Arg Ile Lys Gln Lys Gly
        1490                1495                1500

Ile Leu Gly Tyr Ser Gln Ile Gly Ala Gly Val Tyr Lys Glu Gly Thr
1505                1510                1515                1520

Phe His Thr Met Trp His Val Thr Arg Gly Ala Val Leu Met His Lys
            1525                1530                1535

Gly Lys Arg Ile Glu Pro Ser Trp Ala Asp Val Lys Lys Asp Leu Ile
        1540                1545                1550

Ser Tyr Gly Gly Gly Trp Lys Leu Glu Gly Glu Trp Lys Glu Gly Glu
            1555                1560                1565
```

```
Glu Val Gln Val Leu Ala Leu Glu Pro Gly Lys Asn Pro Arg Ala Val
            1570                1575                1580

Gln Thr Lys Pro Gly Leu Phe Arg Thr Asn Thr Gly Thr Ile Gly Ala
1585                1590                1595                1600

Val Ser Leu Asp Phe Ser Pro Gly Thr Ser Gly Ser Pro Ile Val Asp
            1605                1610                1615

Lys Lys Gly Lys Val Val Gly Leu Tyr Gly Asn Gly Val Val Thr Arg
            1620                1625                1630

Ser Gly Ala Tyr Val Ser Ala Ile Ala Gln Thr Glu Lys Ser Ile Glu
            1635                1640                1645

Asp Asn Pro Glu Ile Glu Asp Asp Ile Phe Arg Lys Arg Arg Leu Thr
            1650                1655                1660

Ile Met Asp Leu His Pro Gly Ala Gly Lys Thr Lys Arg Tyr Leu Pro
1665                1670                1675                1680

Ala Ile Val Arg Glu Ala Ile Lys Arg Gly Leu Arg Thr Leu Ile Leu
            1685                1690                1695

Ala Pro Thr Arg Val Val Ala Ala Glu Met Glu Glu Ala Leu Arg Gly
            1700                1705                1710

Leu Pro Ile Arg Tyr Gln Thr Pro Ala Ile Arg Ala Glu His Thr Gly
            1715                1720                1725

Arg Glu Ile Val Asp Leu Met Cys His Ala Thr Phe Thr Met Arg Leu
            1730                1735                1740

Leu Ser Pro Ile Arg Val Pro Asn Tyr Asn Leu Ile Ile Met Asp Glu
1745                1750                1755                1760

Ala His Phe Thr Asp Pro Ala Ser Ile Ala Ala Arg Gly Tyr Ile Ser
            1765                1770                1775

Thr Arg Val Glu Met Gly Glu Ala Ala Gly Ile Phe Met Thr Ala Thr
            1780                1785                1790

Pro Pro Gly Ser Arg Asp Pro Phe Pro Gln Ser Asn Ala Pro Ile Met
            1795                1800                1805

Asp Glu Glu Arg Glu Ile Pro Glu Arg Ser Trp Asn Ser Gly His Glu
            1810                1815                1820

Trp Val Thr Asp Phe Lys Gly Lys Thr Val Trp Phe Val Pro Ser Ile
1825                1830                1835                1840

Lys Thr Gly Asn Asp Ile Ala Ala Cys Leu Arg Lys Asn Gly Lys Arg
            1845                1850                1855

Val Ile Gln Leu Ser Arg Lys Thr Phe Asp Ser Glu Tyr Val Lys Thr
            1860                1865                1870

Arg Thr Asn Asp Trp Asp Phe Val Val Thr Thr Asp Ile Ser Glu Met
            1875                1880                1885

Gly Ala Asn Phe Lys Ala Glu Arg Val Ile Asp Pro Arg Arg Cys Met
            1890                1895                1900

Lys Pro Val Ile Leu Thr Asp Gly Glu Glu Arg Val Ile Leu Ala Gly
1905                1910                1915                1920

Pro Met Pro Val Thr His Ser Ser Ala Ala Gln Arg Arg Gly Arg Ile
            1925                1930                1935

Gly Arg Asn Pro Arg Asn Glu Asn Asp Gln Tyr Ile Tyr Met Gly Glu
            1940                1945                1950

Pro Leu Glu Asn Asp Glu Asp Cys Ala His Trp Lys Glu Ala Lys Met
            1955                1960                1965

Leu Leu Asp Asn Ile Asn Thr Pro Glu Gly Ile Ile Pro Ser Leu Phe
            1970                1975                1980

Glu Pro Glu Arg Glu Lys Val Asp Ala Ile Asp Gly Glu Tyr Arg Leu
```

```
                1985                1990                1995                2000

Arg Gly Glu Ala Arg Lys Thr Phe Val Asp Leu Met Arg Arg Gly Asp
                    2005                2010                2015

Leu Pro Val Trp Leu Ala Tyr Lys Val Ala Ala Glu Gly Ile Asn Tyr
                    2020                2025                2030

Ala Asp Arg Arg Trp Cys Phe Asp Gly Thr Arg Asn Asn Gln Ile Leu
                    2035                2040                2045

Glu Glu Asn Val Glu Val Glu Ile Trp Thr Lys Glu Gly Glu Arg Lys
                    2050                2055                2060

Lys Leu Lys Pro Arg Trp Leu Asp Ala Arg Ile Tyr Ser Asp Pro Leu
2065                2070                2075                2080

Ala Leu Lys Glu Phe Lys Glu Phe Ala Ala Gly Arg Lys Ser Leu Thr
                    2085                2090                2095

Leu Asn Leu Ile Thr Glu Met Gly Arg Leu Pro Thr Phe Met Thr Gln
                    2100                2105                2110

Lys Ala Arg Asp Ala Leu Asp Asn Leu Ala Val Leu His Thr Ala Glu
                    2115                2120                2125

Ala Gly Gly Lys Ala Tyr Asn His Ala Leu Ser Glu Leu Pro Glu Thr
                    2130                2135                2140

Leu Glu Thr Leu Leu Leu Leu Thr Leu Leu Ala Thr Val Thr Gly Gly
2145                2150                2155                2160

Ile Phe Leu Phe Leu Met Ser Gly Arg Gly Met Gly Lys Met Thr Leu
                    2165                2170                2175

Gly Met Cys Cys Ile Ile Thr Ala Ser Ile Leu Leu Trp Tyr Ala Gln
                    2180                2185                2190

Ile Gln Pro His Trp Ile Ala Ala Ser Ile Ile Leu Glu Phe Phe Leu
                    2195                2200                2205

Ile Val Leu Leu Ile Pro Glu Pro Glu Lys Gln Arg Thr Pro Gln Asp
                    2210                2215                2220

Asn Gln Leu Thr Tyr Val Ile Ile Ala Ile Leu Thr Val Val Ala Ala
2225                2230                2235                2240

Thr Met Ala Asn Glu Met Gly Phe Leu Glu Lys Thr Lys Lys Asp Leu
                    2245                2250                2255

Gly Leu Gly Asn Ile Ala Thr Gln Gln Pro Glu Ser Asn Ile Leu Asp
                    2260                2265                2270

Ile Asp Leu Arg Pro Ala Ser Ala Trp Thr Leu Tyr Ala Val Ala Thr
                    2275                2280                2285

Thr Phe Ile Thr Pro Met Leu Arg His Ser Ile Glu Asn Ser Ser Val
                    2290                2295                2300

Asn Val Ser Leu Thr Ala Ile Ala Asn Gln Ala Thr Val Leu Met Gly
2305                2310                2315                2320

Leu Gly Lys Gly Trp Pro Leu Ser Lys Met Asp Ile Gly Val Pro Leu
                    2325                2330                2335

Leu Ala Ile Gly Cys Tyr Ser Gln Val Asn Pro Ile Thr Leu Thr Ala
                    2340                2345                2350

Ala Leu Leu Leu Leu Val Ala His Tyr Ala Ile Ile Gly Pro Gly Leu
                    2355                2360                2365

Gln Ala Lys Ala Thr Arg Glu Ala Gln Lys Arg Ala Ala Ala Gly Ile
                    2370                2375                2380

Met Lys Asn Pro Thr Val Asp Gly Ile Thr Val Ile Asp Leu Asp Pro
2385                2390                2395                2400

Ile Pro Tyr Asp Pro Lys Phe Glu Lys Gln Leu Gly Gln Val Met Leu
                    2405                2410                2415
```

```
Leu Val Leu Cys Val Thr Gln Val Leu Met Met Arg Thr Thr Trp Ala
            2420                2425                2430

Leu Cys Glu Ala Leu Thr Leu Ala Thr Gly Pro Val Ser Thr Leu Trp
        2435                2440                2445

Glu Gly Asn Pro Gly Arg Phe Trp Asn Thr Thr Ile Ala Val Ser Met
2450                2455                2460

Ala Asn Ile Phe Arg Gly Ser Tyr Leu Ala Gly Ala Gly Leu Leu Phe
2465                2470                2475                2480

Ser Ile Met Lys Asn Thr Thr Ser Thr Arg Arg Gly Thr Gly Asn Ile
            2485                2490                2495

Gly Glu Thr Leu Gly Glu Lys Trp Lys Ser Arg Leu Asn Ala Leu Gly
                2500                2505                2510

Lys Ser Glu Phe Gln Ile Tyr Lys Lys Ser Gly Ile Gln Glu Val Asp
            2515                2520                2525

Arg Thr Leu Ala Lys Glu Gly Ile Lys Arg Gly Glu Thr Asp His His
            2530                2535                2540

Ala Val Ser Arg Gly Ser Ala Lys Leu Arg Trp Phe Val Glu Arg Asn
2545                2550                2555                2560

Leu Val Thr Pro Glu Gly Lys Val Val Asp Leu Gly Cys Gly Arg Gly
                2565                2570                2575

Gly Trp Ser Tyr Tyr Cys Gly Gly Leu Lys Asn Val Arg Glu Val Lys
            2580                2585                2590

Gly Leu Thr Lys Gly Gly Pro Gly His Glu Glu Pro Ile Pro Met Ser
            2595                2600                2605

Thr Tyr Gly Trp Asn Leu Val Arg Leu Gln Ser Gly Val Asp Val Phe
            2610                2615                2620

Phe Val Pro Pro Glu Lys Cys Asp Thr Leu Leu Cys Asp Ile Gly Glu
2625                2630                2635                2640

Ser Ser Pro Asn Pro Thr Val Glu Ala Gly Arg Thr Leu Arg Val Leu
                2645                2650                2655

Asn Leu Val Glu Asn Trp Leu Asn Asn Asn Thr Gln Phe Cys Val Lys
            2660                2665                2670

Val Leu Asn Pro Tyr Met Pro Ser Val Ile Glu Arg Met Glu Thr Leu
            2675                2680                2685

Gln Arg Lys Tyr Gly Gly Ala Leu Val Arg Asn Pro Leu Ser Arg Asn
            2690                2695                2700

Ser Thr His Glu Met Tyr Trp Val Ser Asn Ala Ser Gly Asn Ile Val
2705                2710                2715                2720

Ser Ser Val Asn Met Ile Ser Arg Met Leu Ile Asn Arg Phe Thr Met
                2725                2730                2735

Arg His Lys Lys Ala Thr Tyr Glu Pro Asp Val Asp Leu Gly Ser Gly
            2740                2745                2750

Thr Arg Asn Ile Gly Ile Glu Ser Glu Thr Pro Asn Leu Asp Ile Ile
            2755                2760                2765

Gly Lys Arg Ile Glu Lys Ile Lys Gln Glu His Glu Thr Ser Trp His
            2770                2775                2780

Tyr Asp Gln Asp His Pro Tyr Lys Thr Trp Ala Tyr His Gly Ser Tyr
2785                2790                2795                2800

Glu Thr Lys Gln Thr Gly Ser Ala Ser Ser Met Val Asn Gly Val Val
                2805                2810                2815

Arg Leu Leu Thr Lys Pro Trp Asp Val Val Pro Met Val Thr Gln Met
                2820                2825                2830

Ala Met Thr Asp Thr Thr Pro Phe Gly Gln Gln Arg Val Phe Lys Glu
```

```
                       2835                2840                2845
Lys Val Asp Thr Arg Thr Gln Glu Pro Lys Glu Gly Thr Lys Lys Leu
                  2850                2855                2860
Met Lys Ile Thr Ala Glu Trp Leu Trp Lys Glu Leu Gly Lys Lys Lys
2865                2870                2875                2880
Thr Pro Arg Met Cys Thr Arg Glu Glu Phe Thr Lys Lys Val Arg Ser
                  2885                2890                2895
Asn Ala Ala Leu Gly Ala Ile Phe Thr Asp Glu Asn Lys Trp Lys Ser
                  2900                2905                2910
Ala Arg Glu Ala Val Glu Asp Ser Arg Phe Trp Glu Leu Val Asp Lys
                  2915                2920                2925
Glu Arg Asn Leu His Leu Glu Gly Lys Cys Glu Thr Cys Val Tyr Asn
                  2930                2935                2940
Met Met Gly Lys Arg Glu Lys Lys Leu Gly Glu Phe Gly Lys Ala Lys
2945                2950                2955                2960
Gly Ser Arg Ala Ile Trp Tyr Met Trp Leu Gly Ala Arg Phe Leu Glu
                  2965                2970                2975
Phe Glu Ala Leu Gly Phe Leu Asn Glu Asp His Trp Phe Ser Arg Glu
                  2980                2985                2990
Asn Ser Leu Ser Gly Val Glu Gly Glu Gly Leu His Lys Leu Gly Tyr
                  2995                3000                3005
Ile Leu Arg Glu Val Ser Lys Lys Glu Gly Gly Ala Met Tyr Ala Asp
                  3010                3015                3020
Asp Thr Ala Gly Trp Asp Thr Arg Ile Thr Ile Glu Asp Leu Lys Asn
3025                3030                3035                3040
Glu Glu Met Ile Thr Asn His Met Ala Gly Glu His Lys Lys Leu Ala
                  3045                3050                3055
Glu Ala Ile Phe Lys Leu Thr Tyr Gln Asn Lys Val Val Arg Val Gln
                  3060                3065                3070
Arg Pro Thr Pro Arg Gly Thr Val Met Asp Ile Ile Ser Arg Arg Asp
                  3075                3080                3085
Gln Arg Gly Ser Gly Gln Val Gly Thr Tyr Gly Leu Asn Thr Phe Thr
                  3090                3095                3100
Asn Met Glu Ala Gln Leu Ile Arg Gln Met Glu Gly Glu Gly Ile Phe
3105                3110                3115                3120
Lys Ser Ile Gln His Leu Thr Ala Ser Glu Glu Ile Ala Val Gln Asp
                  3125                3130                3135
Trp Leu Val Arg Val Gly Arg Glu Arg Leu Ser Arg Met Ala Ile Ser
                  3140                3145                3150
Gly Asp Asp Cys Val Val Lys Pro Leu Asp Asp Arg Phe Ala Arg Ala
                  3155                3160                3165
Leu Thr Ala Leu Asn Asp Met Gly Lys Val Arg Lys Asp Ile Gln Gln
                  3170                3175                3180
Trp Glu Pro Ser Arg Gly Trp Asn Asp Trp Thr Gln Val Pro Phe Cys
3185                3190                3195                3200
Ser His His Phe His Glu Leu Ile Met Lys Asp Gly Arg Thr Leu Val
                  3205                3210                3215
Val Pro Cys Arg Asn Gln Asp Glu Leu Ile Gly Arg Ala Arg Ile Ser
                  3220                3225                3230
Gln Gly Ala Gly Trp Ser Leu Arg Glu Thr Ala Cys Leu Gly Lys Ser
                  3235                3240                3245
Tyr Ala Gln Met Trp Ser Leu Met Tyr Phe His Arg Arg Asp Leu Arg
                  3250                3255                3260
```

Leu Ala Ala Asn Ala Ile Cys Ser Ala Val Pro Ser His Trp Ile Pro
3265 3270 3275 3280

Thr Ser Arg Thr Thr Trp Ser Ile His Ala Ser His Glu Trp Met Thr
3285 3290 3295

Thr Glu Asp Met Leu Thr Val Trp Asn Arg Val Trp Ile Leu Glu Asn
3300 3305 3310

Pro Trp Met Glu Asp Lys Thr Pro Val Glu Ser Trp Glu Glu Ile Pro
3315 3320 3325

Tyr Leu Gly Lys Arg Glu Asp Gln Trp Cys Gly Ser Leu Ile Gly Leu
3330 3335 3340

Thr Ser Arg Ala Thr Trp Ala Lys Asn Ile Gln Thr Ala Ile Asn Gln
3345 3350 3355 3360

Val Arg Ser Leu Ile Gly Asn Glu Glu Tyr Thr Asp Tyr Met Pro Ser
3365 3370 3375

Met Lys Arg Phe Arg Arg Glu Glu Glu Glu Ala Gly Val Leu Trp
3380 3385 3390

<210> SEQ ID NO 48
<211> LENGTH: 15153
<212> TYPE: DNA
<213> ORGANISM: Artificial Sequence
<220> FEATURE:
<223> OTHER INFORMATION: Dengue 3 plasmid p3

<400> SEQUENCE: 48
agttgttagt ctacgtggac cgacaagaac agtttcgact cggaagcttg cttaacgtag 60
tactgacagt tttttattag agagcagatc tctgatgaac aaccaacgga aaaagacggg 120
aaaaccgtct atcaatatgc tgaaacgcgt gagaaaccgt gtgtcaactg gatcacagtt 180
ggcgaagaga ttctcaagag gactgctgaa cggccaagga ccaatgaaat tggttatggc 240
gttcatagct ttcctcagat ttctagccat tccaccgaca gcaggagtct tggctagatg 300
gggaaccttt aagaagtcgg gggctattaa ggtcctgaga ggcttcaaga aggagatctc 360
aaacatgctg agcattatca acagacggaa aaagacatcg ctctgtctca tgatgatgtt 420
accagcaaca cttgctttcc acttgacttc acgagatgga gagccgcgca tgattgtggg 480
gaagaatgaa agaggaaaat ccctactttt taagacagcc tctggaatca acatgtgcac 540
actcatagcc atggatttgg gagagatgtg tgatgacacg gtcacctaca aatgccccct 600
cattactgaa gtggagcctg aagacattga ctgctggtgc aaccttacat cgacatgggt 660
gacctacgga acgtgcaatc aagctggaga gcacagacgc gacaaaagat cggtggcgtt 720
agctccccat gtcggcatgg gactggacac acgcacccaa acctggatgt cggctgaagg 780
agcttggaga caggtcgaga aggtagagac atgggccttt aggcacccag ggttcacaat 840
actagcccta tttcttgccc attacatagg cacttccttg acccagaaag tggttatttt 900
catactacta atgctggtca ccccatccat gacaatgaga tgcgtgggag taggaaacag 960
agattttgtg gaaggcctat caggagctac gtgggttgac gtggtgctcg agcacggtgg 1020
gtgtgtgact accatggcta agaacaagcc cacgctggat atagagctcc agaagaccga 1080
ggccacccaa ctggcgaccc taaggaaact atgtattgag ggaaaaatta ccaacgtaac 1140
aaccgactca aggtgcccca cccaagggga agcgatttta cctgaggagc aggaccagaa 1200
ccacgtgtgc aagcacacat acgtggacag aggctgggga aacggttgtg gtttgtttgg 1260
caagggaagc ctggtaacat gcgcgaaatt tcaatgtttg gaatcaatag agggaaaagt 1320
ggtgcagcat gagaacctca aatacaccgt catcatcaca gtgcacacag gagatcaaca 1380

```
ccaggtggga aatgaaacgc agggagtcac ggctgagata acaccccagg catcaaccgt   1440
tgaagccatc ttacctgaat atggaaccct tgggctagaa tgctcaccac ggacaggttt   1500
agatttcaat gaaatgattt tgttgacaat gaagaacaaa gcatggatgg tacatagaca   1560
atggtttttt gacctacctt taccatggac atcaggagct acaacagaaa caccaacctg   1620
gaataagaaa gagcttcttg tgacattcaa aaacgcacat gcaaaaaagc aagaagtagt   1680
agtccttgga tcgcaagagg gagcaatgca cacagcactg acaggagcta cagagatcca   1740
aacctcagga ggcacaagta ttttgcggg gcacttaaaa tgtagactca agatggacaa   1800
attggaactc aaggggatga gctatgcaat gtgcttgaat gcctttgtgt tgaagaaaga   1860
agtctccgaa acgcaacatg gacaatact catcaaggtt gagtacaaag gggaagatgc   1920
accttgcaag attcctttct ccacggagga tggacaaggg aaagcccaca atggcagact   1980
gatcacagct aacccagtgg tgaccaagaa ggaggagcct gtcaatattg aggcagaacc   2040
tccttttggg gaaagcaata tagtaattgg aattggagac aaagccttga aaatcaactg   2100
gtacaagaag ggaagctcga ttgggaagat gttcgaggcc actgccagag gtgcaaggcg   2160
catggccatc ttgggagaca cagcctggga ctttggatca gtaggtggtg tttttaaattc   2220 attaggaaaa atggtgcacc aaatatttgg aagtgcttac acagccctat ttagtggagt   2280
ctcctggata atgaaaattg gaataggtgt ccttttaacc tggatagggt tgaattcaaa   2340
aaacactagt atgagcttta gctgcattgt gataggaatc attacactct atctgggagc   2400
cgtggtgcaa gctgacatgg ggtgtgtcat aaactgaaaa ggcaaagaac tcaaatgtgg   2460
aagtggaatt ttcgtcacta atgaggtcca cacctggaca gagcaataca aatttcaagc   2520
agactccccc aaaagactgg cgacagccat tgcaggcgct tgggagaatg gagtgtgcgg   2580
aatcaggtcg acaaccagaa tggagaacct cttgtggaag caaatagcca atgaactgaa   2640
ctacatatta tgggaaaaca acatcaaatt aacggtagtt gtgggtgata taattgggt   2700 cttagagcaa gggaaaagaa cactaacacc acaacccatg gaactaaaat attcatggaa   2760
aacatgggga aaggcgaaga tagtgacagc tgaaacacaa aattcctctt tcataataga   2820
tgggccaaac acaccagagt gtccaagtgc ctcaagagca tggaatgtgt gggaggtgga   2880
agattacggg ttcggagtct tcacaactaa catatggctg aaactccgag agatgtacac   2940
ccaactatgt gaccacaggc taatgtcggc agccgttaag gatgagaggg ccgtacacgc   3000
cgacatgggc tattggatag aaagccaaaa gaatggaagt tggaagctag aaaaggcatc   3060
cctcatagag gtaaaaacct gcacatggcc aaaatcacac actctttgga gcaatggtgt   3120
gctagagagt gacatgatca tcccaaagag tctggctggt cccatttcgc aacacaacta   3180
caggcccgga taccacaccc aaacggcagg accctggcac ttaggaaaat tggagctgga   3240
cttcaactat tgtgaaggaa caacagttgt catcacagaa aattgtggga caagaggccc   3300
atcactgaga acaacaacag tgtcaggaaa gttgatacac gaatggtgtt gccgctcgtg   3360
tacacttcct cccctgcgat acatgggaga agacggctgc tggtatgcca tggaaattag   3420
acccattaat gagaaagaag agaacatggt aaagtcttta gtctcagcag ggagtggaaa   3480
ggtggataac ttcacaatgg gtgtcttgtg tttggcaatc cttttgaag aggtgatgag   3540 aggaaaattt gggaaaaagc acatgattgc aggggttctc ttcacgtttg tactccttct   3600
ctcagggcaa ataacatgga gagacatggc gcacacactc ataatgattg ggtccaacgc   3660
ctctgacaga atgggaatgg gcgtcactta cctagcattg attgcaacat ttaaaattca   3720 gccattttg gctttgggat tcttcctgag gaaactgaca tctagagaaa atttattgtt   3780
```

```
gggagttggg ttggccatgg caacaacgtt acaactgcca gaggacattg aacaaatggc    3840
gaatggaata gctttagggc tcatggctct taaattaata acacaatttg aaacatacca    3900
actatggacg gcattagtct ccctaatgtg ttcaaataca attttcacgt tgactgttgc    3960
ctggagaaca gccaccctga ttttggccgg aatttctctt ttgccagtgt gccagtcttc    4020
gagcatgagg aaaacagatt ggctcccaat ggctgtggca gctatgggag ttccacccct    4080 accactttt attttcagtt tgaaagatac gctcaaaagg agaagctggc cactgaatga    4140
gggggtgatg gctgttggac ttgtgagtat tctagctagt tctctcctta ggaatgacgt    4200
gcccatggct ggaccattag tggctggggg cttgctgata gcgtgctacg tcataactgg    4260
cacgtcagca gacctcactg tagaaaaagc agcagatgtg acatgggagg aagaggctga    4320
gcaaacagga gtgtcccaca atttaatgat cacagttgat gacgatggaa caatgagaat    4380
aaaagatgat gagactgaga acatcttaac agtgcttttg aaaacagcat tactaatagt    4440
gtcaggcatt tttccatact ccatacccgc aacactgttg gtctggcaca cttggcaaaa    4500
gcaaacccaa agatccggtg tcctatggga cgttcccagc ccccagaga cacagaaagc    4560 agaactggaa aaggggttt ataggatcaa gcagcaagga atttttggga aacccaagt    4620 ggggggttgga gtacaaaaag aaggagtttt ccacaccatg tggcacgtca agaggagc    4680 agtgttgaca cacaatggga aaagactgga accaaactgg gctagcgtga aaaagatct    4740 gatttcatac ggaggaggat ggaaattgag tgcacaatgg caaaaggag aggaggtgca    4800 ggttattgcc gtagagcctg gaagaaccc aaagaacttt caaaccatgc caggcatttt    4860
ccagacaaca cagggagaa taggagcgat tgcactggac ttcaagcctg aacttcagg    4920 atctcccatc ataaacagag agggaaaggt actgggattg tatggcaatg gagtggtcac    4980
aaagaatggt ggctatgtca gtggaatagc acaaacaaat gcagaaccag acggaccgac    5040
accagagttg gaagaagaga tgttcaaaaa gcgaaatcta accataatgg atctccatcc    5100
cgggtcagga aagacgcgga atatcttcc agctattgtt agagaggcaa tcaagagacg    5160
cttaaggact ctaatttgg caccaacaag ggtagttgca gctgagatgg aagaagcatt    5220
gaaagggctc ccaataaggt atcaaacaac tgcaacaaaa tctgaacaca cagggagaga    5280
gattgttgat ctaatgtgcc acgcaacgtt cacaatgcgt ttgctgtcac cagtcagggt    5340
tccaaactac aacttgataa taatggatga ggctcatttc acagacccag ccagtatagc    5400
ggctagaggg tacatatcaa ctcgtgtagg aatgggagag gcagccgcaa ttttcatgac    5460
agccacaccc cctggaacag ctgatgcctt tcctcagagc aacgctccaa ttcaagatga    5520
agaaagagac ataccagaac gctcatggaa ttcaggcaat gaatggatta ccgactttgc    5580
cgggaagacg gtgtggtttg tccctagcat caaagctgga aatgacatag caaactgctt    5640
gcggaaaaat ggaaaaaagg tcattcaact tagtaggaag acttttgaca cagaatatca    5700
aaagactaaa ctaaatgatt gggactttgt ggtgacaaca gacatttcag aaatgggagc    5760
caatttcaaa gcagacagag tgatcgaccc aagaagatgt ctcaagccag tgattttgac    5820
agacggaccc gagcgcgtga tcctggcggg accaatgcca gtcaccgtag cgagcgctgc    5880
gcaaaggaga gggagagttg gcaggaaccc acaaaaagaa aatgaccaat acatattcat    5940
gggccagccc ctcaataatg atgaagacca tgctcactgg acagaagcaa aaatgctgct    6000
agacaacatc aacacaccag aagggatcat accagctctc tttgaaccag aaagggagaa    6060
gtcagccgcc atagacggcg aataccgcct gaagggtgag tccaggaaga ccttcgtgga    6120
actcatgagg agggggtgacc tcccagtttg gctagcccat aaagtagcat cagaagggat    6180
```

```
caaatataca gatagaaagt ggtgttttga tggagaacgc aacaatcaaa ttttagagga   6240
gaatatggat gtggaaatct ggacaaagga aggagaaaag aaaaaattga gacctaggtg   6300
gcttgatgcc cgcacttatt cagatcccTt agcgctcaag gaattcaagg actttgcggc   6360
tggtagaaag tcaattgccc ttgatcttgt gacagaaata ggaagagtgc cttcacactt   6420
agctcacaga acgagaaacg ccctggacaa tctggtgatg ttgcacacgt cagaacatgg   6480
cgggagggcc tacaggcatg cagtggagga actaccagaa acaatggaaa cactcttact   6540
cctgggactc atgatcctgt taacaggtgg agcaatgctt ttcttgatat caggtaaagg   6600
gattggaaag acttcaatag gactcatttg tgtagctgct ccagcggta tgttatggat    6660
ggctgatgtc ccactccaat ggatcgcgtc tgccatagtc ctggagtttt ttatgatggt   6720
gttacttata ccagaaccag aaaagcagag aactccccaa gacaatcaac tcgcatatgt   6780
cgtgataggc atactcacac tggctgcaat agtagcagcc aatgaaatgg gactgttgga   6840
aaccacaaag agagatttag gaatgtccaa agaaccaggt gttgtttctc caaccagcta   6900
tttggatgtg gacttgcacc cagcatcagc ctggacattg tacgctgtgg ccacaacagt   6960
aataacacca atgttgagac ataccataga gaattccaca gcaaatgtgt ccctggcagc   7020
tatagccaac caggcagtgg tcctgatggg tttagacaaa ggatggccga tatcgaaaat   7080
ggacttaggc gtgccactat tggcactggg ttgttattca caagtgaacc cactaactct   7140
cacagcggca gttctcctgc tagtcacgca ttatgctatt ataggtccag gattgcaggc   7200
aaaagccact cgtgaagctc aaaaaaggac agctgctgga ataatgaaga tccaacggt   7260
ggatgggata atgacaatag acctagatcc tgtaatatac gattcaaaat tgaaaagca   7320
actaggacag gttatgctcc tggttctgtg tgcagttcaa cttttgttaa tgagaacatc   7380
atgggctttt tgtgaagctc taacccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
gagagggaca gggtcacagg gtgaaacctt gggagaaaag tggaaaaaga aattgaatca   7620
attaccccgg aaagagtttg acctttacaa gaaatccgga atcactgaag tggatagaac   7680
agaagccaaa gaagggttga aaagaggaga ataacacac catgccgtgt ccagaggcag   7740
cgcaaaactt caatggttcg tggagagaaa catggtcatc cccgaaggaa gagtcataga   7800
cttaggctgt ggaagaggag gctggtcata ttattgtgca ggactgaaaa aagttacaga   7860
agtgcgagga tacacaaaag gcggcccagg acatgaagaa ccagtaccta tgtctacata   7920
cggatgaaac atagtcaagt taatgagtgg aaaggatgtg ttttatcttc cacctgaaaa   7980
gtgtgatact ctattgtgtg acattggaga atcttcacca agcccaacag tggaagaaag   8040
cagaaccata agagtcttga gatggttga accatggcta aaaatatacc agttttgcat   8100
taaagtattg aaccctaca tgccaactgt gattgagcac ctagaaagac tacaaaggaa   8160
acatggagga atgcttgtga gaatccact ctcacgaaac tccacgcacg aaatgtactg   8220
gatatctaat ggcacaggca atatcgtttc ttcagtcaac atggtatcca gattgctact   8280
taacagattc acaatgacac ataggagacc caccatagag aaagatgtgg atttaggagc   8340
ggggaccccga catgtcaatg cggaaccaga acacccaac atggatgtca ttgggggaaag   8400
aataagaagg atcaaggagg agcatagttc aacatggcac tatgatgatg aaatccTta   8460
taaacgtgg gcttaccatg gatcctatga agttaaggcc acaggctcag cctcctccat   8520
gataaatgga gtcgtgaaac tcctcacgaa accatgggat gtggtgccca tggtgacaca   8580
```

```
gatggcaatg acggatacaa ccccattcgg ccagcaaagg gttttttaaag agaaagtgga    8640
caccaggaca cccagaccta tgccaggaac aagaaaggtt atggagatca cagcggaatg    8700
gctttggaga accctgggaa ggaacaaaag acccagatta tgtacgagag aggagttcac    8760
aaaaaaggtc agaaccaacg cagctatggg cgccgttttt acagaggaga accaatggga    8820
cagtgctaga gctgctgttg aggatgaaga attctggaaa ctcgtggaca gagaacgtga    8880
actccacaaa ttgggcaagt gtggaagctg cgtttacaac atgatgggca agagagagaa    8940
gaaacttgga gagtttggca aagcaaaagg cagtagagcc atatggtaca tgtggttggg    9000
agccagatac cttgagttcg aagcactcgg attcttaaat gaagaccatt ggttctcgcg    9060
tgaaaactct tacagtggag tagaaggaga aggactgcac aagctgggat acatcttaag    9120
agacatttcc aagatacccg gaggagctat gtatgctgat gacacagctg ttgggacac    9180
aagaataaca gaagatgacc tgcacaatga ggaaaaaatc acacagcaaa tggaccctga    9240
acacaggcag ttagcaaacg ctatattcaa gctcacatac caaaacaaag tggtcaaagt    9300
tcaacgacca actccaaagg gcacggtaat ggacatcata tctaggaaag accaaagagg    9360
cagtggacag gtgggaactt atggtctgaa tacattcacc aacatggaag cccagttaat    9420
cagacaaatg gaaggagaag gtgtgttgtc gaaggcagac ctcgagaacc ctcatctgct    9480
agagaagaaa gttacacaat ggttggaaac aaaaggagtg gagaggttaa aaagaatggc    9540
catcagcggg gatgattgcg tggtgaaacc aattgatgac aggttcgcca atgccctgct    9600
tgccctgaat gacatgggaa aagttaggaa ggacatacct caatggcagc catcaaaggg    9660
atggcatgat tggcaacagg tcccttcctg ctcccaccac tttcatgaat tgatcatgaa    9720
agatggaaga aagttggtag ttccctgcag acctcaggat gaattaatcg ggagagcgag    9780
aatctctcaa ggagcaggat ggagccttag agaaactgca tgcctaggga agcctacgc    9840
ccaaatgtgg actctcatgt actttcacag aagagatctt agactagcat ccaacgccat    9900
atgttcagca gtaccagtcc attgggtccc cacaagcaga acgacgtggt ctattcatgc    9960
tcaccatcag tggatgacta cagaagacat gcttactgtt tggaacaggg tgtggataga   10020
ggataatcca tggatggaag acaaaactcc agtcaaaacc tgggaagatg ttccatatct   10080
agggaagaga gaagaccaat ggtgcggatc actcattggt ctcacttcca gagcaacctg   10140
ggcccagaac atacttacgg caatccaaca ggtgagaagc cttataggca atgaagagtt   10200
tctggactac atgccttcga tgaagagatt caggaaggag gaggagtcag agggagccat   10260
ttggtaaacg taggaagtga aaaagaggca aactgtcagg ccaccttaag ccacagtacg   10320
gaagaagctg tgcagcctgt gagccccgtc caaggacgtt aaaagaagaa gtcaggccca   10380
aaagccacgg tttgagcaaa ccgtgctgcc tgtggctccg tcgtgggac gtaaaacctg   10440
ggaggctgca aactgtggaa gctgtacgca cggtgtagca gactagcggt tagaggagac   10500
ccctcccatg acacaacgca gcagcggggc ccgagctctg agggaagctg tacctccttg   10560
caaaggacta gaggttagag gagacccccc gcaaataaaa acagcatatt gacgctggga   10620
gagaccagag atcctgctgt ctcctcagca tcattccagg cacagaacgc cagaaaatgg   10680
aatggtgctg ttgaatcaac aggttctggt accggtaggc atcgtggtgt cacgctcgtc   10740
gtttggtatg gcttcattca gctccggttc ccaacgatca aggcgagtta catgatcccc   10800
catgttgtgc aaaaaagcgg ttagctcctt cggtcctccg atcgttgtca gaagtaagtt   10860
ggccgcagtg ttatcactca tggttatggc agcactgcat aattctctta ctgtcatgcc   10920
atccgtaaga tgcttttctg tgactggtga gtactcaacc aagtcattct gagaatagtg   10980
```

```
tatgcggcga ccgagttgct cttgcccggc gtcaacacgg gataataccg cgccacatag   11040
cagaacttta aaagtgctca tcattggaaa acgttcttcg gggcgaaaac tctcaaggat   11100
cttaccgctg ttgagatcca gttcgatgta acccactcgt gcacccaact gatcttcagc   11160
atcttttact ttcaccagcg tttctgggtg agcaaaaaca ggaaggcaaa atgccgcaaa   11220
aaagggaata agggcgacac ggaaatgttg aatactcata ctcttccttt ttcaatatta   11280
ttgaagcatt tatcagggtt attgtctcat gagcggatac atatttgaat gtatttagaa   11340
aaataaacaa ataggggttc cgcgcacatt tccccgaaaa gtgccacctg acgtctaaga   11400
aaccattatt atcatgacat taacctataa aaataggcgt atcacgaggc cctttcgtct   11460
tcaagaattc tcatgtttga cagcttatca tcgataagct ttaatgcggt agtttatcac   11520
agttaaattg ctaacgcagt caggcaccgt gtatgaaatc taacaatgcg ctcatcgtca   11580
tcctcggcac cgtcaccctg gatgctgtag cataggctt ggttatgccg gtactgccgg   11640
gcctcttgcg ggatatcgtc cattccgaca gcatcgccag tcactatggc gtgctgctgg   11700
cgctatatgc gttgatgcaa tttctatgcg cacccgttct cggagcactg tccgaccgct   11760
ttggccgccg cccagtcctg ctcgcttcgc tacttggagc cactatcgac tacgcgatca   11820
tggcgaccac acccgtcctg tggatcctct acgccggacg catcgtggcc ggcatcaccg   11880
gcgccacagg tgcggttgct ggcgcctata tcgccgacat caccgatggg gaagatcggg   11940
ctcgccactt cgggctcatg agcgcttgtt tcggcgtggg tatggtggca ggccccgtgg   12000 ccggggggact gttgggcgcc atctccttgc atgcaccatt ccttgcggcg gcggtgctca   12060
acggcctcaa cctactactg ggctgcttcc taatgcagga gtcgcataag ggagagcgtc   12120
gaccgatgcc cttgagagcc ttcaacccag tcagctcctt ccgtgggcg cggggcatga   12180 ctatcgtcgc cgcacttatg actgtcttct ttatcatgca actcgtagga caggtgccgg   12240
cagcgctctg ggtcattttc ggcgaggacc gctttcgctg gagcgcgacg atgatcggcc   12300
tgtcgcttgc ggtattcgga atcttgcacg ccctcgctca agccttcgtc actggtcccg   12360
ccaccaaacg tttcggcgag aagcaggcca ttatcgccgg catggcggcc gacgcgctgg   12420
gctacgtctt gctggcgttc gcgacgcgag gctggatggc cttccccatt atgattcttc   12480
tcgcttccgg cggcatcggg atgcccgcgt tgcaggccat gctgtccagg caggtagatg   12540
acgaccatca gggacagctt caaggatcgc tcgcggctct taccagccta acttcgatca   12600
ctggaccgct gatcgtcacg gcgatttatg ccgcctcggc gagcacatgg aacgggttgg   12660
catggattgt aggcgccgcc ctataccttg tctgcctccc cgcgttgcgt cgcggtgcat   12720
ggagccgggc cacctcgacc tgaatggaag ccggcggcac ctcgctaacg gattcaccac   12780
tccaagaatt ggagccaatc aattcttgcg gagaactgtg aatgcgcaaa ccaacccttg   12840
gcagaacata tccatcgcgt ccgccatctc cagcagccgc acgcggcgca tctcgggcag   12900
cgttgggtcc tggccacggg tgcgcatgat cgtgctcctg tcgttgagga cccggctagg   12960
ctggcggggt tgccttactg gttagcagaa tgaatcaccg atacgcgagc gaacgtgaag   13020
cgactgctgc tgcaaaacgt ctgcgacctg agcaacaaca tgaatggtct tcggtttccg   13080
tgtttcgtaa agtctggaaa cgcggaagtc agcgccctgc accattatgt tccggatctg   13140
catcgcagga tgctgctggc tacccgtgg aacacctaca tctgtattaa cgaagcgctg   13200
gcattgaccc tgagtgattt ttctctggtc ccgccgcatc cataccgcca gttgtttacc   13260
ctcacaaacg tccagtaacc gggcatgttc atcatcagta acccgtatcg tgagcatcct   13320
ctctcgtttc atcggtatca ttacccccat gaacagaaat cccccttaca cggaggcatc   13380
```

```
agtgaccaaa caggaaaaaa ccgcccttaa catggcccgc tttatcagaa gccagacatt    13440
aacgcttctg gagaaactca acgagctgga cgcggatgaa caggcagaca tctgtgaatc    13500
gcttcacgac cacgctgatg agctttaccg cagctgcctc gcgcgtttcg gtgatgacgg    13560
tgaaaacctc tgacacatgc agctcccgga cacggtcaca gcttgtctgt aagcggatgc    13620
cgggagcaga caagcccgtc agggcgcgtc agcgggtgtt ggcgggtgtc ggggcgcagc    13680
catgacccag tcacgtagcg atagcggagt gtatactggc ttaactatgc ggcatcagag    13740
cagattgtac tgagagtgca ccatatgcgg tgtgaaatac cgcacagatg cgtaaggaga    13800
aaataccgca tcaggcgctc ttccgcttcc tcgctcactg actcgctgcg ctcggtcgtt    13860
cggctgcggc gagcggtatc agctcactca aaggcggtaa tacggttatc cacagaatca    13920
ggggataacg caggaaagaa catgtgagca aaaggccagc aaaaggccag gaaccgtaaa    13980
aaggccgcgt tgctggcgtt tttccatagg ctccgccccc ctgacgagca tcacaaaaat    14040
cgacgctcaa gtcagaggtg gcgaaacccg acaggactat aaagatacca ggcgtttccc    14100
cctggaagct ccctcgtgcg ctctcctgtt ccgaccctgc cgcttaccgg atacctgtcc    14160
gcctttctcc cttcgggaag cgtggcgctt tctcatagct cacgctgtag gtatctcagt    14220
tcggtgtagg tcgttcgctc caagctgggc tgtgtgcacg aaccccccgt tcagcccgac    14280
cgctgcgcct tatccggtaa ctatcgtctt gagtccaacc cggtaagaca cgacttatcg    14340
ccactggcag cagccactgg taacaggatt agcagagcga ggtatgtagg cggtgctaca    14400
gagttcttga agtggtggcc taactacggc tacactagaa ggacagtatt tggtatctgc    14460
gctctgctga agccagttac cttcggaaaa agagttggta gctcttgatc cggcaaacaa    14520
accaccgctg gtagcggtgg tttttttgtt tgcaagcagc agattacgcg cagaaaaaaa    14580
ggatctcaag aagatccttt gatcttttct acggggtctg acgctcagtg gaacgaaaac    14640
tcacgttaag ggattttggt catgagatta tcaaaaagga tcttcaccta gatccttta    14700 aattaaaaat gaagttttaa atcaatctaa agtatatatg agtaaacttg gtctgacagt    14760
taccaatgct taatcagtga ggcacctatc tcagcgatct gtctatttcg ttcatccata    14820
gttgcctgac tccccgtcgt gtagataact acgatacggg agggcttacc atctggcccc    14880
agtgctgcaa tgataccgcg agacccacgc tcaccggctc cagatttatc agcaataaac    14940
cagccagccg gaagggccga gcgcagaagt ggtcctgcaa ctttatccgc ctccatccag    15000
tctattaatt gttgccggga agctagagta agtagttcgc cagttaatag tttgcgcaac    15060
gttgttgcca ttgctgcaag atctggctag cgatgaccct gctgattggt tcgctgacca    15120
tttccgggcg cgccgattta ggtgacacta tag                                 15153
```

<210> SEQ ID NO 49
<211> LENGTH: 3390
<212> TYPE: PRT
<213> ORGANISM: Dengue 3 (Sleman/78) virus

<400> SEQUENCE: 49

Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

```
Val Leu Ala Arg Trp Gly Thr Phe Lys Lys Ser Gly Ala Ile Lys Val
 65                  70                  75                  80

Leu Arg Gly Phe Lys Lys Glu Ile Ser Asn Met Leu Ser Ile Asn
                 85                  90                  95

Arg Arg Lys Lys Thr Ser Leu Cys Leu Met Met Leu Pro Ala Thr
            100                 105                 110

Leu Ala Phe His Leu Thr Ser Arg Asp Gly Glu Pro Arg Met Ile Val
            115                 120                 125

Gly Lys Asn Glu Arg Gly Lys Ser Leu Leu Phe Lys Thr Ala Ser Gly
            130                 135                 140

Ile Asn Met Cys Thr Leu Ile Ala Met Asp Leu Gly Glu Met Cys Asp
145                 150                 155                 160

Asp Thr Val Thr Tyr Lys Cys Pro Leu Ile Thr Glu Val Glu Pro Glu
                165                 170                 175

Asp Ile Asp Cys Trp Cys Asn Leu Thr Ser Thr Trp Val Thr Tyr Gly
                180                 185                 190

Thr Cys Asn Gln Ala Gly Glu His Arg Arg Asp Lys Arg Ser Val Ala
            195                 200                 205

Leu Ala Pro His Val Gly Met Gly Leu Asp Thr Arg Thr Gln Thr Trp
            210                 215                 220

Met Ser Ala Glu Gly Ala Trp Arg Gln Val Glu Lys Val Glu Thr Trp
225                 230                 235                 240

Ala Phe Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
            275                 280                 285

Arg Asp Phe Val Glu Gly Leu Ser Gly Ala Thr Trp Val Asp Val Val
290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
            325                 330                 335

Arg Lys Leu Cys Ile Glu Gly Lys Ile Thr Asn Val Thr Thr Asp Ser
            340                 345                 350

Arg Cys Pro Thr Gln Gly Glu Ala Ile Leu Pro Glu Glu Gln Asp Gln
            355                 360                 365

Asn His Val Cys Lys His Thr Tyr Val Asp Arg Gly Trp Gly Asn Gly
            370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
                420                 425                 430

Asn Glu Thr Gln Gly Val Thr Ala Glu Ile Thr Pro Gln Ala Ser Thr
            435                 440                 445

Val Glu Ala Ile Leu Pro Glu Tyr Gly Thr Leu Gly Leu Glu Cys Ser
            450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
```

-continued

```
                485                 490                 495
Pro Trp Thr Ser Gly Ala Thr Thr Glu Thr Pro Thr Trp Asn Lys Lys
                500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Asn Ala Phe Val Leu Lys Lys Glu Val Ser Glu
                580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
                660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
        740                 745                 750

Met Ser Phe Ser Cys Ile Val Ile Gly Ile Ile Thr Leu Tyr Leu Gly
    755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
        820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Ile Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Asn
        900                 905                 910
```

```
Thr Pro Glu Cys Pro Ser Ala Ser Arg Ala Trp Asn Val Trp Glu Val
            915                 920                 925

Glu Asp Tyr Gly Phe Gly Val Phe Thr Thr Asn Ile Trp Leu Lys Leu
        930                 935                 940

Arg Glu Met Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Leu Ile Glu
            980                 985                 990

Val Lys Thr Cys Thr Trp Pro Lys Ser His Thr Leu Trp Ser Asn Gly
            995                 1000                1005

Val Leu Glu Ser Asp Met Ile Ile Pro Lys Ser Leu Ala Gly Pro Ile
    1010                1015                1020

Ser Gln His Asn Tyr Arg Pro Gly Tyr His Thr Gln Thr Ala Gly Pro
1025                1030                1035                1040

Trp His Leu Gly Lys Leu Glu Leu Asp Phe Asn Tyr Cys Glu Gly Thr
            1045                1050                1055

Thr Val Val Ile Thr Glu Asn Cys Gly Thr Arg Gly Pro Ser Leu Arg
            1060                1065                1070

Thr Thr Thr Val Ser Gly Lys Leu Ile His Glu Trp Cys Cys Arg Ser
        1075                1080                1085

Cys Thr Leu Pro Pro Leu Arg Tyr Met Gly Glu Asp Gly Cys Trp Tyr
        1090                1095                1100

Gly Met Glu Ile Arg Pro Ile Asn Glu Lys Glu Glu Asn Met Val Lys
1105                1110                1115                1120

Ser Leu Val Ser Ala Gly Ser Gly Lys Val Asp Asn Phe Thr Met Gly
            1125                1130                1135

Val Leu Cys Leu Ala Ile Leu Phe Glu Glu Val Met Arg Gly Lys Phe
            1140                1145                1150

Gly Lys Lys His Met Ile Ala Gly Val Leu Phe Thr Phe Val Leu Leu
            1155                1160                1165

Leu Ser Gly Gln Ile Thr Trp Arg Asp Met Ala His Thr Leu Ile Met
        1170                1175                1180

Ile Gly Ser Asn Ala Ser Asp Arg Met Gly Met Gly Val Thr Tyr Leu
1185                1190                1195                1200

Ala Leu Ile Ala Thr Phe Lys Ile Gln Pro Phe Leu Ala Leu Gly Phe
            1205                1210                1215

Phe Leu Arg Lys Leu Thr Ser Arg Glu Asn Leu Leu Leu Gly Val Gly
            1220                1225                1230

Leu Ala Met Ala Thr Thr Leu Gln Leu Pro Glu Asp Ile Glu Gln Met
        1235                1240                1245

Ala Asn Gly Ile Ala Leu Gly Leu Met Ala Leu Lys Leu Ile Thr Gln
        1250                1255                1260

Phe Glu Thr Tyr Gln Leu Trp Thr Ala Leu Val Ser Leu Met Cys Ser
1265                1270                1275                1280

Asn Thr Ile Phe Thr Leu Thr Val Ala Trp Arg Thr Ala Thr Leu Ile
            1285                1290                1295

Leu Ala Gly Ile Ser Leu Leu Pro Val Cys Gln Ser Ser Met Arg
        1300                1305                1310

Lys Thr Asp Trp Leu Pro Met Ala Val Ala Ala Met Gly Val Pro Pro
        1315                1320                1325

Leu Pro Leu Phe Ile Phe Ser Leu Lys Asp Thr Leu Lys Arg Arg Ser
```

```
             1330              1335              1340
Trp Pro Leu Asn Glu Gly Val Met Ala Val Gly Leu Val Ser Ile Leu
1345              1350              1355              1360

Ala Ser Ser Leu Leu Arg Asn Asp Val Pro Met Ala Gly Pro Leu Val
            1365              1370              1375

Ala Gly Gly Leu Leu Ile Ala Cys Tyr Val Ile Thr Gly Thr Ser Ala
            1380              1385              1390

Asp Leu Thr Val Glu Lys Ala Ala Asp Val Thr Trp Glu Glu Ala
        1395              1400              1405

Glu Gln Thr Gly Val Ser His Asn Leu Met Ile Thr Val Asp Asp Asp
        1410              1415              1420

Gly Thr Met Arg Ile Lys Asp Asp Glu Thr Glu Asn Ile Leu Thr Val
1425              1430              1435              1440

Leu Leu Lys Thr Ala Leu Leu Ile Val Ser Gly Ile Phe Pro Tyr Ser
            1445              1450              1455

Ile Pro Ala Thr Leu Leu Val Trp His Thr Trp Gln Lys Gln Thr Gln
            1460              1465              1470

Arg Ser Gly Val Leu Trp Asp Val Pro Ser Pro Glu Thr Gln Lys
        1475              1480              1485

Ala Glu Leu Glu Glu Gly Val Tyr Arg Ile Lys Gln Gln Gly Ile Phe
        1490              1495              1500

Gly Lys Thr Gln Val Gly Val Gly Val Gln Lys Glu Gly Val Phe His
1505              1510              1515              1520

Thr Met Trp His Val Thr Arg Gly Ala Val Leu Thr His Asn Gly Lys
            1525              1530              1535

Arg Leu Glu Pro Asn Trp Ala Ser Val Lys Lys Asp Leu Ile Ser Tyr
            1540              1545              1550

Gly Gly Gly Trp Lys Leu Ser Ala Gln Trp Gln Lys Gly Glu Glu Val
        1555              1560              1565

Gln Val Ile Ala Val Glu Pro Gly Lys Asn Pro Lys Asn Phe Gln Thr
    1570              1575              1580

Met Pro Gly Ile Phe Gln Thr Thr Thr Gly Glu Ile Gly Ala Ile Ala
1585              1590              1595              1600

Leu Asp Phe Lys Pro Gly Thr Ser Gly Ser Pro Ile Ile Asn Arg Glu
            1605              1610              1615

Gly Lys Val Leu Gly Leu Tyr Gly Asn Gly Val Val Thr Lys Asn Gly
            1620              1625              1630

Gly Tyr Val Ser Gly Ile Ala Gln Thr Asn Ala Glu Pro Asp Gly Pro
        1635              1640              1645

Thr Pro Glu Leu Glu Glu Glu Met Phe Lys Lys Arg Asn Leu Thr Ile
        1650              1655              1660

Met Asp Leu His Pro Gly Ser Gly Lys Thr Arg Lys Tyr Leu Pro Ala
1665              1670              1675              1680

Ile Val Arg Glu Ala Ile Lys Arg Arg Leu Arg Thr Leu Ile Leu Ala
            1685              1690              1695

Pro Thr Arg Val Val Ala Ala Glu Met Glu Glu Ala Leu Lys Gly Leu
            1700              1705              1710

Pro Ile Arg Tyr Gln Thr Thr Ala Thr Lys Ser Glu His Thr Gly Arg
        1715              1720              1725

Glu Ile Val Asp Leu Met Cys His Ala Thr Phe Thr Met Arg Leu Leu
        1730              1735              1740

Ser Pro Val Arg Val Pro Asn Tyr Asn Leu Ile Ile Met Asp Glu Ala
1745              1750              1755              1760
```

```
His Phe Thr Asp Pro Ala Ser Ile Ala Ala Arg Gly Tyr Ile Ser Thr
            1765                1770                1775
Arg Val Gly Met Gly Glu Ala Ala Ile Phe Met Thr Ala Thr Pro
        1780                1785                1790
Pro Gly Thr Ala Asp Ala Phe Pro Gln Ser Asn Ala Pro Ile Gln Asp
        1795                1800                1805
Glu Glu Arg Asp Ile Pro Glu Arg Ser Trp Asn Ser Gly Asn Glu Trp
        1810                1815                1820
Ile Thr Asp Phe Ala Gly Lys Thr Val Trp Phe Val Pro Ser Ile Lys
1825                1830                1835                1840
Ala Gly Asn Asp Ile Ala Asn Cys Leu Arg Lys Asn Gly Lys Lys Val
            1845                1850                1855
Ile Gln Leu Ser Arg Lys Thr Phe Asp Thr Glu Tyr Gln Lys Thr Lys
            1860                1865                1870
Leu Asn Asp Trp Asp Phe Val Val Thr Thr Asp Ile Ser Glu Met Gly
        1875                1880                1885
Ala Asn Phe Lys Ala Asp Arg Val Ile Asp Pro Arg Arg Cys Leu Lys
        1890                1895                1900
Pro Val Ile Leu Thr Asp Gly Pro Glu Arg Val Ile Leu Ala Gly Pro
1905                1910                1915                1920
Met Pro Val Thr Val Ala Ser Ala Ala Gln Arg Arg Gly Arg Val Gly
            1925                1930                1935
Arg Asn Pro Gln Lys Glu Asn Asp Gln Tyr Ile Phe Met Gly Gln Pro
            1940                1945                1950
Leu Asn Asn Asp Glu Asp His Ala His Trp Thr Glu Ala Lys Met Leu
        1955                1960                1965
Leu Asp Asn Ile Asn Thr Pro Glu Gly Ile Ile Pro Ala Leu Phe Glu
        1970                1975                1980
Pro Glu Arg Glu Lys Ser Ala Ala Ile Asp Gly Glu Tyr Arg Leu Lys
1985                1990                1995                2000
Gly Glu Ser Arg Lys Thr Phe Val Glu Leu Met Arg Arg Gly Asp Leu
            2005                2010                2015
Pro Val Trp Leu Ala His Lys Val Ala Ser Glu Gly Ile Lys Tyr Thr
            2020                2025                2030
Asp Arg Lys Trp Cys Phe Asp Gly Glu Arg Asn Asn Gln Ile Leu Glu
            2035                2040                2045
Glu Asn Met Asp Val Glu Ile Trp Thr Lys Glu Gly Glu Lys Lys Lys
        2050                2055                2060
Leu Arg Pro Arg Trp Leu Asp Ala Arg Thr Tyr Ser Asp Pro Leu Ala
2065                2070                2075                2080
Leu Lys Glu Phe Lys Asp Phe Ala Ala Gly Arg Lys Ser Ile Ala Leu
            2085                2090                2095
Asp Leu Val Thr Glu Ile Gly Arg Val Pro Ser His Leu Ala His Arg
            2100                2105                2110
Thr Arg Asn Ala Leu Asp Asn Leu Val Met Leu His Thr Ser Glu His
            2115                2120                2125
Gly Gly Arg Ala Tyr Arg His Ala Val Glu Glu Leu Pro Glu Thr Met
        2130                2135                2140
Glu Thr Leu Leu Leu Leu Gly Leu Met Ile Leu Leu Thr Gly Gly Ala
2145                2150                2155                2160
Met Leu Phe Leu Ile Ser Gly Lys Gly Ile Gly Lys Thr Ser Ile Gly
            2165                2170                2175
Leu Ile Cys Val Ala Ala Ser Ser Gly Met Leu Trp Met Ala Asp Val
```

```
                    2180             2185             2190
Pro Leu Gln Trp Ile Ala Ser Ala Ile Val Leu Glu Phe Phe Met Met
                2195             2200             2205
Val Leu Leu Ile Pro Glu Pro Glu Lys Gln Arg Thr Pro Gln Asp Asn
            2210             2215             2220
Gln Leu Ala Tyr Val Val Ile Gly Ile Leu Thr Leu Ala Ala Ile Val
2225             2230             2235             2240
Ala Ala Asn Glu Met Gly Leu Leu Glu Thr Thr Lys Arg Asp Leu Gly
                2245             2250             2255
Met Ser Lys Glu Pro Gly Val Val Ser Pro Thr Ser Tyr Leu Asp Val
                2260             2265             2270
Asp Leu His Pro Ala Ser Ala Trp Thr Leu Tyr Ala Val Ala Thr Thr
            2275             2280             2285
Val Ile Thr Pro Met Leu Arg His Thr Ile Glu Asn Ser Thr Ala Asn
            2290             2295             2300
Val Ser Leu Ala Ala Ile Ala Asn Gln Ala Val Val Leu Met Gly Leu
2305             2310             2315             2320
Asp Lys Gly Trp Pro Ile Ser Lys Met Asp Leu Gly Val Pro Leu Leu
                2325             2330             2335
Ala Leu Gly Cys Tyr Ser Gln Val Asn Pro Leu Thr Leu Thr Ala Ala
                2340             2345             2350
Val Leu Leu Leu Val Thr His Tyr Ala Ile Ile Gly Pro Gly Leu Gln
                2355             2360             2365
Ala Lys Ala Thr Arg Glu Ala Gln Lys Arg Thr Ala Ala Gly Ile Met
            2370             2375             2380
Lys Asn Pro Thr Val Asp Gly Ile Met Thr Ile Asp Leu Asp Pro Val
2385             2390             2395             2400
Ile Tyr Asp Ser Lys Phe Glu Lys Gln Leu Gly Gln Val Met Leu Leu
                2405             2410             2415
Val Leu Cys Ala Val Gln Leu Leu Leu Met Arg Thr Ser Trp Ala Phe
                2420             2425             2430
Cys Glu Ala Leu Thr Leu Ala Thr Gly Pro Ile Thr Thr Leu Trp Glu
                2435             2440             2445
Gly Ser Pro Gly Lys Phe Trp Asn Thr Thr Ile Ala Val Ser Met Ala
                2450             2455             2460
Asn Ile Phe Arg Gly Ser Tyr Leu Ala Gly Ala Gly Leu Ala Phe Ser
2465             2470             2475             2480
Ile Met Lys Ser Val Gly Thr Gly Lys Arg Gly Thr Gly Ser Gln Gly
                2485             2490             2495
Glu Thr Leu Gly Glu Lys Trp Lys Lys Lys Leu Asn Gln Leu Pro Arg
                2500             2505             2510
Lys Glu Phe Asp Leu Tyr Lys Lys Ser Gly Ile Thr Glu Val Asp Arg
            2515             2520             2525
Thr Glu Ala Lys Glu Gly Leu Lys Arg Gly Glu Ile Thr His His Ala
            2530             2535             2540
Val Ser Arg Gly Ser Ala Lys Leu Gln Trp Phe Val Glu Arg Asn Met
2545             2550             2555             2560
Val Ile Pro Glu Gly Arg Val Ile Asp Leu Gly Cys Gly Arg Gly Gly
                2565             2570             2575
Trp Ser Tyr Tyr Cys Ala Gly Leu Lys Lys Val Thr Glu Val Arg Gly
                2580             2585             2590
Tyr Thr Lys Gly Gly Pro Gly His Glu Glu Pro Val Pro Met Ser Thr
                2595             2600             2605
```

```
Tyr Gly Trp Asn Ile Val Lys Leu Met Ser Gly Lys Asp Val Phe Tyr
    2610            2615                2620

Leu Pro Pro Glu Lys Cys Asp Thr Leu Leu Cys Asp Ile Gly Glu Ser
2625            2630                2635                2640

Ser Pro Ser Pro Thr Val Glu Glu Ser Arg Thr Ile Arg Val Leu Lys
                2645                2650                2655

Met Val Glu Pro Trp Leu Lys Asn Asn Gln Phe Cys Ile Lys Val Leu
            2660                2665                2670

Asn Pro Tyr Met Pro Thr Val Ile Glu His Leu Glu Arg Leu Gln Arg
        2675                2680                2685

Lys His Gly Gly Met Leu Val Arg Asn Pro Leu Ser Arg Asn Ser Thr
    2690                2695                2700

His Glu Met Tyr Trp Ile Ser Asn Gly Thr Gly Asn Ile Val Ser Ser
2705                2710                2715                2720

Val Asn Met Val Ser Arg Leu Leu Leu Asn Arg Phe Thr Met Thr His
                2725                2730                2735

Arg Arg Pro Thr Ile Glu Lys Asp Val Asp Leu Gly Ala Gly Thr Arg
            2740                2745                2750

His Val Asn Ala Glu Pro Glu Thr Pro Asn Met Asp Val Ile Gly Glu
        2755                2760                2765

Arg Ile Arg Arg Ile Lys Glu Glu His Ser Ser Thr Trp His Tyr Asp
    2770                2775                2780

Asp Glu Asn Pro Tyr Lys Thr Trp Ala Tyr His Gly Ser Tyr Glu Val
2785                2790                2795                2800

Lys Ala Thr Gly Ser Ala Ser Ser Met Ile Asn Gly Val Val Lys Leu
                2805                2810                2815

Leu Thr Lys Pro Trp Asp Val Val Pro Met Val Thr Gln Met Ala Met
            2820                2825                2830

Thr Asp Thr Thr Pro Phe Gly Gln Gln Arg Val Phe Lys Glu Lys Val
        2835                2840                2845

Asp Thr Arg Thr Pro Arg Pro Met Pro Gly Thr Arg Lys Val Met Glu
    2850                2855                2860

Ile Thr Ala Glu Trp Leu Trp Arg Thr Leu Gly Arg Asn Lys Arg Pro
2865                2870                2875                2880

Arg Leu Cys Thr Arg Glu Glu Phe Thr Lys Lys Val Arg Thr Asn Ala
                2885                2890                2895

Ala Met Gly Ala Val Phe Thr Glu Glu Asn Gln Trp Asp Ser Ala Arg
            2900                2905                2910

Ala Ala Val Glu Asp Glu Glu Phe Trp Lys Leu Val Asp Arg Glu Arg
        2915                2920                2925

Glu Leu His Lys Leu Gly Lys Cys Gly Ser Cys Val Tyr Asn Met Met
    2930                2935                2940

Gly Lys Arg Glu Lys Lys Leu Gly Glu Phe Gly Lys Ala Lys Gly Ser
2945                2950                2955                2960

Arg Ala Ile Trp Tyr Met Trp Leu Gly Ala Arg Tyr Leu Glu Phe Glu
                2965                2970                2975

Ala Leu Gly Phe Leu Asn Glu Asp His Trp Phe Ser Arg Glu Asn Ser
            2980                2985                2990

Tyr Ser Gly Val Glu Gly Glu Gly Leu His Lys Leu Gly Tyr Ile Leu
        2995                3000                3005

Arg Asp Ile Ser Lys Ile Pro Gly Gly Ala Met Tyr Ala Asp Asp Thr
    3010                3015                3020

Ala Gly Trp Asp Thr Arg Ile Thr Glu Asp Asp Leu His Asn Glu Glu
```

```
                3025                3030                3035                3040
Lys Ile Thr Gln Gln Met Asp Pro Glu His Arg Gln Leu Ala Asn Ala
                    3045                3050                3055
Ile Phe Lys Leu Thr Tyr Gln Asn Lys Val Val Lys Val Gln Arg Pro
            3060                3065                3070
Thr Pro Lys Gly Thr Val Met Asp Ile Ile Ser Arg Lys Asp Gln Arg
        3075                3080                3085
Gly Ser Gly Gln Val Gly Thr Tyr Gly Leu Asn Thr Phe Thr Asn Met
    3090                3095                3100
Glu Ala Gln Leu Ile Arg Gln Met Glu Gly Glu Gly Val Leu Ser Lys
3105                3110                3115                3120
Ala Asp Leu Glu Asn Pro His Leu Leu Glu Lys Lys Val Thr Gln Trp
                3125                3130                3135
Leu Glu Thr Lys Gly Val Glu Arg Leu Lys Arg Met Ala Ile Ser Gly
                    3140                3145                3150
Asp Asp Cys Val Val Lys Pro Ile Asp Asp Arg Phe Ala Asn Ala Leu
            3155                3160                3165
Leu Ala Leu Asn Asp Met Gly Lys Val Arg Lys Asp Ile Pro Gln Trp
        3170                3175                3180
Gln Pro Ser Lys Gly Trp His Asp Trp Gln Gln Val Pro Phe Cys Ser
3185                3190                3195                3200
His His Phe His Glu Leu Ile Met Lys Asp Gly Arg Lys Leu Val Val
                3205                3210                3215
Pro Cys Arg Pro Gln Asp Glu Leu Ile Gly Arg Ala Arg Ile Ser Gln
                    3220                3225                3230
Gly Ala Gly Trp Ser Leu Arg Glu Thr Ala Cys Leu Gly Lys Ala Tyr
            3235                3240                3245
Ala Gln Met Trp Thr Leu Met Tyr Phe His Arg Arg Asp Leu Arg Leu
        3250                3255                3260
Ala Ser Asn Ala Ile Cys Ser Ala Val Pro Val His Trp Val Pro Thr
3265                3270                3275                3280
Ser Arg Thr Thr Trp Ser Ile His Ala His His Gln Trp Met Thr Thr
                3285                3290                3295
Glu Asp Met Leu Thr Val Trp Asn Arg Val Trp Ile Glu Asp Asn Pro
                    3300                3305                3310
Trp Met Glu Asp Lys Thr Pro Val Lys Thr Trp Glu Asp Val Pro Tyr
            3315                3320                3325
Leu Gly Lys Arg Glu Asp Gln Trp Cys Gly Ser Leu Ile Gly Leu Thr
        3330                3335                3340
Ser Arg Ala Thr Trp Ala Gln Asn Ile Leu Thr Ala Ile Gln Gln Val
3345                3350                3355                3360
Arg Ser Leu Ile Gly Asn Glu Glu Phe Leu Asp Tyr Met Pro Ser Met
                3365                3370                3375
Lys Arg Phe Arg Lys Glu Glu Glu Ser Glu Gly Ala Ile Trp
                    3380                3385                3390
```

<210> SEQ ID NO 50
<211> LENGTH: 2426
<212> TYPE: DNA
<213> ORGANISM: Artificial Sequence
<220> FEATURE:
<223> OTHER INFORMATION: Dengue 1 CME chimeric region

<400> SEQUENCE: 50
agttgttagt ctgtgtggac cgacaaggac agttccaaat cggaagcttg cttaacacag    60

```
ttctaacagt tgtttgaat agagagcaga tctctggaaa aatgaacaac caacggaaaa    120
agacgggtcg accgtctttc aatatgctga aacgcgcgag aaaccgcgtg tcaactggtt    180
cacagttggc gaagagattc tcaaaaggat tgctttcagg ccaaggaccc atgaaattgg    240
tgatggcttt catagcattt ctaagatttc tagccatacc cccaacagca ggaattttgg    300
ctagatggag ctcattcaag aagaatggag cgatcaaagt gttacggggt ttcaaaaaag    360
agatctcaag catgttgaac attatgaaca ggaggaaaaa atctgtgacc atgctcctca    420
tgctgctgcc cacagccctg gcgttccatt tgaccacacg aggggagag ccacacatga    480 tagttagtaa gcaggaaaga ggaaagtcac tgttgtttaa gacctctgca ggcatcaata    540
tgtgcactct cattgcgatg gatttgggag agttatgcga ggacacaatg acctacaaat    600
gcccccggat cactgaggcg gaaccagatg acgttgactg ctggtgcaat gccacagaca    660
catgggtgac ctatgggacg tgttctcaaa ccggcgaaca ccgacgagac aaacgttccg    720
tggcactggc cccacacgtg ggacttggtc tagaaacaag aaccgaaaca tggatgtcct    780
ctgaaggtgc ctggaaacaa gtacaaaaag tggagacttg gctttgaga cacccaggat    840 tcacggtgac agccctttt ttagcacatg ccataggaac atccattact cagaaaggga    900
tcattttcat tctgctgatg ctagtaacac catcaatggc catgcgatgt gtgggaatag    960
gcaacagaga cttcgttgaa ggactgtcag agcaacgtg ggtggacgtg gtattggagc    1020
atggaagctg cgtcaccacc atggcaaaag ataaaccaac attggacatt gaactcttga    1080
agacggaggt cacaaaccct gccgtcttgc gcaaactgtg cattgaagct aaaatatcaa    1140
acaccaccac cgattcaagg tgtccaacac aaggagaggc tacactggtg gaagaacagg    1200
actcgaactt tgtgtgtcga cgaacgtttg tggacagagg ctggggtaat ggctgcggac    1260
tatttggaaa aggaagccta ctgacgtgtg ctaagttcaa gtgtgtgaca aaactagaag    1320
gaaagatagt tcaatatgaa aacttaaaat attcagtgat agtcactgtc cacactgggg    1380
accagcacca ggtgggaaac gagactacag aacatggaac aattgcaacc ataacacctc    1440
aagctcctac gtcggaaata cagctgactg actacgagc cctcacattg gactgctcgc    1500
ctagaacagg gctggacttt aatgagatgg ttctattgac aatgaaagaa aaatcatggc    1560
ttgtccacaa acaatggttt ctagacttac cactgccttg gacttcagga gcttcaacat    1620
ctcaagagac ttgaacaga caagatttgc tggtcacatt caagacagct catgcaaaga    1680
aacaggaagt agtcgtactg ggatcacagg aaggagcaat gcacactgcg ttgactgggg    1740
cgacagaaat ccagacgtca ggaacgacaa caatctttgc aggacacctg aaatgcagac    1800
taaaaatgga taaactgact ttaaaaggga tgtcatatgt aatgtgcaca ggctcattta    1860
agctagagaa ggaagtggct gagacccagc atggaactgt tttagtgcag gttaaatacg    1920
aaggaacaga tgcgccatgc aagatcccctt tttcggccca agatgagaaa ggagtgaccc    1980
agaatgggag attgataaca gccaaccccca tagtcactga caagaaaaaa ccagtcaaca    2040
ttgagacaga accacctttt ggtgagagct acatcgtggt agggggcagg tgaaaaagctt    2100 tgaaactgag ctggttcaag aaagggagca gcataggaaa aatgttcgaa gcaactgccc    2160
gaggagcgcg aaggatggct atcctgggag acaccgcatg ggactttggc tctataggag    2220
gagtgttcac atcagtggga aaattggtac caggtttt tggagccgca tatgggttc    2280 tgttcagcgg tgtttcttgg accatgaaaa taggaatagg gattctgctg acatggctag    2340
gattaaactc gaggaacact tcaatggcta tgacgtgcat agctgttgga ggaatcactc    2400
tgtttctggg cttcacagtt caagca                                         2426
```

<210> SEQ ID NO 51
<211> LENGTH: 775
<212> TYPE: PRT
<213> ORGANISM: Artificial Sequence
<220> FEATURE:
<223> OTHER INFORMATION: Dengue 1 CME chimeric region

<400> SEQUENCE: 51

Met Asn Asn Gln Arg Lys Lys Thr Gly Arg Pro Ser Phe Asn Met Leu
1 5 10 15

Lys Arg Ala Arg Asn Arg Val Ser Thr Gly Ser Gln Leu Ala Lys Arg
20 25 30

Phe Ser Lys Gly Leu Leu Ser Gly Gln Gly Pro Met Lys Leu Val Met
35 40 45

Ala Phe Ile Ala Phe Leu Arg Phe Leu Ala Ile Pro Pro Thr Ala Gly
50 55 60

Ile Leu Ala Arg Trp Ser Ser Phe Lys Lys Asn Gly Ala Ile Lys Val
65 70 75 80

Leu Arg Gly Phe Lys Lys Glu Ile Ser Ser Met Leu Asn Ile Met Asn
85 90 95

Arg Arg Lys Lys Ser Val Thr Met Leu Leu Met Leu Leu Pro Thr Ala
100 105 110

Leu Ala Phe His Leu Thr Thr Arg Gly Gly Glu Pro His Met Ile Val
115 120 125

Ser Lys Gln Glu Arg Gly Lys Ser Leu Leu Phe Lys Thr Ser Ala Gly
130 135 140

Ile Asn Met Cys Thr Leu Ile Ala Met Asp Leu Gly Glu Leu Cys Glu
145 150 155 160

Asp Thr Met Thr Tyr Lys Cys Pro Arg Ile Thr Glu Ala Glu Pro Asp
165 170 175

Asp Val Asp Cys Trp Cys Asn Ala Thr Asp Thr Trp Val Thr Tyr Gly
180 185 190

Thr Cys Ser Gln Thr Gly Glu His Arg Arg Asp Lys Arg Ser Val Ala
195 200 205

Leu Ala Pro His Val Gly Leu Gly Leu Glu Thr Arg Thr Glu Thr Trp
210 215 220

Met Ser Ser Glu Gly Ala Trp Lys Gln Val Gln Lys Val Glu Thr Trp
225 230 235 240

Ala Leu Arg His Pro Gly Phe Thr Val Thr Ala Leu Phe Leu Ala His
245 250 255

Ala Ile Gly Thr Ser Ile Thr Gln Lys Gly Ile Ile Phe Ile Leu Leu
260 265 270

Met Leu Val Thr Pro Ser Met Ala Met Arg Cys Val Gly Ile Gly Asn
275 280 285

Arg Asp Phe Val Glu Gly Leu Ser Gly Ala Thr Trp Val Asp Val Val
290 295 300

Leu Glu His Gly Ser Cys Val Thr Thr Met Ala Lys Asp Lys Pro Thr
305 310 315 320

Leu Asp Ile Glu Leu Leu Lys Thr Glu Val Thr Asn Pro Ala Val Leu
325 330 335

Arg Lys Leu Cys Ile Glu Ala Lys Ile Ser Asn Thr Thr Thr Asp Ser
340 345 350

Arg Cys Pro Thr Gln Gly Glu Ala Thr Leu Val Glu Glu Gln Asp Ser
355 360 365

```
Asn Phe Val Cys Arg Arg Thr Phe Val Asp Arg Gly Trp Gly Asn Gly
    370                 375                 380

Cys Gly Leu Phe Gly Lys Gly Ser Leu Leu Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Ile Ala Thr Ile Thr Pro Gln Ala
        435                 440                 445

Pro Thr Ser Glu Ile Gln Leu Thr Asp Tyr Gly Ala Leu Thr Leu Asp
    450                 455                 460

Cys Ser Pro Arg Thr Gly Leu Asp Phe Asn Glu Met Val Leu Leu Thr
465                 470                 475                 480

Met Lys Glu Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Leu Gly Ser Gln Glu Gly Ala Met His Thr Ala Leu
    530                 535                 540

Thr Gly Ala Thr Glu Ile Gln Thr Ser Gly Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Ala Gln Asp Glu Lys Gly
    610                 615                 620

Val Thr Gln Asn Gly Arg Leu Ile Thr Ala Asn Pro Ile Val Thr Asp
625                 630                 635                 640

Lys Glu Lys Pro Val Asn Ile Glu Thr Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Val Gly Lys Leu Val His Gln Val Phe
705                 710                 715                 720

Gly Ala Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Met Ala Met Thr Cys Ile Ala Val Gly Gly Ile Thr Leu Phe
        755                 760                 765

Leu Gly Phe Thr Val Gln Ala
    770                 775
```

<210> SEQ ID NO 52
<211> LENGTH: 2423
<212> TYPE: DNA
<213> ORGANISM: Artificial Sequence
<220> FEATURE:
<223> OTHER INFORMATION: Dengue 1 ME chimeric region

<400> SEQUENCE: 52

```
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatcccacc aacagcaggg attctgaaga    300
gatggggaca gttgaagaaa aataaggcca tcaagatact gattggattc aggaaggaga    360
taggccgcat gctgaacatc ttgaacggga gaaaaaggtc tgcagccatg ctcctcatgc    420
tgctgcccac agccctggcg ttccatttga ccacacgagg gggagagcca cacatgatag    480
ttagtaagca ggaaagagga aagtcactgt tgtttaagac ctctgcaggc atcaatatgt    540
gcactctcat tgcgatggat ttgggagagt tatgcgagga cacaatgacc tacaaatgcc    600
cccggatcac tgaggcggaa ccagatgacg ttgactgctg gtgcaatgcc acagacacat    660
gggtgaccta tgggacgtgt tctcaaaccg gcgaacaccg acgagacaaa cgttccgtgg    720
cactggcccc acacgtggga cttggtctag aaacaagaac cgaaacatgg atgtcctctg    780
aaggtgcctg gaaacaagta caaaaagtgg agacttgggc tttgagacac ccaggattca    840
cggtgacagc ccttttttta gcacatgcca taggaacatc cattactcag aaagggatca    900
ttttcattct gctgatgcta gtaacaccat caatggccat gcgatgtgtg ggaataggca    960
acagagactt cgttgaagga ctgtcaggag caacgtgggt ggacgtggta ttggagcatg   1020
gaagctgcgt caccaccatg gcaaaagata aaccaacatt ggacattgaa ctcttgaaga   1080
cggaggtcac aaaccctgcc gtcttgcgca aactgtgcat tgaagctaaa atatcaaaca   1140
ccaccaccga ttcaaggtgt ccaacacaag gagaggctac actggtggaa gaacaggact   1200
cgaactttgt gtgtcgacga acgtttgtgg acagaggctg gggtaatggc tgcggactat   1260
ttggaaaagg aagcctactg acgtgtgcta agttcaagtg tgtgacaaaa ctagaaggaa   1320
agatagttca atatgaaaac ttaaaatatt cagtgatagt cactgtccac actggggacc   1380
agcaccaggt gggaaacgag actacagaac atggaacaat tgcaaccata acacctcaag   1440
ctcctacgtc ggaaatacag ctgactgact acggagccct cacattggac tgctcgccta   1500
gaacagggct ggactttaat gagatggttc tattgacaat gaaagaaaaa tcatggcttg   1560
tccacaaaca atggtttcta gacttaccac tgccttggac ttcaggagct tcaacatctc   1620
aagagacttg gaacagacaa gatttgctgg tcacattcaa gacagctcat gcaaagaaac   1680
aggaagtagt cgtactggga tcacaggaag gagcaatgca cactgcgttg actggggcga   1740
cagaaatcca gacgtcagga acgacaacaa tctttgcagg acacctgaaa tgcagactaa   1800
aaatggataa actgacttta aaagggatgt catatgtaat gtgcacaggc tcatttaagc   1860
tagagaagga agtggctgag acccagcatg gaactgtttt agtgcaggtt aaatacgaag   1920
gaacagatgc gccatgcaag atcccttttt cggcccaaga tgagaaagga gtgacccaga   1980
atgggagatt gataacagcc aaccccatag tcactgacaa agaaaaacca gtcaacattg   2040
agacagaacc accttttggt gagagctaca tcgtggtagg ggcaggtgaa aaagctttga   2100

-continued

```
aactgagctg gttcaagaaa gggagcagca tagggaaaat gttcgaagca actgcccgag    2160
gagcgcgaag gatggctatc ctgggagaca ccgcatggga ctttggctct ataggaggag    2220
tgttcacatc agtgggaaaa ttggtacacc aggttttttgg agccgcatat ggggttctgt   2280
tcagcggtgt ttcttggacc atgaaaatag gaatagggat tctgctgaca tggctaggat    2340
taaactcgag gaacacttca atggctatga cgtgcatagc tgttggagga atcactctgt    2400
ttctgggctt cacagttcaa gca                                            2423
```

<210> SEQ ID NO 53
<211> LENGTH: 774
<212> TYPE: PRT
<213> ORGANISM: Artificial Sequence
<220> FEATURE:
<223> OTHER INFORMATION: Dengue 1 ME chimeric region

<400> SEQUENCE: 53

```
Met Asn Gln Arg Lys Lys Val Val Arg Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Lys Ile Leu
65                  70                  75                  80

Ile Gly Phe Arg Lys Glu Ile Gly Arg Met Leu Asn Ile Leu Asn Gly
                85                  90                  95

Arg Lys Arg Ser Ala Ala Met Leu Leu Met Leu Leu Pro Thr Ala Leu
            100                 105                 110

Ala Phe His Leu Thr Thr Arg Gly Gly Glu Pro His Met Ile Val Ser
        115                 120                 125

Lys Gln Glu Arg Gly Lys Ser Leu Leu Phe Lys Thr Ser Ala Gly Ile
    130                 135                 140

Asn Met Cys Thr Leu Ile Ala Met Asp Leu Gly Glu Leu Cys Glu Asp
145                 150                 155                 160

Thr Met Thr Tyr Lys Cys Pro Arg Ile Thr Glu Ala Glu Pro Asp Asp
                165                 170                 175

Val Asp Cys Trp Cys Asn Ala Thr Asp Thr Trp Val Thr Tyr Gly Thr
            180                 185                 190

Cys Ser Gln Thr Gly Glu His Arg Arg Asp Lys Arg Ser Val Ala Leu
        195                 200                 205

Ala Pro His Val Gly Leu Gly Leu Glu Thr Arg Thr Glu Thr Trp Met
    210                 215                 220

Ser Ser Glu Gly Ala Trp Lys Gln Val Gln Lys Val Glu Thr Trp Ala
225                 230                 235                 240

Leu Arg His Pro Gly Phe Thr Val Thr Ala Leu Phe Leu Ala His Ala
                245                 250                 255

Ile Gly Thr Ser Ile Thr Gln Lys Gly Ile Ile Phe Ile Leu Leu Met
            260                 265                 270

Leu Val Thr Pro Ser Met Ala Met Arg Cys Val Gly Ile Gly Asn Arg
        275                 280                 285

Asp Phe Val Glu Gly Leu Ser Gly Ala Thr Trp Val Asp Val Val Leu
    290                 295                 300
```

-continued

```
Glu His Gly Ser Cys Val Thr Thr Met Ala Lys Asp Lys Pro Thr Leu
305                 310                 315                 320

Asp Ile Glu Leu Leu Lys Thr Glu Val Thr Asn Pro Ala Val Leu Arg
            325                 330                 335

Lys Leu Cys Ile Glu Ala Lys Ile Ser Asn Thr Thr Asp Ser Arg
        340                 345                 350

Cys Pro Thr Gln Gly Glu Ala Thr Leu Val Glu Glu Gln Asp Ser Asn
        355                 360                 365

Phe Val Cys Arg Arg Thr Phe Val Asp Arg Gly Trp Gly Asn Gly Cys
370                 375                 380

Gly Leu Phe Gly Lys Gly Ser Leu Leu Thr Cys Ala Lys Phe Lys Cys
385                 390                 395                 400

Val Thr Lys Leu Glu Gly Lys Ile Val Gln Tyr Glu Asn Leu Lys Tyr
                405                 410                 415

Ser Val Ile Val Thr Val His Thr Gly Asp Gln His Gln Val Gly Asn
            420                 425                 430

Glu Thr Thr Glu His Gly Thr Ile Ala Thr Ile Thr Pro Gln Ala Pro
                435                 440                 445

Thr Ser Glu Ile Gln Leu Thr Asp Tyr Gly Ala Leu Thr Leu Asp Cys
450                 455                 460

Ser Pro Arg Thr Gly Leu Asp Phe Asn Glu Met Val Leu Leu Thr Met
465                 470                 475                 480

Lys Glu Lys Ser Trp Leu Val His Lys Gln Trp Phe Leu Asp Leu Pro
                485                 490                 495

Leu Pro Trp Thr Ser Gly Ala Ser Ser Gln Glu Thr Trp Asn Arg
            500                 505                 510

Gln Asp Leu Leu Val Thr Phe Lys Thr Ala His Ala Lys Lys Gln Glu
                515                 520                 525

Val Val Val Leu Gly Ser Gln Glu Gly Ala Met His Thr Ala Leu Thr
530                 535                 540

Gly Ala Thr Glu Ile Gln Thr Ser Gly Thr Thr Thr Ile Phe Ala Gly
545                 550                 555                 560

His Leu Lys Cys Arg Leu Lys Met Asp Lys Leu Thr Leu Lys Gly Met
                565                 570                 575

Ser Tyr Val Met Cys Thr Gly Ser Phe Lys Leu Glu Lys Glu Val Ala
            580                 585                 590

Glu Thr Gln His Gly Thr Val Leu Val Gln Val Lys Tyr Glu Gly Thr
                595                 600                 605

Asp Ala Pro Cys Lys Ile Pro Phe Ser Ala Gln Asp Glu Lys Gly Val
610                 615                 620

Thr Gln Asn Gly Arg Leu Ile Thr Ala Asn Pro Ile Val Thr Asp Lys
625                 630                 635                 640

Glu Lys Pro Val Asn Ile Glu Thr Glu Pro Pro Phe Gly Glu Ser Tyr
                645                 650                 655

Ile Val Val Gly Ala Gly Glu Lys Ala Leu Lys Leu Ser Trp Phe Lys
            660                 665                 670

Lys Gly Ser Ser Ile Gly Lys Met Phe Glu Ala Thr Ala Arg Gly Ala
                675                 680                 685

Arg Arg Met Ala Ile Leu Gly Asp Thr Ala Trp Asp Phe Gly Ser Ile
690                 695                 700

Gly Gly Val Phe Thr Ser Val Gly Lys Leu Val His Gln Val Phe Gly
705                 710                 715                 720

Ala Ala Tyr Gly Val Leu Phe Ser Gly Val Ser Trp Thr Met Lys Ile
                725                 730                 735
```

```
Gly Ile Gly Ile Leu Leu Thr Trp Leu Gly Leu Asn Ser Arg Asn Thr
            740                 745                 750
Ser Met Ala Met Thr Cys Ile Ala Val Gly Gly Ile Thr Leu Phe Leu
            755                 760                 765
Gly Phe Thr Val Gln Ala
        770
```

What is claimed is:

1. A tetravalent immunogenic composition comprising
   a) a first attenuated virus that is immunogenic against dengue serotype 1 comprising a nucleic acid that encodes at least one structural protein from dengue serotype 1 and nonstructural proteins from dengue serotype 1 or dengue serotype 4;
   b) a second attenuated virus that is immunogenic against dengue serotype 2 comprising a nucleic acid that encodes at least one structural protein from dengue serotype 2 and nonstructural proteins from dengue serotype 4;
   c) a third attenuated virus that is immunogenic against dengue serotype 3 comprising a nucleic acid that encodes at least one structural protein from dengue serotype 3 and nonstructural proteins from dengue serotype 3 or dengue serotype 4; and
   d) a fourth attenuated virus that is immunogenic against dengue serotype 4 comprising a nucleic acid that encodes at least one structural protein from dengue serotype 4 and nonstructural proteins from dengue serotype 4,
   wherein the first attenuated virus, the second attenuated virus, the third attenuated virus, and the fourth attenuated virus each comprise a 3' untranslated region, and
   wherein the 3' untranslated region contains a deletion of about 30 nucleotides corresponding to the TL2 stem-loop structure of dengue serotype 1, dengue serotype 3, or dengue serotype 4;
   wherein the tetravalent immunogenic composition is not a combination of rDEN1/4Δ30, rDEN2/4Δ30, rDEN3/4Δ30, and rDEN4Δ30.

2. The tetravalent immunogenic composition of claim 1, wherein the nucleic acid of at least one of a), b), c) or d) further comprises a mutation that confers a phenotype wherein the phenotype is host-cell adaptation for improved replication in Vero cells, or attenuation in mice or monkeys.

3. The composition of claim 1, wherein the 3' untranslated region of a) comprises a deletion of about 30 nucleotides from the 3' untranslated region of the dengue type 1 genome corresponding to the TL2 stem-loop structure between about nucleotides 10562-10591.

4. The composition of claim 1, wherein the 3' untranslated region of a) comprises a deletion of about 30 nucleotides from the 3' untranslated region of the dengue type 4 genome corresponding to the TL2 stem-loop structure between about nucleotides 10478-10507.

5. The composition of claim 1, wherein the 3' untranslated region of b) comprises a deletion of about 30 nucleotides from the 3' untranslated region of the dengue type 4 genome corresponding to the TL2 stem-loop structure between about nucleotides 10478-10507.

6. The composition of claim 1, wherein the 3' untranslated region of c) comprises a deletion of about 30 nucleotides from the 3' untranslated region of the dengue type 4 genome corresponding to the TL2 stem-loop structure between about nucleotides 10478-10507.

7. The composition of claim 1, wherein the 3' untranslated region of d) comprises a deletion of about 30 nucleotides from the 3' untranslated region of the dengue type 4 genome corresponding to the TL2 stem-loop structure between about nucleotides 10478-10507.

8. The composition of claim 1, wherein the nucleic acid that encodes at least one structural protein from dengue serotype 1 encodes at least two structural proteins from dengue serotype 1.

9. The composition of claim 1, wherein the nucleic acid that encodes at least one structural protein from dengue serotype 2 encodes at least two structural proteins from dengue serotype 2.

10. The composition of claim 1, wherein the nucleic acid that encodes at least one structural protein from dengue serotype 3 encodes at least two structural proteins from dengue serotype 3.

11. The composition of claim 1, wherein the nucleic acid that encodes at least one structural protein from dengue serotype 4 encodes at least two structural proteins from dengue serotype 4.

12. The composition of claim 8, wherein the at least two structural proteins from dengue serotype 1 are prM and E proteins.

13. The composition of claim 8, wherein the at least two structural proteins from dengue serotype 1 are C, prM and E proteins.

14. The composition of claim 9, wherein the at least two structural proteins from dengue serotype 2 are prM and E proteins.

15. The composition of claim 10, wherein the at least two structural proteins from dengue serotype 3 are C, prM and E proteins.

16. The composition of claim 11, wherein the at least two structural proteins from dengue serotype 4 are C, prM and E proteins.

17. The composition of claim 12,
   wherein the at least one structural protein from dengue serotype 2 is prM and E proteins;
   wherein the at least one structural protein from dengue serotype 3 is C, prM and E proteins;
   wherein the at least one structural protein from dengue serotype 4 is C, prM and E proteins;
   wherein the deletion of a) is a deletion of about 30 nucleotides from the 3' untranslated region of the dengue type 4 genome corresponding to the TL2 stem-loop structure between about nucleotides 10478-10507;
   wherein the deletion of b) is a deletion of about 30 nucleotides from the 3' untranslated region of the dengue type 4 genome corresponding to the TL2 stem-loop structure between about nucleotides 10478-10507;

wherein the deletion of c) is a deletion of about 30 nucleotides from the 3' untranslated region of the dengue type 4 genome corresponding to the TL2 stem-loop structure between about nucleotides 10478-10507;

wherein the deletion of d) is a deletion of about 30 nucleotides from the 3' untranslated region of the dengue type 4 genome corresponding to the TL2 stem-loop structure between about nucleotides 10478-10507.

18. The composition of claim 13, wherein the at least one structural protein from dengue serotype 2 is prM and E proteins, wherein the at least one structural protein from dengue serotype 3 is C, prM and E proteins;

wherein the at least one structural protein from dengue serotype 4 is C, prM and E proteins;

wherein the deletion of a) is a deletion of about 30 nucleotides from the 3' untranslated region of the dengue type 1 genome corresponding to the TL2 stem-loop structure between about nucleotides 10562-10591;

wherein the deletion of b) is a deletion of about 30 nucleotides from the 3' untranslated region of the dengue type 4 genome corresponding to the TL2 stem-loop structure between about nucleotides 10478-10507;

wherein the deletion of c) is a deletion of about 30 nucleotides from the 3' untranslated region of the dengue type 4 genome corresponding to the TL2 stem-loop structure between about nucleotides 10478-10507;

wherein the deletion of d) is a deletion of about 30 nucleotides from the 3' untranslated region of the dengue type 4 genome corresponding to the TL2 stem-loop structure between about nucleotides 10478-10507.

19. The composition of claim 1 which is a combination of rDEN1/4Δ30, rDEN2/4Δ30, rDEN3Δ30, and rDEN4Δ30.

20. The composition of claim 1 which is a combination of rDEN1/4Δ30, rDEN2/4Δ30, rDEN3Δ30, and rDEN4Δ30.

21. The composition of claim 1 which is a combination of rDEN1/4Δ30, rDEN2/4Δ30, rDEN3Δ30, and rDEN4Δ30.

22. A method of inducing an immune response in a subject comprising administering an effective amount of the composition of claim 1 to the subject.

23. The method of claim 22 wherein the subject is a human.

24. A method of inducing an immune response in a subject comprising administering an effective amount of the composition of claim 17 to the subject.

25. The method of claim 24 wherein the subject is a human.

26. A method of inducing an immune response in a subject comprising administering an effective amount of the composition of claim 18 to the subject.

27. The method of claim 26 wherein the subject is a human.

28. A tetravalent vaccine comprising the composition of claim 1.

29. A tetravalent vaccine comprising the composition of claim 17.

30. A tetravalent vaccine comprising the composition of claim 18.

31. A method of preventing disease caused by dengue virus in a subject comprising administering an effective amount of the vaccine of claim 28 to the subject.

32. The method of claim 31 wherein the subject is a human.

33. A method of preventing disease caused by dengue virus in a subject comprising administering an effective amount of the vaccine of claim 17 to the subject.

34. The method of claim 33 wherein the subject is a human.

35. A method of preventing disease caused by dengue virus in a subject comprising administering an effective amount of the vaccine of claim 18 to the subject.

36. The method of claim 35 wherein the subject is a human.

* * * * *